(12) United States Patent  
Edmunds

(10) Patent No.: US 7,407,972 B2  
(45) Date of Patent: Aug. 5, 2008

(54) INHIBITORS OF FACTOR XA AND OTHER SERINE PROTEASES INVOLVED IN THE COAGULATION CASCADE

(75) Inventor: Jeremy John Edmunds, Ypsilanti, MI (US)

(73) Assignee: Pfizer Inc., New York, NY (US)

( * ) Notice: Subject to any disclaimer, the term of this patent is extended or adjusted under 35 U.S.C. 154(b) by 532 days.

(21) Appl. No.: 11/017,598

(22) Filed: Dec. 20, 2004

(65) Prior Publication Data

US 2005/0267118 A1    Dec. 1, 2005

Related U.S. Application Data

(62) Division of application No. 10/278,643, filed on Oct. 23, 2002, now Pat. No. 7,030,141.

(60) Provisional application No. 60/384,895, filed on May 31, 2002, provisional application No. 60/334,168, filed on Nov. 29, 2001.

(51) Int. Cl.
```
A61K 31/454      (2006.01)
A61K 31/4439     (2006.01)
A61K 31/4155     (2006.01)
C07D 401/14      (2006.01)
C07D 403/14      (2006.01)
C07D 405/14      (2006.01)
C07D 409/14      (2006.01)
C07D 411/14      (2006.01)
C07D 413/14      (2006.01)
C07D 417/14      (2006.01)
C07D 419/14      (2006.01)
C07D 421/14      (2006.01)
C07D 249/14      (2006.01)
C07D 231/04      (2006.01)
C07D 231/06      (2006.01)
C07D 231/08      (2006.01)
C07D 217/24      (2006.01)
C07D 471/04      (2006.01)
C07D 491/04      (2006.01)
C07D 498/04      (2006.01)
A61K 31/4412     (2006.01)
A61K 31/4725     (2006.01)
```

(52) U.S. Cl. .................. 514/326; 514/340; 514/341; 514/343; 514/406; 514/302; 514/309; 514/301; 514/332; 514/333; 544/405; 546/208; 546/211; 546/275.4; 546/256; 546/278.4; 546/146; 546/116; 546/114; 548/100; 548/265.6; 548/266.2; 548/314.7; 548/379.4

(58) Field of Classification Search ................. 514/326, 514/406, 340, 341, 343, 302, 309, 301.333; 546/211, 275.4, 208, 256, 278.4, 141, 116.114; 548/379.4, 100, 265.6, 266.2, 314.7, 364.1; 544/405

See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,807,875 A | 9/1998 | Rudolf et al. | |
| 6,835,739 B2 * | 12/2004 | Zhu et al. | 514/318 |
| 2002/0091116 A1 | 7/2002 | Zhu et al. | |

FOREIGN PATENT DOCUMENTS

| | | |
|---|---|---|
| CA | 23/99018 A1 | 2/2001 |
| WO | WO 95/28420 A1 | 10/1995 |
| WO | WO 97/05161 A1 | 2/1997 |
| WO | WO97/19911 A1 | 6/1997 |
| WO | WO 97/46576 A1 | 12/1997 |
| WO | WO 98/50029 A1 | 11/1998 |
| WO | WO 01/19788 A2 | 3/2001 |
| WO | WO 01/19798 A2 | 3/2001 |
| WO | WO 01/64642 A2 | 9/2001 |
| WO | WO 01/96296 A1 | 12/2001 |
| WO | WO 02/00651 A2 | 1/2002 |
| WO | WO 02/08177 A2 | 1/2002 |
| WO | WO 02/24654 A1 | 3/2002 |
| WO | WO 02/30880 A2 | 4/2002 |

(Continued)

OTHER PUBLICATIONS

Lapatto et al., Embo. J, 1997:5151-5161.

(Continued)

*Primary Examiner*—Mark L. Berch  
*Assistant Examiner*—Cecilia M Jaisle  
(74) *Attorney, Agent, or Firm*—Gregg C. Benson; Rona A. Nardone

(57) ABSTRACT

The present invention provides compounds of Formula (I):

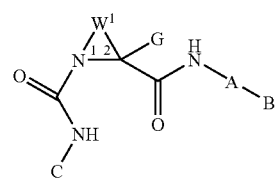

wherein A, B, C, G, and $W^1$ have any of the values defined in the specification, and pharmaceutically acceptable salt thereof, that are useful to treat thrombotic disorders. Also disclosed are pharmaceutical compositions comprising one or more compounds of Formula I, processes for preparing compounds of Formula I, and intermediates useful for preparing compounds of Formula I.

13 Claims, No Drawings

FOREIGN PATENT DOCUMENTS

| | | |
|---|---|---|
| WO | WO 02/48099 A1 | 6/2002 |
| WO | WO 02/057236 A1 | 7/2002 |

OTHER PUBLICATIONS

Mellott et al, Fibrinolysis, 1993: 195-202.
Lynch et al., Thromb. Haemostasis, 1995:640-645.
Schaffer et al., Circulation, 1991: 1741-1748.
Fioravanti et al., Thromb. Res., 1993: 317-324.
Wong et al., Thromb. Res., 1996: 117-126.
Leadley, Curr. Top. Med. Chem., 2001: v. 1, 151-159.
Edmunds et al., Annual Reports in Medicinal Chemistry, 1996:51.
Kunitada and Nagahara, Curr. Pharm. Des., 1996:531-542.
Berge S.M. et al.,Pharmaceutical Salts, Journal of Pharmaceutical Science, 1977;66:1-19.
F Al-Obeidi & Jaostrem: "Factor Xa Inhibitors" Expert Opinion on Therapeutic Patents., vol. 9, No. 7, 1999, pp. 931-953, XP001000512.
Erik Verner et al.: "Development of Serine Protease Inhibitors Displaying a Multicenter Short Hydrogen Bond Binding Mode: Inhibitors of Urokinase-Type Plasminogen Activator and Factor Xa" Journal of Medicinal Chemistry vol. 44, No. 17, 2001, pp. 2753-2771, XP002216503.
Michael R Wiley et al., "Structure-Based Design of Potent, Amidine-Derived Inhibitors of Factor Xa: Evaluation of Selectivity, Anticoagulant Activity, and Antithrombotic Activity" Journal of Medicinal Chemistry, vol. 43, No. 5, 2000, pp. 883-899. XP002186966.
Ying K. Yee et al.,: "N-Aroylanthranilamide Inhibitors of Human Factor Xa" Journal of Medicinal Chemistry., vol. 43, No. 5, 2000, pp. 873-882. XP002186965.

* cited by examiner

INHIBITORS OF FACTOR XA AND OTHER SERINE PROTEASES INVOLVED IN THE COAGULATION CASCADE

This application is a division of U.S. Ser. No. 10/278,643, filed Oct. 23, 2002, now U.S. Pat. No. 7,030,141, which claims the benefit of U.S. provisional application 60/334,168, filed Nov. 29, 2001, and U.S. provisional application 60/384,895, filed May 31, 2002.

FIELD OF THE INVENTION

The present invention relates to cyclic amino acid and proline derivatives which display inhibitory effects of the serine protease factor Xa. The invention also discloses pharmaceutically acceptable salts of the compounds, pharmaceutically acceptable compositions comprising the compounds or their salts, and methods of using them as therapeutic agents for treating or preventing disease states in mammals characterized by abnormal thrombosis.

BACKGROUND OF THE INVENTION

In economically developed countries, cardiovascular disease represents a major cause of mortality. In particular, abnormal coagulation and inappropriate thrombus formation within blood vessels precipitates many acute cardiovascular disease states. While it has long been recognized that a variety of plasma proteins such as fibrinogen, serine proteases, and cellular receptors are involved in hemostasis, it is abnormal regulation that has emerged as important contributing factors to cardiovascular disease.

Thrombin can be considered the key or principal regulatory enzyme in the coagulation cascade; it serves a pluralistic role as both a positive and negative feedback regulator in normal hemostasis. However, in some pathologic conditions, the positive feedback regulation is amplified through catalytic activation of cofactors required for thrombin generation. Such cofactors include factor Xa, a serine protease which occupies a pivotal position in the coagulation cascade. Factor X is the zymogen of factor Xa. Factor X can be activated either the intrinsic or extrinsic pathways of the coagulation system. Initiation of coagulation by either pathway in response to vascular injury activates factor X to factor Xa. Factor Xa and its cofactor, factor Va, combine on a phospholipid membrane to form the "prothombinase" complex, which activates prothrombin to thrombin. Thrombin cleaves fibrinogen to fibrin, activates platelets, and converts factor XIII to XIIIa which is the principal enzyme involved in thrombus generation, growth, and stabilization. Accordingly, the location of the prothrombinase complex at the convergence of both the intrinsic and extrinsic coagulation pathways suggests that inhibition of factor Xa, and hence thrombin generation, may be a viable approach to limiting the procoagulant activity of thrombin.

Evidence exists for the role of factor Xa inhibitors as anticoagulants. Antistasin, a potent inhibitor of blood coagulation factor Xa from the Mexican leech, *Haementeria officinalis*, displays antithrombotic activity in various models of arterial and venous thrombosis (Lapatto et al., *Embo. J*, 1997:5151-5161). Other protein or polypeptide factor Xa inhibitors include recombinant tick anticoagulant peptide (rTAP), which is known to accelerate the recombinant tissue plasminogen activator mediated clot lysis and prevent acute reocclusion in the dog, hence indicating factor Xa inhibitors may be useful as an adjunct to thrombolytic therapy (Mellott et al., *Fibrinolysis*, 1993: 195-202). Furthermore, in a canine coronary artery electrolytic lesion model, rTAP was demonstrated to reduce thrombus mass and time to occlusion in the absence of dramatic hemodynamic or hemostatic changes indicating the primary role for factor Xa in the process of arterial thrombosis (Lynch et al., *Thromb. Haemostasis*, 1995:640-645; Schaffer et al., *Circulation*, 1991: 1741-1748). On the venous side, rTAP was also demonstrated to reduce fibrin deposition in a rabbit model of venous thrombosis while having little affect on systemic hemostatic parameters (Fioravanti et al., *Thromb. Res.*, 1993: 317-324). In addition to these relatively high molecular weight proteins that are not suitable as oral antithrombotic agents, there also exist examples of low molecular weight factor Xa inhibitors. In particular DX9065a, a low molecular weight synthetic factor Xa inhibitor, has also shown antithrombotic potential in various experimental thrombosis rat models. In both arteriovenous shunt and venous stasis models, inhibition of thrombus formation was achieved at doses that had little effect on APTT, indicating that DX9065a is effective in preventing thrombosis and hence has therapeutic antithrombotic potential (Wong et al., *Thromb. Res.*, 1996: 117-126).

Recently, it has been appreciated that factor Xa inhibition may provide sustained antithrombotic protection. Specifically, several animal studies show that inhibition of short term exposure to factor Xa produces a sustained antithrombotic. (Leadley, *Curr. Top. Med. Chem.*, 2001: v. 1, 151-159.) Finally, the article by Leadley observes that factor Xa inhibition potentially provides a large therapeutical window between antithrombotic efficacy and bleeding tendency. Consequently, there may exist a range in which factor Xa inhibition is achieved without an concurrent increase in a patients susceptibility to bleeding.

The majority of factor Xa inhibitors known to date have been summarized in two reviews (Edmunds et al., *Annual Reports in Medicinal Chemistry*, 1996:51 and Kunitada and Nagahara, *Curr. Pharm. Des.*, 1996:531-542). However, it is readily apparent that there still exists a need for more effective agents that regulate factor Xa proteolytic activity.

SUMMARY OF THE INVENTION

These and other needs are met by the present invention which is directed to a compound of Formula I

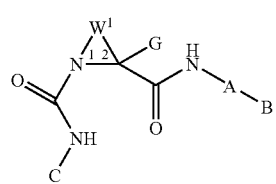

I or a pharmaceutically acceptable salt thereof wherein:

A is aryl or substituted aryl or monocyclic heteroaryl or substituted monocyclic heteroaryl; be opt

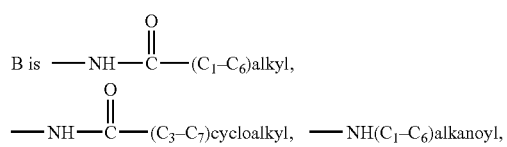

-continued

($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, or heteroaryl, any of which may ionally substituted by halo, ($C_1$-$C_6$)alkyl, or halo($C_1$-$C_6$)alkyl, ($C_1$-$C_6$)alkoxy, —CN, haloalkyl, amino, alkylamino, amidino, amido, or sulfonamido;

C is phenyl or heteroaryl, wherein phenyl or heteroaryl is optionally substituted with one or more substituents selected from halogen, hydroxy, -$CO_2R^2$, —$COR^2$, —$CONR^2R^{2'}$, alkoxy, alkyl, —CN, haloalkyl, amino, alkylamino, amidino, amido, or sulfonamido;

G is H, halo, ($C_1$-$C_6$)alkyl, halo($C_1$-$C_6$)alkyl, hydroxy($C_1$-$C_6$)alkyl, —$CH_2O$—($C_1$-$C_6$)alkyl, —$CH_2$—$CO_2$($C_1$-$C_6$)alkyl, —$CH_2$—$NR2R2'$, or —$CH_2$—$CONH(C_1$-$C_6$)alkyl;

$W^1$ is a saturated or unsaturated, substituted or unsubstituted hydrocarbon chain or hydrocarbon-heteroatom chain having from 2 to 6 atoms, wherein $W^1$ connects the nitrogen atom at position 1 to the carbon atom at position 2 to form a four to eight membered ring;

$R^1$ is ($C_1$-$C_6$)alkoxy, ($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, monocyclic heteroaryl, or —$NR^3R^4$;

$R^2$ and $R^{2'}$ are each independently H or ($C_1$-$C_6$)alkyl; and $R^3$ and $R^4$ are each independently H, ($C_1$-$C_6$)alkyl, aralkyl, aryl, monocyclic heteroaryl, alkoxycarbonyl, aralkoxycarbonyl, —$SO_2$alkyl, or joined together to form a saturated or unsaturated 3 to 7 membered ring.

The invention is also directed to a compound of formula II:

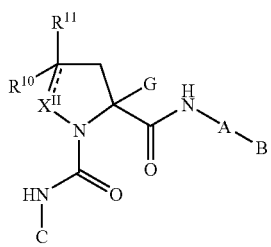

II or a pharmaceutically acceptable salt thereof wherein

" - - - " is a bond or is absent;

$X^{II}$ is $CH_2$, CH, NH or N;

$R^{10}$ and $R^{11}$ are each independently H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$ or are taken together to form =O, =$NOR^2$, =$C(C_1$-$C_6$alkyl$)_2$, or =$CR^2H$, with the proviso that when " - - - " is a bond, $R^{11}$ is absent, and $X^{II}$ is CH or N, and $R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$;

A is aryl and substituted aryl or monocyclic heteroaryl or substituted monocyclic heteroaryl;

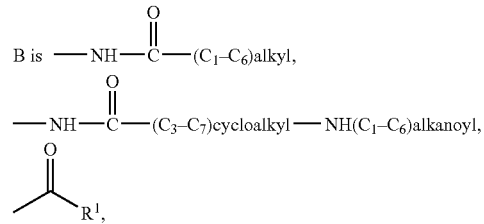

($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, or heteroaryl, any of which may be optionally substituted;

C is phenyl or heteroaryl, wherein phenyl or heteroaryl is optionally substituted with one or more substituents selected from halogen, hydroxy, —$CO_2R^2$, —$COR^2$, —$CONR^2R^{2'}$, alkoxy, alkyl, —CN, haloalkyl, amino, alkylamino, amidino, amido, or sulfonamido;

G is H, halo, ($C_1$-$C_6$)alkyl, halo($C_1$-$C_6$)alkyl, hydroxy($C_1$-$C_6$)alkyl,
—$CH_2O$—($C_1$-$C_6$)alkyl, —$CH_2$—$CO_2(C_1$-$C_6$)alkyl, —$CH_2$—$NR^2R^{2'}$, or —$CH_2$—$CONH(C_1$-$C_6$)alkyl; or —$CH_2$—$CONH(C_1$-$C_6$)alkyl;

$R^1$ is ($C_1$-$C_6$)alkoxy, ($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, monocyclic heteroaryl, or —$NR^3R^4$;

$R^2$ and $R^{2'}$ are each independently H or ($C_1$-$C_6$)alkyl; and $R^3$ and $R^4$ are each independently H, ($C_1$-$C_6$)alkyl, aralkyl, aryl, monocyclic heteroaryl, alkoxycarbonyl, aralkoxycarbonyl, —$SO_2$alkyl, or joined together to form a saturated or unsaturated 5 to 7 membered ring.

The invention is also directed to a compound of Formula III

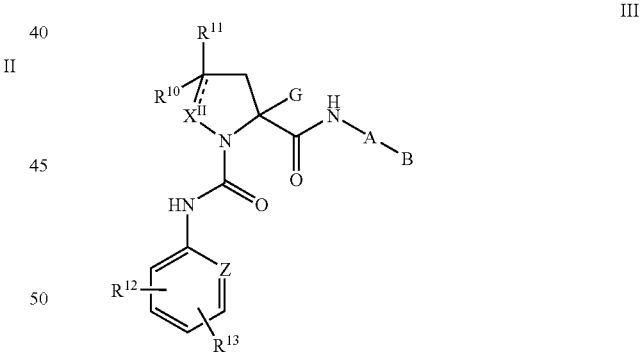

III or a pharmaceutically acceptable salt thereof wherein

" - - - " is a bond or is absent;

Z is C—H, C-halo, C—($C_1$-$C_6$)alkyl, C-halo($C_1$-$C_6$)alkyl, C—($C_1$-$C_6$)alkoxy, or N;

$X^{II}$ is $CH_2$, CH, NH or N;

$R^{10}$ and $R^{11}$ are each independently H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$ or are taken together to form =O, =$NOR^2$, =$C(C_1$-$C_6$alkyl$)_2$, or =$CR^2H$, with the proviso that when " - - - " is a bond, $R^{11}$ is absent, and $X^{II}$ is CH or N, and $R^{10}$ is H, —OH, halo, alkyl, haloalkyl, —$NR^8R^9$, —$OR^2$, —CN, —$CH_2OH$, —$CH_2$—

NR³R⁴, aryl, monocyclic heteroaryl, alkylaryl, —CH=O, —CH₂OR², —COR², —CO₂R², or —CONR³R⁴;

A is aryl and substituted aryl or monocyclic heteroaryl or substituted monocyclic heteroaryl;

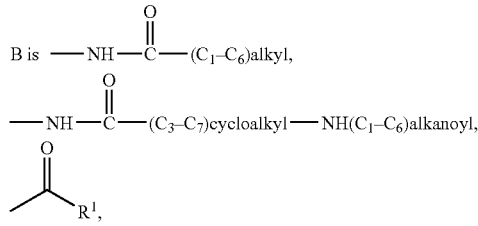

$(C_3-C_7)$cycloalkyl, $(C_3-C_7)$heterocycloalkyl, $(C_4-C_7)$cycloalkenyl, $(C_4-C_7)$heterocycloalkenyl, aryl, or heteroaryl, any of which may be optionally substituted, wherein $R^1$ is $(C_1-C_6)$alkoxy, $(C_3-C_7)$cycloalkyl, $(C_3-C_7)$heterocycloalkyl, $(C_4-C_7)$cycloalkenyl, $(C_4-C_7)$heterocycloalkenyl, aryl, monocyclic heteroaryl, or —NR³R⁴;

G is H, halo, $(C_1-C_6)$alkyl, halo$(C_1-C_6)$alkyl, hydroxy$(C_1-C_6)$alkyl, —CH₂O—$(C_1-C_6)$alkyl, —CH₂—CO₂$(C_1-C_6)$alkyl, —CH₂—CONH₂, or —CH₂—CONH$(C_1-C_6)$alkyl;

R² and R²' are each independently H or $(C_1-C_6)$alkyl; and

R³ and R⁴ are independently H, $(C_1-C_6)$alkyl, aralkyl, aryl, monocyclic heteroaryl, alkoxycarbonyl, aralkoxycarbonyl, —SO₂alkyl, or joined together to form a saturated or unsaturated 5 to 7 membered ring; and R¹² and R¹³ are each independently H, halo, $(C_1-C_6)$alkyl, halo$(C_1-C_6)$alkyl, or $(C_1-C_6)$alkoxy.

What is also provided is a compound of Formula IV

IV

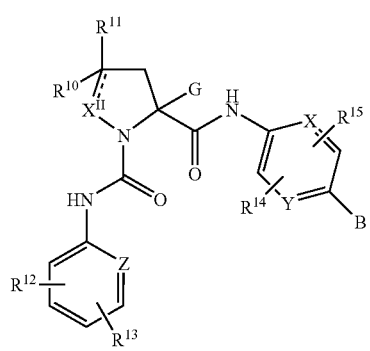

or a pharmaceutically acceptable salt thereof wherein

" - - - " is a bond or is absent;

Z is C—H, C-halo, C—$(C_1-C_6)$alkyl, C-halo$(C_1-C_6)$alkyl, C—$(C_1-C_6)$alkoxy, or N;

$X^{II}$ is CH₂, CH, NH or N;

R¹⁰ and R¹¹ are each independently H, —OH, halo, alkyl, haloalkyl, —NR⁸R⁹, —OR², —CN, —CH₂OH, —CH₂—NR³R⁴, aryl, monocyclic heteroaryl, alkylaryl, —CH=O, —CH₂OR², —COR², —CO₂R², or —CONR³R⁴ or are taken together to form =O, =NOR², =C$(C_1-C_6$alkyl$)_2$, or =CR²H, with the proviso that when " - - - " is a bond, R¹¹ is absent, and $X^{II}$ is CH or N, and R¹⁰ is H, —OH, halo, alkyl, haloalkyl, —NR⁸R⁹, —OR², —CN, —CH₂OH, —CH₂—NR³R⁴, aryl, monocyclic heteroaryl, alkylaryl, —CH=O, —CH₂OR², —COR², —CO₂R², or —CONR³R⁴;

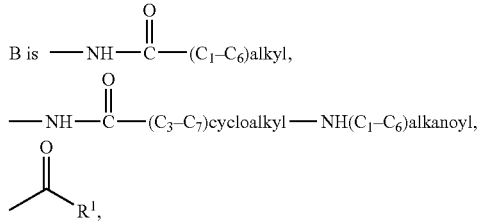

$(C_3-C_7)$cycloalkyl, $(C_3-C_7)$heterocycloalkyl, $(C_4-C_7)$cycloalkenyl, $(C_4-C_7)$heterocycloalkenyl, aryl, or heteroaryl, any of which may be optionally substituted, wherein $R^1$ is $(C_1-C_6)$alkoxy, $(C_3-C_7)$cycloalkyl, $(C_3-C_7)$heterocycloalkyl, $(z_4-C_7)$cycloalkenyl, $(C_4-C_7)$heterocycloalkenyl, aryl, monocyclic heteroaryl, or —NR³R⁴;

G is H, halo, $(C_1-C_6)$alkyl, halo$(C_1-C_6)$alkyl, hydroxy$(C_1-C_6)$alkyl, —CH₂O—$(C_1-C_6)$alkyl, —CH₂—CO₂$(C_1-C_6)$alkyl, —CH₂—CONH₂, or —CH₂—CONH$(C_1-C_6)$alkyl;

R² and R²' are each independently H or $(C_1-C_6)$alkyl; and

R³ and R⁴ are independently H, $(C_1-C_6)$alkyl, aralkyl, aryl, monocyclic heteroaryl, alkoxycarbonyl, aralkoxycarbonyl, —SO₂alkyl, or joined together to form a saturated or unsaturated 5 to 7 membered ring;

R¹² and R¹³ are each independently H, halo, $(C_1-C_6)$alkyl, or halo$(C_1-C_6)$alkyl, or $(C_1-C_6)$alkoxy;

R¹⁴ and R¹⁵ are each independently H, halo, alkyl, or haloalkyl, or NR⁸R⁹ wherein R⁸ and R⁹ are as defined for R³ and R⁴;

X and Y are each C, or one of X and Y is C and the other is N, provided that when one of X or Y is N, R¹⁴ or R¹⁵ is absent at that position.

What is also provided is a compound of Formula V

V

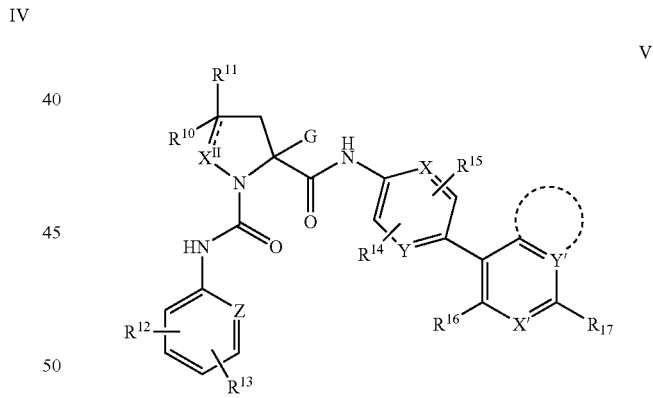

or a pharmaceutically acceptable salt thereof wherein

" - - - " is a bond or is absent;

Z is C—H, C-halo, C—$(C_1-C_6)$alkyl, C-halo$(C_1-C_6)$alkyl, C—$(C_1-C_6)$alkoxy, or N;

G is H, halo, $(C_1-C_6)$alkyl, halo$(C_1-C_6)$alkyl, hydroxy$(C_1-C_6)$alkyl, —CH₂O—$(C_1-C_6)$alkyl, —CH₂—CO₂$(C_1-C_6)$alkyl, —CH₂—CONH₂, or —CH₂—CONH$(C_1-C_6)$alkyl;

$X^{II}$ is CH₂, CH, NH or N;

R¹⁰ and R¹¹ are each independently H, —OH, halo, alkyl, haloalkyl, —NR⁸R⁹, —OR², —CN, —CH₂OH, —CH₂—NR³R⁴, aryl, monocyclic heteroaryl, alkylaryl, —CH=O, —CH₂OR², —COR², —CO₂R², or —CONR³R⁴ or are taken together to form =O, =NOR², =C$(C_1-C_6$alkyl$)_2$, or =CR²H, with the proviso that when " - - - " is a bond, R¹¹ is absent, and $X^{II}$ is CH or N, and $R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, -$CO_2R^2$, or —$CONR^3R^4$;

$R^2$ is H or $(C_1$-$C_6)$alkyl; and $R^3$ and $R^4$ are independently H, $(C_1$-$C_6)$alkyl, aralkyl, aryl, monocyclic heteroaryl, alkoxycarbonyl, aralkoxycarbonyl, —$SO_2$alkyl, or joined together to form a saturated or unsaturated 5 to 7 membered ring;

$R^{12}$ and $R^{13}$ are each independently H, halo, $(C_1$-$C_6)$alkyl, or halo$(C_1$-$C_6)$alkyl, or $(C_1$-$C_6)$alkoxy;

$R^{14}$ and $R^{15}$ are each independently H, halo, alkyl, or haloalkyl, or $NR^8R^9$ wherein $R^8$ and $R^9$ are as defined for $R^3$ and $R^4$;

X and Y are each independently C or N, provided that when one of X or Y is N, $R^{14}$ or $R^{15}$ is absent at that position.

X' and Y' are each independently CH or N;

is absent or is a fused heterocyclic or fused heteroaryl ring, provided that when is present, Y' is C; and $R^{16}$ and $R^{17}$ are each independently H, halo, cyano, $(C_1$-$C_6)$alkoxy carbonyl, aminomethyl, t-butyl, $H_2NSO_2$—, $Me_2NSO_2$—, $(C_1$-$C_6)$alkoxy, $MeSO_2$—, MeSO—, MeS—, $NR^8R^9$, or hydroxy What is also provided is a compound of Formula VI or a pharmaceutically acceptable salt thereof wherein " - - - " is a bond or is absent;

Z is C—H, C-halo, C—$(C_1$-$C_6)$alkyl, C-halo$(C_1$-$C_6)$alkyl, C—$(C_1$-$C_6)$alkoxy, or N;

G is H, halo, $(C_1$-$C_6)$alkyl, halo$(C_1$-$C_6)$alkyl, hydroxy$(C_1$-$C_6)$alkyl, —$CH_2O$—$(C_1$-$C_6)$alkyl, —$CH_2$—$CO_2(C_1$-$C_6)$alkyl, —$CH_2$—$CONH_2$, or —$CH_2$—$CONH(C_1$-$C_6)$alkyl;

Q is NH or is absent;

$X^{II}$ is $CH_2$, CH, NH or N;

$R^{10}$ and $R^{11}$ are each independently H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$ or are taken together to form =O, =$NOR^2$, =$C(C_1$-$C_6$alkyl$)_2$, or =$CR^2H$, with the proviso that when " - - - " is a bond, $R^{11}$ is absent, and $X^{II}$ is CH or N, and $R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$;

$R^1$ is OH, —O—$(C_1$-$C_6)$alkyl, $(C_3$-$C_7)$cycloalkyl, $(C_3$-$C_7)$heterocycloalkyl, $(C_4$-$C_7)$cycloalkenyl, $(C_4$-$C_7)$heterocloalkenyl, aryl, monocyclic heteroaryl, or —$NR^3R^4$, wherein $R^3$ and $R^4$ are independently H, $(C_1$-$C_6)$alkyl, aralkyl, aryl, monocyclic heteroaryl, alkoxycarbonyl, aralkoxycarbonyl, —$SO_2$alkyl, or joined together to form a saturated or unsaturated 5 to 7 membered ring;

$R^2$ is H or $(C_1$-$C_6)$alkyl; and $R^3$ and $R^4$ are independently H, $(C_1$-$C_6)$alkyl, aralkyl, aryl, monocyclic heteroaryl, alkoxycarbonyl, aralkoxycarbonyl, —$SO_2$alkyl, or joined together to form a 5 to 7 membered ring;

$R^{12}$ and $R^{13}$ are each independently H, halo, $(C_1$-$C_6)$alkyl, or halo$(C_1$-$C_6)$alkyl, or $(C_1$-$C_6)$alkoxy;

$R^{14}$ and $R^{15}$ are each independently H, halo, alkyl, or haloalkyl, or $NR^8R^9$ wherein $R^8$ and $R^9$ are as defined for $R^3$ and $R^4$;

X and Y are each independently C or N, provided that when one of X or Y is N, $R^{14}$ or $R^{15}$ is absent at that position.

What is also provided is a compound of Formula VII or a pharmaceutically acceptable salt thereof wherein G is H, halo, $(C_1$-$C_6)$alkyl, halo$(C_1$-$C_6)$alkyl, hydroxy$(C_1$-$C_6)$alkyl, —$CH_2O$—$(C_1$-$C_6)$alkyl, —$CH_2$—$CO_2(C_1$-$C_6)$alkyl, —$CH_2$—$CONH_2$, or —$CH_2$—$CONH(C_1$-$C_6)$alkyl;

$X^{II}$ is $CH_2$, CH, NH or N;

$R^{10}$ and $R^{11}$ are each independently H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$ or are taken together to form =O, =$NOR^2$, =$C(C_1$-$C_6$alkyl$)_2$, or =$CR^2H$, with the proviso that when " - - - " is a bond, $R^{11}$ is absent, and $X^{II}$ is CH or N, and $R^{10}$ is H, —OH, halo, alkyl, haloalkyl, —NR$^8$R$^9$, —OR$^2$, —CN, —CH$_2$OH, —CH$_2$—NR$^3$R$^4$, aryl, monocyclic heteroaryl, alkylaryl, —CH=O, —CH$_2$OR$^2$, —COR$^2$, -CO$_2$R$^2$, or —CONR$^3$R$^4$;

R$^{12}$ and R$^{13}$ are each independently H, halo, (C$_1$-C$_6$)alkyl, or halo(C$_1$-C$_6$)alkyl, or (C$_1$-C$_6$)alkoxy;

R$^{14}$ and R$^{15}$ are each independently H, halo, alkyl, or haloalkyl, or NR$^8$R$^9$ wherein R$^8$ and R$^9$ are as defined for R$^3$ and R$^4$;

X and Y are each independently C or N, provided that when one of X or Y is N, R$^{14}$ or R$^{15}$ is absent at that position; and

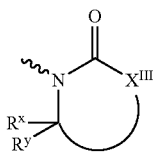

is an optionally substituted 4, 5, 6 or 7-membered ring;

wherein R$^x$ and R$^y$ are H, halo, hydroxymethyl, (C$_1$-C$_6$) alkyl, (C$_1$-C$_6$)alkoxy, or wherein R$^x$ and R$^y$ are H, halo, (C$_1$-C$_6$)alkyl, (C$_1$-C$_6$)alkoxy, (C$_1$-C$_6$)carboxyalkyl, or taken together are O=;

X$^{III}$ is CH$_2$, O, S, NH, or N(C$_1$-C$_6$)alkyl, provided that when R$^x$ and R$^y$ taken together are O=, X$^{III}$ is CH$_2$.

What is also provided is a compound of Formula VIII

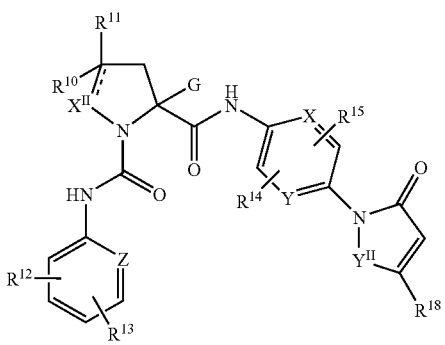

VIII or a pharmaceutically acceptable salt or tautomer thereof wherein

" - - - " is a bond or is absent;

Z is C—H, C-halo, C—(C$_1$-C$_6$)alkyl, C-halo(C$_1$-C$_6$)alkyl, C—(C$_1$-C$_6$)alkoxy, or N;

G is H, halo, (C$_1$-C$_6$)alkyl, halo(C$_1$-C$_6$)alkyl, hydroxy(C$_1$-C$_6$)alkyl, —CH$_2$O—(C$_1$-C$_6$)alkyl, —CH$_2$—CO$_2$(C$_1$-C$_6$)alkyl, —CH$_2$—CONH$_2$, or —CH$_2$—CONH(C$_1$-C$_6$)alkyl;

X$^{II}$ is CH$_2$, CH, NH or N;

R$^{10}$ and R$^{11}$ are each independently H, —OH, halo, alkyl, haloalkyl, —NR$^8$R$^9$, —OR$^2$, —CN, —CH$_2$OH, —CH$_2$—NR$^3$R$^4$, aryl, monocyclic heteroaryl, alkylaryl, —CH=O, —CH$_2$OR$^2$, —COR$^2$, —CO$_2$R$^2$, or —CONR$^3$R$^4$ or are taken together to form =O, =NOR$^2$, =C(C$_1$-C$_6$alkyl)$_2$, or =CR$^2$H, with the proviso that when " - - - " is a bond, R$^{11}$ is absent, and X$^{II}$ is CH or N, and R$^{10}$ is H, —OH, halo, alkyl, haloalkyl, —NR$^8$R$^9$, —OR$^2$, —CN, —CH$_2$OH, —CH$_2$—NR$^3$R$^4$, aryl, monocyclic heteroaryl, alkylaryl, —CH=O, —CH$_2$OR$^2$, —COR$^2$, —CO$_2$R$^2$, or —CONR$^3$R$^4$;

R$^{12}$ and R$^{13}$ are each independently H, halo, (C$_1$-C$_6$)alkyl, or halo(C$_1$-C$_6$)alkyl, or (C$_1$-C$_6$)alkoxy;

R$^{14}$ and R$^{15}$ are each independently H, halo, alkyl, or haloalkyl, or NR$^8$R$^9$ wherein R$^8$ and R$^9$ are as defined for R$^3$ and R$^4$;

X and Y are each independently C or N, provided that when one of X or Y is N, R$^{14}$ or R$^{15}$ is absent at that position; and Y$^{II}$ is CH$_2$, CH(C$_1$-C$_6$alkyl), or N; and R$^{18}$ is H, (C$_1$-C$_6$)alkyl, hydroxymethyl, CH$_2$O—(C$_1$-C$_6$)alkyl, or NR$^3$R$^4$.

What is also provided is a compound of Formula IX

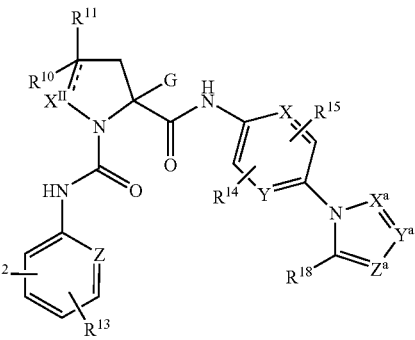

IX or a pharmaceutically acceptable salt thereof wherein

" - - - " is a bond or is absent;

Z is C—H, C-halo, C—(C$_1$-C$_6$)alkyl, C-halo(C$_1$-C$_6$)alkyl, C—(C$_1$-C$_6$)alkoxy, or N;

G is H, halo, (C$_1$-C$_6$)alkyl, halo(C$_1$-C$_6$)alkyl, hydroxy(C$_1$-C$_6$)alkyl, —CH$_2$O—(C$_1$-C$_6$)alkyl, —CH$_2$—CO$_2$(C$_1$-C$_6$)alkyl, —CH$_2$—CONH$_2$, or —CH$_2$—CONH(C$_1$-C$_6$)alkyl;

X$^{II}$ is CH$_2$, CH, NH or N;

R$^{10}$ and R$^{11}$ are each independently H, —OH, halo, alkyl, haloalkyl, —NR$^8$R$^9$, —OR$^2$, —CN, —CH$_2$OH, —CH$_2$—NR$^3$R$^4$, aryl, monocyclic heteroaryl, alkylaryl, —CH=O, —CH$_2$OR$^2$, —COR$^2$, —CO$_2$R$^2$, or —CONR$^3$R$^4$ or are taken together to form =O, =NOR$^2$, =C(C$_1$-C$_6$alkyl)$_2$, or =CR$^2$H, with the proviso that when " - - - " is a bond, R$^{11}$ is absent, and X$^{II}$ is CH or N, and R$^{10}$ is H, —OH, halo, alkyl, haloalkyl, —NR$^8$R$^9$, —OR$^2$, —CN, —CH$_2$OH, —CH$_2$—NR$^3$R$^4$, aryl, monocyclic heteroaryl, alkylaryl, —CH=O, —CH$_2$OR$^2$, —COR$^2$, —CO$_2$R$^2$, or —CONR$^3$R$^4$;

R$^{12}$ and R$^{13}$ are each independently H, halo, (C$_1$-C$_6$)alkyl, or halo(C$_1$-C$_6$)alkyl, or (C$_1$-C$_6$)alkoxy;

R$^{14}$ and R$^{15}$ are each independently H, halo, alkyl, or haloalkyl, or NR$^8$R$^9$ wherein R$^8$ and R$^9$ are as defined for R$^3$ and R$^4$;

X and Y are each independently C or N, provided that when one of X or Y is N, R$^{14}$ or R$^{15}$ is absent at that position;

X$^a$, Y$^a$, and Z$^a$ are each independently CH, CR$^{18}$ or N; and

R$^{18}$ is H, (C$_1$-C$_6$)alkyl, hydroxymethyl, CH$_2$O—(C$_1$-C$_6$)alkyl, or NR$^3$R$^4$.

The invention also provides a compound of Formula X

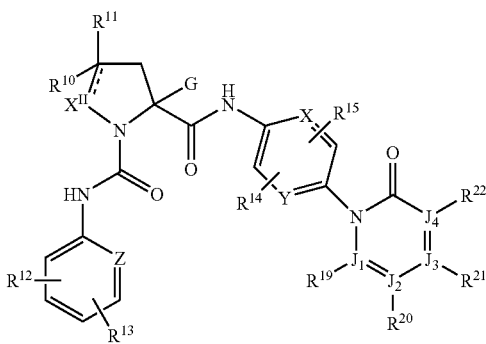

or a pharmaceutically acceptable salt thereof wherein

" - - - " is a bond or is absent;

Z is C—H, C-halo, C—($C_1$-$C_6$)alkyl, C-halo($C_1$-$C_6$)alkyl, C—($C_1$-$C_6$)alkoxy, or N;

G is H, halo, ($C_1$-$C_6$)alkyl, halo($C_1$-$C_6$)alkyl, hydroxy($C_1$-$C_6$)alkyl, —$CH_2O$—($C_1$-$C_6$)alkyl, —$CH_2$—$CO_2$($C_1$-$C_6$)alkyl, —$CH_2$—$CONH_2$, or —$CH_2$—$CONH$($C_1$-$C_6$)alkyl;

$X^{II}$ is $CH_2$, CH, NH or N;

$R^{10}$ and $R^{11}$ are each independently H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$ or are taken together to form =O, =$NOR^2$, =C($C_1$-$C_6$alkyl)$_2$, or =$CR^2H$, with the proviso that when " - - - " is a bond, $R^{11}$ is absent, and $X^{II}$ is CH or N, and $R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, -$CO_2R^2$, or —$CONR^3R^4$;

$R^{12}$ and $R^{13}$ are each independently H, halo, ($C_1$-$C_6$)alkyl, or halo($C_1$-$C_6$)alkyl, or ($C_1$-$C_6$)alkoxy;

$R^{14}$ and $R^{15}$ are each independently H, halo, alkyl, or haloalkyl, or $NR^8R^9$ wherein $R^8$ and $R^9$ are as defined for $R^3$ and $R^4$;

X and Y are each independently C or N, provided that when one of X or Y is N, $R^{14}$ or $R^{15}$ is absent at that position;

$J_1$, $J_2$, $J_3$, and $J_4$ are C or one of $J_1$, $J_2$, $J_3$, and $J_4$ is N;

$R^{19}$, $R^{20}$, $R^{21}$, and $R^{22}$ are each independently H, halo, hydroxy, $NH_2$, $NR^{23}R^{24}$, $NO_2$, SH, ($C_1$-$C_6$)alkyl, halo($C_1$-$C_6$)alkyl, ($C_1$-$C_6$)alkanoyl, ($C_1$-$C_6$)alkoxycarbonyl, or ($C_1$-$C_6$)alkoxy, wherein $R^{23}$ and $R^{24}$ are each independently H, ($C_1$-$C_6$)alkyl, aralkyl, aryl, monocyclic heteroaryl, alkoxycarbonyl, aralkoxycarbonyl, —$SO_2$alkyl, or joined together to form a saturated or unsaturated 3 to 7 membered ring, or $R^{19}$ and $R^{20}$, $R^{20}$ and $R^{21}$, or $R^{21}$ and $R^{22}$, together with the carbons to which they are attached, form a 5, 6, or 7 membered saturated or unsaturated cycloalkyl or heterocycloalkyl ring, or an aryl or heteroaryl ring;

provided that when any of $J_1$, $J_2$, $J_3$, or $J_4$ is N, $R^{19}$, $R^{20}$, $R^{21}$, or $R^{22}$ is absent at that position.

The invention is also directed to a compound which is:

Pyrrolidine-1,2-dicarboxylic acid 1-[(4-chloro-phenyl)-amide]2-[(3-fluoro-2'-sulfamoyl-biphenyl-4-yl)-amide];

Pyrrolidine-1,2-dicarboxylic acid 1-[(4-chloro-phenyl)-amide]2-[(3-fluoro-2'-sulfamoyl-biphenyl-4-yl)-amide];

Pyrrolidine-1,2-dicarboxylic acid 1-[(5-chloro-pyridin-2-yl)-amide]2-[(3-fluoro-2'-sulfamoyl-biphenyl-4-yl)-amide];

Pyrrolidine-1,2-dicarboxylic acid 1-[(2,4-difluoro-phenyl)-amide]2-[(3-fluoro-2'-sulfamoyl-biphenyl-4-yl)-amide];

Pyrrolidine-1,2-dicarboxylic acid 2-[(3-fluoro-2'-sulfamoyl-biphenyl-4-yl)-amide]1-p-tolylamide;

Pyrrolidine-1,2-dicarboxylic acid 2-[(3-fluoro-2'-sulfamoyl-biphenyl-4-yl)-amide]1-[(4-methoxy-phenyl)-amide];

Pyrrolidine-1,2-dicarboxylic acid 1-[(4-bromo-phenyl)-amide]2-[(3-fluoro-2'-sulfamoyl-biphenyl-4-yl)-amide];

Pyrrolidine-1,2-dicarboxylic acid 2-[(3-fluoro-2'-sulfamoyl-biphenyl-4-yl)-amide]1-[(4-isopropyl-phenyl)-amide];

Pyrrolidine-1,2-dicarboxylic acid 2-[(3-fluoro-2'-sulfamoyl-biphenyl-4-yl)-amide]1-phenylamide;

Pyrrolidine-1,2-dicarboxylic acid 2-[(3-fluoro-2'-sulfamoyl-biphenyl-4-yl)-amide]1-[(4-trifluoromethyl-phenyl)-amide];

Pyrrolidine-1,2-dicarboxylic acid 2-[(3-fluoro-2'-sulfamoyl-biphenyl-4-yl)-amide]1-[(3-methoxy-phenyl)-amide];

Pyrrolidine-1,2-dicarboxylic acid 1-[(5-chloro-pyridin-2-yl)-amide]2-[(3-fluoro-2'-methanesulfonyl-biphenyl-4-yl)-amide];

Pyrrolidine-1,2-dicarboxylic acid 1-[(4-chloro-phenyl)-amide]2-[(3-fluoro-2'-methanesulfonyl-biphenyl-4-yl)-amide];

Pyrrolidine-1,2-dicarboxylic acid 1-[(4-ethyl-phenyl)-amide]2-[(3-fluoro-2'-sulfamoyl-biphenyl-4-yl)-amide];

Pyrrolidine-1,2-dicarboxylic acid 1-[(3,4-difluoro-phenyl)-amide]2-[(3-fluoro-2'-sulfamoyl-biphenyl-4-yl)-amide];

Pyrrolidine-1,2-dicarboxylic acid 1-[(3-fluoro4-methyl-phenyl)-amide]2-[(3-fluoro-2'-sulfamoyl-biphenyl-4-yl)-amide];

Pyrrolidine-1,2-dicarboxylic acid 1-[(4-chloro-phenyl)-amide]2-{[5-(2-sulfamoyl-phenyl)-pyridin-2-yl]-amide};

Pyrrolidine-1,2-dicarboxylic acid 2-[(3-chloro-2'-methanesulfonyl-biphenyl-4-yl)-amide]1-[(5-chloro-pyridin-2-yl)-amide];

Pyrrolidine-1,2-dicarboxylic acid 1-[(4-chloro-phenyl)-amide]2-[(3-fluoro-2'-sulfamoyl-biphenyl-4-yl)-amide];

Pyrrolidine-1,2-dicarboxylic acid 2-[(3-chloro-2'-methanesulfonyl-biphenyl-4-yl)-amide]1-[(4-chloro-phenyl)-amide];

Pyrrolidine-1,2-dicarboxylic acid 1-[(5-chloro-pyridin-2-yl)-amide]2-{[5-(2-sulfamoyl-phenyl)-pyridin-2-yl]-amide};

Pyrrolidine-1,2-dicarboxylic acid 1-[(4-chloro-phenyl)-amide]2-{[4-(1H-tetrazol-5-yl)-phenyl]-amide};

4-Hydroxy-pyrrolidine-1,2-dicarboxylic acid 1-[(4-chloro-phenyl)-amide]2-[(3-fluoro-2'-methanesulfonyl-biphenyl-4-yl)-amide];

4-Hydroxy-pyrrolidine-1,2-dicarboxylic acid 1-[(4-chloro-phenyl)-amide]2-[(3-fluoro-2'-methanesulfonyl-biphenyl4-yl)-amide];

4-Methoxy-pyrrolidine-1,2-dicarboxylic acid 1-[(4-chloro-phenyl)-amide]2-[(3-fluoro-2'-methanesulfonyl-biphenyl-4-yl)-amide];

4-Oxo-pyrrolidine-1,2-dicarboxylic acid 1-[(4-chloro-phenyl)-amide]2-[(3-fluoro-2'-methanesulfonyl-biphenyl4-yl)-amide];

4-Methylene-pyrrolidine-1,2-dicarboxylic acid 1-[(4-chloro-phenyl)-amide]2-[(3-fluoro-2'-methanesulfonyl-biphenyl-4-yl)-amide];

4-Methyl-pyrrolidine-1,2-dicarboxylic acid 1-[(4-chloro-phenyl)-amide]2-[(3-fluoro-2'-methanesulfonyl-biphenyl4-yl)-amide];

4,4-Difluoro-pyrrolidine-1,2-dicarboxylic acid 1-[(4-chloro-phenyl)-amide]2-[(3-fluoro-2'-methanesulfonyl-biphenyl-4-yl)-amide];

4-Amino-pyrrolidine-1,2-dicarboxylic acid 1-[(4-chloro-phenyl)-amide]2-[(3-fluoro-2'-methanesulfonyl-biphenyl4-yl)-amide];

4-Hydroxymethyl-pyrrolidine-1,2-dicarboxylic acid 1-[(4-chloro-phenyl)-amide]2-[(3-fluoro-2'-methanesulfonyl-biphenyl-4-yl)-amide];

1-(4-Chloro-phenylcarbamoyl)-5-(3-fluoro-2'-methanesulfonyl-biphenyl-4-ylcarbamoyl)-pyrrolidine-3-carboxylic acid;

1-(4-Chloro-phenylcarbamoyl)-5-(3-fluoro-2'-methanesulfonyl-biphenyl-4-ylcarbamoyl)-pyrrolidine-3-carboxylic acid methyl ester;

Pyrrolidine-1,2,4-tricarboxylic acid 4-amide 1-[(4-chloro-phenyl)-amide]2-[(3-fluoro-2'-methanesulfonyl-biphenyl-4-yl)-amide];

4-Aminomethyl-pyrrolidine-1,2-dicarboxylic acid 1-[(4-chloro-phenyl)-amide]2-[(3-fluoro-2'-methanesulfonyl-biphenyl-4-yl)-amide];

4-Methoxymethyl-pyrrolidine-1,2-dicarboxylic acid 1-[(4-chloro-phenyl)-amide]2-[(3-fluoro-2'-methanesulfonyl-biphenyl-4-yl)-amide];

4-Ethoxy-pyrrolidine-1,2-dicarboxylic acid 1-[(4-chloro-phenyl)-amide]2-[(3-fluoro-2'-methanesulfonyl-biphenyl-4-yl)-amide];

4-Methylamino-pyrrolidine-1,2-dicarboxylic acid 1-[(4-chloro-phenyl)-amide]2-[(3-fluoro-2'-methanesulfonyl-biphenyl-4-yl)-amide];

4-Acetylamino-pyrrolidine-1,2-dicarboxylic acid 1-[(4-chloro-phenyl)-amide]2-[(3-fluoro-2'-methanesulfonyl-biphenyl-4-yl)-amide];

4-Methanesulfonylamino-pyrrolidine-1,2-dicarboxylic acid 1-[(4-chloro-phenyl)-amide]2-[(3-fluoro-2'-methanesulfonyl-biphenyl-4-yl)-amide];

5-Oxo-pyrrolidine-1,2-dicarboxylic acid 1-[(4-chloro-phenyl)-amide]2-[(3-fluoro-2'-methanesulfonyl-biphenyl-4-yl)-amide];

Piperidine-1,2-dicarboxylic acid 1-[(4-chloro-phenyl)-amide]2-[(3-fluoro-2'-methanesulfonyl-biphenyl-4-yl)-amide];

Morpholine-3,4-dicarboxylic acid 4-[(4-chloro-phenyl)-amide]3-[(3-fluoro-2'-methanesulfonyl-biphenyl-4-yl)-amide];

Piperazine-1,2-dicarboxylic acid 1-[(4-chloro-phenyl)-amide]2-[(3-fluoro-2'-methanesulfonyl-biphenyl-4-yl)-amide];

2,5-Dihydro-pyrrole-1,2-dicarboxylic acid 1-[(4-chloro-phenyl)-amide]2-[(3-fluoro-2'-sulfamoyl-biphenyl-4-yl)-amide];

Pyrrolidine-1,2-dicarboxylic acid 1-[(4-chloro-phenyl)-amide]2-[(2'-methanesulfonyl-3-methyl-biphenyl-4-yl)-amide];

4-Hydroxy-pyrrolidine-1,2-dicarboxylic acid 1-[(4-chloro-phenyl)-amide]2-[(2'-methanesulfonyl-3-methyl-biphenyl4-yl)-amide];

Pyrrolidine-1,2-dicarboxylic acid 1-[(4-chloro-phenyl)-amide]2-[(2'-methanesulfonyl-biphenyl-4-yl)-amide];

4-Hydroxy-pyrrolidine-1,2-dicarboxylic acid 1-[(4-chloro-phenyl)-amide]2-[(2'-methanesulfonyl-biphenyl4-yl)-amide];

Pyrrolidine-1,2-dicarboxylic acid 1-[(4-chloro-phenyl)-amide]2-{[5-(2-methanesulfonyl-phenyl)-pyrimidin-2-yl]-amide};

4-Hydroxy-pyrrolidine-1,2-dicarboxylic acid 1-[(4-chloro-phenyl)-amide]2-{[5-(2-methanesulfonyl-phenyl)-pyrimidin-2-yl]-amide};

Pyrrolidine-1,2-dicarboxylic acid 1-[(4-chloro-phenyl)-amide]2-{[5-(2-methanesulfonyl-phenyl)-3-methyl-pyridin-2-yl]-amide};

4-Hydroxy-pyrrolidine-1,2-dicarboxylic acid 1-[(4-chloro-phenyl)-amide]2-{[5-(2-methanesulfonyl-phenyl)-3-methyl-pyridin-2-yl]-amide};

Pyrrolidine-1,2-dicarboxylic acid 1-[(4-chloro-phenyl)-amide]2-[(2'-methanesulfonyl-3-trifluoromethyl-biphenyl-4-yl)-amide];

4-Hydroxy-pyrrolidine-1,2-dicarboxylic acid 1-[(4-chloro-phenyl)-amide]2-[(2'-methanesulfonyl-3-trifluoromethyl-biphenyl-4-yl)-amide];

Pyrrolidine-1,2-dicarboxylic acid 1-[(4-chloro-phenyl)-amide]2-{[5-(2-methanesulfonyl-phenyl)-6-methyl-pyridin-2-yl]-amide};

4-Hydroxy-pyrrolidine-1,2-dicarboxylic acid 1-[(4-chloro-phenyl)-amide]2-{[5-(2-methanesulfonyl-phenyl)-6-methyl-pyridin-2-yl]-amide};

Pyrrolidine-1,2-dicarboxylic acid 1-[(4-chloro-phenyl)-amide]2-[(3-ethyl-2'-methanesulfonyl-biphenyl-4-yl)-amide];

4-Hydroxy-pyrrolidine-1,2-dicarboxylic acid 1-[(4-chloro-phenyl)-amide]2-[(3-ethyl-2'-methanesulfonyl-biphenyl-4-yl)-amide];

4-Hydroxy-pyrrolidine-1,2-dicarboxylic acid 1-[(4-chloro-phenyl)-amide]2-[(3,5-difluoro-2'-methanesulfonyl-biphenyl-4-yl)-amide];

Pyrrolidine-1,2-dicarboxylic acid 1-[(4-chloro-phenyl)-amide]2-[(3,5-dichloro-2'-methanesulfonyl-biphenyl-4-yl)-amide];

4-Hydroxy-pyrrolidine-1,2-dicarboxylic acid 1-[(4-chloro-phenyl)-amide]2-[(3,5-dichloro-2'-methanesulfonyl-biphenyl-4-yl)-amide];

Pyrrolidine-1,2-dicarboxylic acid 1-[(4-chloro-phenyl)-amide]2-[(2'-methanesulfonyl-3,5-dimethyl-biphenyl-4-yl)-amide];

4-Hydroxy-pyrrolidine-1,2-dicarboxylic acid 1-[(4-chloro-phenyl)-amide]2-[(2'-methanesulfonyl-3,5-dimethyl-biphenyl-4-yl)-amide];

Pyrrolidine-1,2-dicarboxylic acid 2-[(3-chloro-2'-methanesulfonyl-5-methyl-biphenyl4-yl)-amide]1-[(4-chloro-phenyl)-amide];

4-Hydroxy-pyrrolidine-1,2-dicarboxylic acid 2-[(3-chloro-2'-methanesulfonyl-5-methyl-biphenyl-4-yl)-amide]1-[(4-chloro-phenyl)-amide];

Pyrrolidine-1,2-dicarboxylic acid 2-[(2-chloro-2'-methanesulfonyl-biphenyl-4-yl)-amide]1-[(4-chloro-phenyl)-amide];

4-Hydroxy-pyrrolidine-1,2-dicarboxylic acid 2-[(2-chloro-2'-methanesulfonyl-biphenyl4-yl)-amide]1-[(4-chloro-phenyl)-amide];

Pyrrolidine-1,2-dicarboxylic acid 1-[(4-chloro-phenyl)-amide]2-[(2'-methanesulfonyl-2-methyl-biphenyl-4-yl)-amide];

4-Hydroxy-pyrrolidine-1,2-dicarboxylic acid 1-[(4-chloro-phenyl)-amide]2-[(2'-methanesulfonyl-2-methyl-biphenyl-4-yl)-amide];

Pyrrolidine-1,2-dicarboxylic acid 1-[(4-chloro-phenyl)-amide]2-[(2-fluoro-2'-methanesulfonyl-biphenyl-4-yl)-amide];

4-Hydroxy-pyrrolidine-1,2-dicarboxylic acid 1-[(4-chloro-phenyl)-amide]2-[(2-fluoro-2'-methanesulfonyl-biphenyl-4-yl)-amide];

4-{[1-(4-Chloro-phenylcarbamoyl)-pyrrolidine-2-carbonyl]-amino}-2'-methanesulfonyl-biphenyl-3-carboxylic acid methyl ester;

4-{[1-(4-Chloro-phenylcarbamoyl)-4-hydroxy-pyrrolidine-2-carbonyl]-amino}-2'-methanesulfonyl-biphenyl-3-carboxylic acid methyl ester;

Pyrrolidine-1,2-dicarboxylic acid 2-[(3-fluoro-2'-sulfamoyl-biphenyl-4-yl)-amide]1-[(4-trifluoromethyl-phenyl)-amide];

Pyrrolidine-1,2-dicarboxylic acid 2-[(3-fluoro-2'-sulfamoyl-biphenyl-4-yl)-amide]1-m-tolylamide;

Pyrrolidine-1,2-dicarboxylic acid 1-[(3-acetyl-phenyl)-amide]2-[(3-fluoro-2'-sulfamoyl-biphenyl-4-yl)-amide];

Pyrrolidine-1,2-dicarboxylic acid 1-[(5-chloro-2-methyl-phenyl)-amide]2-[(3-fluoro-2'-sulfamoyl-biphenyl-4-yl)-amide];

Pyrrolidine-1,2-dicarboxylic acid 1-[(2-fluoro-phenyl)-amide]2-[(3-fluoro-2'-sulfamoyl-biphenyl-4-yl)-amide];

Pyrrolidine-1,2-dicarboxylic acid 1-[(3-chloro4-fluoro-phenyl)-amide]2-[(3-fluoro-2'-sulfamoyl-biphenyl-4-yl)-amide];

Pyrrolidine-1,2-dicarboxylic acid 1-[(3-chloro-phenyl)-amide]2-[(3-fluoro-2'-sulfamoyl-biphenyl-4-yl)-amide];

Pyrrolidine-1,2-dicarboxylic acid 1-[(4-cyano-phenyl)-amide]2-[(3-fluoro-2'-sulfamoyl-biphenyl-4-yl)-amide];

Pyrrolidine-1,2-dicarboxylic acid 1-[(4-chloro-2-methyl-phenyl)-amide]2-[(3-fluoro-2'-sulfamoyl-biphenyl-4-yl)-amide];

Pyrrolidine-1,2-dicarboxylic acid 1-[(3,4-dichloro-phenyl)-amide]2-[(3-fluoro-2'-sulfamoyl-biphenyl-4-yl)-amide];

Pyrrolidine-1,2-dicarboxylic acid 2-[(3-fluoro-2'-sulfamoyl-biphenyl-4-yl)-amide]1-[(3-trifluoromethyl-phenyl)-amide];

Pyrrolidine-1,2-dicarboxylic acid 1-[(4-dimethylamino-phenyl)-amide]2-[(3-fluoro-2'-sulfamoyl-biphenyl-4-yl)-amide];

(2S)-Pyrrolidine-1,2-dicarboxylic acid 1-[(4-chloro-phenyl)-amide]2-[(3-fluoro-2'-sulfamoyl-biphenyl-4-yl)-amide];

Pyrrolidine-1,2-dicarboxylic acid 1-[(4-chloro-phenyl)-amide]2-[(4-cyano-phenyl)-amide];

4-Methoxy-pyrrolidine-1,2-dicarboxylic acid 1-[(4-chloro-phenyl)-amide]2-[(3-fluoro-2'-methanesulfonyl-biphenyl-4-yl)-amide];

4-Hydroxy-pyrrolidine-1,2-dicarboxylic acid 2-[(3-fluoro-2'-methanesulfonyl-biphenyl-4-yl)-amide]1-[(4-fluoro-phenyl)-amide];

4-Hydroxy-pyrrolidine-1,2-dicarboxylic acid 1-[(5-chloro-pyridin-2-yl)-amide]2-[(3-fluoro-2'-methanesulfonyl-biphenyl-4-yl)-amide];

4-Hydroxy-pyrrolidine-1,2-dicarboxylic acid 2-[(3-fluoro-2'-methanesulfonyl-biphenyl-4-yl)-amide]1-p-tolylamide;

4-Oxo-pyrrolidine-1,2-dicarboxylic acid 1-[(4-chloro-phenyl)-amide]2-[(3-fluoro-2'-methanesulfonyl-biphenyl-4-yl)-amide]; and 4-Fluoro-pyrrolidine-1,2-dicarboxylic acid 1-[(4-chloro-phenyl)-amide]2-[(3-fluoro-2'-methanesulfonyl-biphenyl-4-yl)-amide]; or a pharmaceutically acceptable salt thereof.

A compound which is:

(R)-Pyrrolidine-1,2-dicarboxylic acid 1-[(4-chloro-phenyl)-amide]2-[(3-fluoro-2'-sulfamoyl-biphenyl-4-yl)-amide];

(S)-Pyrrolidine-1,2-dicarboxylic acid 1-[(4-chloro-phenyl)-amide]2-[(3-fluoro-2'-sulfamoyl-biphenyl-4-yl)-amide];

(2R,4R)-4-Hydroxy-pyrrolidine-1,2-dicarboxylic acid 1-[(4-chloro-phenyl)-amide]2-[(3-fluoro-2'-methanesulfonyl-biphenyl-4-yl)-amide];

(2R,4S)-4-Hydroxy-pyrrolidine-1,2-dicarboxylic acid 1-[(4-chloro-phenyl)-amide]2-[(3-fluoro-2'-methanesulfonyl-biphenyl-4-yl)-amide];

(2R,4R)4-Methoxy-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Hydroxy-pyrrolidine-1,2-dicarboxylic acid 2-[(3-fluoro-2'-methanesulfonyl-biphenyl-4-yl)-amide]1-[(4-fluoro-phenyl)-amide];

(2R,4R)-4-Hydroxy-pyrrolidine-1,2-dicarboxylic acid 1-[(5-chloro-pyridin-2-yl)-amide]2-[(3-fluoro-2'-methanesulfonyl-biphenyl-4-yl)-amide];

(2R,4R)-4-Hydroxy-pyrrolidine-1,2-dicarboxylic acid 2-[(3-fluoro-2'-methanesulfonyl-biphenyl-4-yl)-amide]1-p-tolylamide;

(2R)-4-Oxo-pyrrolidine-1,2-dicarboxylic acid 1-[(4-chloro-phenyl)-amide]2-[(3-fluoro-2'-methanesulfonyl-biphenyl-4-yl)-amide]; and (2R,4S)4-Fluoro-pyrrolidine-1,2-dicarboxylic acid 1-[(4-chloro-phenyl)-amide]2-[(3-fluoro-2'-methanesulfonyl-biphenyl-4-yl)-amide]; or a pharmaceutically acceptable salt thereof.

The invention is also directed to a compound which is:

(2R,4R)-4-Methoxy-pyrrolidine-1,2-dicarboxylic acid 1-[(4-chloro-phenyl)-amide]2-{[2-fluoro4-(2-oxo-piperidin-1-yl)-phenyl]-amide};

(2R,4R)4-Hydroxy-pyrrolidine-1,2-dicarboxylic acid 1-[(4-chloro-phenyl)-amide]2-{[4-(2-oxo-piperidin-1-yl)-phenyl]-amide};

(2R,4R)4-Hydroxy-pyrrolidine-1,2-dicarboxylic acid 1-[(4-chloro-phenyl)-amide]2-{[2-fluoro4-(2-oxo-piperidin-1-yl)-phenyl]-amide};

(2R,4R)4-Hydroxy-pyrrolidine-1,2-dicarboxylic acid 1-[(5-chloro-pyridin-2-yl)-amide]2-{[2-fluoro4-(2-oxo-piperidin-1-yl)-phenyl]-amide};

(2R,4R)4-Methoxy-pyrrolidine-1,2-dicarboxylic acid 1-[(5-chloro-pyridin-2-yl)-amide]2-{[2-fluoro4-(2-oxo-piperidin-1-yl)-phenyl]-amide};

(2R,4R)-4-Ethoxy-pyrrolidine-1,2-dicarboxylic acid 1-[(5-chloro-pyridin-2-yl)-amide]2-{[2-fluoro-4-(2-oxo-piperidin-1-yl)-phenyl]-amide};

(2R,4R)4-Ethoxy-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Propoxy-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Propoxy-pyrrolidine-1,2-dicarboxylic acid 1-[(5-chloro-pyridin-2-yl)-amide]2-{[2-fluoro-4-(2-oxo-piperidin-1-yl)-phenyl]-amide};

(2R,4R)-4-Fluoro-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-azetidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(2-oxo-azetidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-pyrrolidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(2-oxo-pyrrolidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-azepan-1-yl)-phenyl]-amide};

(2R,4R)-4-Methoxy-pyrrolidine-1,2-dicarboxylic acid 1-[(5-chloro-pyridin-2-yl)-amide]2-{[2-fluoro4-(2-oxo-azepan-1-yl)-phenyl]-amide};

(2R,4R)-4-Methoxy-pyrrolidine-1,2-dicarboxylic acid 1-[(5-chloro-pyridin-2-yl)-amide]2-{[4-(2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[4-(2-oxo-2H-pyridin-1-yl)-phenyl]-amide};

(2R,4R)4-Ethoxy-pyrrolidine-1,2-dicarboxylic acid 1-[(5-chloro-pyridin-2-yl)-amide]2-{[2-fluoro4-(2-oxo-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro4-(2-hydroxymethyl-5-oxo-pyrrolidin-1-yl)-phenyl]-amide};

(2R,4R)-4-Hydroxy-pyrrolidine-1,2-dicarboxylic acid 1-[(4-chloro-phenyl)-amide]2-{[4-(2,3-dimethyl-5-oxo-2,5-dihydro-pyrazol-1-yl)-phenyl]-amide};

4-Hydroxy-pyrrolidine-1,2-dicarboxylic acid 1-[(4-chloro-phenyl)-amide]2-{[4-(2-hydroxymethyl-pyrrolidin-1-yl)-phenyl]-amide};

(2R,4R)-4-Hydroxy-pyrrolidine-1,2-dicarboxylic acid 1-[(4-chloro-phenyl)-amide]2-[(4-pyrrolidin-1-yl-phenyl)-amide];

(2R,4R)-4-Hydroxy-pyrrolidine-1,2-dicarboxylic acid 1-[(4-chloro-phenyl)-amide]2-[(4-pyrazol-1-yl-phenyl)-amide];

(2R,4R)-4-Hydroxy-pyrrolidine-1,2-dicarboxylic acid 1-[(4-chloro-phenyl)-amide]2-[(2-fluoro-4-pyrazol-1-yl-phenyl)-amide];

(2R,4R)4-Hydroxy-pyrrolidine-1,2-dicarboxylic acid 1-[(4-chloro-phenyl)-amide]2-[(4-[1,2,4]triazol-1-yl-phenyl)-amide];

(2R,4R)-4-Hydroxy-pyrrolidine-1,2-dicarboxylic acid 1-[(4-chloro-phenyl)-amide]2-[(4-[1,2,3]triazol-2-yl-phenyl)-amide];

(2R,4R)-4-Hydroxy-pyrrolidine-1,2-dicarboxylic acid 1-[(4-chloro-phenyl)-amide]2-[(4-[1,2,3]triazol-1-yl-phenyl)-amide];

(2R,4R)-4-Hydroxy-pyrrolidine-1,2-dicarboxylic acid 2-[(4-acetylamino-phenyl)-amide]1-[(4-chloro-phenyl)-amide];

(2R,4R)4-Hydroxy-pyrrolidine-1,2-dicarboxylic acid 1-[(4-chloro-phenyl)-amide]2-{[4-(cyclopentanecarbonyl-amino)-phenyl]-amide}; and 4-Hydroxy-pyrrolidine-1,2-dicarboxylic acid 1-[(4-chloro-phenyl)-amide]2-[(4-pyrimidin-5-yl-phenyl)-amide]; or a pharmaceutically acceptable salt thereof.

A compound which is:

1-(4-Chloro-phenylcarbamoyl)-5-[2-fluoro4-(2-oxo-piperidin-1-yl)-phenylcarbamoyl]-pyrrolidine-3-carboxylic acid;

1-(4-Chloro-phenylcarbamoyl)-5-[2-fluoro4-(2-oxo-piperidin-1-yl)-phenylcarbamoyl]-pyrrolidine-3-carboxylic acid methyl ester;

1-(4-Chloro-phenylcarbamoyl)-5-[2-fluoro4-(2-oxo-piperidin-1-yl)-phenylcarbamoyl]-pyrrolidine-3-carboxylic acid ethyl ester;

Pyrrolidine-1,2,4-tricarboxylic acid 4-amide 1-[(4-chloro-phenyl)-amide]2-{[2-fluoro-4-(2-oxo-piperidin-1-yl)-phenyl]-amide};

4-Cyano-pyrrolidine-1,2-dicarboxylic acid 1-[(4-chloro-phenyl)-amide]2-{[2-fluoro-4-(2-oxo-piperidin-1-yl)-phenyl]-amide};

4-(1H-Tetrazol-5-yl)-pyrrolidine-1,2-dicarboxylic acid 1-[(4-chloro-phenyl)-amide]2-{[2-fluoro-4-(2-oxo-piperidin-1-yl)-phenyl]-amide};

4-Aminomethyl-pyrrolidine-1,2-dicarboxylic acid 1-[(4-chloro-phenyl)-amide]2-{[2-fluoro-4-(2-oxo-piperidin-1-yl)-phenyl]-amide};

4-Methylaminomethyl-pyrrolidine-1,2-dicarboxylic acid 1-[(4-chloro-phenyl)-amide]2-{[2-fluoro-4-(2-oxo-piperidin-1-yl)-phenyl]-amide};

4-Dimethylaminomethyl-pyrrolidine-1,2-dicarboxylic acid 1-[(4-chloro-phenyl)-amide]2-{[2-fluoro-4-(2-oxo-piperidin-1-yl)-phenyl]-amide};

4-Acetyl-pyrrolidine-1,2-dicarboxylic acid 1-[(4-chloro-phenyl)-amide]2-{[2-fluoro-4-(2-oxo-piperidin-1-yl)-phenyl]-amide};

Pyrrolidine-1,2,4-tricarboxylic acid 1-[(4-chloro-phenyl)-amide]2-{[2-fluoro-4-(2-oxo-piperidin-1-yl)-phenyl]-amide}4-methylamide;

Pyrrolidine-1,2,4-tricarboxylic acid 1-[(4-chloro-phenyl)-amide]4-dimethylamide 2-{[2-fluoro-4-(2-oxo-piperidin-1-yl)-phenyl]-amide};

4-Trifluoromethyl-pyrrolidine-1,2-dicarboxylic acid 1-[(4-chloro-phenyl)-amide]2-{[2-fluoro-4-(2-oxo-piperidin-1-yl)-phenyl]-amide};

4-Methyl-pyrrolidine-1,2-dicarboxylic acid 1-[(4-chloro-phenyl)-amide]2-{[2-fluoro-4-(2-oxo-piperidin-1-yl)-phenyl]-amide};

4-Isopropoxy-pyrrolidine-1,2-dicarboxylic acid 1-[(4-chloro-phenyl)-amide]2-{[2-fluoro-4-(2-oxo-piperidin-1-yl)-phenyl]-amide};

4-Fluoro-pyrrolidine-1,2-dicarboxylic acid 1-[(4-chloro-phenyl)-amide]2-{[2-fluoro-4-(2-oxo-piperidin-1-yl)-phenyl]-amide};

4,4-Difluoro-pyrrolidine-1,2-dicarboxylic acid 1-[(4-chloro-phenyl)-amide]2-{[2-fluoro-4-(2-oxo-piperidin-1-yl)-phenyl]-amide};

1-(4-{[1-(4-Chloro-phenylcarbamoyl)4-methoxy-pyrrolidine-2-carbonyl]-amino}-phenyl)-pyrrolidine-2-carboxylic acid;

1-(4-{[1-(4-Chloro-phenylcarbamoyl)-4-hydroxy-pyrrolidine-2-carbonyl]-amino}-phenyl)-pyrrolidine-2-carboxylic acid;

4-Methoxy-pyrrolidine-1,2-dicarboxylic acid 1-[(5-chloro-pyridin-2-yl)-amide]2-[(oxo-3,4,5,6-tetrahydro-2H-[1,3']bipyridinyl-6'-yl)-amide];

4-Methoxy-pyrrolidine-1,2-dicarboxylic acid 1-[(4-chloro-phenyl)-amide]2-[(2-oxo-3,4,5,6-tetrahydro-2H-[1,2']bipyridinyl-5'-yl)-amide];

4-Methoxy-pyrrolidine-1,2-dicarboxylic acid 1-[(5-chloro-pyridin-2-yl)-amide]2-{[5-(2-oxo-piperidin-1-yl)-pyrimidin-2-yl]-amide};

4-Methoxy-pyrrolidine-1,2-dicarboxylic acid 1-[(5-chloro-pyridin-2-yl)-amide]2-{[2-(2-oxo-piperidin-1-yl)-pyrimidin-5-yl]-amide};

4-Methoxy-pyrrolidine-1,2-dicarboxylic acid 1-[(4-chloro-phenyl)-amide]2-{[5-(2-oxo-piperidin-1-yl)-pyrimidin-2-yl]-amide};

4-Methoxy-pyrrolidine-1,2-dicarboxylic acid 1-[(4-chloro-phenyl)-amide]2-{[2-(2-oxo-piperidin-1-yl)-pyrimidin-5-yl]-amide};

4-Methoxy-pyrrolidine-1,2-dicarboxylic acid 2-{[2-fluoro-4-(2-oxo-piperidin-1-yl)-phenyl]-amide}1-[(5-fluoro-pyridin-2-yl)-amide];

4-Methoxy-pyrrolidine-1,2-dicarboxylic acid 1-[(5-fluoro-pyridin-2-yl)-amide]2-[(2-oxo-3,4,5,6-tetrahydro-2H-[1,3']bipyridinyl-6'-yl)-amide];

4-Methoxy-pyrrolidine-1,2-dicarboxylic acid 1-[(5-fluoro-pyridin-2-yl)-amide]2-[(2-oxo-3,4,5,6-tetrahydro-2H-[1,2']bipyridinyl-5'-yl)-amide];

4-Fluoro-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide];

4-Fluoro-pyrrolidine-1,2-dicarboxylic acid 1-[(5-chloro-pyridin-2-yl)-amide]2-[(2-oxo-3,4,5,6-tetrahydro-2H-[1,3']bipyridinyl-6'-yl)-amide];

4-Fluoro-pyrrolidine-1,2-dicarboxylic acid 1-[(5-fluoro-pyridin-2-yl)-amide]2-[(2-oxo-3,4,5,6-tetrahydro-2H-[1,3']bipyridinyl-6'-yl)-amide];

4-Fluoro-pyrrolidine-1,2-dicarboxylic acid 1-[(4-chloro-phenyl)-amide]2-[(2-oxo-3,4,5,6-tetrahydro-2H-[1,2']bipyridinyl-5'-yl)-amide];

4-Fluoro-pyrrolidine-1,2-dicarboxylic acid 1-[(5-chloro-pyridin-2-yl)-amide]2-[(2-oxo-3,4,5,6-tetrahydro-2H-[1,2']bipyridinyl-5'-yl)-amide];

4-Fluoro-pyrrolidine-1,2-dicarboxylic acid 1-[(5-fluoro-pyridin-2-yl)-amide]2-[(2-oxo-3,4,5,6-tetrahydro-2H-[1,2']bipyridinyl-5'-yl)-amide];

4-Methoxy-pyrrolidine-1,2-dicarboxylic acid 1-[(4-chloro-phenyl)-amide]2-{[2-fluoro-4-(2-hydroxymethyl-5-oxo-pyrrolidin-1-yl)-phenyl]-amide};

1-(4-{[1-(4-Chloro-phenylcarbamoyl)-4-methoxy-pyrrolidine-2-carbonyl]-amino}-3-fluoro-phenyl)-5-oxo-pyrrolidine-2-carboxylic acid;

1-(4-{[1-(4-Chloro-phenylcarbamoyl)4-methoxy-pyrrolidine-2-carbonyl]-amino}-3-fluoro-phenyl)-5-oxo-pyrrolidine-2-carboxylic acid;

4-Methoxy-pyrrolidine-1,2-dicarboxylic acid 1-[(4-chloro-phenyl)-amide]2-{[4-(4,4-dimethyl-2,5-dioxo-imidazolidin-1-yl)-2-fluoro-phenyl]-amide};

[1-(4-{[1-(4-Chloro-phenylcarbamoyl)-4-methoxy-pyrrolidine-2-carbonyl]-amino}-3-fluoro-phenyl)-2,5-dioxo-imidazolidin-4-yl]-acetic acid;

4-Methoxy-pyrrolidine-1,2-dicarboxylic acid 1-[(4-chloro-phenyl)-amide]2-{[4-(5,5-dimethyl-2,4-dioxo-oxazolidin-3-yl)-2-fluoro-phenyl]-amide};

4-Methoxy-pyrrolidine-1,2-dicarboxylic acid 1-[(4-chloro-phenyl)-amide]2-{[4-(2,5-dioxo-pyrrolidin-1-yl)-2-fluoro-phenyl]-amide};

4-Methoxy-pyrrolidine-1,2-dicarboxylic acid 1-[(4-chloro-phenyl)-amide]2-{[2-fluoro-4-(2-oxo-oxazolidin-3-yl)-phenyl]-amide};

4-Methoxy-pyrrolidine-1,2-dicarboxylic acid 1-[(4-chloro-phenyl)-amide]2-{[4-(2,5-dioxo-oxazolidin-3-yl)-2-fluoro-phenyl]-amide};

4-Methoxy-pyrrolidine-1,2-dicarboxylic acid 1-[(4-chloro-phenyl)-amide]2-{[2-fluoro4-(2-oxo-imidazolidin-1-yl)-phenyl]-amide};

4-Methoxy-pyrrolidine-1,2-dicarboxylic acid 1-[(4-chloro-phenyl)-amide]2-{[4-(2,5-dioxo-imidazolidin-1-yl)-2-fluoro-phenyl]-amide};

4-Methoxy-pyrrolidine-1,2-dicarboxylic acid 1-[(4-chloro-phenyl)-amide]2-{[2-fluoro-4-(3-methyl-2,5-dioxo-imidazolidin-1-yl)-phenyl]-amide};

3-(4-{[1-(4-Chloro-phenylcarbamoyl)-4-methoxy-pyrrolidine-2-carbonyl]-amino}-3-fluoro-phenyl)-2-oxo-imidazolidine4-carboxylic acid;

4-Methoxy-pyrrolidine-1,2-dicarboxylic acid 1-[(4-chloro-phenyl)-amide]2-{[2-fluoro4-(2,4,5-trioxo-imidazolidin-1-yl)-phenyl]-amide};

4-Methoxy-pyrrolidine-1,2-dicarboxylic acid 1-[(4-chloro-phenyl)-amide]2-{[4-(2,5-dioxo-2,5-dihydro-pyrrol-1-yl)-2-fluoro-phenyl]-amide};

4-Methoxy-pyrrolidine-1,2-dicarboxylic acid 2-{[4-(2-aminomethyl-5-oxo-pyrrolidin-1-yl)-2-fluoro-phenyl]-amide}1-[(4-chloro-phenyl)-amide];

4-Methoxy-pyrrolidine-1,2-dicarboxylic acid 2-{[4-(2-aminomethyl-5-oxo-pyrrolidin-1-yl)-2-fluoro-phenyl]-amide}1-[(4-chloro-phenyl)-amide];

4-Methoxy-pyrrolidine-1,2-dicarboxylic acid 2-{[4-(2-carbamoyl-5-oxo-pyrrolidin-1-yl)-2-fluoro-phenyl]-amide}1-[(4-chloro-phenyl)-amide];

4-Methoxy-pyrrolidine-1,2-dicarboxylic acid 2-{[4-(2-carbamoyl-5-oxo-pyrrolidin-1-yl)-2-fluoro-phenyl]-amide}1-[(4-chloro-phenyl)-amide];

4-Methoxy-pyrrolidine-1,2-dicarboxylic acid 2-{[4-(2,2-bis-hydroxymethyl-5-oxo-pyrrolidin-1-yl)-2-fluoro-phenyl]-amide}1-[(4-chloro-phenyl)-amide];

3-(4-{[1-(4-Chloro-phenylcarbamoyl)-4-methoxy-pyrrolidine-2-carbonyl]-amino}-3-fluoro-phenyl)-2-oxo-imidazolidine-4-carboxylic acid;

4-Methoxy-pyrrolidine-1,2-dicarboxylic acid 1-[(4-chloro-phenyl)-amide]2-{[4-(3,3-dimethyl-2,5-dioxo-pyrrolidin-1-yl)-2-fluoro-phenyl]-amide};

4-Methoxy-pyrrolidine-1,2-dicarboxylic acid 1-[(4-chloro-phenyl)-amide]2-{[2-fluoro-4-(3,3,4-trimethyl-2,5-dioxo-pyrrolidin-1-yl)-phenyl]-amide};

1-(4-{[1-(4-Chloro-phenylcarbamoyl)-4-methoxy-pyrrolidine-2-carbonyl]-amino}-3-fluoro-phenyl)-5-oxo-pyrrolidine-2,2-dicarboxylic acid;

4-Methoxy-pyrrolidine-1,2-dicarboxylic acid 1-[(4-chloro-phenyl)-amide]2-{[2-fluoro-4-(2-methyl-5-oxo-pyrrolidin-1-yl)-phenyl]-amide};

4-Methoxy-pyrrolidine-1,2-dicarboxylic acid 1-[(4-chloro-phenyl)-amide]2-{[2-fluoro-4-(2-methyl-6-oxo-piperidin-1-yl)-phenyl]-amide};

4-Methoxy-pyrrolidine-1,2-dicarboxylic acid 1-[(4-chloro-phenyl)-amide]2-{[2-fluoro-4-(3-hydroxy-2-oxo-piperidin-1-yl)-phenyl]-amide};

4-Methoxy-pyrrolidine-1,2-dicarboxylic acid 1-[(4-chloro-phenyl)-amide]2-{[2-fluoro4-(5-methyl-2,6-dioxo-tetrahydro-pyrimidin-1-yl)-phenyl]-amide};

4-Methoxy-pyrrolidine-1,2-dicarboxylic acid 1-[(4-chloro-phenyl)-amide]2-{[2-fluoro-4-(2-oxo-tetrahydro-pyrimidin-1-yl)-phenyl]-amide};

4-Methoxy-pyrrolidine-1,2-dicarboxylic acid 1-[(4-chloro-phenyl)-amide]2-{[2-fluoro4-(3-methyl-2-oxo-2H-pyridin-1-yl)-phenyl]-amide};

4-Methoxy-pyrrolidine-1,2-dicarboxylic acid 1-[(4-chloro-phenyl)-amide]2-{[4-(2,5-dioxo-piperazin-1-yl)-2-fluoro-phenyl]-amide};

4-Methoxy-pyrrolidine-1,2-dicarboxylic acid 1-[(4-chloro-phenyl)-amide]2-{[2-fluoro4-(3-hydroxy-2-oxo-2H-pyridin-1-yl)-phenyl]-amide};

4-Methoxy-pyrrolidine-1,2-dicarboxylic acid 1-[(4-chloro-phenyl)-amide]2-{[2-fluoro-4-(3-methoxy-2-oxo-2H-pyridin-1-yl)-phenyl]-amide};

4-Methoxy-pyrrolidine-1,2-dicarboxylic acid 1-[(4-chloro-phenyl)-amide]2-{[2-fluoro-4-(6-methyl-2-oxo-4-trifluoromethyl-2H-pyridin-1-yl)-phenyl]-amide};

4-Methoxy-pyrrolidine-1,2-dicarboxylic acid 1-[(4-chloro-phenyl)-amide]2-{[4-(2,6-dioxo-piperidin-1-yl)-2-fluoro-phenyl]-amide};

1-(4-{[1-(4-Chloro-phenylcarbamoyl)-4-methoxy-pyrrolidine-2-carbonyl]-amino}-3-fluoro-phenyl)-2-oxo-piperidine-3-carboxylic acid;

4-Methoxy-pyrrolidine-1,2-dicarboxylic acid 1-[(4-chloro-phenyl)-amide]2-{[4-(5,5-dihydroxy-2,4,6-trioxo-tetrahydro-pyrimidin-1-yl)-2-fluoro-phenyl]-amide};

4-Methoxy-pyrrolidine-1,2-dicarboxylic acid 1-[(4-chloro-phenyl)-amide]2-{[2-fluoro-4-(2,4,6-trioxo-tetrahydro-pyrimidin-1-yl)-phenyl]-amide};

4-Methoxy-pyrrolidine-1,2-dicarboxylic acid 1-[(4-chloro-phenyl)-amide]2-{[4-(4,4-dimethyl-2,6-dioxo-piperidin-1-yl)-2-fluoro-phenyl]-amide};

4-Methoxy-pyrrolidine-1,2-dicarboxylic acid 1-[(4-chloro-phenyl)-amide]2-{[2-fluoro-4-(2-hydroxy-4-oxo-azetidin-1-yl)-phenyl]-amide};

4-Methoxy-pyrrolidine-1,2-dicarboxylic acid 2-{[4-(acetyl-methyl-amino)-2-fluoro-phenyl]-amide}1-[(4-chloro-phenyl)-amide];

4-(4-{[1-(4-Chloro-phenylcarbamoyl)-4-methoxy-pyrrolidine-2-carbonyl]-amino}-3-fluoro-phenyl)-1H-pyrrole-3-carboxylic acid;

2-(4-{[1-(4-Chloro-phenylcarbamoyl)-4-methoxy-pyrrolidine-2-carbonyl]-amino}-3-fluoro-phenyl)-2H-pyrazole-3-carboxylic acid;

1-(4-{[1-(4-Chloro-phenylcarbamoyl)4-methoxy-pyrrolidine-2-carbonyl]-amino}-3-fluoro-phenyl)-1H-imidazole-2-carboxylic acid;

1-(4-{[1-(4-Chloro-phenylcarbamoyl)4-methoxy-pyrrolidine-2-carbonyl]-amino}-3-fluoro-phenyl)-1H-pyrrole-2-carboxylic acid;

3-(4-{[1-(4-Chloro-phenylcarbamoyl)4-methoxy-pyrrolidine-2-carbonyl]-amino}-3-fluoro-phenyl)-1H-pyrrole-2-carboxylic acid;

3-(4-{[1-(4-Chloro-phenylcarbamoyl)4-methoxy-pyrrolidine-2-carbonyl]-amino}-3-fluoro-phenyl)-furan-2-carboxylic acid;

3-(4-{[1-(4-Chloro-phenylcarbamoyl)-4-methoxy-pyrrolidine-2-carbonyl]-amino}-3-fluoro-phenyl)-thiophene-2-carboxylic acid;

4-(4-{[1-(4-Chloro-phenylcarbamoyl)-4-methoxy-pyrrolidine-2-carbonyl]-amino}-3-fluoro-phenyl)-furan-3-carboxylic acid;

4-(4-{[1-(4-Chloro-phenylcarbamoyl)-4-methoxy-pyrrolidine-2-carbonyl]-amino}-3-fluoro-phenyl)-thiophene-3-carboxylic acid;

4,5-Dihydro-pyrazole-1,5-dicarboxylic acid 1-[(4-chloro-phenyl)-amide]5-[(3-fluoro-2'-methanesulfonyl-biphenyl-4-yl)-amide];

3-Oxo-pyrazolidine-1,5-dicarboxylic acid 1-[(4-chloro-phenyl)-amide]5-[(3-fluoro-2'-sulfamoyl-biphenyl-4-yl)-amide];

3-Oxo-pyrazolidine-1,5-dicarboxylic acid 1-[(4-chloro-phenyl)-amide]5-{[2-fluoro4-(2-oxo-piperidin-1-yl)-phenyl]-amide};

4,5-Dihydro-pyrazole-1,5-dicarboxylic acid 1-[(4-chloro-phenyl)-amide]5-{[4-(2-oxo-piperidin-1-yl)-phenyl]-amide};

4,5-Dihydro-pyrazole-1,5-dicarboxylic acid 1-[(5-chloro-pyridin-2-yl)-amide]5-{[2-fluoro-4-(2-oxo-piperidin-1-yl)-phenyl]-amide};

4,5-Dihydro-pyrazole-1,5-dicarboxylic acid 1-[(5-chloro-pyridin-2-yl)-amide]5-{[4-(2-oxo-piperidin-1-yl)-phenyl]-amide};

4,5-Dihydro-pyrazole-1,5-dicarboxylic acid 1-[(4-chloro-phenyl)-amide]5-[(2-oxo-3,4,5,6-tetrahydro-2H-[1,3']bipyridinyl-6'-yl)-amide];

4,5-Dihydro-pyrazole-1,5-dicarboxylic acid 1-[(5-chloro-pyridin-2-yl)-amide]5-[(2-oxo-3,4,5,6-tetrahydro-2H-[1,3'] bipyridinyl-6'-yl)-amide];

4-Methoxy-pyrrolidine-1,2-dicarboxylic acid 1-[(5-chloro-pyridin-2-yl)-amide]2-[(3,5'-difluoro-2'-sulfamoyl-biphenyl-4-yl)-amide];

4-Methoxy-pyrrolidine-1,2-dicarboxylic acid 1-[(4-chloro-phenyl)-amide]2-[(5'-fluoro-2'-sulfamoyl-biphenyl-4-yl)-amide];

4-Methoxy-pyrrolidine-1,2-dicarboxylic acid 1-[(5-chloro-pyridin-2-yl)-amide]2-[(3,5'-difluoro-2'-sulfamoyl-biphenyl-4-yl)-amide];

4-Methoxy-pyrrolidine-1,2-dicarboxylic acid 1-[(4-chloro-phenyl)-amide]2-[(3,5'-difluoro-2'-sulfamoyl-biphenyl-4-yl)-amide];

4-Methoxy-pyrrolidine-1,2-dicarboxylic acid 1-[(4-chloro-phenyl)-amide]2-[(5'-fluoro-2'-methanesulfonyl-biphenyl-4-yl)-amide];

4-Methoxy-pyrrolidine-1,2-dicarboxylic acid 1-[(4-chloro-phenyl)-amide]2-[(3,5'-difluoro-2'-methanesulfonyl-biphenyl-4-yl)-amide];

4-Methoxy-pyrrolidine-1,2-dicarboxylic acid 1-[(5-chloro-pyridin-2-yl)-amide]2-[(3,5'-difluoro-2'-methanesulfonyl-biphenyl-4-yl)-amide];

4-Hydroxy-pyrrolidine-1,2-dicarboxylic acid 1-[(4-chloro-phenyl)-amide]2-[(3,5'-difluoro-2'-sulfamoyl-biphenyl-4-yl)-amide];

4-Hydroxy-pyrrolidine-1,2-dicarboxylic acid 1-[(4-chloro-phenyl)-amide]2-[(3,5'-difluoro-2'-methanesulfonyl-biphenyl-4-yl)-amide], or a pharmaceutically acceptable salt thereof.

The invention is also directed to a compound which is:

(2R,4R)-4-Methoxy-pyrrolidine-1,2-dicarboxylic acid 1-[(4-chloro-phenyl)-amide]2-[(4-pyrazol-1-yl-phenyl)-amide];

(2R,4R)-4-Methoxy-pyrrolidine-1,2-dicarboxylic acid 1-[(4-chloro-phenyl)-amide]2-[(2-fluoro-4-pyrazol-1-yl-phenyl)-amide];

(2R,4R)-4-Ethoxy-pyrrolidine-1,2-dicarboxylic acid 1-[(4-chloro-phenyl)-amide]2-[(2-fluoro-4-pyrazol-1-yl-phenyl)-amide];

(2R,4R)-4-Ethoxy-pyrrolidine-1,2-dicarboxylic acid 1-[(4-chloro-phenyl)-amide]2-[(4-pyrazol-1-yl-phenyl)-amide];

(2R,4R)-4-Methoxy-pyrrolidine-1,2-dicarboxylic acid 1-[(4-chloro-phenyl)-amide]2-{[2-fluoro-4-(3-methyl-pyrazol-1-yl)-phenyl]-amide};

(2R,4R)4-Hydroxy-pyrrolidine-1,2-dicarboxylic acid 1-[(4-chloro-phenyl)-amide]2-{[2-fluoro-4-(5-methyl-pyrazol-1-yl)-phenyl]-amide};

(2R,4R)-4-Methoxy-pyrrolidine-1,2-dicarboxylic acid 1-[(4-chloro-phenyl)-amide]2-{[4-(5-methyl-pyrazol-1-yl)-phenyl]-amide};

(2R,4R)-4-Hydroxy-pyrrolidine-1,2-dicarboxylic acid 1-[(4-chloro-phenyl)-amide]2-{[4-(3,5-dimethyl-pyrazol-1-yl)-phenyl]-amide};

(2R,4R)4-Methoxy-pyrrolidine-1,2-dicarboxylic acid 1-[(4-chloro-phenyl)-amide]2-{[4-(3,5-dimethyl-pyrazol-1-yl)-phenyl]-amide};

(2R,4R)4-Methoxy-pyrrolidine-1,2-dicarboxylic acid 1-[(4-chloro-phenyl)-amide]2-{[4-(3,5-dimethyl-pyrazol-1-yl)-2-fluoro-phenyl]-amide};

(2R,4S)-4-Amino-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Amino-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Hydroxy-pyrrolidine-1,2-dicarboxylic acid 1-[(4-chloro-phenyl)-amide]2-[(3-fluoro-2'-sulfamoyl-biphenyl-4-yl)-amide];

(2R)-4-Hydroxyimino-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Hydroxy-pyrrolidine-1,2-dicarboxylic acid 1-[(4-chloro-phenyl)-amide]2-[(3-fluoro-2'-methylsulfamoyl-biphenyl-4-yl)-amide];

(2R,4R)-4-Hydroxy-pyrrolidine-1,2-dicarboxylic acid 1-[(4-chloro-phenyl)-amide]2-[(2'-dimethylsulfamoyl-3-fluoro-biphenyl-4-yl)-amide];

(2R,4R)-4-Methoxy-pyrrolidine-1,2-dicarboxylic acid 1-[(5-chloro-pyridin-2-yl)-amide]2-[(3-fluoro-2'-methanesulfonyl-biphenyl-4-yl)-amide];

(2R,4R)-4-Methoxy-pyrrolidine-1,2-dicarboxylic acid 1-[(4-chloro-phenyl)-amide]2-[(3-fluoro-2'-sulfamoyl-biphenyl-4-yl)-amide];

(2R,4R)-4-Ethoxy-pyrrolidine-1,2-dicarboxylic acid 1-[(5-chloro-pyridin-2-yl)-amide]2-[(3-fluoro-2'-methanesulfonyl-biphenyl-4-yl)-amide];

(2R,4R)-4-Ethoxy-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Ethoxy-pyrrolidine-1,2-dicarboxylic acid 1-[(4-chloro-phenyl)-amide]2-[(3-fluoro-2'-sulfamoyl-biphenyl-4-yl)-amide];

(2R,4S)4-Methoxy-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Fluoro-pyrrolidine-1,2-dicarboxylic acid 1-[(4-chloro-phenyl)-amide]2-[(3-fluoro-2'-methanesulfonyl-biphenyl-4-yl)-amide];

(2R)-4,4-Difluoro-pyrrolidine-1,2-dicarboxylic acid 1-[(4-chloro-phenyl)-amide]2-[(3-fluoro-2'-methanesulfonyl-biphenyl-4-yl)-amide];

(2R,4R)4-Methoxy-pyrrolidine-1,2-dicarboxylic acid 2-[(3-fluoro-2'-methanesulfonyl-biphenyl4-yl)-amide]1-[(4-fluoro-phenyl)-amide];

(2R,4R)4-Acetylamino-pyrrolidine-1,2-dicarboxylic acid 1-[(4-chloro-phenyl)-amide]2-[(3-fluoro-2'-methanesulfonyl-biphenyl-4-yl)-amide];

(2R,4R)-4-Methanesulfonylamino-pyrrolidine-1,2-dicarboxylic acid 1-[(4-chloro-phenyl)-amide]2-[(3-fluoro-2'-methanesulfonyl-biphenyl-4-yl)-amide];

(2R,4S)-4-(1H-Tetrazol-5-yl)-pyrrolidine-1,2-dicarboxylic acid 1-[(4-chloro-phenyl)-amide]2-{[2-fluoro4-(2-oxo-piperidin-1-yl)-phenyl]-amide};

(2R,4S)4-Methoxy-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Cyano-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-(1H-Tetrazol-5-yl)-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Trifluoromethyl-pyrrolidine-1,2-dicarboxylic acid 1-[(4-chloro-phenyl)-amide]2-{[2-fluoro-4-(2-oxo-piperidin-1-yl)-phenyl]-amide};

(2R,4R)-4-Methoxy-pyrrolidine-1,2-dicarboxylic acid 1-[(4-chloro-phenyl)-amide]2-[(2'-cyano-3-fluoro-biphenyl-4-yl)-amide];

(2R,4R)-4-Methoxy-pyrrolidine-1,2-dicarboxylic acid 2-[(2'-aminomethyl-3-fluoro-biphenyl-4-yl)-amide]1-[(4-chloro-phenyl)-amide];

(2R,4R)-4'-{[1-(4-Chloro-phenylcarbamoyl)-4-methoxy-pyrrolidine-2-carbonyl]-amino}-3'-fluoro-biphenyl-2-carboxylic acid methyl ester;

(2R,4R)4-Methoxy-pyrrolidine-1,2-dicarboxylic acid 1-[(4-chloro-phenyl)-amide]2-{[4-(2,5-dihydro-pyrrole-1-carbonyl)-phenyl]-amide};

(2R,4R)-4-Hydroxy-pyrrolidine-1,2-dicarboxylic acid 1-[(4-chloro-phenyl)-amide]2-[(4-dimethylcarbamoyl-2-fluoro-phenyl)-amide];

(2R,4R)-4-Hydroxy-pyrrolidine-1,2-dicarboxylic acid 1-[(4-chloro-phenyl)-amide]2-{[4-(pyrrolidine-1-carbonyl)-phenyl]-amide};

Pyrrolidine-1,2-dicarboxylic acid 1-[(4-chloro-phenyl)-amide]2-{[4-(pyrrolidine-1-carbonyl)-phenyl]-amide};

(2R,4R)4-Hydroxy-pyrrolidine-1,2-dicarboxylic acid 1-[(4-chloro-phenyl)-amide]2-{[4-(2-methyl-pyrrolidine-1-carbonyl)-phenyl]-amide};

(2R,4R)4-Hydroxy-pyrrolidine-1,2-dicarboxylic acid 1-[(4-chloro-phenyl)-amide]2-{[4-(ethyl-methyl-carbamoyl)-phenyl]-amide};

(2R,4R)4-Hydroxy-pyrrolidine-1,2-dicarboxylic acid 1-[(4-chloro-phenyl)-amide]2-[(4-dimethylcarbamoyl-phenyl)-amide];

(2R,4R)4-Hydroxy-pyrrolidine-1,2-dicarboxylic acid 1-[(4-chloro-phenyl)-amide]2-{[4-(2R-methyl-pyrrolidine-1-carbonyl)-phenyl]-amide};

(2R,4R)-4-Hydroxy-pyrrolidine-1,2-dicarboxylic acid 1-[(4-chloro-phenyl)-amide]2-{[4-(2S-methyl-pyrrolidine-1-carbonyl)-phenyl]-amide};

(2R,4R)-4-Hydroxy-pyrrolidine-1,2-dicarboxylic acid 1-[(4-chloro-phenyl)-amide]2-{[2-fluoro-4-(pyrrolidine-1-carbonyl)-phenyl]-amide};

(2R,4R)-4-Hydroxy-pyrrolidine-1,2-dicarboxylic acid 1-[(4-chloro-phenyl)-amide]2-{[4-(pyrrolidine-1-carbonyl)-2-pyrrolidin-1-yl-phenyl]-amide};

(2R,4R)-4-{[1-(4-Chloro-phenylcarbamoyl)-4-hydroxy-pyrrolidine-2-carbonyl]-amino}-3-pyrrolidin-1-yl-benzoic acid methyl ester;

(2R,4R)-4-Hydroxy-pyrrolidine-1,2-dicarboxylic acid 2-{[4-(azetidine-1-carbonyl)-phenyl]-amide}1-[(4-chloro-phenyl)-amide];

(2R,4R)-4-Hydroxy-pyrrolidine-1,2-dicarboxylic acid 1-[(5-chloro-pyridin-2-yl)-amide]2-{[2-fluoro-4-(pyrrolidine-1-carbonyl)-phenyl]-amide};

(2R,4R)-4-Hydroxy-pyrrolidine-1,2-dicarboxylic acid 1-[(5-chloro-pyridin-2-yl)-amide]2-{[4-(pyrrolidine-1-carbonyl)-phenyl]-amide};

(2R,4R)-4-Hydroxy-pyrrolidine-1,2-dicarboxylic acid 1-[(5-chloro-pyridin-2-yl)-amide]2-[(4-dimethylcarbamoyl-phenyl)-amide];

(2R,4R)4-{[1-(4-Chloro-phenylcarbamoyl)-4-hydroxy-pyrrolidine-2-carbonyl]-amino}-3-dimethylamino-benzoic acid methyl ester;

(2R,4R)-4-Methoxy-pyrrolidine-1,2-dicarboxylic acid 1-[(4-chloro-phenyl)-amide]2-{[4-(pyrrolidine-1-carbonyl)-phenyl]-amide};

(2R,4R)4-Methoxy-pyrrolidine-1,2-dicarboxylic acid 1-[(4-chloro-phenyl)-amide]2-[(4-dimethylcarbamoyl-phenyl)-amide];

(2R,4R)4-Ethoxy-pyrrolidine-1,2-dicarboxylic acid 1-[(4-chloro-phenyl)-amide]2-{[4-(pyrrolidine-1-carbonyl)-phenyl]-amide};

(2R,4R)-4-Ethoxy-pyrrolidine-1,2-dicarboxylic acid 1-[(4-chloro-phenyl)-amide]2-[(4-dimethylcarbamoyl-phenyl)-amide];

(2R,4R)4-Methoxy-pyrrolidine-1,2-dicarboxylic acid 1-[(4-chloro-phenyl)-amide]2-{[2-fluoro4-(pyrrolidine-1-carbonyl)-phenyl]-amide};

(2R,4R)-4-Ethoxy-pyrrolidine-1,2-dicarboxylic acid 1-[(4-chloro-phenyl)-amide]2-{[2-fluoro4-(pyrrolidine-1-carbonyl)-phenyl]-amide};

(2R,4R)-4-Ethoxy-pyrrolidine-1,2-dicarboxylic acid 1-[(4-chloro-phenyl)-amide]2-[(4-dimethylcarbamoyl-2-fluoro-phenyl)-amide];

(2R,4R)4-Methoxy-pyrrolidine-1,2-dicarboxylic acid 1-[(4-chloro-phenyl)-amide]2-{[2-methyl-4-(2-oxo-piperidin-1-yl)-phenyl]-amide};

(2R,4R)-4-Ethoxy-pyrrolidine-1,2-dicarboxylic acid 1-[(4-chloro-phenyl)-amide]2-{[2-methyl-4-(2-oxo-piperidin-1-yl)-phenyl]-amide};

Pyrrolidine-1,2-dicarboxylic acid 1-[(4-chloro-phenyl)-amide]2-[(2-fluoro-4-quinolin-8-yl-phenyl)-amide];

Pyrrolidine-1,2-dicarboxylic acid 1-[(4-chloro-phenyl)-amide]2-[(3,5-difluoro-2'-methanesulfonyl-biphenyl-4-yl)-amide];

Pyrrolidine-1,2-dicarboxylic acid 1-[(4-chloro-phenyl)-amide]2-[(2'-methanesulfonyl-2-methyl-biphenyl-4-yl)-amide];

(2R,4R)-4-Hydroxy-pyrrolidine-1,2-dicarboxylic acid 1-[(4-chloro-phenyl)-amide]2-[(2'-methanesulfonyl-biphenyl-4-yl)-amide];

(2R,4R)-4-Hydroxy-pyrrolidine-1,2-dicarboxylic acid 1-[(4-chloro-phenyl)-amide]2-[(2'-methanesulfinyl-biphenyl-4-yl)-amide];

(2R,4R)-4-Hydroxy-pyrrolidine-1,2-dicarboxylic acid 1-[(4-chloro-phenyl)-amide]2-[(3-methyl-2'-methylsulfanyl-biphenyl-4-yl)-amide];

(2R,4R)-4-Hydroxy-pyrrolidine-1,2-dicarboxylic acid 1-[(4-chloro-phenyl)-amide]2-[(2-fluoro-2'-methanesulfonyl-biphenyl-4-yl)-amide];

(2R,4R)-4-Hydroxy-pyrrolidine-1,2-dicarboxylic acid 1-[(4-chloro-phenyl)-amide]2-[(2'-methanesulfonyl-3-methyl-biphenyl-4-yl)-amide];

(2R,4R)4-Hydroxy-pyrrolidine-1,2-dicarboxylic acid 1-[(4-chloro-phenyl)-amide]2-[(2'-methanesulfonyl-3-trifluoromethyl-biphenyl-4-yl)-amide];

5-Methyl4,5-dihydro-pyrazole-1,5-dicarboxylic acid 1-[(4-chloro-phenyl)-amide]5-[(3-fluoro-2'-sulfamoyl-biphenyl-4-yl)-amide];

3-Hydroxymethyl4,5-dihydro-pyrazole-1,5-dicarboxylic acid 1-[(4-chloro-phenyl)-amide]5-[(3-fluoro-2'-methanesulfonyl-biphenyl-4-yl)-amide];

4,5-Dihydro-pyrazole-1,5-dicarboxylic acid 1-[(4-chloro-phenyl)-amide]5-[(3-fluoro-2'-sulfamoyl-biphenyl-4-yl)-amide];

(R)4,5-Dihydro-pyrazole-1,5-dicarboxylic acid 1-[(4-chloro-phenyl)-amide]5-[(3-fluoro-2'-sulfamoyl-biphenyl-4-yl)-amide];

4,5-Dihydro-pyrazole-1,5-dicarboxylic acid 1-[(4-chloro-phenyl)-amide]5-{[2-fluoro-4-(2-oxo-piperidin-1-yl)-phenyl]-amide};

4,5-Dihydro-pyrazole-1,5-dicarboxylic acid 1-[(4-chloro-phenyl)-amide]5-[(3-fluoro-2'-methanesulfonyl-biphenyl-4-yl)-amide];

1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester;

(2R,4R)-4-Hydroxy-pyrrolidine-1,2-dicarboxylic acid 1-[(4-chloro-phenyl)-amide]2-[(2'-methoxy-biphenyl-4-yl)-amide];

(2R,4R)-4-Hydroxy-pyrrolidine-1,2-dicarboxylic acid 1-[(4-chloro-phenyl)-amide]2-[(2'-hydroxy-biphenyl-4-yl)-amide];

(2R,4R)-4-Methoxy-pyrrolidine-1,2-dicarboxylic acid 1-[(4-chloro-phenyl)-amide]2-[(2-fluoro-4-iodo-phenyl)-amide];

(2R,4R)-4-Methoxy-pyrrolidine-1,2-dicarboxylic acid 1-[(4-chloro-phenyl)-amide]2-{[2-fluoro-4-(3-hydroxy-2-oxo-piperidin-1-yl)-phenyl]-amide};

(2R,4R)4-Methoxy-pyrrolidine-1,2-dicarboxylic acid 1-[(4-chloro-phenyl)-amide]2-{[2-fluoro4-(2-oxo-tetrahydro-pyrimidin-1-yl)-phenyl]-amide};

(2R,4R)-4-Methoxy-pyrrolidine-1,2-dicarboxylic acid 1-[(4-chloro-phenyl)-amide]2-{[2-fluoro4-(2-oxo-imidazolidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-oxazolidin-3-yl)-phenyl]-amide};

(2R,4R)-1-(4-{[1-(4-Chloro-phenylcarbamoyl)-4-methoxy-pyrrolidine-2-carbonyl]-amino}-3-fluoro-phenyl)-2-oxo-piperidine-3-carboxylic acid ethyl ester;

(2R,4R)4-Methoxy-pyrrolidine-1,2-dicarboxylic acid 1-[(4-chloro-phenyl)-amide]2-{[2-fluoro-4-(3-methoxy-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro4-(3-methoxy-2-oxo-2H-pyridin-1-yl)-phenyl]-amide};

(2R,4R)4-Methoxy-pyrrolidine-1,2-dicarboxylic acid 1-[(5-chloro-pyridin-2-yl)-amide]2-{[4-(3-methyl-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-[(4-morpholin-4-yl-phenyl)-amide];

(2R,4R)-4-Methoxy-pyrrolidine-1,2-dicarboxylic acid 1-[(4-chloro-phenyl)-amide]2-{[4-(2-methyl-5-oxo-pyrrolidin-1-yl)-phenyl]-amide};

(2R,4R)-4-Methoxy-pyrrolidine-1,2-dicarboxylic acid 1-[(5-chloro-pyridin-2-yl)-amide]2-{[4-(2-methyl-5-oxo-pyrrolidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(4-methoxy-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(4-methoxy-2-oxo-2H-pyridin-1-yl)-phenyl]-amide};

(2R,4R)-4-Methoxy-pyrrolidine-1,2-dicarboxylic acid 2-{[4-(5-chloro-2-oxo-2H-pyridin-1-yl)-2-fluoro-phenyl]-amide}1-[(4-chloro-phenyl)-amide];

4-Hydroxy-pyrrolidine-1,2-dicarboxylic acid 2-[(4-tert-butyl-phenyl)-amide]1-[(4-chloro-phenyl)-amide];

4-Hydroxy-pyrrolidine-1,2-dicarboxylic acid 1-[(4-chloro-phenyl)-amide]2[(3,5'difluoro-2'-sulfamoyl-biphenyl-4-yl)-amide];

4-Methoxy-pyrrolidine-1,2-dicarboxylic acid 1-[(4-chloro-phenyl)-amide]2-[(2-oxo-3,4,5,6-tetrahydro-2H-[1,2']bipyridinyl-5'-yl)-amide];

4-Methoxy-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide];

4-Methoxy-pyrrolidine-1,2-dicarboxylic acid 1-[(5-chloro-pyridin-2-yl)-amide]2-{[4-(2,3-dimethyl-5-oxo-2,5-dihydro-pyrazol-1-yl)-phenyl]-amide};

4-Methoxy-pyrrolidine-1,2-dicarboxylic acid 1-[(4-chloro-phenyl)-amide]2-{[4-(2,3-dimethyl-5-oxo-2,5-dihydro-pyrazol-1-yl)-phenyl]-amide};

4-Methoxy-pyrrolidine-1,2-dicarboxylic acid 1-[(4-chloro-phenyl)-amide]2-[(2-oxo-2H-[1,3']bipyridinyl-6'-yl)-amide];

4-Methoxy-pyrrolidine-1,2-dicarboxylic acid 1-[(5-chloro-pyridin-2-yl)-amide]2-[(2-oxo-3,4,5,6-tetrahydro-2H-[1,3']bipyridinyl-6'-yl)-amide]-TFA Salt;

4-Ethoxy-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide];

4-Ethoxy-pyrrolidine-1,2-dicarboxylic acid 1-[(4-chloro-phenyl)-amide]2-[(2-oxo-2H-[1,3']bipyridinyl-6'-yl)-amide]; or 4-Methoxy-pyrrolidine-1,2-dicarboxylic acid 1-[(4-chloro-phenyl)-amide]2-{[2-fluoro4-(6-oxo-6H-pyridazin-1-yl)-phenyl]-amide};

(2R,4R)-4-Methoxy-pyrrolidine-1,2-dicarboxylic acid 1-[(4-chloro-phenyl)-amide]2-{[2-fluoro-4-(6-methyl-5-oxo-5H-[1,2,4]triazin-4-yl)-phenyl]-amide};

(2R,4R)4-Methoxy-pyrrolidine-1,2-dicarboxylic acid 2-{[4-(3-chloro-5-methyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[4-(3-methyl-5-oxo-4,5-dihydro-pyrazol-1-yl)-phenyl]-amide};

(2R,4R)-4-Methoxy-pyrrolidine-1,2-dicarboxylic acid 2-{[4-(5-chloro-3-methyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[4-(3,5-dimethoxy-2-oxo-2H-pyridin-1-yl)-2-fluoro-phenyl]-amide};

(2R,4R)4-Methoxy-pyrrolidine-1,2-dicarboxylic acid 1-[(4-chloro-phenyl)-amide]2-{[2-fluoro-4-(5-methoxy-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro4-(2-oxo-3-pyrrol-1-yl-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro-4-(2-oxo-3-phenyl-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro4-(3-methyl-2-oxo-pyrrolidin-1-yl)-phenyl]-amide};

(2R,4R)4-Methoxy-pyrrolidine-1,2-dicarboxylic acid 1-[(4-chloro-phenyl)-amide]2-{[2-fluoro4-(3-methyl-2-oxo-imidazolidin-1-yl)-phenyl]-amide};

(2R,4R)-4-Methoxy-pyrrolidine-1,2-dicarboxylic acid 1-[(4-chloro-phenyl)-amide]2-{[4-(3,5-dimethyl-2-oxo-imidazolidin-1-yl)-2-fluoro-phenyl]-amide};

(2R,4R)-4-Methoxy-pyrrolidine-1,2-dicarboxylic acid 1-[(4-chloro-phenyl)-amide]2-{[2-fluoro-4-(3,5,5-trimethyl-2-oxo-imidazolidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(3-isopropyl-5,5-dimethyl-2-oxo-imidazolidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(5-methyl-2-oxo-imidazolidin-1-yl)-phenyl]-amide};

(2R,4R)-4-Methoxy-pyrrolidine-1,2-dicarboxylic acid 1-[(4-chloro-phenyl)-amide]2-{[4-(5,5-dimethyl-2-oxo-imidazolidin-1-yl)-2-fluoro-phenyl]-amide};

(2R,4R)-4-Methoxy-pyrrolidine-1,2-dicarboxylic acid 1-[(4-chloro-phenyl)-amide]2-{[4-(3,4-dimethyl-2-oxo-2H-pyridin-1-yl)-2-fluoro-phenyl]-amide};

(2R,4R)-4-Methoxy-pyrrolidine-1,2-dicarboxylic acid 2-{[4-(4-chloro-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(5-chloro-pyridin-2-yl)-amide]2-{[2-fluoro-4-(3-methyl-2-oxo-pyrrolidin-1-yl)-phenyl]-amide};

(2R,4R)4-Methoxy-pyrrolidine-1,2-dicarboxylic acid 1-[(5-chloro-pyridin-2-yl)-amide]2-{[2-fluoro4-(3-methyl-2-oxo-imidazolidin-1-yl)-phenyl]-amide};

(2R,4R)4-Methoxy-pyrrolidine-1,2-dicarboxylic acid 1-[(5-chloro-pyridin-2-yl)-amide]2-{[4-(3,5-dimethyl-2-oxo-imidazolidin-1-yl)-2-fluoro-phenyl]-amide};

(2R,4R)4-Methoxy-pyrrolidine-1,2-dicarboxylic acid 1-[(5-chloro-pyridin-2-yl)-amide]2-{[2-fluoro4-(3,5,5-trimethyl-2-oxo-imidazolidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(3-isopropyl-5,5-dimethyl-2-oxo-imidazolidin-1-yl)-phenyl]-amide};

(2R,4R)4-Methoxy-pyrrolidine-1,2-dicarboxylic acid 1-[(5-chloro-pyridin-2-yl)-amide]2-{[2-fluoro-4-(5-methyl-2-oxo-imidazolidin-1-yl)-phenyl]-amide};

(2R,4R)-4-Methoxy-pyrrolidine-1,2-dicarboxylic acid 1-[(5-chloro-pyridin-2-yl)-amide]2-{[4-(5,5-dimethyl-2-oxo-imidazolidin-1-yl)-2-fluoro-phenyl]-amide};

(2R,4R)-4-Methoxy-pyrrolidine-1,2-dicarboxylic acid 1-[(5-chloro-pyridin-2-yl)-amide]2-{[4-(3,4-dimethyl-2-oxo-2H-pyridin-1-yl)-2-fluoro-phenyl]-amide};

(2R,4R)4-Methoxy-pyrrolidine-1,2-dicarboxylic acid 2-{[4-(4-chloro-2-oxo-2H-pyridin-1-yl)-2-fluoro-phenyl]-amide}1-[(5-chloro-pyridin-2-yl)-amide];

or a pharmaceutically acceptable salt thereof.

The invention is also directed to a compound which is:

(2R,4R)-4-Methoxy-pyrrolidine-1,2-dicarboxylic acid 1-[(4-chloro-phenyl)-amide]2-{[2-fluoro-4-(2-oxo-2H-quinolin-1-yl)-phenyl]-amide};

(2R,4R)4-Methoxy-pyrrolidine-1,2-dicarboxylic acid 1-[(4-chloro-phenyl)-amide]2-{[2-fluoro-4-(3-oxo-3H-isoquinolin-2-yl)-phenyl]-amide};

(2R,4R)-4-Methoxy-pyrrolidine-1,2-dicarboxylic acid 1-[(4-chloro-phenyl)-amide]2-{[2-fluoro-4-(1-oxo-1H-isoquinolin-2-yl)-phenyl]-amide};

(2R,4R)-4-Methoxy-pyrrolidine-1,2-dicarboxylic acid 1-[(4-chloro-phenyl)-amide]2-{[2-fluoro4-(5-oxo-5H-[1,2,4]triazin-4-yl)-phenyl]-amide};

(2R,4R)-4-Methoxy-pyrrolidine-1,2-dicarboxylic acid 1-[(4-chloro-phenyl)-amide]2-{[2-fluoro-4-(6-oxo-6H-pyrimidin-1-yl)-phenyl]-amide};

2R,4R)4-Methoxy-pyrrolidine-1,2-dicarboxylic acid 1-[(4-chloro-phenyl)-amide]2-{[2-fluoro4-(2-oxo-2H-pyrazin-1-yl)-phenyl]-amide};

(2R,4R)-4-Methoxy-pyrrolidine-1,2-dicarboxylic acid 1-[(4-chloro-phenyl)-amide]2-{[2-fluoro4-(2-oxo-2H-pyrimidin-1-yl)-phenyl]-amide};

(2R,4R)4-Methoxy-pyrrolidine-1,2-dicarboxylic acid 1-[(4-chloro-phenyl)-amide]2-{[2-fluoro-4-(2-oxo-2H-[1,3,5]triazin-1-yl)-phenyl]-amide};

(2R,4R)-4-Methoxy-pyrrolidine-1,2-dicarboxylic acid 1-[(4-chloro-phenyl)-amide]2-[(6-methyl-2-oxo-2H-[1,3']bipyridinyl-6'-yl)-amide];

(2R,4R)-4-Methoxy-pyrrolidine-1,2-dicarboxylic acid 1-[(4-chloro-phenyl)-amide]2-{[2-fluoro-4-(1-methyl-1H-imidazol-2-yl)-phenyl]-amide};

(2R,4R)-4-Methoxy-pyrrolidine-1,2-dicarboxylic acid 1-[(4-chloro-phenyl)-amide]2-{[2-fluoro-4-(1-methyl-1H-pyrrol-2-yl)-phenyl]-amide};

(2R,4R)-5-Aza-spiro[2.4]heptane-5,6-dicarboxylic acid 5-[(4-chloro-phenyl)-amide]6-{[2-fluoro-4-(2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-2H-pyridine-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(3-methyl-3H-imidazol-4-yl)-phenyl]-amide};

(2R,4R)-4-Methoxy-pyrrolidine-1,2-dicarboxylic acid 1-[(4-chloro-phenyl)-amide]2-{[2-fluoro-4-(2-methyl-2H-pyrazol-3-yl)-phenyl]-amide};

(2R,4R)-4-Methoxy-pyrrolidine-1,2-dicarboxylic acid 1-[(4-chloro-phenyl)-amide]2-{[5-(2,5-dihydro-pyrrole-1-carbonyl)-pyridin-2-yl]-amide};

(2R,4R)-4-Methoxy-pyrrolidine-1,2-dicarboxylic acid 1-[(4-chloro-phenyl)-amide]2-{[2-fluoro-4-(3-methyl-5-oxo-2,5-dihydro-pyrazol-1-yl)-phenyl]-amide};

(2R,4R)4-Methoxy-pyrrolidine-1,2-dicarboxylic acid 1-[(4-chloro-phenyl)-amide]2-{[2-fluoro-4-(5-methoxymethyl-3-methyl-pyrazol-1-yl)-phenyl]-amide};

(2R,4R)4-Methoxy-pyrrolidine-1,2-dicarboxylic acid 1-[(4-chloro-phenyl)-amide]2-{[2-fluoro4-(3-methoxymethyl-5-methyl-pyrazol-1-yl)-phenyl]-amide};

(2R,4R)4-Methoxy-pyrrolidine-1,2-dicarboxylic acid 1-[(4-chloro-phenyl)-amide]2-{[2-fluoro4-(5-ethyl-3-methyl-pyrazol-1-yl)-phenyl]-amide};

(2R,4R)4-Methoxy-pyrrolidine-1,2-dicarboxylic acid 1-[(4-chloro-phenyl)-amide]2-{[2-fluoro4-(5-isobutyl-3-methyl-pyrazol-1-yl)-phenyl]-amide};

(2R,4R)-4-Methoxy-pyrrolidine-1,2-dicarboxylic acid 1-[(4-chloro-phenyl)-amide]2-{[2-fluoro-4-(5-isopropyl-pyrazol-1-yl)-phenyl]-amide};

(2R,4R)-4-Methoxy-pyrrolidine-1,2-dicarboxylic acid 1-[(4-chloro-phenyl)-amide]2-{[2-fluoro-4-(5-ethyl-pyrazol-1-yl)-phenyl]-amide};

(2R,4R)-4-Methoxy-pyrrolidine-1,2-dicarboxylic acid 1-[(4-chloro-phenyl)-amide]2-{[2-fluoro-4-(5-isobutyl-pyrazol-1-yl)-phenyl]-amide};

(2R,4R)-2-(4-{[1-(4-Chloro-phenylcarbamoyl)4-methoxy-pyrrolodine-2-carbonyl]-amino}-3-fluoro-phenyl)-2H-pyrazole-3-carboxylic acid methyl ester;

(2R,4R)-2-(4-{[1-(4-Chloro-phenylcarbamoyl)-4-methoxy-pyrrolodine-2-carbonyl]-amino}-3-fluoro-phenyl)-2H-pyrazole-3-carboxylic acid;

(2R,4R)-4-Methoxy-pyrrolidine-1,2-dicarboxylic acid 1-[(4-chloro-phenyl)-amide]2-{[2-fluoro-4-(5-methoxymethyl-pyrazol-1-yl)-phenyl]-amide};

(2R,4R)-5-(4-{[1-(4-Chloro-phenylcarbamoyl)-4-methoxy-pyrrolidine-2-carbonyl]-amino}-3-fluoro-phenyl)-oxazole-4-carboxylic acid ethyl ester;

(2R,4R)-5-(4-{[1-(4-Chloro-phenylcarbamoyl)-4-hydroxy-pyrrolidine-2-carbonyl]-amino}-3-fluoro-phenyl)-oxazole-4-carboxylic acid ethyl ester;

(2R,4R)-5-(4-{[1-(4-Chloro-phenylcarbamoyl)-4-methoxy-pyrrolidine-2-carbonyl]-amino}-3-fluoro-phenyl)-oxazole-4-carboxylic acid;

(2R,4R)-4-Methoxy-pyrrolidine-1,2-dicarboxylic acid 1-[(4-chloro-phenyl)-amide]2-{[2-fluoro-4-(4-methoxymethyl-oxazol-5-yl)-phenyl]-amide};

(2R,4R)-4-Methoxy-pyrrolidine-1,2-dicarboxylic acid 1-[(4-chloro-phenyl)-amide]2-{[4-(4-ethyl-oxazol-5-yl)-2-fluoro-phenyl]-amide};

(2R,4R)4-Methoxy-pyrrolidine-1,2-dicarboxylic acid 1-[(4-chloro-phenyl)-amide]2-{[2-fluoro4-(4-isopropyl-oxazol-5-yl)-phenyl]-amide};

(2R,4R)-5-(6-{[1-(4-Chloro-phenylcarbamoyl)4-methoxy-pyrrolidine-2-carbonyl]-amino}-pyridin-3-yl)-oxazole4-carboxylic acid ethyl ester;

(2R,4R)-5-(6-{[1-(4-Chloro-phenylcarbamoyl)4-methoxy-pyrrolidine-2-carbonyl]-amino}-pyridin-3-yl)-oxazole4-carboxylic acid;

(2R,4R)4-Methoxy-pyrrolidine-1,2-dicarboxylic acid 1-[(4-chloro-phenyl)-amide]2-{[5-(4-methoxymethyl-oxazol-5-yl)-pyridin-2-yl]-amide};

(2R,4R)4-Methoxy-pyrrolidine-1,2-dicarboxylic acid 1-[(4-chloro-phenyl)-amide]2-{[5-(4-ethyl-oxazol-5-yl)-pyridin-2-yl]-amide};

(2R,4R)4-Methoxy-pyrrolidine-1,2-dicarboxylic acid 1-[(4-chloro-phenyl)-amide]2-{[5-(4-vinyl-oxazol-5-yl)-pyridin-2-yl]-amide};

(2R,4R)-4-Methoxy-pyrrolidine-1,2-dicarboxylic acid 1-[(4-chloro-phenyl)-amide]2-{[5-(4-isobutyl-oxazol-5-yl)-pyridin-2-yl]-amide};

(2R,4R)-4-Methoxy-pyrrolidine-1,2-dicarboxylic acid 1-[(4-chloro-phenyl)-amide]2-{[2-fluoro-4-(4-methyl-isoxazol-3-yl)-phenyl]-amide};

(2R,4R)-4-Methoxy-pyrrolidine-1,2-dicarboxylic acid 1-[(4-chloro-phenyl)-amide]2-{[4-(4-methyl-isoxazol-3-yl)-phenyl]-amide};

(2R,4R)-3-(4-{[1-(4-Chloro-phenylcarbamoyl)-4-methoxy-pyrrolidine-2-carbonyl]-amino}-3-fluoro-phenyl)-isoxazole-4-carboxylic acid methyl ester;

(2R,4R)-3-(4-{[1-(4-Chloro-phenylcarbamoyl)4-methoxy-pyrrolidine-2-carbonyl]-amino}-3-fluoro-phenyl)-isoxazole-4-carboxylic acid;

(2R,4R)-4-Methoxy-pyrrolidine-1,2-dicarboxylic acid 1-[(4-chloro-phenyl)-amide]2-{[4-(4-methoxymethyl-isoxazol-3-yl)-phenyl]-amide};

(2R,4R)-4-Methoxy-pyrrolidine-1,2-dicarboxylic acid 1-[(4-chloro-phenyl)-amide]2-{[2-fluoro-4-(4-isopropyl-isoxazol-3-yl)-phenyl]-amide};

(2R,4R)-4-Methoxy-pyrrolidine-1,2-dicarboxylic acid 1-[(4-chloro-phenyl)-amide]2-{[2-fluoro4-(4-cyclopropyl-isoxazol-3-yl)-phenyl]-amide};

(2R,4R)-4-Methoxy-pyrrolidine-1,2-dicarboxylic acid 1-[(4-chloro-phenyl)-amide]2-{[4-(4-cyclopropyl-isoxazol-3-yl)-phenyl]-amide};

(2R,4R)-4-Methoxy-pyrrolidine-1,2-dicarboxylic acid 1-[(5-chloro-pyridin-2-yl)-amide]2-{[2-methyl4-(2-oxo-2H-pyridin-1-yl)-phenyl]-amide};

(2R,4R)4-Ethoxy-pyrrolidine-1,2-dicarboxylic acid 1-[(4-chloro-phenyl)-amide]2-{[2-methyl4-(2-oxo-2H-pyridin-1-yl)-phenyl]-amide};

(2R,4R)4-Ethoxy-pyrrolidine-1,2-dicarboxylic acid 1-[(5-chloro-pyridin-2-yl)-amide]2-{[2-methyl4-(2-oxo-2H-pyridin-1-yl)-phenyl]-amide};

(2R,4R)-4-Methoxy-pyrrolidine-1,2-dicarboxylic acid 2-[(4-chloro-phenyl)-amide]1-{[2,6-difluoro4-(2-oxo-2H-pyridin-1-yl)-phenyl]-amide};

(2R,4R)4-Methoxy-pyrrolidine-1,2-dicarboxylic acid 2-[(5-chloro-pyridin-2-yl)-amide]1-{[2,6-difluoro4-(2-oxo-2H-pyridin-1-yl)-phenyl]-amide};

(2R,4R)4-Ethoxy-pyrrolidine-1,2-dicarboxylic acid 2-[(4-chloro-phenyl)-amide]1-{[2,6-difluoro4-(2-oxo-2H-pyridin-1-yl)-phenyl]-amide};

(2R,4R)-4-Ethoxy-pyrrolidine-1,2-dicarboxylic acid 2-[(5-chloro-pyridin-2-yl)-amide]1-{[2,6-difluoro4-(2-oxo-2H-pyridin-1-yl)-phenyl]-amide};

(2R,4R)4-Methoxy-pyrrolidine-1,2-dicarboxylic acid 1-[(4-chloro-phenyl)-amide]2-[(5'-methyl-2-oxo-2H-[1,3']bipyridinyl-6'-yl)-amide];

(2R,4R)4-Methoxy-pyrrolidine-1,2-dicarboxylic acid 1-[(5-chloro-pyridin-2-yl)-amide]2-[(5'-methyl-2-oxo-2H-[1,3']bipyridinyl-6'-yl)-amide];

(2R,4R)-4-Ethoxy-pyrrolidine-1,2-dicarboxylic acid 1-[(4-chloro-phenyl)-amide]2-[(5'-methyl-2-oxo-2H-[1,3']bipyridinyl-6'-yl)-amide];

(2R,4R)-4-Ethoxy-pyrrolidine-1,2-dicarboxylic acid 1-[(5-chloro-pyridin-2-yl)-amide]2-[(5'-methyl-2-oxo-2H-[1,3']bipyridinyl-6'-yl)-amide];

(2R,4R)4-Methoxy-pyrrolidine-1,2-dicarboxylic acid 1-[(4-chloro-phenyl)-amide]2-[(2'-methyl-2-oxo-2H-[1,3']bipyridinyl-6'-yl)-amide];

(2R,4R)4-Methoxy-pyrrolidine-1,2-dicarboxylic acid 1-[(5-chloro-pyridin-2-yl)-amide]2-[(2'-methyl-2-oxo-2H-[1,3']bipyridinyl-6'-yl)-amide];

(2R,4R)-4-Ethoxy-pyrrolidine-1,2-dicarboxylic acid 1-[(4-chloro-phenyl)-amide]2-[(2'-methyl-2-oxo-2H-[1,3']bipyridinyl-6'-yl)-amide];

(2R,4R)4-Ethoxy-pyrrolidine-1,2-dicarboxylic acid 1-[(5-chloro-pyridin-2-yl)-amide]2-[(2'-methyl-2-oxo-2H-[1,3']bipyridinyl-6'-yl)-amide];

(2R,4R)4-Methoxy-pyrrolidine-1,2-dicarboxylic acid 1-[(4-chloro-phenyl)-amide]2-{[4-(ethyl-isopropyl-carbamoyl)-phenyl]-amide};

(2R,4R)-4-Methoxy-pyrrolidine-1,2-dicarboxylic acid 1-[(4-chloro-phenyl)-amide]2-{[4-(ethyl-isopropyl-carbamoyl)-2-fluoro-phenyl]-amide};

(2R,4R)-4-Methoxy-pyrrolidine-1,2-dicarboxylic acid 1-[(4-chloro-phenyl)-amide]2-{[4-(3-ethyl-pyrrolidine-1-carbonyl)-phenyl]-amide};

(2R,4R)-4-Methoxy-pyrrolidine-1,2-dicarboxylic acid 1-[(4-chloro-phenyl)-amide]2-{[4-(3-ethyl-pyrrolidine-1-carbonyl)-2-fluoro-phenyl]-amide};

(2R,4R)4-Methoxy-pyrrolidine-1,2-dicarboxylic acid 2-{[4-(3R-amino-pyrrolidine-1-carbonyl)-phenyl]-amide}1-[(4-chloro-phenyl)-amide];

(2R,4R)4-Methoxy-pyrrolidine-1,2-dicarboxylic acid 2-{[4-(3R-amino-pyrrolidine-1-carbonyl)-2-fluoro-phenyl]-amide}1-[(4-chloro-phenyl)-amide];

(2R,4R)4-Methoxy-pyrrolidine-1,2-dicarboxylic acid 2-{[4-(3S-amino-pyrrolidine-1-carbonyl)-phenyl]-amide}1-[(4-chloro-phenyl)-amide];

(2R,4R)4-Methoxy-pyrrolidine-1,2-dicarboxylic acid 2-{[4-(3S-amino-pyrrolidine-1-carbonyl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[4-(3R-methylamino-pyrrolidine-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(3R-methylamino-pyrrolidine-1-carbonyl)-phenyl]-amide};

(2R,4R)-4-Methoxy-pyrrolidine-1,2-dicarboxylic acid 1-[(4-chloro-phenyl)-amide]2-{[4-(3S-methylamino-pyrrolidine-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(3S-methylamino-pyrrolidine-1-carbonyl)-phenyl]-amide};

(2R,4R)4-Methoxy-pyrrolidine-1,2-dicarboxylic acid 1-[(4-chloro-phenyl)-amide]2-{[4-(3R-ethylamino-pyrrolidine-1-carbonyl)-phenyl]-amide};

(2R,4R)4-Methoxy-pyrrolidine-1,2-dicarboxylic acid 1-[(4-chloro-phenyl)-amide]2-{[2-fluoro-4-(3R-ethylamino-pyrrolidine-1-carbonyl)-phenyl]-amide};

(2R,4R)-4-Methoxy-pyrrolidine-1,2-dicarboxylic acid 1-[(4-chloro-phenyl)-amide]2-{[4-(3S-ethylamino-pyrrolidine-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(3S-ethylamino-pyrrolidine-1-carbonyl)-phenyl]-amide};

(2R,4R)-4-Methoxy-pyrrolidine-1,2-dicarboxylic acid 1-[(5-chloro-pyridin-2-yl)-amide]2-{[4-(2,5-dihydro-pyrrole-1-carbonyl)-phenyl]-amide};

(2R,4R)4-Methoxy-pyrrolidine-1,2-dicarboxylic acid 1-[(4-chloro-phenyl)-amide]2-{[4-(2,5-dihydro-pyrrole-1-carbonyl)-2-fluoro-phenyl]-amide};

(2R,4R)4-Methoxy-pyrrolidine-1,2-dicarboxylic acid 1-[(5-chloro-pyridin-2-yl)-amide]2-{[4-(2,5-dihydro-pyrrole-1-carbonyl)-2-fluoro-phenyl]-amide};

(2R,4R)4-Methoxy-pyrrolidine-1,2-dicarboxylic acid 1-[(4-chloro-phenyl)-amide]2-{[4-(pyrrole-1-carbonyl)-phenyl]-amide};

(2R,4R)4-Methoxy-pyrrolidine-1,2-dicarboxylic acid 1-[(4-chloro-phenyl)-amide]2-{[2-fluoro4-(pyrrole-1-carbonyl)-phenyl]-amide};

(2R,4R)-4-Methoxy-pyrrolidine-1,2-dicarboxylic acid 1-[(5-chloro-pyridin-2-yl)-amide]2-{[4-(pyrrole-1-carbonyl)-phenyl]-amide};

(2R,4R)-4-Methoxy-pyrrolidine-1,2-dicarboxylic acid 1-[(5-chloro-pyridin-2-yl)-amide]2-{[2-fluoro-4-(pyrrole-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(5-fluoro-2-oxo-2H-pyridin-1-yl)-phenyl]-amide};

(2R,4R)-1-(4-{[1-(4-Chloro-phenylcarbamoyl)-4-methoxy-pyrrolidine-2-carbonyl]-amino}-3-fluoro-phenyl)-6-oxo-1,6-dihydro-pyridine-3-carboxylic acid;

(2R,4R)-4-Methoxy-pyrrolidine-1,2-dicarboxylic acid 1-[(4-chloro-phenyl)-amide]2-{[2-fluoro-4-(6-hydroxy-2-oxo-2H-pyridin-1-yl)-phenyl]-amide};

(2R,4R)-1-(4-{[1-(4-Chloro-phenylcarbamoyl)-4-methoxy-pyrrolidine-2-carbonyl]-amino}-3-fluoro-phenyl)-2-oxo-1,2-dihydro-pyridine-3-carboxylic acid;

(2R,4R)-1-(4-{[1-(4-Chloro-phenylcarbamoyl)-4-methoxy-pyrrolidine-2-carbonyl]-amino}-3-fluoro-phenyl)-6-oxo-1,6-dihydro-pyridine-2-carboxylic acid methyl ester;

(2R,4R)-[1-(4-1{[1-(4-Chloro-phenylcarbamoyl)4-methoxy-pyrrolidine-2-carbonyl]-amino}-phenyl)-2,5-dioxo-imidazolidin-4-yl]-acetic acid;

(2R,4R)-1-(4-{[1-(4-Chloro-phenylcarbamoyl)4-methoxy-pyrrolidine-2-carbonyl]-amino}-3-fluoro-phenyl)-2-oxo-1,2-dihydro-pyridine-3-carboxylic acid methyl ester;

(2R,4R)-4-Methoxy-pyrrolidine-1,2-dicarboxylic acid 1-[(4-chloro-phenyl)-amide]2-{[2-fluoro4-(2-oxo-3-trifluoromethyl-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro4-(4-hydroxy-2-oxo-2H-pyridin-1-yl)-phenyl]-amide};

(2R,4R)-1-(4-{[1-(4-Chloro-phenylcarbamoyl)4-methoxy-pyrrolidine-2-carbonyl]-amino}-3-fluoro-phenyl)-6-oxo-1,6-dihydro-pyridine-2-carboxylic acid;

(2R,4R)-4-Methoxy-pyrrolidine-1,2-dicarboxylic acid 1-[(4-chloro-phenyl)-amide]2-{[2-fluoro-4-(2-oxo-5-trifluoromethyl-2H-pyridin-1-yl)-phenyl]-amide};

(2R,4R)-4-Methoxy-pyrrolidine-1,2-dicarboxylic acid 1-[(4-chloro-phenyl)-amide]2-{[4-(6-cyclopropyl-2-oxo-2H-pyridin-1-yl)-2-fluoro-phenyl]-amide};

(2R,4R)-1-(4-{[1-(4-Chloro-phenylcarbamoyl)-4-methoxy-pyrrolidine-2-carbonyl]-amino}-3-fluoro-phenyl)-6-oxo-1,6-dihydro-pyridine-3-carboxylic acid ethyl ester;

(2R,4R)-4-Methoxy-pyrrolidine-1,2-dicarboxylic acid 1-[(4-chloro-phenyl)-amide]2-{[4-(3,3-dimethyl-2-oxo-azetidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(7-oxo-7H-thieno[2,3-c]pyridin-6-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-1-azaspiro[4.5]dec-1-yl)-phenyl]-amide};

(2R,4R)-4-Methoxy-pyrrolidine-1,2-dicarboxylic acid 2-{[4-(3-benzoyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-acetylsulfamoyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[2-fluoro4-(2-oxo-thiazolidin-3-yl)-phenyl]-amide};

(2R,4R)-4-Methoxy-pyrrolidine-1,2-dicarboxylic acid 1-[(4-chloro-phenyl)-amide]2-{[2-fluoro4-(3-methyl-2-oxo-piperidin-1-yl)-phenyl]-amide};

(2R,4R)4-Methoxy-pyrrolidine-1,2-dicarboxylic acid 1-[(4-chloro-phenyl)-amide]2-{[2-fluoro4-(2-oxo-3-sulfamoyl-2H-pyridin-1-yl)-phenyl]-amide};

(2R,4R)4-Methoxy-pyrrolidine-1,2-dicarboxylic acid 1-[(4-chloro-phenyl)-amide]2-{[4-(2,5-dioxo-2,5-dihydro-pyrrol-1-yl)-phenyl]-amide};

(2R,4R)4-Methoxy-pyrrolidine-1,2-dicarboxylic acid 2-{[4-(3-amino-2-oxo-2H-pyridin-1-yl)-2-fluoro-phenyl]-amide}1-[(4-chloro-phenyl)-amide];

(2R,4R)4-Methoxy-pyrrolidine-1,2-dicarboxylic acid 1-[(4-chloro-phenyl)-amide]2-{[2-fluoro-4-(2-oxo-3-phenoxy-2H-pyridin-1-yl)-phenyl]-amide};

(2R,4R)-4-Methoxy-pyrrolidine-1,2-dicarboxylic acid 1-[(4-chloro-phenyl)-amide]2-{[4-(2,2-dimethyl-5-oxo-pyrrolidin-1-yl)-2-fluoro-phenyl]-amide};

(2R,4R)-4-Methoxy-pyrrolidine-1,2-dicarboxylic acid 1-[(4-chloro-phenyl)-amide]2-{[2-fluoro-4-(3-nitro-2-oxo-2H-pyridin-1-yl)-phenyl]-amide};

(2R,4R)-1-(4-{[1-(4-Chloro-phenylcarbamoyl)-4-methoxy-pyrrolidine-2-carbonyl]-amino}-3-fluoro-phenyl)-2-oxo-1,2-dihydro-pyridine-3-carboxylic acid tert-butyl ester;

(2R,4R)-4-Methoxy-pyrrolidine-1,2-dicarboxylic acid 1-[(4-chloro-phenyl)-amide]2-{[4-(2,5-dioxo-pyrrolidin-1-yl)-phenyl]-amide};

(2R,4R)-4-Methoxy-pyrrolidine-1,2-dicarboxylic acid 2-{[4-(3-benzothiazol-2-yl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-amino-4,6-dimethyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[4-(3-diethylaminomethyl-2-oxo-2H-pyridin-1-yl)-2-fluoro-phenyl]-amide};

(2R,4R)4-Methoxy-pyrrolidine-1,2-dicarboxylic acid 2-{[4-(3-aminomethyl-2-oxo-2H-pyridin-1-yl)-2-fluoro-phenyl]-amide}1-[(4-chloro-phenyl)-amide];

(2R,4R)4-Methoxy-pyrrolidine-1,2-dicarboxylic acid 1-[(4-chloro-phenyl)-amide]2-{[2-fluoro4-(3-methyl-5-nitro-2-oxo-2H-pyridin-1-yl)-phenyl]-amide};

(2R,4R)-Acetic acid 1-(4-1{[1-(4-chloro-phenylcarbamoyl)4-methoxy-pyrrolidine-2-carbonyl]-amino}-3-fluoro-phenyl)-2-oxo-1,2-dihydro-pyridin-3-yl ester;

(2R,4R)-4-Methoxy-pyrrolidine-1,2-dicarboxylic acid 1-[(4-chloro-phenyl)-amide]2-( {4-[3-(cyclopentanecarbonyl-amino)-2-oxo-2H-pyridin-1-yl]-2-fluoro-phenyl}-amide);

(2R,4R)-4-Methoxy-pyrrolidine-1,2-dicarboxylic acid 2-{[4-(5-amino-3-methyl-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-({2-fluoro-4-[2-oxo-3-(pyridin-4-ylcarbamoyl)-2H-pyridin-1-yl]-phenyl}-amide);

(2R,4R)-4-Methoxy-pyrrolidine-1,2-dicarboxylic acid 1-[(4-chloro-phenyl)-amide]2-{[4-(3,5-dichloro-2-oxo-2H-pyridin-1-yl)-2-fluoro-phenyl]-amide};

(2R,4R)-4-Methoxy-pyrrolidine-1,2-dicarboxylic acid 2-{[4-(3-amino-5-bromo-2-oxo-2H-pyridin-1-yl)-2-fluoro-phenyl]-amide}1-[(4-chloro-phenyl)-amide];

(2R,4R)4-Methoxy-pyrrolidine-1,2-dicarboxylic acid 1-[(4-chloro-phenyl)-amide]2-{[4-(3-cyano-2-oxo-2H-pyridin-1-yl)-2-fluoro-phenyl]-amide};

(2R,4R)-4-Methoxy-pyrrolidine-1,2-dicarboxylic acid 1-[(4-chloro-phenyl)-amide]2-{[4-(3-cyano-2-oxo-5-phenyl-2H-pyridin-1-yl)-2-fluoro-phenyl]-amide};

(2R,4R)-4-Methoxy-pyrrolidine-1,2-dicarboxylic acid 1-[(4-chloro-phenyl)-amide]2-{[4-(3-ethyl-6-methyl-2-oxo-2H-pyridin-1-yl)-2-fluoro-phenyl]-amide};

(2R,4R)4-Methoxy-pyrrolidine-1,2-dicarboxylic acid 1-[(4-chloro-phenyl)-amide]2-{[4-(3-cyano-4-dimethylamino-2-oxo-2H-pyridin-1-yl)-2-fluoro-phenyl]-amide};

(2R,4R)4-Methoxy-pyrrolidine-1,2-dicarboxylic acid 1-[(4-chloro-phenyl)-amide]2-{[2-fluoro4-(4-methyl-3-nitro-2-oxo-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro4-(5-nitro-2-oxo-3-trifluoromethyl-2H-pyridin-1-yl)-phenyl]-amide};

(2R,4R)-4-Methoxy-pyrrolidine-1,2-dicarboxylic acid 2-{[4-(5-amino-6-oxo-6H-[3,4']bipyridinyl-1-yl)-2-fluoro-phenyl]-amide}1-[(4-chloro-phenyl)-amide];

(2R,4R)4-Methoxy-pyrrolidine-1,2-dicarboxylic acid 2-{[4-(5-chloro-3-nitro-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-carbamoyl-2-oxo-5-trifluoromethyl-2H-pyridin-1-yl)-2-fluoro-phenyl]-amide}1-[(4-chloro-phenyl)-amide];

(2R,4R)-5-Bromo-1-(4-{[1-(4-chloro-phenylcarbamoyl)-4-methoxy-pyrrolidine-2-carbonyl]-amino}-3-fluoro-phenyl)-2-oxo-1,2-dihydro-pyridine-3-carboxylic acid isobutyl ester;

(2R,4R)-4-Methoxy-pyrrolidine-1,2-dicarboxylic acid 2-{[4-(3-chloro-2-oxo-5-trifluoromethyl-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-bromo-5-chloro-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(5-bromo-3-nitro-2-oxo-2H-pyridin-1-yl)-2-fluoro-phenyl]-amide}1-[(4-chloro-phenyl)-amide];

(2R,4R)4-Methoxy-pyrrolidine-1,2-dicarboxylic acid 1-[(4-chloro-phenyl)-amide]2-{[2-fluoro-4-(3-nitro-2-oxo-5-trifluoromethyl-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro4-(5-methyl-3-nitro-2-oxo-2H-pyridin-1-yl)-phenyl]-amide};

(2R,4R)-5-Chloro-1-(4-{[1-(4-chloro-phenylcarbamoyl)-4-methoxy-pyrrolidine-2-carbonyl]-amino}-3-fluoro-phenyl)-2-oxo-1,2-dihydro-pyridine-3-carboxylic acid methyl ester;

(2R,4R)-5-Chloro-1-(4-1{[1-(4-chloro-phenylcarbamoyl)-4-methoxy-pyrrolidine-2-carbonyl]-amino}-3-fluoro-phenyl)-2-oxo-1,2-dihydro-pyridine-3-carboxylic acid;

(2R,4R)-4-Methoxy-pyrrolidine-1,2-dicarboxylic acid 2-{[4-(4-benzyloxy-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(4-amino-5-fluoro-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[2-fluoro-4-(6-methyl-3-oxo-3H-isoquinolin-2-yl)-phenyl]-amide};

(2R,4R)-4-Methoxy-pyrrolidine-1,2-dicarboxylic acid 1-[(4-chloro-phenyl)-amide]2-{[2-fluoro4-(4-methyl-5-nitro-2-oxo-2H-pyridin-1-yl)-phenyl]-amide};

(2R,4R)-4-Methoxy-pyrrolidine-1,2-dicarboxylic acid 2-{[4-(5-acetylamino-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(4-amino-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[2-fluoro4-(6-oxo-6H-[3,4']bipyridinyl-1-yl)-phenyl]-amide};

(2R,4R)-4-Methoxy-pyrrolidine-1,2-dicarboxylic acid 2-{[4-(4-bromo-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[2-fluoro-4-(4-oxo4H-furo[3,2-c]pyridin-5-yl)-phenyl]-amide};

(2R,4R)4-Methoxy-pyrrolidine-1,2-dicarboxylic acid 1-[(4-chloro-phenyl)-amide]2-{[2-fluoro4-(1-oxo-1H-[2,6]naphthyridin-2-yl)-phenyl]-amide};

(2R,4R)4-Methoxy-pyrrolidine-1,2-dicarboxylic acid 2-{[4-(5-bromo-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 1-[(4-chloro-phenyl)-amide]2-{[2-fluoro4-(4-oxo-4H-thieno[3,2-c]pyridin-5-yl)-phenyl]-amide};

(2R,4R)-4-Methoxy-pyrrolidine-1,2-dicarboxylic acid 1-[(4-chloro-phenyl)-amide]2-{[2-fluoro-4-(4-oxo-1,4-dihydro-imidazo[4,5-c]pyridin-5-yl)-phenyl]-amide};

(2R,4R)-4-Methoxy-pyrrolidine-1,2-dicarboxylic acid 2-{[4-(5-chloro-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[2-fluoro-4-(5-fluoro-2-oxo-2H-pyridin-1-yl)-phenyl]-amide};

(2R,4R)-1-(4-{[1-(5-Chloro-pyridin-2-ylcarbamoyl)-4-methoxy-pyrrolidine-2-carbonyl]-amino }-3-fluoro-phenyl)-6-oxo-1,6-dihydro-pyridine-3-carboxylic acid;

(2R,4R)-4-Methoxy-pyrrolidine-1,2-dicarboxylic acid 1-[(5-chloro-pyridin-2-yl)-amide]2-{[2-fluoro4-(6-hydroxy-2-oxo-2H-pyridin-1-yl)-phenyl]-amide};

(2R,4R)-1-(4-{[1-(5-Chloro-pyridin-2-ylcarbamoyl)-4-methoxy-pyrrolidine-2-carbonyl]-amino}-3-fluoro-phenyl)-2-oxo-1,2-dihydro-pyridine-3-carboxylic acid;

(2R,4R)-1-(4-{[1-(5-Chloro-pyridin-2-ylcarbamoyl)-4-methoxy-pyrrolidine-2-carbonyl]-amino}-3-fluoro-phenyl)-6-oxo-1,6-dihydro-pyridine-2-carboxylic acid methyl ester;

(2R,4R)-1-[1-(4-{[1-(5-Chloro-pyridin-2-ylcarbamoyl)4-methoxy-pyrrolidine-2-carbonyl]-amino}-phenyl)-2,5-dioxo-imidazolidin-4-yl]-acetic acid;

(2R,4R)-1-(4-{[1-(5-Chloro-pyridin-2-ylcarbamoyl)4-methoxy-pyrrolidine-2-carbonyl]-amino}-3-fluoro-phenyl)-2-oxo-1,2-dihydro-pyridine-3-carboxylic acid methyl ester;

(2R,4R)4-Methoxy-pyrrolidine-1,2-dicarboxylic acid 1-[(5-chloro-pyridin-2-yl)-amide]2-{[2-fluoro4-(2-oxo-3-trifluoromethyl-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(4-hydroxy-2-oxo-2H-pyridin-1-yl)-phenyl]-amide};

(2R,4R)-1-(4-{[1-(5-Chloro-pyridin-2-ylcarbamoyl)-4-methoxy-pyrrolidine-2-carbonyl]-amino}-3-fluoro-phenyl)-6-oxo-1,6-dihydro-pyridine-2-carboxylic acid;

(2R,4R)-4-Methoxy-pyrrolidine-1,2-dicarboxylic acid 1-[(5-chloro-pyridin-2-yl)-amide]2-{[2-fluoro-4-(2-oxo-5-trifluoromethyl-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[4-(6-cyclopropyl-2-oxo-2H-pyridin-1-yl)-2-fluoro-phenyl]-amide};

(2R,4R)-1-(4-{[1-(5-Chloro-pyridin-2-ylcarbamoyl)-4-methoxy-pyrrolidine-2-carbonyl]-amino }-3-fluoro-phenyl)-6-oxo-1,6-dihydro-pyridine-3-carboxylic acid ethyl ester;

(2R,4R)-4-Methoxy-pyrrolidine-1,2-dicarboxylic acid 1-[(5-chloro-pyridin-2-yl)-amide]2-{[2-fluoro-4-(3-hydroxy-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[4-(3,3-dimethyl-2-oxo-azetidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(7-oxo-7H-thieno[2,3-c]pyridin-6-yl)-phenyl]-amide};

(2R,4R)4-Methoxy-pyrrolidine-1,2-dicarboxylic acid 1-[(5-chloro-pyridin-2-yl)-amide]2-{[2-fluoro-4-(2-oxo-1-aza-spiro[4.5]dec-1-yl)-phenyl]-amide};

(2R,4R)4-Methoxy-pyrrolidine-1,2-dicarboxylic acid 2-{[4-(3-benzoyl-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro4-(2-methyl-5-oxo-pyrrolidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(2-methyl-6-oxo-piperidin-1-yl)-phenyl]-amide};

(2R,4R)-4-Methoxy-pyrrolidine-1,2-dicarboxylic acid 2-{[4-(3-acetylsulfamoyl-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[2-fluoro-4-(2-oxo-thiazolidin-3-yl)-phenyl]-amide};

(2R,4R)4-Methoxy-pyrrolidine-1,2-dicarboxylic acid 1-[(5-chloro-pyridin-2-yl)-amide]2-{[2-fluoro-4-(3-methyl-2-oxo-piperidin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro4-(2-oxo-3-sulfamoyl-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[4-(2,5-dioxo-2,5-dihydro-pyrrol-1-yl)-phenyl]-amide};

(2R,4R)-4-Methoxy-pyrrolidine-1,2-dicarboxylic acid 2-{[4-(3-amino-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro-4-(2-oxo-3-phenoxy-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[4-(2,2-dimethyl-5-oxo-pyrrolidin-1-yl)-2-fluoro-phenyl]-amide};

(2R,4R)4-Methoxy-pyrrolidine-1,2-dicarboxylic acid 1-[(5-chloro-pyridin-2-yl)-amide]2-{[2-fluoro4-(3-nitro-2-oxo-2H-pyridin-1-yl)-phenyl]-amide};

(2R,4R)-1-(4-{[1-(5-Chloro-pyridin-2-ylcarbamoyl)4-methoxy-pyrrolidine-2-carbonyl]-amino}-3-fluoro-phenyl)-2-oxo-1,2-dihydro-pyridine-3-carboxylic acid tert-butyl ester;

(2R,4R)4-Methoxy-pyrrolidine-1,2-dicarboxylic acid 1-[(5-chloro-pyridin-2-yl)-amide]2-{[4-(2,5-dioxo-pyrrolidin-1-yl)-phenyl]-amide};

(2R,4R)-4-Methoxy-pyrrolidine-1,2-dicarboxylic acid 2-{[4-(3-benzothiazol-2-yl-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(3-amino-4,6-dimethyl-2-oxo-2H-pyridin-1-yl)-2-fluoro-phenyl]-amide }1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[4-(3-diethyaminomethyl-2-oxo-2H-pyridin-1-yl)-2-fluoro-phenyl]-amide};

(2R,4R)-4-Methoxy-pyrrolidine-1,2-dicarboxylic acid 2-{[4-(3-aminomethyl-2-oxo-2H-pyridin-1-yl)-2-fluoro-phenyl]-amide }1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[2-fluoro-4-(3-methyl-5-nitro-2-oxo-2H-pyridin-1-yl)-phenyl]-amide};

(2R,4R)-Acetic acid 1-(4-{[1-(5-chloro-pyridin-2-ylcarbamoyl)-4-methoxy-pyrrolidine-2-carbonyl]-amino}-3-fluoro-phenyl)-2-oxo-1,2-dihydro-pyridin-3-yl ester;

(2R,4R)4-Methoxy-pyrrolidine-1,2-dicarboxylic acid 1-[(5-chloro-pyridin-2-yl)-amide]2-({4-[3-(cyclopentanecarbonyl-amino)-2-oxo-2H-pyridin-1-yl]-2-fluoro-phenyl}-amide);

(2R,4R)-4-Methoxy-pyrrolidine-1,2-dicarboxylic acid 2-{[4-(5-amino-3-methyl-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-( {2-fluoro4-[2-oxo-3-(pyridin-4-ylcarbamoyl)-2H-pyridin-1-yl]-phenyl}-amide);

(2R,4R)4-Methoxy-pyrrolidine-1,2-dicarboxylic acid 1-[(5-chloro-pyridin-2-yl)-amide]2-{[4-(3,5-dichloro-2-oxo-2H-pyridin-1-yl)-2-fluoro-phenyl]-amide};

(2R,4R)-4-Methoxy-pyrrolidine-1,2-dicarboxylic acid 2-{[4-(3-amino-5-bromo-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[4-(3-cyano-2-oxo-2H-pyridin-1-yl)-2-fluoro-phenyl]-amide};

(2R,4R)-4-Methoxy-pyrrolidine-1,2-dicarboxylic acid 1-[(5-chloro-pyridin-2-yl)-amide]2-{[4-(3-cyano-2-oxo-5-phenyl-2H-pyridin-1-yl)-2-fluoro-phenyl]-amide};

(2R,4R)4-Methoxy-pyrrolidine-1,2-dicarboxylic acid 1-[(5-chloro-pyridin-2-yl)-amide]2-{[4-(3-ethyl-6-methyl-2-oxo-2H-pyridin-1-yl)-2-fluoro-phenyl]-amide};

(2R,4R)-4-Methoxy-pyrrolidine-1,2-dicarboxylic acid 1-[(5-chloro-pyridin-2-yl)-amide]2-{[4-(3-cyano4-dimethylamino-2-oxo-2H-pyridin- I -yl)-2-fluoro-phenyl]-amide};

(2R,4R)-4-Methoxy-pyrrolidine-1,2-dicarboxylic acid 1-[(5-chloro-pyridin-2-yl)-amide]2-{[2-fluoro-4-(4-methyl-3-nitro-2-oxo-2H-pyridin-1 phenyl]-amide};

(2R,4R)-4-Methoxy-pyrrolidine-1,2-dicarboxylic acid 1-[(5-chloro-pyridin-2-yl)-amide]2-{[2-fluoro-4-(5-nitro-2-oxo-3-trifluoromethyl-2H-pyridin-1-yl)-phenyl]-amide};

(2R,4R)-4-Methoxy-pyrrolidine-1,2-dicarboxylic acid 2-{[4-(5-amino-6-oxo-6H-[3,4']bipyridinyl-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(5-chloro-3-nitro-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 2-{[4-(3-carbamoyl-2-oxo-5-trifluoromethyl-2H-pyridin-1-yl)-2-fluoro-phenyl]-amide}1-[(5-chloro-pyridin-2-yl)-amide];

(2R,4R)-5-Bromo-1-(4-{[1-(5-chloro-pyridin-2-ylcarbamoyl)4-methoxy-pyrrolidine-2-carbonyl]-amino}-3-fluoro-phenyl)-2-oxo-1,2-dihydro-pyridine-3-carboxylic acid isobutyl ester;

(2R,4R)-4-Methoxy-pyrrolidine-1,2-dicarboxylic acid 2-{[4-(3-chloro-2-oxo-5-trifluoromethyl-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(3-bromo-5-chloro-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(5-bromo-3-nitro-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro-4-(3-nitro-2-oxo-5-trifluoromethyl-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(5-methyl-3-nitro-2-oxo-2H-pyridin-1 phenyl]-amide};

(2R,4R)-5-Chloro-1-(4-{[1-(5-chloro-pyridin-2-ylcarbamoyl)-4-methoxy-pyrrolidine-2-carbonyl]-amino}-3-fluoro-phenyl)-2-oxo-1,2-dihydro-pyridine-3-carboxylic acid methyl ester;

(2R,4R)-5-Chloro-1-(4-{[1-(5-chloro-pyridin-2-ylcarbamoyl)4-methoxy-pyrrolidine-2-carbonyl]-amino}-3-fluoro-phenyl)-2-oxo-1,2-dihydro-pyridine-3-carboxylic acid;

(2R,4R)4-Methoxy-pyrrolidine-1,2-dicarboxylic acid 2-{[4-(4-benzyloxy-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(4-amino-5-fluoro-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro-4-(5-nitro-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(6-methyl-3-oxo-3H-isoquinolin-2-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(4-methyl-5-nitro-2-oxo-2H-pyridin-1-yl)-phenyl]-amide};

(2R,4R)-4-Methoxy-pyrrolidine-1,2-dicarboxylic acid 2-{[4-(5-acetylamino-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[2-fluoro-4-(1-oxo-1H-isoquinolin-2-yl)-phenyl]-amide};

(2R,4R)-4-Methoxy-pyrrolidine-1,2-dicarboxylic acid 2-{[4-(4-amino-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(5-chloro-pyridin-2-yl)-amide]2-{[2-fluoro4-(6-oxo-6H-[3,4']bipyridinyl-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(3-oxo-3H-isoquinolin-2-yl)-phenyl]-amide};

(2R,4R)4-Methoxy-pyrrolidine-1,2-dicarboxylic acid 2-{[4-(4-bromo-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro4-(4-oxo4H-furo[3,2-c]pyridin-5-yl)-phenyl]-amide};

(2R,4R)4-Methoxy-pyrrolidine-1,2-dicarboxylic acid 1-[(5-chloro-pyridin-2-yl)-amide]2-{[2-fluoro4-(1-oxo-1H-[2,6]naphthyridin-2-yl)-phenyl]-amide};

(2R,4R)4-Methoxy-pyrrolidine-1,2-dicarboxylic acid 2-{[4-(5-bromo-2-oxo-2H-pyridin-1-yl)-2-fluoro-phenyl]-amide}1-[(5-chloro-pyridin-2-yl)-amide];

(2R,4R)4-Methoxy-pyrrolidine-1,2-dicarboxylic acid 1-[(5-chloro-pyridin-2-yl)-amide]2-{[2-fluoro4-(4-oxo4H-thieno[3,2-c]pyridin-5-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(4-oxo-1,4-dihydro-imidazo[4,5-c]pyridin-5-yl)-phenyl]-amide};

4,5-Dihydro-pyrazole-1,5-dicarboxylic acid 1-[(4-chloro-phenyl)-amide]5-{[2-fluoro-4-(2-oxo-2H-pyridin-1-yl)-phenyl]-amide};

3-Hydroxymethyl-4,5-dihydro-pyrazole-1,5-dicarboxylic acid 1-[(4-chloro-phenyl)-amide]5-{[2-fluoro-4-(2-oxo-2H-pyridin-1-yl)-phenyl]-amide};

5-Methyl-4,5-dihydro-pyrazole-1,5-dicarboxylic acid 1-[(4-chloro-phenyl)-amide]5-{[2-fluoro-4-(2-oxo-2H-pyridin-1-yl)-phenyl]-amide};

3-Methoxymethyl-4,5-dihydro-pyrazole-1,5-dicarboxylic acid 1-[(4-chloro-phenyl)-amide]5-{[2-fluoro-4-(2-oxo-2H-pyridin-1-yl)-phenyl]-amide};

4,5-Dihydro-pyrazole-1,5-dicarboxylic acid 1-[(5-chloro-pyridin-2-yl)-amide]5-{[2-fluoro4-(2-oxo-2H-pyridin-1-yl)-phenyl]-amide};

3-Hydroxymethyl-4,5-dihydro-pyrazole-1,5-dicarboxylic acid 1-[(5-chloro-pyridin-2-yl)-amide]5-{[2-fluoro-4-(2-oxo-2H-pyridin-1-yl)-phenyl]-amide};

5-Methyl-4,5-dihydro-pyrazole-1,5-dicarboxylic acid 1-[(5-chloro-pyridin-2-yl)-amide]5-{[2-fluoro4-(2-oxo-2H-pyridin-1-yl)-phenyl]-amide};

3-Methoxymethyl4,5-dihydro-pyrazole-1,5-dicarboxylic acid 1-[(5-chloro-pyridin-2-yl)-amide]5-{[2-fluoro-4-(2-oxo-2H-pyridin-1-yl)-phenyl]-amide};

4,5-Dihydro-pyrazole-1,5-dicarboxylic acid 1-[(4-chloro-phenyl)-amide]5-{[4-(2-methyl-thiazol-4-yl)-phenyl]-amide};

(2R,4R)4-Methoxy-2-methyl-pyrrolidine-1,2-dicarboxylic acid 1-[(4-chloro-phenyl)-amide]2-{[2-fluoro4-(2-oxo-piperidin-1-yl)-phenyl]-amide};

(2R,4R)4-Methoxy-pyrrolidine-1,2-dicarboxylic acid 1-[(4-chloro-phenyl)-amide]2-[(3,4,5,6-tetrahydro-2H-[1,4']bipyridinyl-4-ylmethyl)-amide];

(2R,4R)-4-Methoxy-pyrrolidine-1,2-dicarboxylic acid 1-[(4-chloro-phenyl)-amide]2-{[4-(2-dimethylaminomethyl-imidazol-1-yl)-2-fluoro-phenyl]-amide};

(2R,4R)-4-Methoxy-pyrrolidine-1,2-dicarboxylic acid 2-{[2-chloro4-(2-oxo-2H-pyridin-1-yl)-phenyl]-amide}1-[(4-chloro-phenyl)-amide];

(2R,4R)-4-Methoxy-pyrrolidine-1,2-dicarboxylic acid 2-{[2-chloro-4-(2-oxo-2H-pyridin-1-yl)-phenyl]-amide}1-[(5-chloro-pyridin-2-yl)-amide];

(2R,4R)-4-Methyl-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-methylamino-imidazol-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(2-isopropyl-imidazol-1-yl)-phenyl]-amide};

(2R,4R)-4-Methoxy-pyrrolidine-1,2-dicarboxylic acid 1-[(4-chloro-phenyl)-amide]2-{[4-(2-ethyl-imidazol-1-yl)-2-fluoro-phenyl]-amide};

(2R,4R)-4-Methoxy-pyrrolidine-1,2-dicarboxylic acid 1-[(5-chloro-pyridin-2-yl)-amide]2-{[4-(2-ethyl-imidazol-1-yl)-2-fluoro-phenyl]-amide};

(2R,4R)-4-Methoxy-pyrrolidine-1,2-dicarboxylic acid 1-[(4-chloro-phenyl)-amide]2-{[2-fluoro-4-(2-isopropyl-imidazol-1-yl)-phenyl]-amide};

(2R,4R)-2-Ethyl-4-methoxy-pyrrolidine-1,2-dicarboxylic acid 1-[(4-chloro-phenyl)-amide]2-{[2-fluoro4-(2-oxo-piperidin-1-yl)-phenyl]-amide};

4-Methoxy-2-methoxymethyl-pyrrolidine-1,2-dicarboxylic acid 1-[(4-chloro-phenyl)-amide]2-{[2-fluoro4-(2-oxo-piperidin-1-yl)-phenyl]-amide};

2-Hydroxymethyl4-methoxy-pyrrolidine-1,2-dicarboxylic acid 1-[(4-chloro-phenyl)-amide]2-{[2-fluoro4-(2-oxo-piperidin-1-yl)-phenyl]-amide};

{1-(4-Chloro-phenylcarbamoyl)-2-[2-fluoro-4-(2-oxo-piperidin-1-yl)-phenylcarbamoyl]-4-methoxy-pyrrolidin-2-yl}-acetic acid methyl ester;

{1-(4-Chloro-phenylcarbamoyl)-2-[2-fluoro4-(2-oxo-piperidin-1-yl)-phenylcarbamoyl]4-methoxy-pyrrolidin-2-yl}-acetic acid;

4-Hydroxymethyl-pyrrolidine-1,2-dicarboxylic acid 1-[(4-chloro-phenyl)-amide]2-{[2-fluoro4-(2-oxo-piperidin-1-yl)-phenyl]-amide};

{1-(4-Chloro-phenylcarbamoyl)-5-[2-fluoro-4-(2-oxo-piperidin-1-yl)-phenylcarbamoyl]-pyrrolidin-3-yl}-acetic acid;

{1-(4-Chloro-phenylcarbamoyl)-5-[2-fluoro-4-(2-oxo-piperidin-1-yl)-phenylcarbamoyl]-pyrrolidin-3-yl}-acetic acid methyl ester;

(2R,4R)4-Ethyl-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R)-4-Isopropyl-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(3-fluoro-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(3-fluoro-2-oxo-2H-pyridin-1-yl)-phenyl]-amide};

(2R,4R)4-Methoxy-pyrrolidine-1,2-dicarboxylic acid 2-{[4-(3-chloro-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 2-{[4-(3-chloro-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-bromo-2-oxo-2H-pyridin-1-yl)-2-fluoro-phenyl]-amide}1-[(4-chloro-phenyl)-amide];

(2R,4R)-4-Methoxy-pyrrolidine-1,2-dicarboxylic acid 2-{[4-(3-bromo-2-oxo-2H-pyridin-1-yl)-2-fluoro-phenyl]-amide}1-[(5-chloro-pyridin-2-yl)-amide];

(2R,4R)-4-Methoxy-pyrrolidine-1,2-dicarboxylic acid 1-[(4-chloro-phenyl)-amide]2-{[2-fluoro-4-(3-iodo-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro4-(3-iodo-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[4-(3-ethyl-2-oxo-2H-pyridin-1-yl)-2-fluoro-phenyl]-amide}; and (2R,4R)4-Methoxy-pyrrolidine-1,2-dicarboxylic acid 1-[(4-chloro-phenyl)-amide]2-{[4-(3-ethyl-2-oxo-2H-pyridin-1-yl)-2-fluoro-phenyl]-amide;

a pharmaceutically acceptable salt thereof.

The invention is also directed to a compound which is:

(2R,4R) 4-Methoxy-pyrrolidine-1,2-dicarboxylic acid 1-[(4-chloro-phenyl)-amide]2-{[2-fluoro-4-(2-oxo-piperidin-1-yl)-phenyl]-amide};

(2R,4R) 4-Ethoxy-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R) 4-Methoxy-pyrrolidine-1,2-dicarboxylic acid 1-[(4-chloro-phenyl)-amide]2-{[2-fluoro4-(2-oxo-2H-pyridin-1-yl)-phenyl]-amide};

(2R,4R) 4-Methoxy-pyrrolidine-1,2-dicarboxylic acid 1-[(5-chloro-pyridin-2-yl)-amide]2-{[2-fluoro-4-(2-oxo-2H-pyridin-1-yl)-phenyl]-amide};

(2R,4R) 4-Methoxy-pyrrolidine-1,2-dicarboxylic acid 1-[(4-chloro-phenyl)-amide]2-[(2-oxo-2H-[1,3']bipyridinyl-6'-yl)-amide];

(2R,4R) 4-Methoxy-pyrrolidine-1,2-dicarboxylic acid 1-[(4-chloro-phenyl)-amide]2-{[2-fluoro-4-(3-methoxy-2-oxo-2H-pyridin-1-yl)-phenyl]-amide};

(2R,4R) 4-Methoxy-pyrrolidine-1,2-dicarboxylic acid 1-[(4-chloro-phenyl)-amide]2-{[4-(3-methyl-2-oxo-2H-pyridin-1-yl)-phenyl]-amide};

(2R,4R) 4-Methoxy-pyrrolidine-1,2-dicarboxylic acid 1-[(4-chloro-phenyl)-amide]2-{[2-fluoro-4-(2-methyl-imidazol-1-yl)-phenyl]-amide};

(2R,4R) 4-Methoxy-pyrrolidine-1,2-dicarboxylic acid 1-[(4-chloro-phenyl)-amide]2-[(4-dimethylcarbamoyl-2-fluoro-phenyl)-amide];

(2R,4R) 4-Methoxy-pyrrolidine-1,2-dicarboxylic acid 1-[(4-chloro-phenyl)-amide]2-{[2-fluoro-4-(5-methyl-pyrazol-1-yl)-phenyl]-amide};

(2R,4R) 4,5-Dihydro-pyrazole-1,5-dicarboxylic acid 1-[(4-chloro-phenyl)-amide]5-[(3-fluoro-2'-sulfamoyl-biphenyl-4-yl)-amide];

(2R,4R) 4-Methoxy-pyrrolidine-1,2-dicarboxylic acid 1-[(4-chloro-phenyl)-amide]2-[(2-fluoro4-pyrazol-1-yl-phenyl)-amide];

(2R,4R) 4-Methoxy-pyrrolidine-1,2-dicarboxylic acid 1-[(4-chloro-phenyl)-amide]2-{[2-fluoro4-(pyrrolidine-1-carbonyl)-phenyl]-amide};

(2R,4R)4-Methoxy-pyrrolidine-1,2-dicarboxylic acid 1-[(4-chloro-phenyl)-amide]2-{[2-fluoro4-(2-oxo-piperidin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro4-(2-oxo-2H-pyridin-1-yl)-phenyl]-amide}

(2R,4R)-4-Methoxy-pyrrolidine-1,2-dicarboxylic acid 1-[(4-chloro-phenyl)-amide]2-{[4-(3-methyl-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(2-methyl-imidazol-1-yl)-phenyl]-amide};

(2R,4R)-4-Methoxy-pyrrolidine-1,2-dicarboxylic acid 1-[(4-chloro-phenyl)-amide]2-[(2-oxo-2H-[1,3']bipyridinyl-6'-yl)-amide];

(2R,4R)-4-Ethoxy-pyrrolidine-1,2-dicarboxylic acid 1-[(4-chloro-phenyl)-amide]2-{[2-fluoro-4-(2-oxo-2H-pyridin-1-yl)-phenyl]-amide};

(2R,4R)-4-Methoxy-pyrrolidine-1,2-dicarboxylic acid 1-[(4-chloro-phenyl)-amide]2-[(4-dimethylcarbamoyl-2-fluoro-phenyl)-amide];

(2R,4R)-4-Methoxy-pyrrolidine-1,2-dicarboxylic acid 1-[(4-chloro-phenyl)-amide]2-{[2-fluoro-4-(5-methyl-pyrazol-1-yl)-phenyl]-amide};

5-Methyl-4,5-dihydro-pyrazole-1,5-dicarboxylic acid 1-[(4-chloro-phenyl)-amide]5-[(3-fluoro-2'-sulfamoyl-biphenyl-4-yl)-amide];

(2R,4R)-4-Methoxy-pyrrolidine-1,2-dicarboxylic acid 1-[(4-chloro-phenyl)-amide]2-{[2-fluoro-4-(4-methyl-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(3-methyl-2-oxo-2H-pyridin-1-yl)-phenyl]-amide};

(2R,4R)-4-Methoxy-pyrrolidine-1,2-dicarboxylic acid 2-{[2-chloro4-(2-oxo-2H-pyridin-1-yl)-phenyl]-amide}1-[(4-chloro-phenyl)-amide];

(2R,4R)4-Methoxy-pyrrolidine-1,2-dicarboxylic acid 1-[(4-chloro-phenyl)-amide]2-{[2-methyl4-(2-oxo-2H-pyridin-1-yl)-phenyl]-amide};

(2R,4R)4-Methoxy-pyrrolidine-1,2-dicarboxylic acid 1-[(4-chloro-phenyl)-amide]2-{[2-fluoro4-(6-methyl-2-oxo-2H-pyridin-1-yl)-phenyl]-amide};

(2R,4R)4-Methoxy-pyrrolidine-1,2-dicarboxylic acid 1-[(5-chloro-pyridin-2-yl)-amide]2-{[2-fluoro4-(3-methyl-2-oxo-2H-pyridin-1-yl)-phenyl]-amide};

(2R,4R)4-Methoxy-pyrrolidine-1,2-dicarboxylic acid 1-[(5-chloro-pyridin-2-yl)-amide]2-{[2-fluoro4-(5-methyl-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[2-fluoro-4-(5-methyl-2-oxo-2H-pyridin-1-yl)-phenyl]-amide};

(2R,4R)-4-Methoxy-pyrrolidine-1,2-dicarboxylic acid 1-[(5-chloro-pyridin-2-yl)-amide]2-{[2-fluoro-4-(4-methyl-2-oxo-2H-pyridin-1-yl)-phenyl]-amide;

(2R,4R)-4-Methoxy-pyrrolidine-1,2-dicarboxylic acid 1-[(4-chloro-phenyl)-amide]2-{[4-(2,5-dihydrom-pyyrole-1-carbonyl)-2-fluoro-phenyl-amide};

(2R,4R)-4-Methoxy-pyrrolidine-1,2-dicarboxylic acid 1-[(4-chloro-phenyl)-amide]2-{[4-(2,5-dihydrom-pyyrole-1-carbonyl)-phenyl-amide};

(2R,4R)-4-Methoxy-pyrrolidine-1,2-dicarboxylic acid 1-[(4-chloro-phenyl)-amide]2-{[4-(2-methyl-5-oxo-pyrrolidin-1-yl)-phenyl]-amide};

(2R,4R)-4-Methoxy-pyrrolidine-1,2-dicarboxylic acid 1-[(4-chloro-phenyl)-amide]2-{[4-(2,5-dihydro-pyrrole-1-carbonyl)-phenyl]-amide};

(2R,4R)-4-Methoxy-pyrrolidine-1,2-dicarboxylic acid 1-[(4-chloro-phenyl)-amide]2-{[2-fluoro-4-(4-methyl-2-oxo-2H-pyridin-1-yl)-phenyl]-amide};

(2R,4R)-4-Methoxy-pyrrolidine-1,2-dicarboxylic acid 1-[(4-chloro-phenyl)-amide]2-{[4-(2,5-dihydro-pyrrole-1-carbonyl)-2-fluoro-phenyl]-amide};

(2R,4R)4-Methoxy-pyrrolidine-1,2-dicarboxylic acid 1-[(4-chloro-phenyl)-amide]2-{[4-(2-methyl-5-oxo-pyrrolidin-1-yl)-phenyl]-amide};

(2R,4R)4-Methoxy-pyrrolidine-1,2-dicarboxylic acid 1-[(4-chloro-phenyl)-amide]2-{[4-(2,5-dihydro-pyrrole-1-carbonyl)-phenyl]-amide};

(2R,4R)4-Methoxy-pyrrolidine-1,2-dicarboxylic acid 1-[(4-chloro-phenyl)-amide]2-{[2-fluoro4-(4-methyl-2-oxo-2H-pyridin-1-yl)-phenyl]-amide};

(2R,4R)4-Methoxy-pyrrolidine-1,2-dicarboxylic acid 1-[(4-chloro-phenyl)-amide]2-{[4-(2,5-dihydro-pyrrole-1-carbonyl)-2-fluoro-phenyl]-amide} or a pharmaceutically acceptable salt thereof.

The invention is also directed to a pharmaceutical composition comprising a compound of formula I admixed with a carrier, diluent, or excipient.

The invention is also directed to a method for preventing or treating acute, subacute, and chronic thrombotic disorder in a mammal is comprising administering to a mammal in need thereof a therapeutically effective amount of a compound of any of formulas I-X.

The invention is also directed to a method of inhibiting Factor Xa in a mammal, comprising administering to a mammal in need of Factor Xa inhibition a Factor Xa inhibition amount of a compound of any of formulas I-X.

The invention is also directed to a process for preparing a compound of Formula I comprising:

(a) reacting an amino acid of formula IA

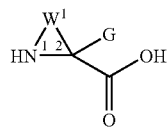

IA with a reagent capable of placing a protecting group $P^1$ on the amino group of an amino acid to form a protected amino acid given by formula IB:

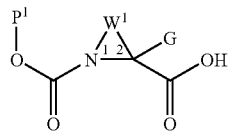

IB wherein $P^1$ is a protecting group and $W^1$ is the same as defined above;

(b) converting the acid moiety in the compound of formula IB to a acid halide;

(c) reacting the acid halide with a haloaniline or a haloamino-heterocycle to form a compound having formula IC:

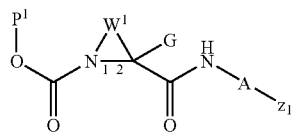

IC wherein $Z^1$ is a halogen and A is as defined above;

(d) coupling the compound of formula IC with a compound H-B to give a compound having formula ID:

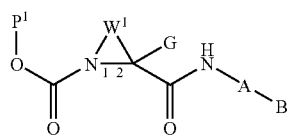

ID (e) removing the protecting group from Compound ID and reacting the resulting acid moiety with a C-isocyanate to form a compound of the invention.

DETAILED DESCRIPTION OF THE INVENTION

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, halogen, nitro, cyano, oxo, thio, —OH, —SH, —F, —CF$_3$, —OCF$_3$, —NO$_2$, —CO$_2$H, —CO$_2$C$_1$—C$_6$alkyl, —NH$_2$, —NHC$_1$—C$_6$ alkyl,

—CONR$^8$R$^9$, or —N(C$_1$-C$_6$alkyl)$_2$. Preferred alkyl groups have from 1 to 6 carbon atoms (C$_1$-C$_6$ alkyl).

The term "(C$_1$-C$_6$)alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Sometimes herein lower alkyl is referred to as "C$_1$-C$_6$alkyl."

The term "(C$_1$-C$_6$)hydroxyalkyl" or "hydroxy(C$_1$-C$_6$) alkyl" as used herein means a straight or branched alcohol having from 1 to 6 carbon atoms and includes, for example, hydroxymethyl, hydroxyethyl, hydroxy-propyl and the like.

The term "(C$_2$-C$_6$)alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-Octenyl, 1-nonenyl, 1-decenyl, 1-undecenyl, 1-dodecenyl, and the like.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2- dimethylpropylene, and the like. The alkylene groups of this invention can be optionally substituted. The alkylene group can also be substituted with one or more of the substituents selected from lower alkyl, lower alkoxy, lower thioalkoxy, halogen, nitro, cyano, oxo, thio, —OH, —SH, —F, —CF$_3$, —OCF$_3$, —NO$_2$, —CO$_2$H, —CO$_2$C$_1$-C$_6$ alkyl, —NH2, —NHC$_1$—C$_6$ alkyl,

—CONR⁸R⁹, or —N(C₁-C₆alkyl)₂. Preferred alkylene groups have from 1 to 6 carbon atoms (C₁-C₆ alkyl).

The term "heteroatom" as used herein represents oxygen, nitrogen, or sulfur (O, N, or S) as well as sulfoxyl or sulfonyl (SO or SO₂), unless otherwise indicated. It is to be understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl.

The term "hetero(C₁-C₆)alkyl" as used herein, refers to an alkyl group that includes one or more heteroatoms such as oxygen, sulfur, or nitrogen (with valence completed by hydrogen or oxygen) in the carbon chain or terminating the carbon chain.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, halogen, nitro, cyano, oxo, thio, —OH, —SH, —F, —CF₃, —OCF₃, —NO₂, —CO₂H, —CO₂C₁-C₆ alkyl, —NH₂, —NHC₁-C₆ alkyl,

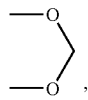

—CONR⁸R⁹, or —N(C₁-C₆alkyl)₂.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower alkoxy, lower thioalkoxy, halogen, nitro, cyano, oxo, thio,

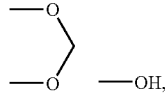

—SH, —F, —CF₃, —OCF₃, —NO₂, —CO₂H, —CO₂C₁-C₆ alkyl, —NH₂, —NHC₁-C₆ alkyl, —CONR⁸R⁹, or —N(C₁-C₆alkyl)₂.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The term "(C₃-C₇)cycloalkyl" means a cyclopropyl, cyclobutyl, cylopentyl, cyclohexyl, or cycloheptyl ring, respectively. The (C₃-C₇)cycloalkyl ring may be optionally substituted with one or more substituents selected from lower alkyl, lower alkoxy, lower thioalkoxy, halogen, nitro, cyano, oxo, thio,

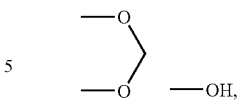

—SH, —F, —CF₃, —OCF₃, —NO₂, —CO₂H, —CO₂C₁-C₆ alkyl, —NH₂, —NHC₁-C₆ alkyl, —CONR⁸R⁹, or —N(C₁-C₆alkyl)₂.

The term "halo(C₁-C₆)alkyl" as used herein means a lower alkyl radical, as defined above, bearing at least one halogen substituent, for example, chloromethyl, fluoroethyl, or trifluoromethyl, and the like. Haloalkyl can also include perfluoroalkyl wherein all hydrogens of a lower alkyl group are replaced with fluorides.

The term "heterocycle" means a saturated or unsaturated mono- or polycyclic (i.e. bicyclic) fused, bridged, or spiro bicyclic heterocyclic ring system ring incorporating one or more (i.e. 1-4) heteroatoms selected from N, O, and S. It is to be understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or C1-6 alkyl. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from 7 to 17 member atoms, preferably 7 to 12 member atoms, in the ring. Bicyclic heterocyclics contain from about 7 to about 17 ring atoms, preferably from 7 to 12 ring atoms. Bicyclic heterocyclics rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycloalkyl groups containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiepin-4-yl. Other commonly employed heterocycles include dihydro-oxathiol-4-yl, tetrahydro-oxazolyl, tetrahydro-oxadiazolyl, tetrahydro-dioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO₂ groups are also included. Examples include the sulfoxide and sulfone forms of tetrahydrothiophene.

The term "aryl" as used herein refers to an aromatic ring which is unsubstituted or optionally substituted by 1 to 4 substituents selected from lower alkyl, lower alkoxy, lower thioalkoxy, halogen, nitro, cyano —OH, —SH, —F, —CF₃, —OCF₃, —NO₂,

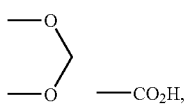

—$CO_2C_1$-$C_6$ alkyl, —$NH_2$, —$NHC_1$-$C_6$ alkyl, —$CONR^8R^9$, —$SO_2$alkyl, —$SO_2NH_2$, or —$N(C_1$-$C_6$alkyl$)_2$. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, thienyl, furanyl, pyrrolyl, pyridyl, pyrimidyl, imidazoyl, pyrazinyl, oxazolyl, thiazolyl, naphthyl, benzothienyl, benzofuranyl, indolyl, quinolinyl, isoquinolinyl, and quinazolinyl, and the like.

The term "aralkyl" as used herein refers to an alkyl radical to which is appended an aryl group. Representative arylalkyl groups include benzyl, phenylethyl, hydroxybenzyl, fluorobenzyl, fluorophenylethyl, and the like. The arylalkyl groups of this invention can be optionally substituted.

The term "arylene" as used herein refers to a divalent group derived from an aromatic ring. The arylene group can also be substituted with one or more of the substituents listed above for aryl.

The term "heteroaryl" means an aromatic cyclic or fused polycyclic ring system having from 1 to 8 heteroatoms selected from N, O, and S. The heteroaryl groups or fused heteroaryl groups may be unsubstituted or substituted by 1 to 3 substituents selected from those described above for alkyl, alkenyl, and alkynyl, for example, cyanothienyl and formylpyrrolyl.

Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

Aromatic fused heteroaryl groups of from 8 to 20 atoms include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or l-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10 -, or 11-7H-pyrazino[2,3-c]carbazolyl,2-, 3-, 5-, 6-, or 7-2H-furo [3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo [1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

Other heteroaryl groups include the following groups wherein "~" indicates the point of attachment, and any of which may be substituted as provided above.

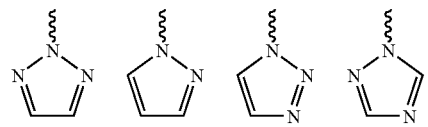

The term "monocyclic heteroarylene" as used herein refers to a divalent group derived from a monocyclic heteroaryl. The arylene group can also be substituted with one or more of the substituents listed above for aryl.

The term "cycloalkenyl" means a cycloalkyl group having one or more carbon-carbon double or triple bond. Example includes cyclobutene, cyclopentene, cyclohexene, cycloheptene, cyclobutadiene, cyclopentadiene, and the like.

The symbol "—" means a bond. If an asymmetric carbon is created by such a bond, a particular stereochemistry is not to be implied.

The symbol "=" means a double bond.

The symbol "∿∿" indicates covalent points of attachment.

The following abbreviations are used herein:
HOAc=Acetic acid
DCM=Dichlormmetbane
TFA=Trifluoroacetic acid
THF=tetrahydrofuran
Me=Methyl
APCI=Atmospheric pressure chemical ionization
Et=Ethyl
EtOAc=Ethyl acetate
MeOH=Methanol
HPLC=High Pressure Liquid Chromatography When a bond to a substituent is shown to cross the bond connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring.

When a bond from a substituent is shown to cross the bond connecting 2 atoms in a ring of the substituent, then such substituent may be bonded from any atom in the ring that is available.

When a bond is represented by a line such as " - - - " this is meant to represent that the bond may be absent or present, provided that the resultant compound is stable and of satisfactory valency.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of thrombotic disorders, venous thrombosis, arterial thrombosis, pulmonary embolism, myocardial infarction, cerebral infarction, restenosis, cancer, angina, diabetes, atrial fibrillation, or heart failure. A therapeutically effective amount of a compound of the present invention can be easily determined by one skilled in the art by administering a quantity of a compound to a patient and observing the result. In addition, those skilled in the art are familiar with identifying patients having thrombotic disorders, venous thrombosis, arterial thrombosis, pulmonary embolism, myocardial infarction, cerebral infarction, restenosis, cancer, angina, diabetes, atrial fibrillation, or heart failure.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed.

In some situations, compounds of the invention may exist in isomeric form; for example, as tautomers, enantiomers, or diastereomers. Some compounds may exhibit polymorphism. All tautomers, enantiomers, and diastereomers are incorporated within the definition of the compounds of the invention. It is further to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity or cytotoxicity using the standard tests described herein, or using other similar tests which are well known in the art.

Certain compounds of the present invention can exist in unsolvated form as well as solvated form including hydrated form. In general, the solvated form including hydrated form is equivalent to unsolvated form and is intended to be encompassed within the scope of the present invention.

Referring now to a compound of Formula I,

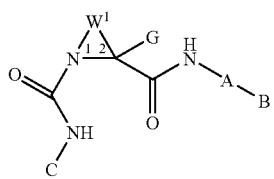

I

A specific value for G is H, F, or methyl.

A specific value for $W^1$ is

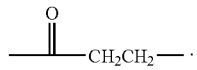

Other specific values for $W^1$ are —CH$_2$—CH$_2$—CH$_2$—, —CH$_2$—CH$_2$—O—CH$_2$—, CH$_2$—HC=CH—CH$_2$—, —CH$_2$—CH$_2$CR$^5$R$^6$—, —CH$_2$CR$^5$R$^6$CH$_2$—, —CH$_2$—CH$_2$CR$^7$R$^8$—, —CH$_2$CR$^7$R$^8$CH$_2$—, —CH$_2$—C=R$^9$CH$_2$—, —CH$_2$—CH$_2$C=R$^9$—, —CH$_2$CH$_2$CH$_2$CH$_2$—, —CH$_2$—HC=CH—, —CH$_2$CH$_2$NR$^5$—, —CH$_2$NR$^5$CH$_2$—, —CH$_2$CH$_2$—NH—CH$_2$—, —CO—CHR$^5$—CH$_2$—, —O—CH$_2$—CHR$^5$—, —N=CR$^5$—CH=, —N=CR$^5$—CH$_2$—, —N=CH—CR$^5$=, —O—CHR$^5$—CH=, —O—CHR$^5$—CH$_2$—, and —O—CH$_2$—CR$^5$=, wherein $R^5$ is —OH, alkyl, halo(C$_1$-C$_6$)alkyl, —NR$^3$R$^4$, —OR$^2$, halo, —CN, —CH$_2$OR$^2$, —CH$_2$—NR$^3$R$^4$, aryl, monocyclic heteroaryl, alkylaryl, —CONR$^3$R$^4$, —COR$^2$, halo(C$_1$-C$_6$)alkyl, or —CO$_2$R$^2$; $R^6$ is H, alkyl, aralkyl, aryl, or monocyclic heteroaryl; $R^7$ and $R^8$ are each independently halo; and $R^9$ is =O or =NOR$^2$;

A specific value for A is phenyl. Another specific value for A is pyridyl. Other specific values for A include the following:

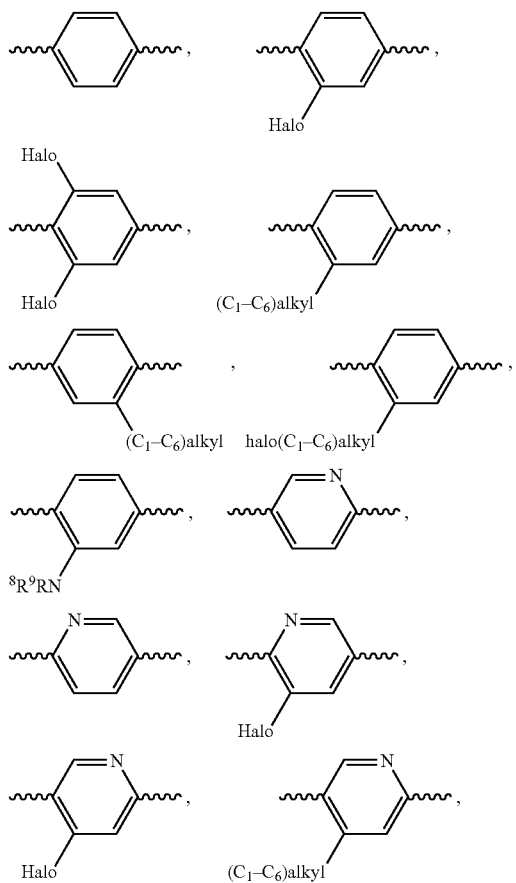

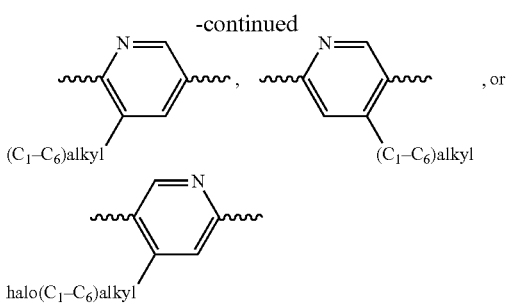

wherein

"—"

indicate points of attachment, and halo, $(C_1$-$C_6)$alkyl, and halo$(C_1$-$C_6)$alkyl are as defined earlier in the definitions section.

A specific value for C is phenyl. Another specific value for C is pyridyl. Other specific values for C include ortho- and para-halo phenyl, ortho, para-dihalophenyl, ortho, meta-dihalophenyl, para-$(C_1$-$C_6)$alkoxyphenyl, para-$(C_1$-$C_6)$alkylphenyl, and meta-halo, para-$(C_1$-$C_6)$alkylphenyl.

One specific value for B is

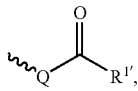

wherein

"—"

indicates the point of attachment; Q is NH or is absent; and wherein $R^{1'}$ is OH, —O—$(C_1$-$C_6)$alkyl, or $NR^{3'}R^{4'}$, wherein $R^{3'}$ and $R^{4'}$ are independently H, $(C_1$-$C_{-6})$alkyl, or are joined together to form a optionally substituted saturated or unsaturated 5 to 7 membered ring.

Another specific value for B is phenyl or phenyl which is substituted at an ortho position with formyl, $H_2NSO_2$, $MeSO_2$, MeSO, MeS, $(C_{1-6})$alkoxycarbonyl, cyano, $H_2N$—$CH_2$—, HN—$(C_1$-$C_6)$alkyl-$CH_2$-, $(C_1$-$C_6)$alkyl$_2$N—$CH_2$—.

Another specific value for B is pyridyl or pyridyl substituted as provided in the previous position.

Another specific value for B is

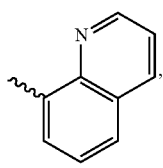

wherein

"~~~"

indicates the point of attachment.

Another specific value for B is

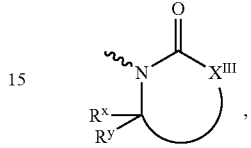

wherein

"~~~"

indicates the point of attachment and which is an optionally substituted 4, 5, 6 or 7-membered ring. When B is

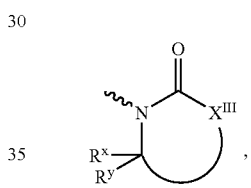

$R^x$ and $R^y$ can be H, halo, $(C_1$-$C_6)$alkyl, $(C_1$-$C_6)$alkoxy, $(C_1$-$C_6)$carboxyalkyl, or taken together can be O=. $X^{III}$ can be $CH_2$, CH—OH, CH—$CO_2(C_1$-$C_6)$alkyl, O, S, NH, or $N(C_1$-$C_6)$alkyl, provided that when $R^x$ and $R^y$ taken together are O=, $X^{III}$ is $CH_2$.

Another specific value for B is

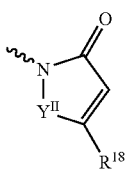

or a tautomer thereof such as

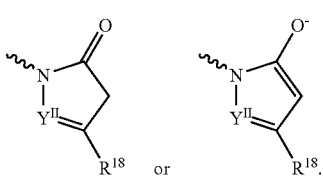

When B is

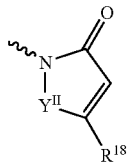

or a tautomer thereof, $Y^{II}$ can be $CH_2$, $CH(C_1\text{-}C_6)$alkyl, $C\text{---}CH_2OH$, $C\text{---}CH_2O\text{---}(C_1\text{-}C_6)$alkyl, NH, or $N(C_1\text{-}C_6)$alkyl. $R^{18}$ is H, $(C_1\text{-}C_6)$alkyl, hydroxymethyl, $CH_2O\text{---}(C_1\text{-}C_6)$alkyl, or $NR^3R^4$.

Another specific value for B is a 5-membered heteroaryl ting which contains at least one nitrogen atom such as imidazolyl, pyrazolyl, triazolyl, tetrazolyl, oxadiazolyl, thiadiazolyl, oxazolyl, isoxazolyl, thiazolyl, or isothiazolyl, any of which may be optionally substituted with halo, $(C_1\text{-}C_6)$alkyl, hydroxy$(C_1\text{-}C_6)$alkyl, $CH_2O\text{---}(C_1\text{-}C_6)$alkyl, or halo$(C_1\text{-}C_6)$alkyl. B can also be

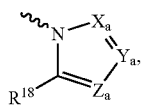

wherein

" $\sim\!\sim\!\sim$ "

indicates the point of attachment;

$X^a$, $Y^a$, and $Z^a$ are each independently $CR^c$ or N, wherein $R^c$ is H or $(C_1\text{-}C_6)$alkyl; and $R^{18}$ is H, $(C_1\text{-}C_6)$alkyl, hydroxymethyl, $CH_2O\text{---}(C_1\text{-}C_6)$alkyl, or $NR^3R^4$.

Another specific value for B is

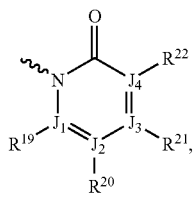

wherein

" $\sim\!\sim\!\sim$ "

indicates the point of attachment. When B is

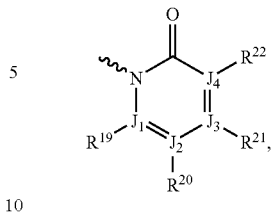

$J_1$, $J_2$, $J_3$, and $J_4$ can each be C, or one or more of $J_1$, $J_2$, $J_3$, or $J_4$ can be N. $R^{19}$, $R^{20}$, $R^{21}$, and $R^{22}$ are each independently H, halo, hydroxy, $NH_2$, $NR^{23}R^{24}$, $NO_2$, SH, $(C_1\text{-}C_6)$alkyl, $(C_1\text{-}C_6)$alkoxy, halo$(C_1\text{-}C_6)$alkyl, $(C_1\text{-}C_6)$alkanoyl, $(C_1\text{-}C_6)$alkoxycarbonyl, or $(C_1\text{-}C_6)$alkoxy, wherein $R^{23}$ and $R^{24}$ are each independently H, $(C_1\text{-}C_6)$alkyl, aralkyl, aryl, monocyclic heteroaryl, alkoxycarbonyl, aralkoxycarbonyl, $\text{---}SO_2$alkyl, or joined together to form a saturated or unsaturated 3 to 7 membered ring. Alternatively, $R^{19}$ and $R^{20}$, $R^{20}$ and $R^{21}$, or $R^{21}$ and $R^{22}$, can be together with the carbons to which they are attached to form a 5, 6, or seven membered saturated or unsaturated cycloalkyl or heterocycloalkyl ring, or an aryl or heteroaryl ring. When any of $J_1$, $J_2$, $J_3$, or $J_4$ is N, $R^{19}$, $R^{20}$, $R^{21}$ or $R^{22}$, respectively, is absent at that position. Thus, specific values for B include

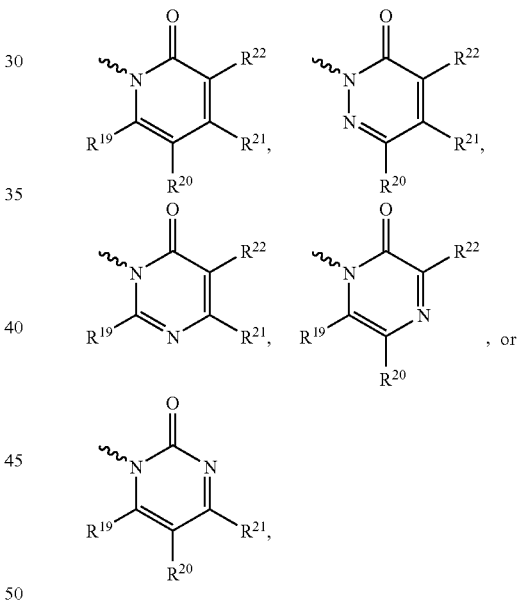

wherein

" $\sim\!\sim\!\sim$ "

indicates the point of attachment; and $R^{19}$, $R^{21}$, and $R^{21}$, $R^{22}$ are each independently H, halo, hydroxy, $NH_2$, $NR^{23}R^{24}$, $NO_2$, SH, $(C_1\text{-}C_6)$alkyl, $(C_1\text{-}C_6)$alkoxy, halo$(C_1\text{-}C_6)$alkyl, $(C_1\text{-}C_6)$alkanoyl, $(C_1\text{-}C_6)$alkoxycarbonyl, or $(C_1\text{-}C_6)$alkoxy, wherein $R^{23}$ and $R^{24}$ are each independently H, $(C_1\text{-}C_6)$alkyl, aralkyl, aryl, monocyclic heteroaryl, alkoxycarbonyl, aralkoxycarbonyl, $\text{---}SO_2$alkyl, or joined together to form a saturated or unsaturated 3 to 7 membered ring, or $R^{19}$ and $R^{20}$, $R^{20}$ and $R^{21}$, or $R^{21}$ and $R^{22}$, together with the carbons to which they are attached, form a 5, 6, or seven membered saturated or unsaturated cycloalkyl or heterocycloalkyl ring, or an aryl or heteroaryl ring.

Reference will now be made to a compound of Formula II.

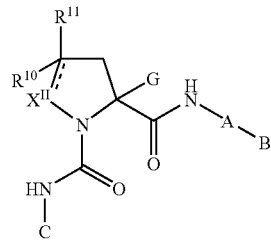

II

In

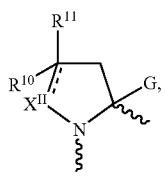

" - - - " is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

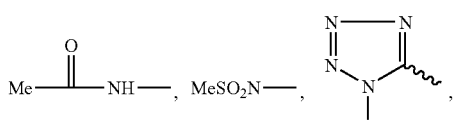

wherein "∿∿∿" indicates the point of attachment. Also, $R^{10}$ and $R^{11}$ can be taken together to form =O or =NOH. Thus, specific values for

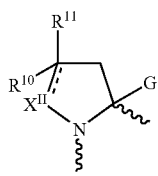

include

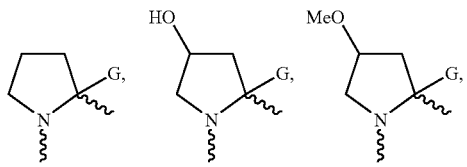

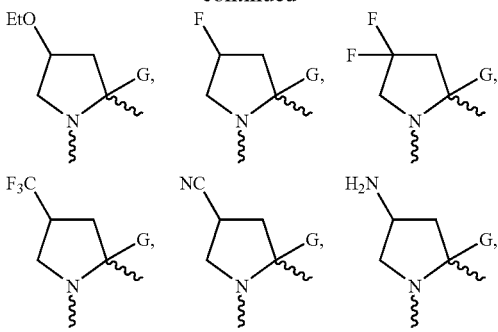

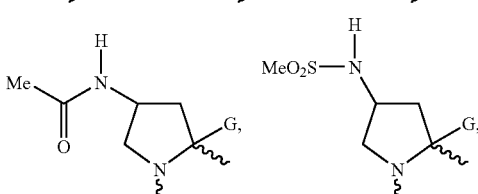

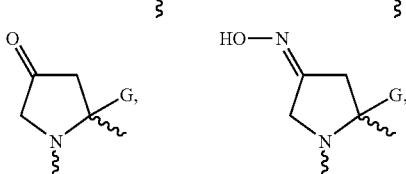

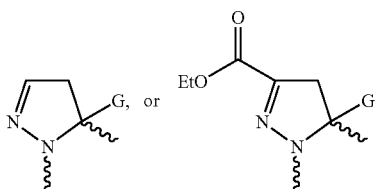

A specific value for G is H, F, or methyl.

A specific value for C is phenyl. Another specific value for C is pyridyl. Other specific values for C include ortho- and para-halo phenyl, ortho, para-dihalophenyl, ortho, meta-dihalophenyl, para-($C_1$-$C_6$)alkoxyphenyl, para-($C_1$-$C_6$)alkylphenyl, and meta-halo, para-($C_1$-$C_6$)alkylphenyl.

A specific value for A is phenyl. Another specific value for A is pyridyl. Other specific values for A include the following:

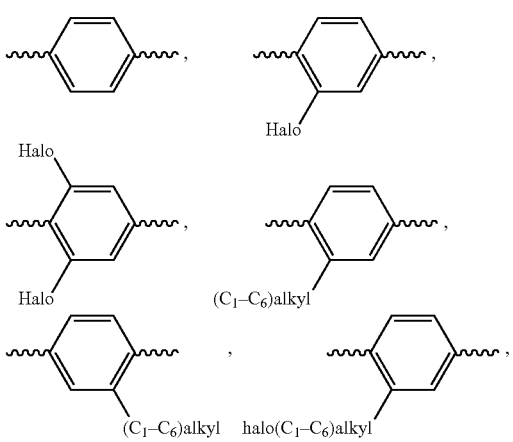

-continued

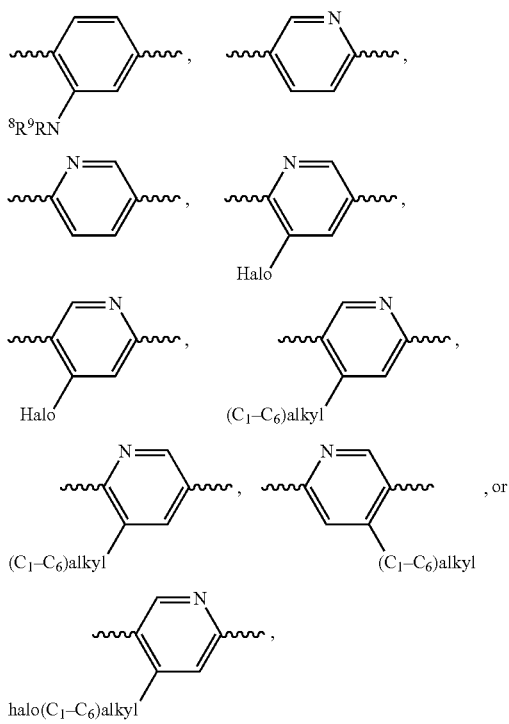

wherein

" ~~~ "

indicate points of attachment, and halo, $(C_1-C_6)$alkyl, and halo$(C_1-C_6)$alkyl are as defined earlier in the definitions section.

One specific value for B is

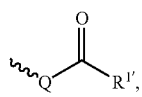

wherein

" ~~~ "

indicates the point of attachment; Q is NH or is absent; and wherein $R^{1'}$ is OH, —O—$(C_1-C_6)$alkyl, or $NR^{3'}R^{4'}$, wherein $R^{3'}$ and $R^{4'}$ are independently H, $(C_1-C_6)$alkyl, or are joined together to form a optionally substituted saturated or unsaturated 5 to 7 membered ring.

Another specific value for B is phenyl or phenyl which is substituted at an ortho position with formyl, $H_2NSO_2$, $MeSO_2$, MeSO, MeS, $(C_{1-6})$alkoxycarbonyl, cyano, $H_2N$—CH, HN—$(C_1-C_6)$alkyl-$CH_2$—, $(C_1-C_6)$alkyl$_2$N—$CH_2$—.

Another specific value for B is pyridyl or pyridyl substituted as provided in the previous position.

Another specific value for B is

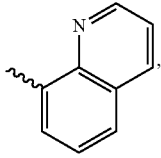

wherein

" ~~~ "

indicates the point of attachment.

Another specific value for B is

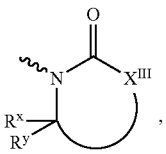

wherein

" ~~~ "

indicates the point of attachment and which is an optionally substituted 4, 5, 6 or 7-membered ring. When B is

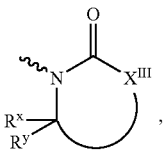

$R^x$ and $R^y$ can be H, halo, $(C_1-C_6)$alkyl, $(C_1-C_6)$alkoxy, $(C_1-C_6)$carboxyalkyl, or taken together can be O=. $X^{III}$ can be $CH_2$, CH—OH, CH—$CO_2(C_1-C_6)$alkyl, O, S, NH, or N$(C_1-C_6)$alkyl, provided that when $R^x$ and $R^y$ taken together are O=, $X^{III}$ is $CH_2$.

Another specific value for B is

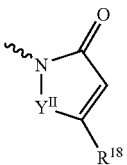

or a tautomer thereof such as

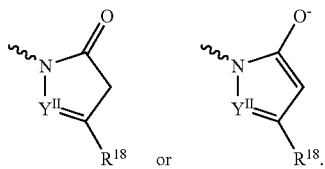

When B is

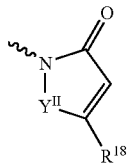

or a tautomer thereof, $Y^{II}$ can be $CH_2$, $CH(C_1-C_6)$alkyl, $C$—$CH_2OH$, $C$—$CH_2O$—$(C_1-C_6)$alkyl, NH, or $N(C_1-C_6)$alkyl. $R^{18}$ is H, $(C_1-C_6)$alkyl, hydroxymethyl, $CH_2O$-$(C_1-C_6)$alkyl, or $NR^3R^4$.

Another specific value for B is a 5-membered heteroaryl ting which contains at least one nitrogen atom such as imidazolyl, pyrazolyl, triazolyl, tetrazolyl, oxadiazolyl, thiadiazolyl, oxazolyl, isoxazolyl, thiazolyl, or isothiazolyl, any of which may be optionally substituted with halo, $(C_1-C_6)$alkyl, hydroxy$(C_1-C_6)$alkyl, $CH_2O$—$(C_1-C_6)$alkyl, or halo$(C_1-C_6)$alkyl. B can also be

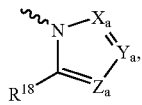

wherein

" ∿∿∿ "

indicates the point of attachment;

$X^a$, $Y^a$, and $Z^a$ are each independently $CR^c$ or N, wherein $R^c$ is H or $(C_1-C_6)$alkyl; and $R^{18}$ is H, $(C_1-C_6)$alkyl, hydroxymethyl, $CH_2O$—$(C_1-C_6)$alkyl, or $NR^3R^4$.

Another specific value for B is

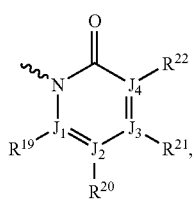

wherein

" ∿∿∿ "

indicates the point of attachment. When B is

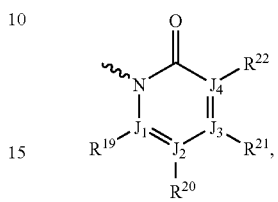

$J_1$, $J_2$, $J_3$, and $J_4$ can each be C, or one or more of $J_1$, $J_2$, $J_3$, or $J_4$ can be N. $R^{19}$, $R^{20}$, $R^{21}$, and $R^{22}$ are each independently H, halo, hydroxy, $NH_2$, $NR^{23}R^{24}$, $NO_2$, SH, $(C_1-C_6)$alkyl, $(C_1-C_6)$alkoxy, halo$(C_1-C_6)$alkyl, $(C_1-C_6)$alkanoyl, $(C_1-C_6)$alkoxycarbonyl, or $(C_1-C_6)$alkoxy, wherein $R^{23}$ and $R^{24}$ are each independently H, $(C_1-C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring. Alternatively, $R^{19}$ and $R^{20}$, $R^{20}$ and $R^{21}$, or $R^{21}$ and $R^{22}$, can be together with the carbons to which they are attached to form a 5, 6, or seven membered saturated or unsaturated cycloalkyl or heterocycloalkyl ring, or an aryl or heteroaryl ring. When any of $J_1$, $J_2$, $J_3$, or $J_4$ is N, $R^{19}$, $R^{20}$, $R^{21}$ or $R^{22}$, respectively, is absent at that position. Thus, specific values for B include

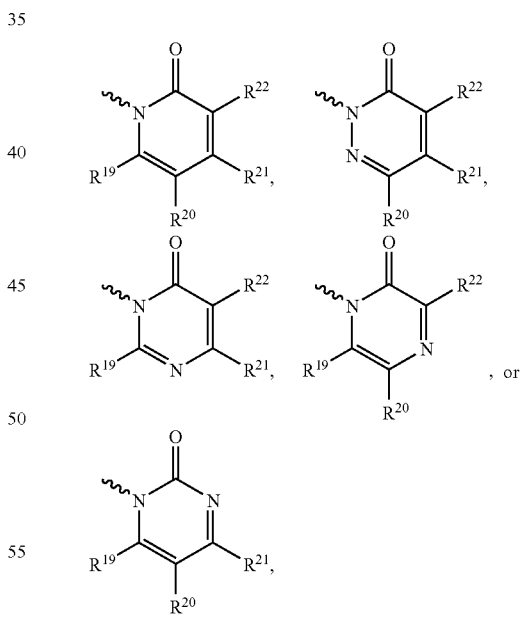

wherein

" ∿∿∿ "

indicates the point of attachment; and $R^{19}$, $R^{20}$, and $R^{21}$, $R^{22}$ are each independently H, halo, hydroxy, $NH_2$, $NR^{23}R^{24}$, NO$_2$, SH, (C$_1$-C$_6$)alkyl, (C$_1$-C$_6$)alkoxy, halo(C$_1$-C$_6$)alkyl, (C$_1$-C$_6$)alkanoyl, (C$_1$-C$_6$)alkoxycarbonyl, or (C$_1$-C$_6$)alkoxy, wherein R$^{23}$ and R$^{24}$ are each independently H, (C$_1$-C$_6$)alkyl, aralkyl, aryl, monocyclic heteroaryl, alkoxycarbonyl, aralkoxycarbonyl, —SO$_2$alkyl, or joined together to form a saturated or unsaturated 3 to 7 membered ring, or R$^{19}$ and R$^{20}$, R$^{20}$ and R$^{21}$, or R$^{21}$ and R$^{22}$, together with the carbons to which they are attached, form a 5, 6, or seven membered saturated or unsaturated cycloalkyl or heterocycloalkyl ring, or an aryl or heteroaryl ring.

Reference will now be made to a compound of Formula III:

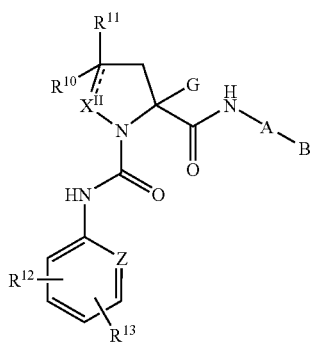

III

In

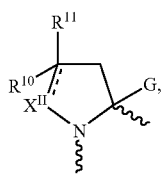

" - - - " is a bond or is absent. A specific value for X$^{II}$ is CH$_2$. Other specific values for X$^{II}$ include CH, NH and N. Specific values for R$^{10}$ and R$^{11}$ include H, hydroxy, methoxy, ethoxy, cyano, trifluoromethyl, fluoro, NH$_2$, carboethoxy, $$\text{Me}-\overset{O}{\underset{\|}{C}}-\text{NH}-,$$

MeSO$_2$N—, $$\text{Me}-\overset{O}{\underset{\|}{C}}-\text{NH}-, \quad \text{MeSO}_2\text{N}-, \quad \underset{\underset{H}{N}}{\overset{N=N}{\underset{N}{\|}}}\overset{}{\nwarrow},$$

wherein

" ∿∿∿ "

indicates the point of attachment. Also, R$^{10}$ and R$^{11}$ taken together can be =O or =NOH. Thus, specific values for

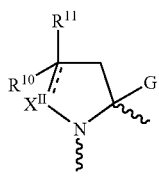

include

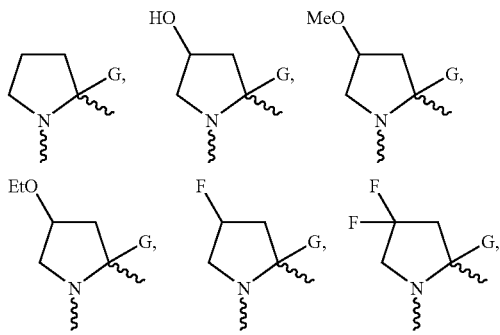

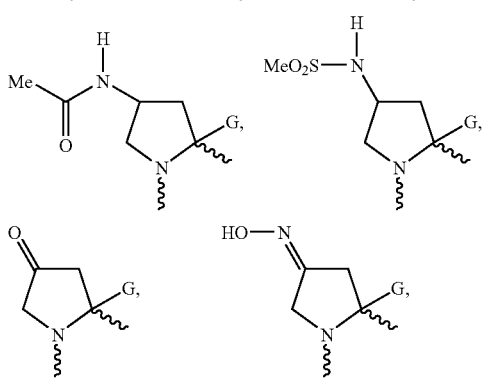

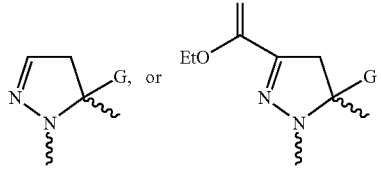

In

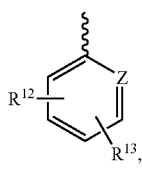

Z is N, CH, C(C-$C_6$)alkyl, C(C-$C_6$)alkoxy, or C-halo. R12 and R13 are each independently H, halo, ($C_1$-$C_6$)alkyl, or ($C_1$-$C_6$)alkoxy. Specific values for

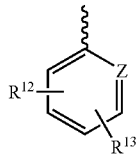

therefore include phenyl, pyridyl, para-chlorophenyl, para-fluorophenyl, para-bromophenyl, para-methoxyphenyl, para-toluyl, para-chloropyridyl, ortho, para-difluorophenyl, meta, para-difluorophenyl, and meta fluoro, paratoluyl.

A specific value for G is H, F, or methyl.

A specific value for A is phenyl. Another specific value for A is pyridyl. Other specific values for A include the following:

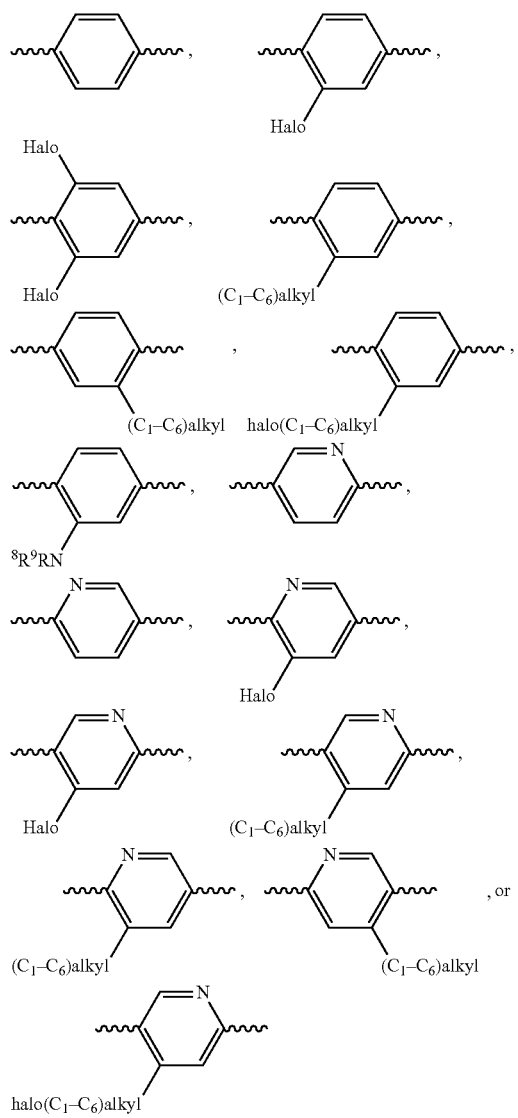

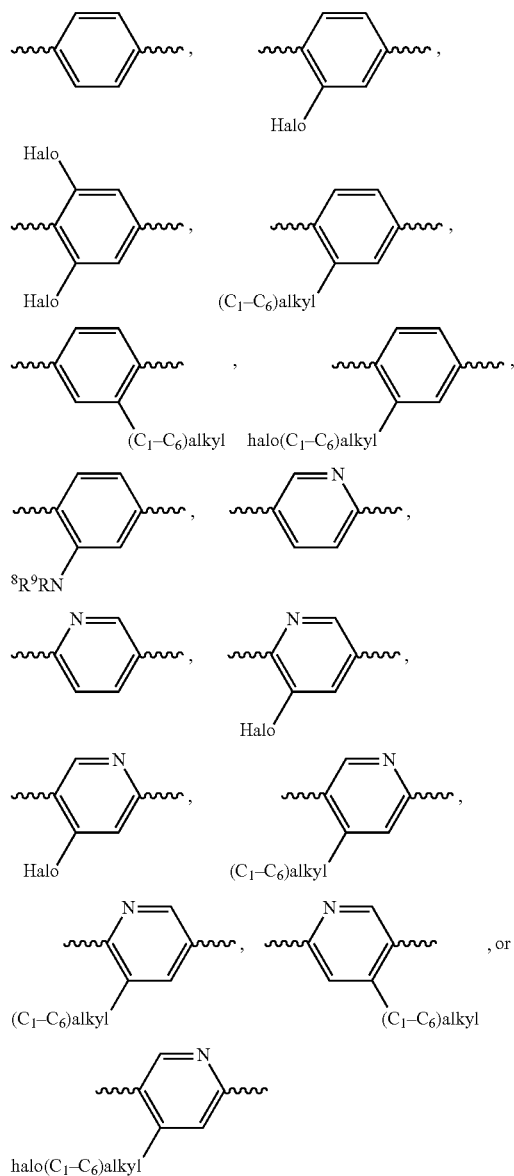

wherein

" ∿∿∿ "

indicate points of attachment, and halo, ($C_1$-$C_6$)alkyl, and halo($C_1$-$C_6$)alkyl are as defined earlier in the definitions section.

One specific value for B is

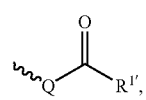

wherein

"∼∼∼"

indicates the point of attachment; Q is NH or is absent; and wherein $R^{1'}$ is OH, —O—$(C_1$-$C_6)$alkyl, or $NR^{3'}R^{4'}$, wherein $R^{3'}$ and $R^{4'}$ are independently H, $(C_1$-$C_6)$alkyl, or are joined together to form a optionally substituted saturated or unsaturated 5 to 7 membered ring.

Another specific value for B is phenyl or phenyl which is substituted at an ortho position with formyl, $H_2NSO_2$, $MeSO_2$, MeSO, MeS, $(C_{1\text{-}6})$alkoxycarbonyl, cyano, $H_2N$—$CH_2$—, HN—$(C_1$-$C_6)$alkyl-$CH_2$—, $(C_1$-$C_6)$alkyl$_2$N—$CH_2$—.

Another specific value for B is pyridyl or pyridyl substituted as provided in the previous position.

Another specific value for B is

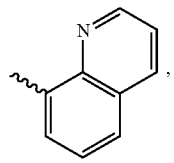

wherein

"∼∼∼"

indicates the point of attachment.

Another specific value for B is

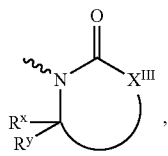

wherein

"∼∼∼"

indicates the point of attachment and which is an optionally substituted 4, 5, 6 or 7-membered ring. When B is

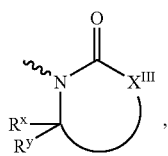

$R^x$ and $R^y$ can be H, halo, $(C_1$-$C_6)$alkyl, $(C_1$-$C_6)$alkoxy, $(C_1$-$C_6)$carboxyalkyl, or taken together can be O=. $X^{III}$ can be $CH_2$, CH—OH, CH—$CO_2(C_1$-$C_6)$alkyl, O, S, NH, or $N(C_1$-$C_6)$alkyl, provided that when $R^x$ and $R^y$ taken together are O=, $X^{III}$ is $CH_2$.

Another specific value for B is

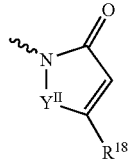

or a tautomer thereof such as

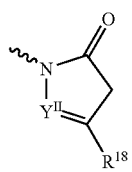 or 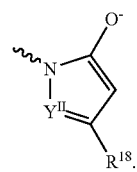.

When B is

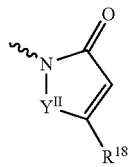

or a tautomer thereof, $Y^{II}$ can be $CH_2$, $CH(C_1$-$C_6)$alkyl, C—$CH_2OH$, C—$CH_2O$—$(C_1$-$C_6)$alkyl, NH, or $N(C_1$-$C_6)$alkyl. $R^{18}$ is H, $(C_1$-$C_6)$alkyl, hydroxymethyl, $CH_2O$—$(C_1$-$C_6)$alkyl, or $NR^3R^4$.

Another specific value for B is a 5-membered heteroaryl ring which contains at least one nitrogen atom such as imidazolyl, pyrazolyl, triazolyl, tetrazolyl, oxadiazolyl, thiadiazolyl, oxazolyl, isoxazolyl, thiazolyl, or isothiazolyl, any of which may be optionally substituted with halo, $(C_1$-$C_6)$alkyl, hydroxy$(C_1$-$C_6)$alkyl, $CH_2O$—$(C_1$-$C_6)$alkyl, or halo$(C_1$-$C_6)$alkyl. B can also be

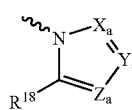

wherein

"∼∼∼"

indicates the point of attachment;

$X^a$, $Y^a$, and $Z^a$ are each independently $CR^c$ or N, wherein $R^c$ is H or $(C_1$-$C_6)$alkyl; and $R^{18}$ is H, $(C_1$-$C_6)$alkyl, hydroxymethyl, $CH_2O$—$(C_1$-$C_6)$alkyl, or $NR^3R^4$.

Another specific value for B is

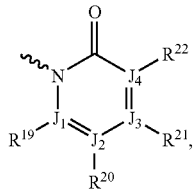

wherein

" $\sim\!\sim\!\sim$ "

indicates the point of attachment. When B is

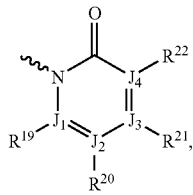

$J_1$, $J_2$, $J_3$, and $J_4$ can each be C, or one or more of $J_1$, $J_2$, $J_3$, or $J_4$ can be N. $R^{19}$, $R^{20}$, $R^{21}$, and $R^{22}$ are each independently H, halo, hydroxy, $NH_2$, $NR^{23}R^{24}$, $NO_2$, SH, $(C_1$-$C_6)$alkyl, $(C_1$-$C_6)$alkoxy, halo$(C_1$-$C_6)$alkyl, $(C_1$-$C_6)$alkanoyl, $(C_1$-$C_6)$alkoxycarbonyl, or $(C_1$-$C_6)$alkoxy, wherein $R^{23}$ and $R^{24}$ are each independently H, $(C_1$-$C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring. Alternatively, $R^{19}$ and $R^{10}$, $R^{20}$ and $R^{21}$, or $R^{21}$ and $R^{22}$, can be together with the carbons to which they are attached to form a 5, 6, or seven membered saturated or unsaturated cycloalkyl or heterocycloalkyl ring, or an aryl or heteroaryl ring. When any of $J_1$, $J_2$, $J_3$, or $J_4$ is N, $R^{19}$, $R^{20}$, $R^{21}$ or $R^{22}$, respectively, is absent at that position. Thus, specific values for B include

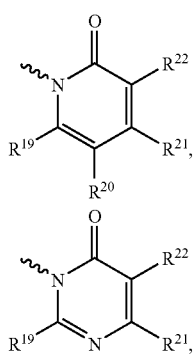

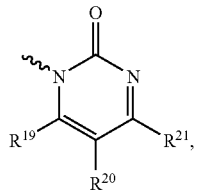

wherein

" $\sim\!\sim\!\sim$ "

indicates the point of attachment; and $R^{19}$, $R^{20}$, and $R^{21}$, $R^{22}$ are each independently H, halo, hydroxy, $NH_2$, $NR^{23}R^{24}$, $NO_2$, SH, $(C_1$-$C_6)$alkyl, $(C_1$-$C_6)$alkoxy, halo$(C_1$-$C_6)$alkyl, $(C_1$-$C_6)$alkanoyl, $(C_1$-$C_6)$alkoxycarbonyl, or $(C_1$-$C_6)$alkoxy, wherein $R^{23}$ and $R^{24}$ are each independently H, $(C_1$-$C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring, or $R^{19}$ and $R^{20}$, $R^{20}$ and $R^{21}$, or $R^{21}$ and $R^{22}$, together with the carbons to which they are attached, form a 5, 6, or seven membered saturated or unsaturated cycloalkyl or heterocycloalkyl ring, or an aryl or heteroaryl ring.

Reference will now be made to a compound of Formula IV:

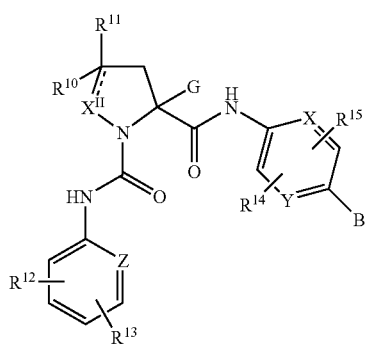

In

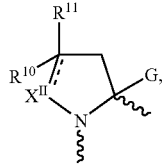

" - - - " is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

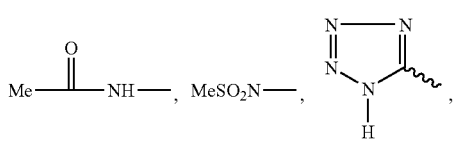

wherein

"⌇"

indicates the point of attachment. Also, $R^{10}$ and $R^{11}$ taken together can be =O or =NOH. Thus, specific values for

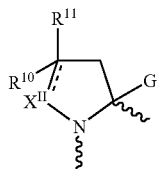

include

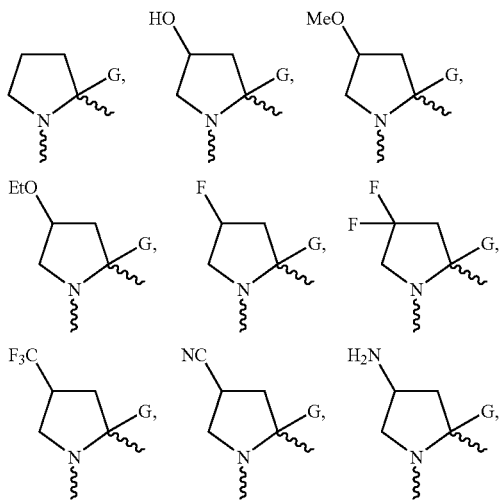

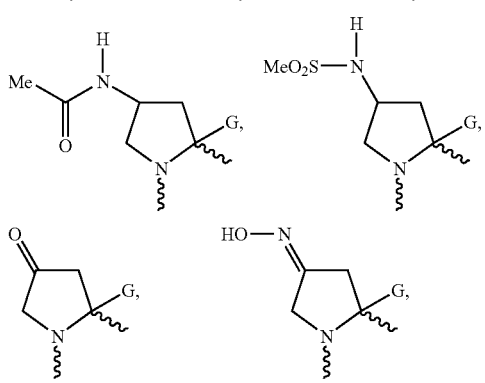

-continued

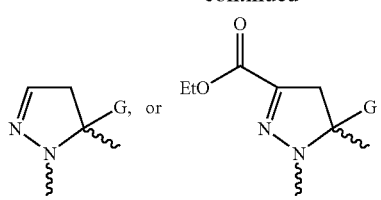

In

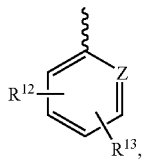

Z is N, CH, C($C_1$-$C_6$)alkyl, C—($C_1$-$C_6$)alkoxy, or C-halo. $R^{12}$ and $R^{13}$ are each independently H, halo, ($C_1$-$C_6$)alkyl, ($C_1$-$C_6$)alkoxy. Specific values for

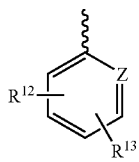

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

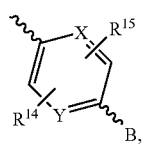

X and Y are each independently N, CH, C-halo, C($C_1$-$C_6$) alkyl, C-halo($C_1$-$C_6$)alkyl, or C-heterocycloalkyl. $R^{14}$ and $R^{15}$ are each independently H, halo, ($C_1$-$C_6$)alkyl, halo($C_1$-$C_6$) alkyl, or heterocycloalkyl. Specific values for

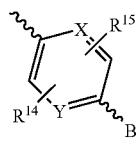

include

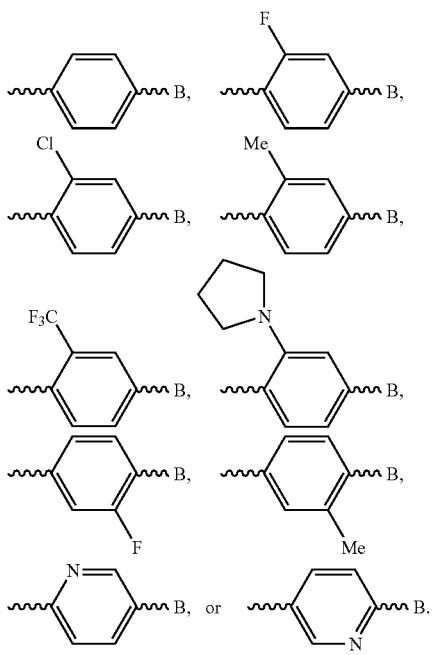

A specific value for G is H, F, or methyl.
One specific value for B is

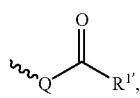

wherein

" ~~~ "

indicates the point of attachment; Q is NH or is absent; and wherein $R^{1'}$ is OH, —O—($C_1$-$C_6$)alkyl, or $NR^{3'}R^{4'}$, wherein $R^{3'}$ and $R^{4'}$ are independently H, ($C_1$-$C_6$)alkyl, or are joined together to form a optionally substituted saturated or unsaturated 5 to 7 membered ring.

Another specific value for B is phenyl or phenyl which is substituted at an ortho position with formyl, $H_2NSO_2$, $MeSO_2$, MeSO, MeS, ($C_{1-6}$)alkoxycarbonyl, cyano, $H_2N$—$CH_2$—, HN—($C_1$-$C_6$)alkyl-$CH_2$—, ($C_1$-$C_6$)alkyl$_2$N—$CH_2$—.

Another specific value for B is pyridyl or pyridyl substituted as provided in the previous position.

Another specific value for B is

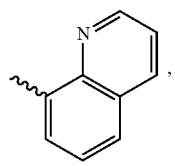

wherein

" ~~~ "

indicates the point of attachment.
Another specific value for B is

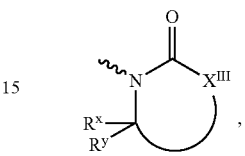

wherein

" ~~~ "

indicates the point of attachment and which is an optionally substituted 4, 5, 6 or 7-membered ring. When B is

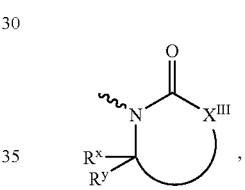

$R^x$ and $R^y$ can be H, halo, ($C_1$-$C_6$)alkyl, ($C_1$-$C_6$)alkoxy, ($C_1$-$C_6$)carboxyalkyl, or taken together can be O=. $X^{III}$ can be $CH_2$, CH—OH, CH—$CO_2$($C_1$-$C_6$)alkyl, O, S, NH, or N($C_1$-$C_6$)alkyl, provided that when $R^x$ and $R^y$ taken together are O=, $X^{III}$ is $CH_2$.

Another specific value for B is

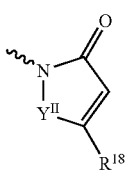

or a tautomer thereof such as

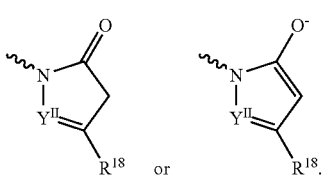

When B is

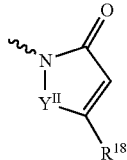

or a tautomer thereof, $Y^{II}$ can be $CH_2$, $CH(C_1-C_6)$alkyl, $C-CH_2OH$, $C-CH_2O-(C_1-C_6)$alkyl, NH, or $N(C_1-C_6)$alkyl. $R^{18}$ is H, $(C_1-C_6)$alkyl, hydroxymethyl, $CH_2-(C_1-C_6)$alkyl, or $NR^3R^4$.

Another specific value for B is a 5-membered heteroaryl ting which contains at least one nitrogen atom such as imidazolyl, pyrazolyl, triazolyl, tetrazolyl, oxadiazolyl, thiadiazolyl, oxazolyl, isoxazolyl, thiazolyl, or isothiazolyl, any of which may be optionally substituted with halo, $(C_1-C_6)$alkyl, hydroxy$(C_1-C_6)$alkyl, $CH_2O-(C_1-C_6)$alkyl, or halo$(C_1-C_6)$alkyl. B can also be

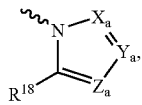

wherein

" ∿∿∿ "

indicates the point of attachment;

$X^a$, $Y^a$, and $Z^a$ are each independently $CR^c$ or N, wherein $R^c$ is H or $(C_1-C_6)$alkyl; and $R^{18}$ is H, $(C_1-C_6)$alkyl, hydroxymethyl, $CH_2O-(C_1-C_6)$alkyl, or $NR^3R^4$.

Another specific value for B is

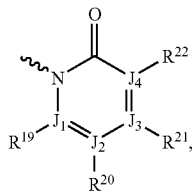

wherein

" ∿∿∿ "

indicates the point of attachment. When B is

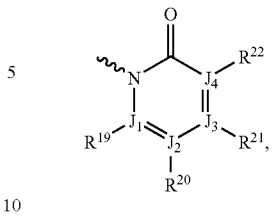

$J_1$, $J_2$, $J_3$, and $J_4$ can each be C, or one or more of $J_1$, $J_2$, $J_3$, or $J_4$ can be N. $R^{19}$, $R^{20}$, $R^{21}$, and $R^{22}$ are each independently H, halo, hydroxy, $NH_2$, $NR^{23}R^{24}$, $NO_2$, SH, $(C_1-C_6)$alkyl, $(C_1-C_6)$alkoxy, halo$(C_1-C_6)$alkyl, $(C_1-C_6)$alkanoyl, $(C_1-C_6)$alkoxycarbonyl, or $(C_1-C_6)$alkoxy, wherein $R^{23}$ and $R^{24}$ are each independently H, $(C_1-C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring. Alternatively, $R^{19}$ and $R^{20}$, $R^{20}$ and $R^{21}$, or $R^{21}$ and $R^{22}$, can be together with the carbons to which they are attached to form a 5, 6, or seven membered saturated or unsaturated cycloalkyl or heterocycloalkyl ring, or an aryl or heteroaryl ring. When any of $J_1$, $J_2$, $J_3$, or $J_4$ is N, $R^{19}$, $R^{20}$, $R^{21}$ or $R^{22}$, respectively, is absent at that position. Thus, specific values for B include

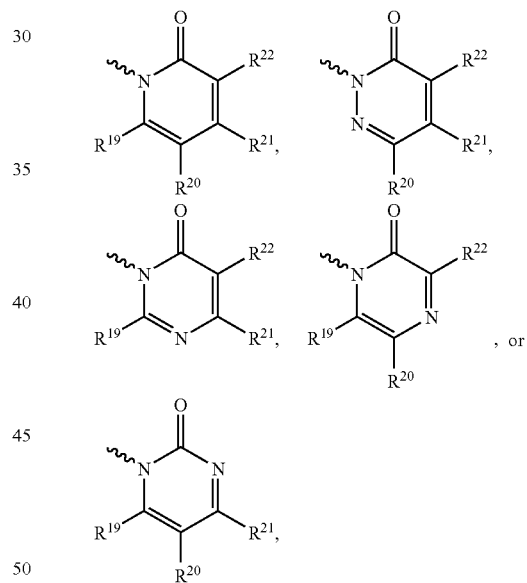

wherein

" ∿∿∿ "

indicates the point of attachment; and $R^{19}$, $R^{20}$, and $R^{21}$, $R^{22}$ are each independently H, halo, hydroxy, $NH_2$, $NR^{23}R^{24}$, $NO_2$, SH, $(C_1-C_6)$alkyl, $(C_1-C_6)$alkoxy, halo$(C_1-C_6)$alkyl, $(C_1-C_6)$alkanoyl, $(C_1-C_6)$alkoxycarbonyl, or $(C_1-C_6)$alkoxy, wherein $R^{23}$ and $R^{24}$ are each independently H, $(C_1-C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring, or $R^{19}$ and $R^{20}$, $R^{20}$ and $R^{21}$, or $R^{21}$ and $R^{22}$, together with the carbons to which they are attached, form a 5, 6, or seven membered saturated or unsaturated cycloalkyl or heterocycloalkyl ring, or an aryl or heteroaryl ring.

Reference will now be made to a compound of Formula V:

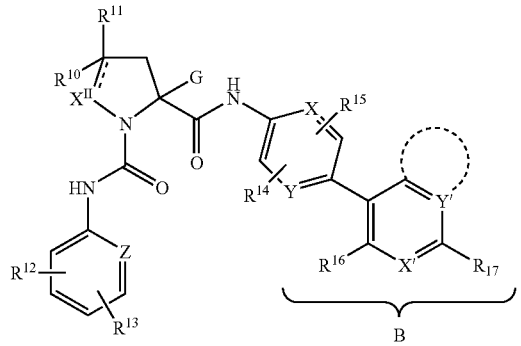

In

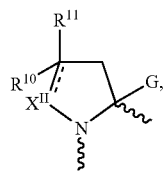

" - - - " is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

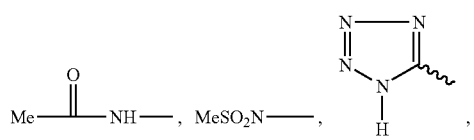

wherein

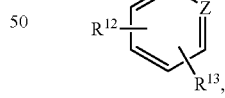

indicates the point of attachment. Also, $R^{10}$ and $R^{11}$ taken together can be =O or =NOH. Thus, specific values for

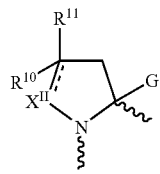

include

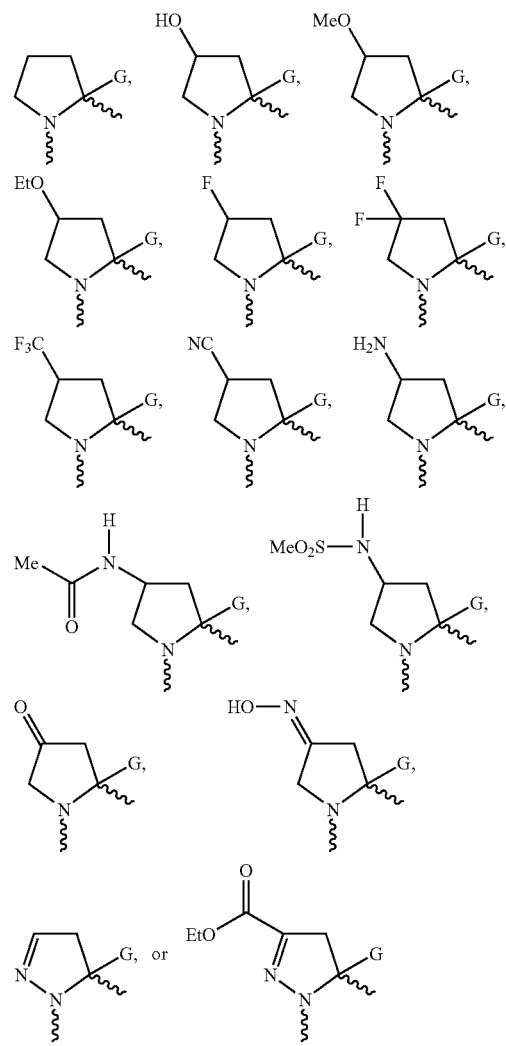

In

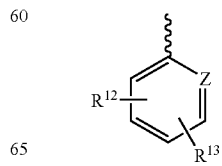

Z is N, CH, C($C_1$-$C_6$)alkyl, C—($C_1$-$C_6$)alkoxy, or C-halo. $R^{12}$ and $R^{13}$ are each independently H, halo, ($C_1$-$C_6$)alkyl, ($C_1$-$C_6$)alkoxy. Specific values for therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

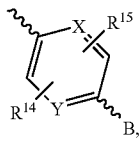

X and Y are each independantly N, CH, C-halo, C($C_1$-$C_6$)alkyl, C-halo($C_1$-$C_6$)alkyl, or C-heterocycloalkyl. $R^{14}$ and $R^{15}$ are each independently H, halo, ($C_1$-$C_6$)alkyl, halo($C_1$-$C_6$)alkyl, or heterocycloalkyl. Specific values for

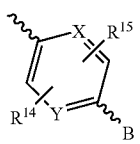

include

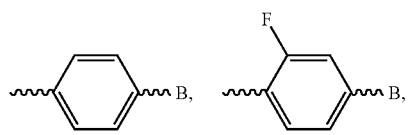

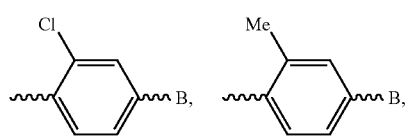

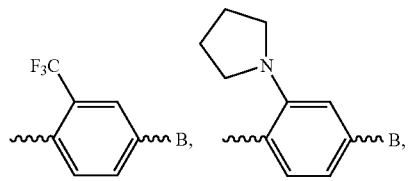

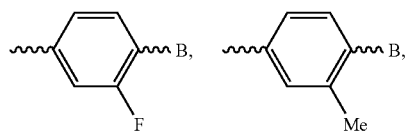

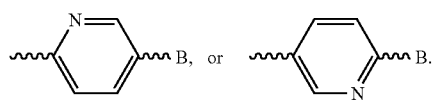

A specific value for G is H, F, or methyl.

In

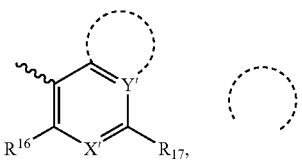

is absent or is a fused heterocyclic or fused heteroaryl ring, provided that when

is present, Y' is C. X' and Y' are each independently N, CH, C-halo, C-halo, C—($C_1$-$C_6$)alkyl, C-halo($C_1$-$C_6$)alkyl, C—($C_1$-$C_6$)alkoxy, C—OH, C—$SO_2$Me, C—$SO_2NH_2$, C—SOMe, C—SMe, C—$CO_2$($C_1$-$C_6$)alkyl, C—CN, or C—$CH_2NH_2$. Specific values for

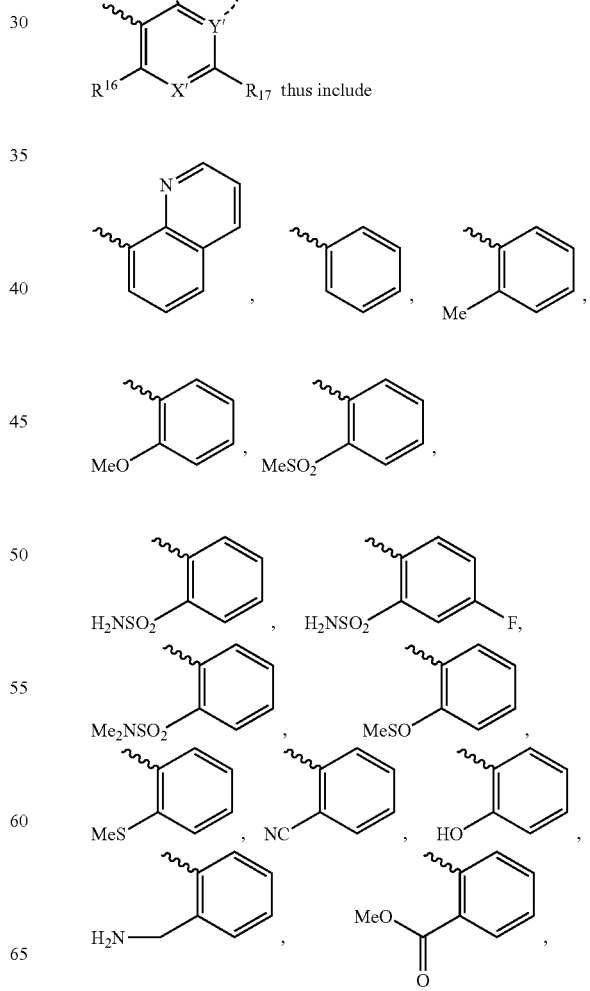

thus include

-continued

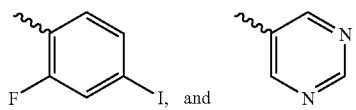

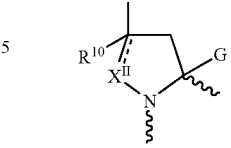

Reference will now be made to a compound of Formula VI.

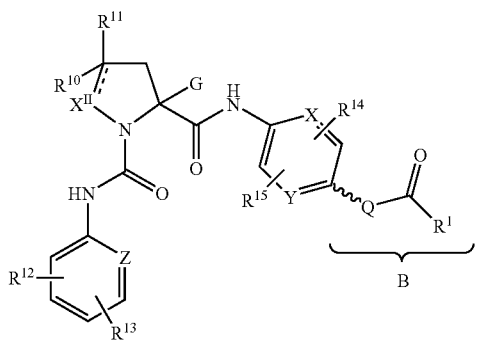

include

In

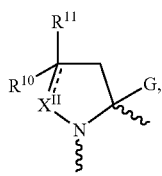

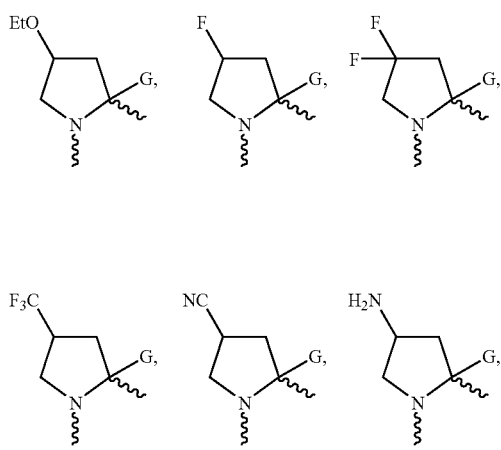

" - - - " is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

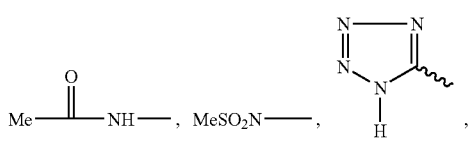

wherein

" ~~~ "

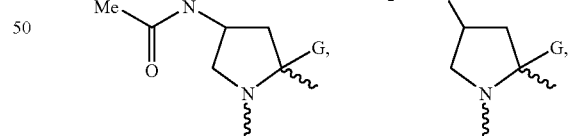

indicates the point of attachment. Also, $R^{10}$ and $R^{11}$ taken together can be =O or =NOH. Thus, specific values for

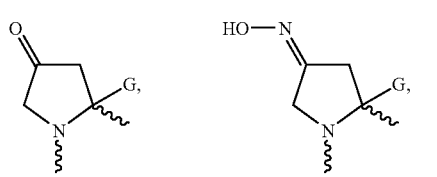

-continued

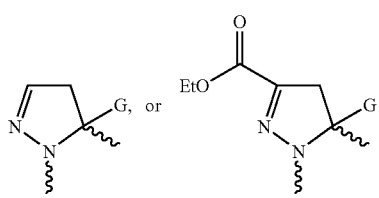

In

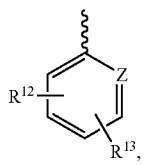

Z is N, CH, C(C$_1$-C$_6$)alkyl, C—(C$_1$-C$_6$)alkoxy, or C-halo. R$^{12}$ and R$^{13}$ are each independently H, halo, (C$_1$-C$_6$)alkyl, (C$_1$-C$_6$)alkoxy. Specific values for

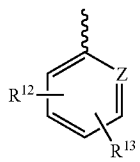

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

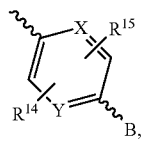

X and Y are each independantly N, CH, C-halo, C(C$_1$-C$_6$) alkyl, C-halo(C$_1$-C$_6$)alkyl, or C-heterocycloalkyl. R$^{14}$ and R$^{15}$ are each independently H, halo, (C$_1$-C$_6$)alkyl, halo(C$_1$-C$_6$) alkyl, or heterocycloalkyl. Specific values for

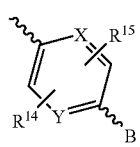

include

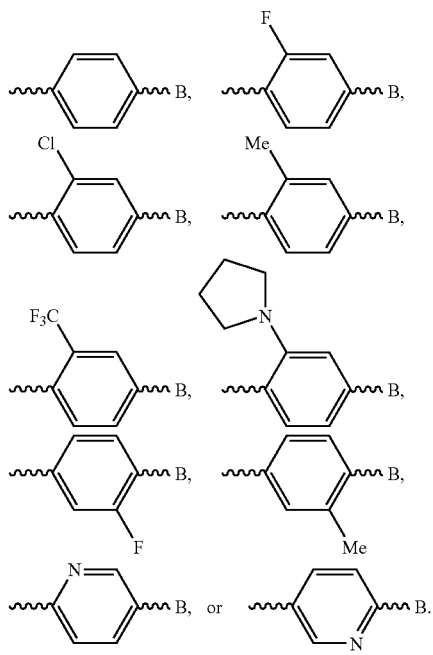

A specific value for G is H, F, or methyl.

In

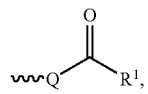

Q is NH or is absent. R$^1$ is OH, —O—(C$_1$-C$_6$)alkyl, (C$_3$-C$_7$) cycloalkyl, (C$_3$-C$_7$)heterocycloalkyl, (C$_4$-C$_7$)cycloalkenyl, (C$_4$-C$_7$)heterocycloalkenyl, aryl, monocyclic heteroaryl, or —NR$^3$R$^4$, wherein R$^3$ and R$^4$ are independently H, (C$_1$-C$_6$) alkyl, aralkyl, aryl, monocyclic heteroaryl, alkoxycarbonyl, aralkoxycarbonyl, —SO$_2$alkyl, or joined together to form a saturated or unsaturated 5 to 7 membered ring. Thus, specific values for

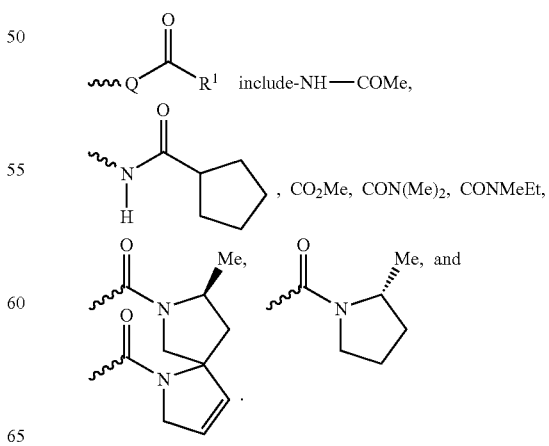

Reference will now be made to a compound of Formula VII.

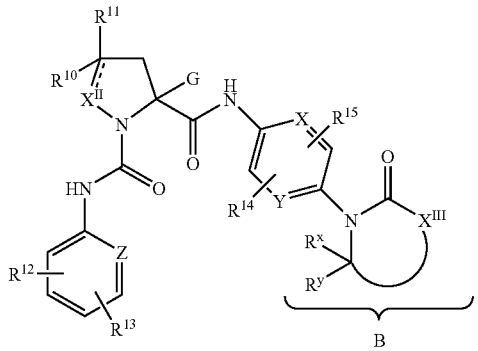

In

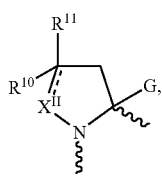

"---" is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

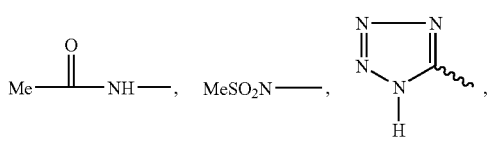

wherein

" 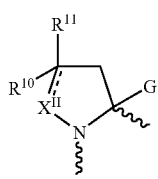 "

indicates the point of attachment. Also, $R^{10}$ and $R^{11}$ taken together can be =O or =NOH. Thus, specific values for

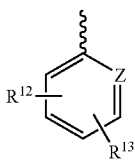

include

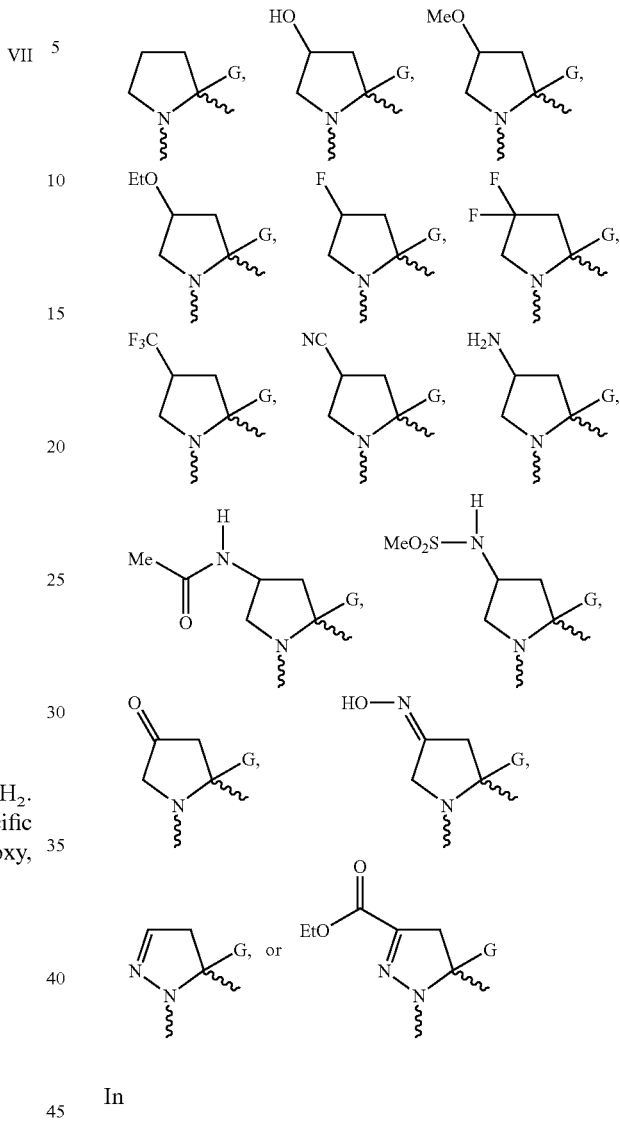

In

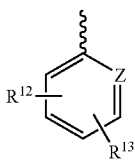

Z is N, CH, $C(C_1-C_6)$alkyl, $C(C_1-C_6)$alkoxy, or C-halo. $R^{12}$ and $R^{13}$ are each independently H, halo, $(C_1-C_6)$alkyl, $(C_1-C_6)$alkoxy. Specific values for

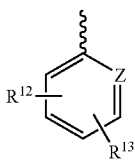

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

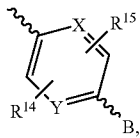

X and Y are each independantly N, CH, C-halo, $C(C_1$-$C_6)$ alkyl, C-halo$(C_1$-$C_6)$alkyl, or C-heterocycloalkyl. $R^{14}$ and $R^{15}$ are each independently H, halo, $(C_1$-$C_6)$alkyl, halo$(C_1$-$C_6)$alkyl, or heterocycloalkyl. Specific values for

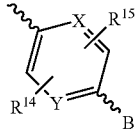

include

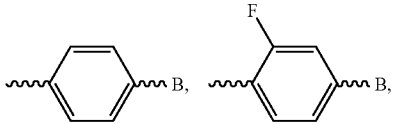

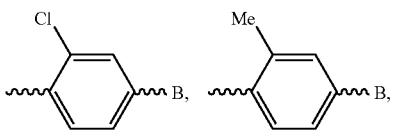

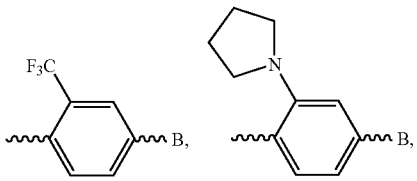

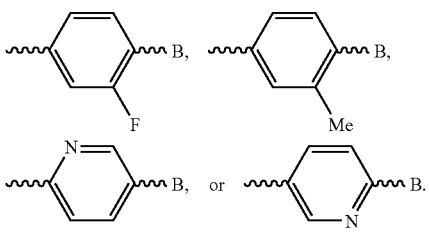

A specific value for G is H, F, or methyl.

In compounds of Formula VII,

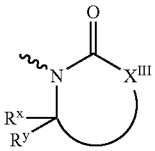

is an optionally substituted 4, 5, 6 or 7-membered ring, wherein $R^x$ and $R^y$ are H, halo, hydroxymethyl, $(C_1$-$C_6)$alkyl, $(C_1$-$C_6)$alkoxy, or wherein $R^x$ and $R^y$ are H, halo, $(C_1$-$C_6)$ alkyl, $(C_1$-$C_6)$alkoxy, $(C_1$-$C_6)$carboxyalkyl, or taken together are O=. $X^{III}$ is $CH_2$, CH—OH, CH—$CO_2(C_1$-$C_6)$alkyl, O, S, NH, or $N(C_1$-$C_6)$alkyl, provided that when $R^x$ and $R^y$ taken together are O=, $X^{III}$ is $CH_2$. Thus, specific values for

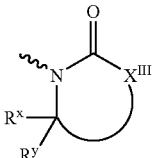

include

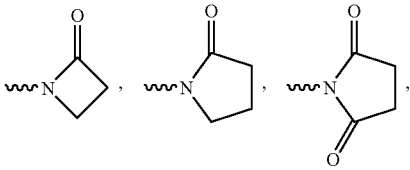

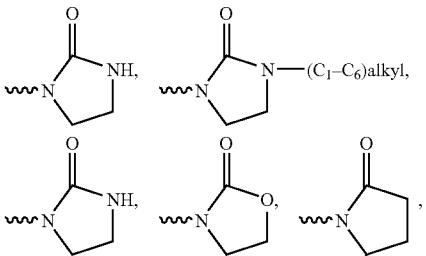

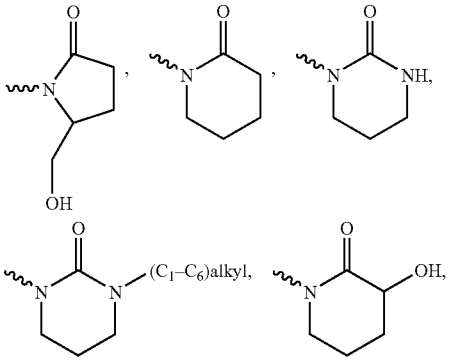

-continued

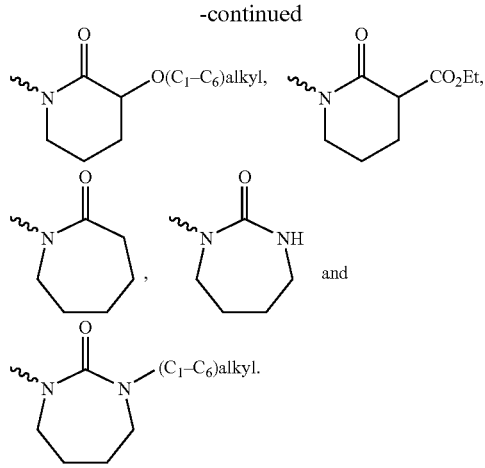

Any of the specific values for

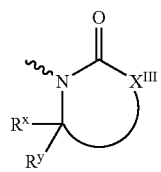

may be further optionally substituted with one, two or three substitutent groups selected from the group consisting of halo, $(C_1-C_6)$alkyl, halo$(C_1-C_6)$alkyl, or hydroxymethyl.

Reference will now be made to a compound of Formula VIII.

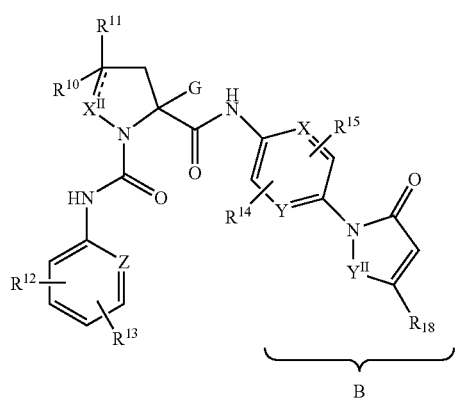

In

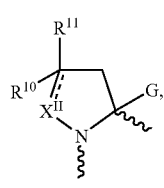

"- - -" is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

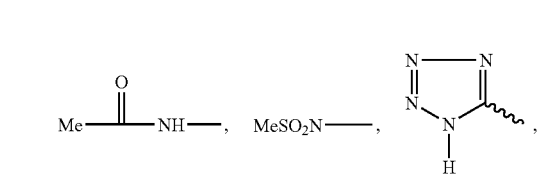

wherein

"〜〜〜"

indicates the point of attachment. Also, $R^{10}$ and $R^{11}$ taken together can be =O or =NOH. Thus, specific values for

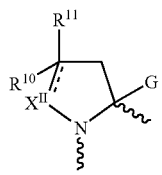

include

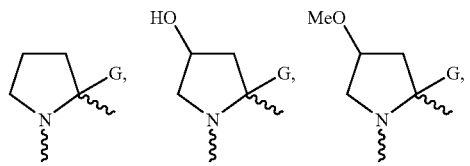

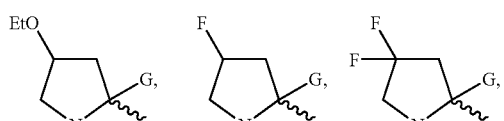

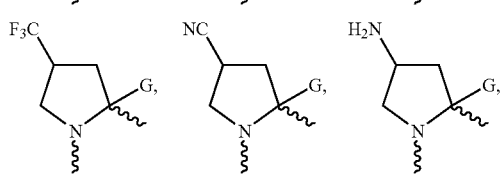

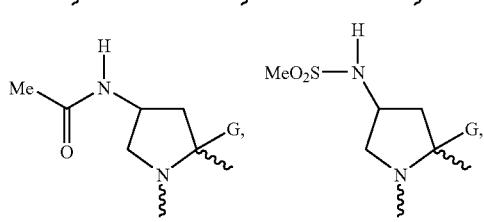

-continued

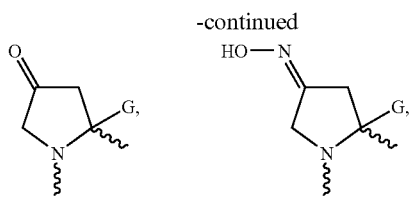 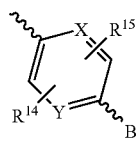

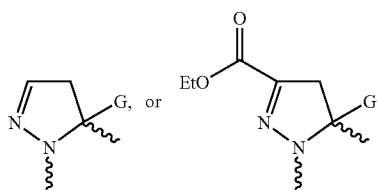

In

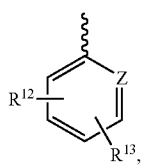

Z is N, CH, C($C_1$-$C_6$)alkyl, C($C_1$-$C_6$)alkoxy, or C-halo. $R^{12}$ and $R^{13}$ are each independently H, halo, ($C_1$-$C_6$)alkyl, ($C_1$-$C_6$)alkoxy. Specific values for

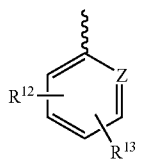

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

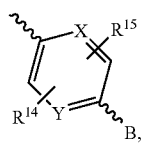 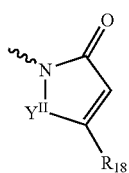

X and Y are each independantly N, CH, C-halo, C($C_1$-$C_6$) alkyl, C-halo($C_1$-$C_6$)alkyl, or C-heterocycloalkyl. $R^{14}$ and $R^{15}$ are each independently H, halo, ($C_1$-$C_6$)alkyl, halo($C_1$-$C_6$) alkyl, or heterocycloalkyl. Specific values for include

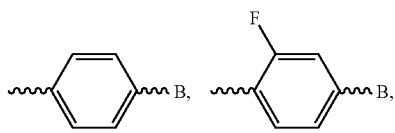

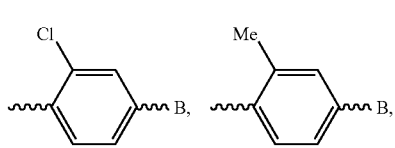

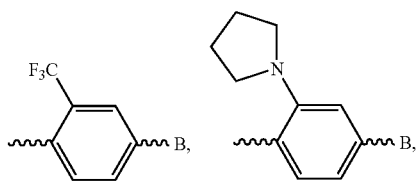

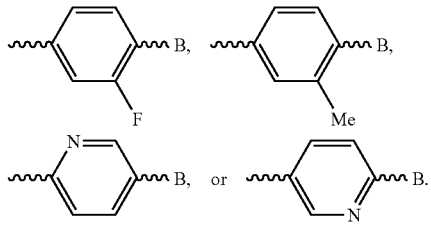

In compounds of Formula VIII,

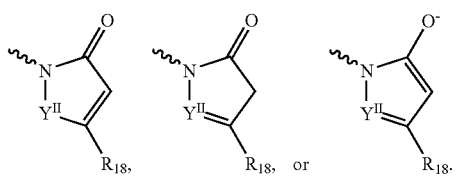

can exist in tautomeric form as

Furthermore, in

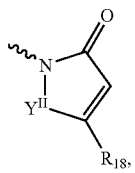

$Y^{II}$ is CH, $CR^{18}$, or N. $R^{18}$ is H, $(C_1-C_6)$alkyl, hydroxymethyl, $CH_2O—(C_1-C_6)$alkyl, or $NR^3R^4$, wherein $R^3$ and $R^4$ are each independently H, $(C_1-C_6)$alkyl, aralkyl, aryl, monocyclic heteroaryl, alkoxycarbonyl, aralkoxycarbonyl, —$SO_2$alkyl, or joined together to form a saturated or unsaturated 3 to 7 membered ring. Thus, specific values for

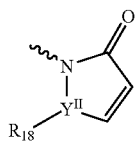

include

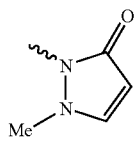

A specific value for G is H, F, or methyl.
Reference will now be made to a compound of Formula IX.

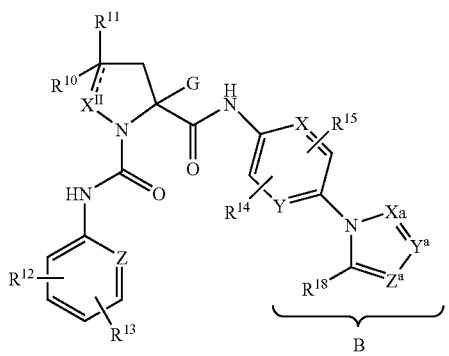

In

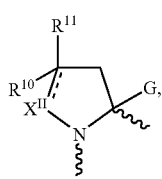

"---" is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

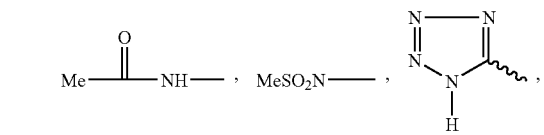

wherein

" ⁓ "

indicates the point of attachment. Also, $R^{10}$ and $R^1$ taken together can be =O or =NOH. Thus, specific values for

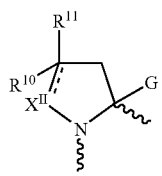

include

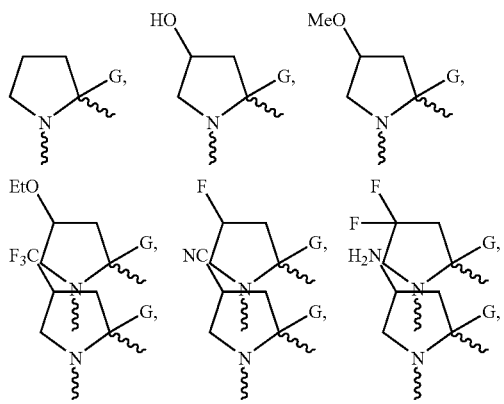

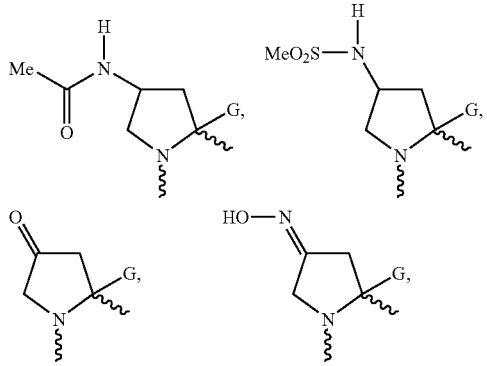

-continued

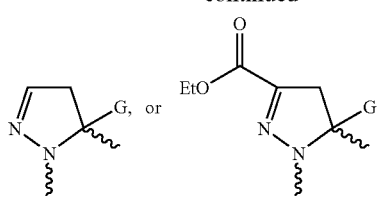

In

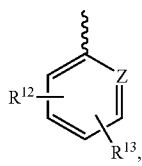

Z is N, CH, C(C$_1$-C$_6$)alkyl, or C-halo. R$^{12}$ and R$^{13}$ are each independently H, halo, (C$_1$-C$_6$)alkyl, (C$_1$-C$_6$)alkoxy. Specific values for

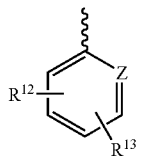

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

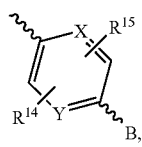

X and Y are each independantly N, CH, C-halo, C(C$_1$-C$_6$) alkyl, C-halo(C$_1$-C$_6$)alkyl, or C-heterocycloalkyl. R$^{14}$ and R$^{15}$ are each independently H, halo, (C$_1$-C$_6$)alkyl, halo(C$_1$-C$_6$) alkyl, or heterocycloalkyl. Specific values for

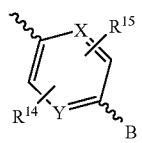

include

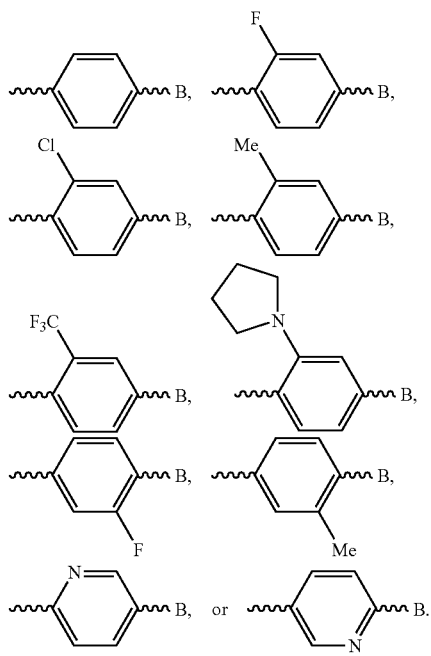

In

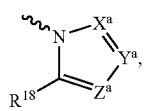

X$^a$, Y$^a$, and Z$^a$ are each independently CH, CR$^{18}$ or N; and R$^{18}$ is H, (C$_1$-C$_6$)alkyl, hydroxymethyl, CH$_2$O—(C$_1$-C$_6$)alkyl, or NR$^3$R$^4$, wherein R$^3$ and R$^4$ are each independently H, (C$_1$-C$_6$)alkyl, aralkyl, aryl, monocyclic heteroaryl, alkoxycarbonyl, aralkoxycarbonyl, —SO$_2$alkyl, or joined together to form a saturated or unsaturated 3 to 7 membered ring. Thus, specific values for

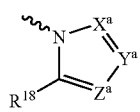

include imidazolyl, pyrazolyl, triazolyl, tetrazolyl, oxadiazolyl, thiadiazolyl, oxazolyl, isoxazolyl, thiazolyl, and isothiazolyl, any of which may be optionally substituted with halo, (C$_1$-C$_6$)alkyl, hydroxy(C$_1$-C$_6$)alkyl, CH$_2$O—(C$_1$-C$_6$)alkyl, or halo(C$_1$-C$_6$)alkyl. Other values for

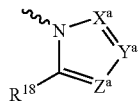

include

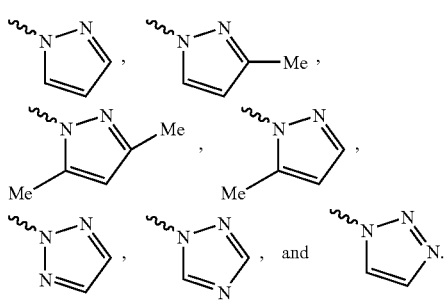

A specific value for G is H, F, or methyl.
Reference will now be made to a compound of Formula X.

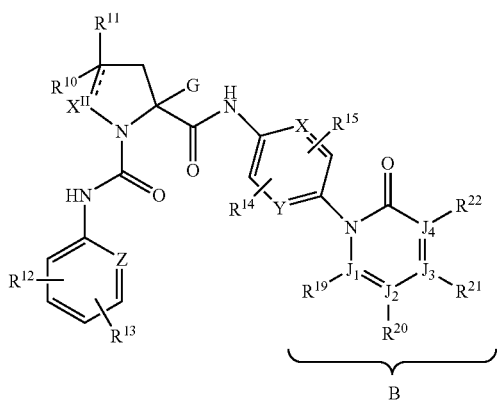

In

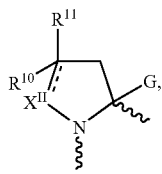

" --- " is a bond or is absent. A specific value for $X^{II}$ is $CH_2$. Other specific values for $X^{II}$ include CH, NH and N. Specific values for $R^{10}$ and $R^{11}$ include H, hydroxy, methoxy, ethoxy, cyano, trifluoromethyl, fluoro, $NH_2$, carboethoxy,

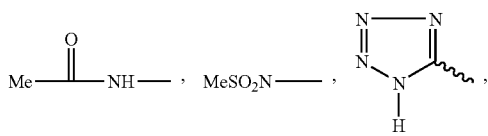

wherein

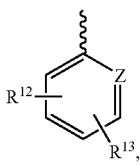

indicates the point of attachment. Also, $R^{10}$ and $R^{11}$ taken together can be =O or =NOH. Thus, specific values

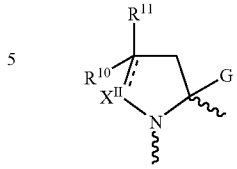

for include

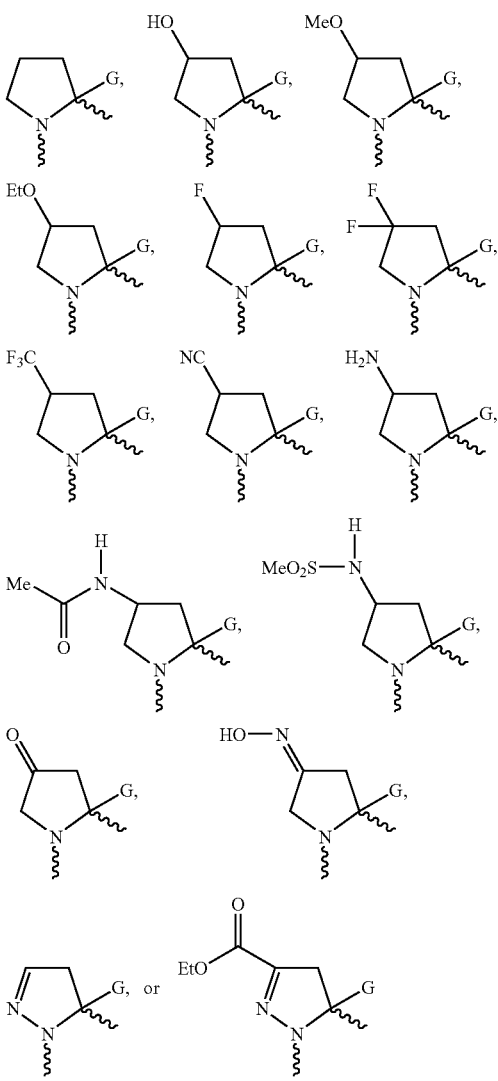

In

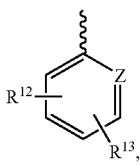

Z is N, CH, C(C$_1$-C$_6$)alkyl, —(C$_1$-C$_6$)alkoxy, or C-halo. R$^{12}$ and R$^{13}$ are each independently H, halo, (C$_1$-C$_6$)alkyl, (C$_1$-C$_6$)alkoxy. Specific values for

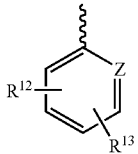

therefore include phenyl, pyridyl, parachlorophenyl, parafluorophenyl, parabromophenyl, paramethoxyphenyl, paratoluyl, parachloropyridyl, ortho, para-difluorophenyl, meta, para-difluorophenyl, and meta fluoro, paramethyl phenyl.

In

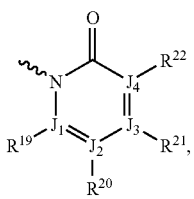

$J_1$, $J_2$, $J_3$, and $J_4$ are each C, or one of $J_1$, $J_2$, $J_3$, and $J_4$ is N. R$^{19}$, R$^{20}$, R$^{21}$, and R$^{22}$ are each independently H, halo, hydroxy, NH$_2$, NR$^{23}$R$^{24}$, NO$_2$, SH, (C$_1$-C$_6$)alkyl, (C$_1$-C$_6$)alkoxy, halo (C$_1$-C$_6$)alkyl, (C$_1$-C$_6$)alkanoyl, (C$_1$-C$_6$)alkoxycarbonyl, or (C$_1$-C$_6$)alkoxy, wherein R$^{23}$ and R$^{24}$ are each independently H, (C$_1$-C$_6$)alkyl, aralkyl, aryl, monocyclic heteroaryl, alkoxycarbonyl, aralkoxycarbonyl, —SO$_2$alkyl, or joined together to form a saturated or unsaturated 3 to 7 membered ring, or R$^{19}$ and R$^{20}$, R$^{20}$ and R$^{21}$, or R$^{21}$ and R$^{22}$, together with the carbons to which they are attached, form a 5, 6, or 7 membered saturated or unsaturated cycloalkyl or heterocycloalkyl ring, or an aryl or heteroaryl ring. Also, when any of $J_1$, $J_2$, $J_3$, or $J_4$ is N, R$^{19}$, R$^{20}$, R$^{21}$ or R$^{22}$, respectively, is absent at that position. Thus, specific values for

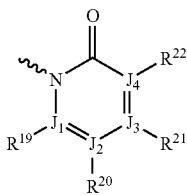

include

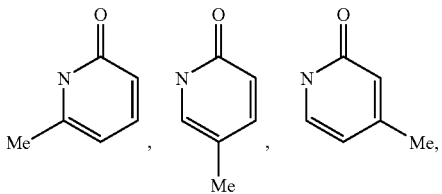

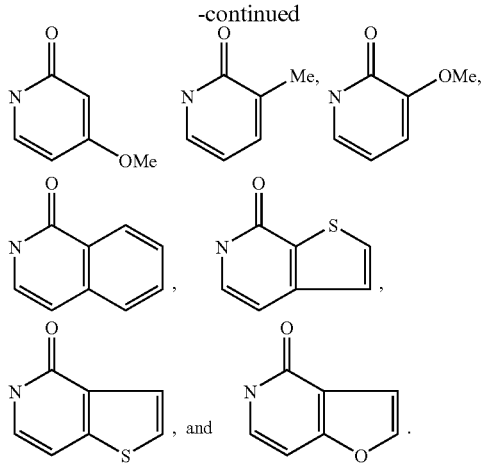

A specific value for G is H, F, or methyl.

PREPARATION OF COMPOUNDS OF THE INVENTION

Processes and novel intermediates for preparing compounds of formula I are provided as further embodiments of the invention and are illustrated by the following procedures in which the meanings of the generic radicals are as given above unless otherwise qualified. Certain compounds of formula I are useful as intermediates for preparing other compounds of formula I.

It is also noted that compounds of formula I can be prepared using protecting groups. It is to be noted that the appropriate use and choice of protecting groups is well-known by one skilled in the art, and is not limited to the specific examples below. It is also to be understood that such groups not only serve to protect chemically reactive sites, but also to enhance solubility or otherwise change physical properties. A good general reference for protecting group preparation and deprotection is "Protecting Groups in Organic Synthesis" by T. W. Green and P. G. Wuts. A number of general reactions such as oxidations and reductions etc. are not shown in detail but can be done by methods understood by one skilled in the art. General transformations are well-reviewed in "Comprehensive Organic Transformation" by Richard Larock, and the series "Compendium of Organic Synthetic Methods" published by Wiley-Interscience. In general, the starting materials are obtained from commercial sources unless otherwise indicated.

It will be appreciated by those skilled in the art that compounds of the invention having one or more chiral centers may exist in and be isolated in optically active and racemic forms. Some compounds may exhibit polymorphism. It is to be understood that the present invention encompasses any racemic, optically-active, polymorphic, geometric, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity or cytotoxicity using the standard tests described herein, or using other similar tests which are well known in the art.

It will be further appreciated by the skilled artisan that the following schemes depict the synthesis of some compounds of the invention. It is to be understood, however, that compounds of the invention other than those specifically disclosed can be prepared using the strategies depicted in the schemes.

One method for making compounds of the invention is disclosed in Scheme 1. The route is useful for a wide variety of starting materials with variable $W^1$ groups, provided the appropriate protecting group is utilized, if necessary. The scheme is also employed for both racemic mixtures and enantiomerically pure compounds. The method comprises reacting an amino acid having Formula With a reagent capable of forming a protecting group on the amino group of an amino acid to form compound with Formula B. In Scheme 1, $P^1$ is a protecting group and $W^1$ is the same as defined above. The compound of Formula B is next converted into an acid halide. Alternatively the carboxyliz acid may be activated by a number of coupling reagents, but not limited to, such as BOP, HATU, EEDQ, or CDI. The acid halide is then reacted with a haloaniline or a haloaminoheterocycle to form a halide having Formula D, where $Y^1$ is a halogen and A is as defined above. The compound with Formula D is then subjected to a coupling reaction with a compound having B to give a compound of Formula E. The protecting group is then removed from compound E and the resulting compound reacted with an isocyanate having C to from a compound of Formula I. Finally, as relating to Scheme 1 and subsequent schemes, it is to be noted that compounds of the invention wherein G has any of the provided meanings other than H can be easily prepared by techniques available to the skilled artisan. For example, compounds wherein G is alkyl can be prepared by alkylation of I, or by alkylation of a corresponding ester of A, B D, or E.

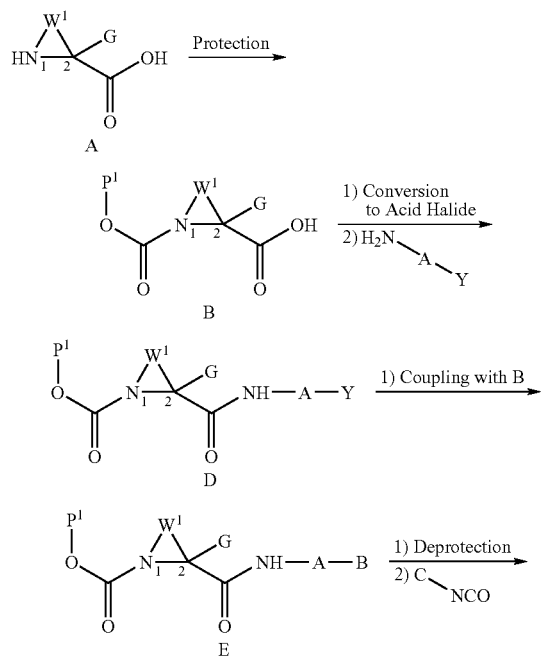

Scheme 1

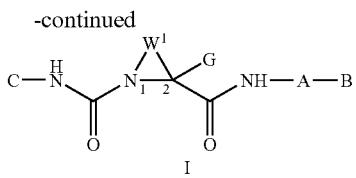

I

Scheme 2 provides a more detailed approach to the preparation of compounds of the invention. The synthetic route starts by protecting an amino acid A with di-tert-butyl dicarbonate in tetrahydrofuran with 2M NaOH as the base. The resulting BOC-protected amino acid B-1 is converted into the acid chloride using oxalyl chloride, with pyridine added to prevent deprotection. The acid chloride or acid is then immediately reacted with a bromoaniline or bromoaminoheterocycle of choice. The resulting bromide is then typically subjected to a Suzuki coupling with a boronic acid, although other coupling conditions may be used to provide D-1. Compound D-1 is then deprotected with 33% trifluoroacetic acid in dichloromethane and allowed to reacted with an isocyanate in the presence of an amine base such as triethylamine in tetrahydrofuran or the like. This route is useful for preparing compounds containing biaryl A-B groups; i.e., where both A and B are aryl.

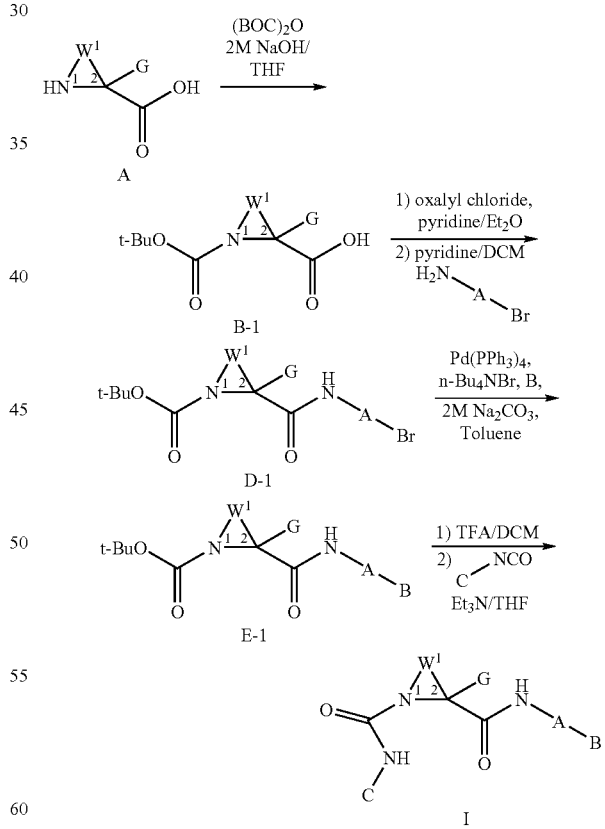

Another method of making compounds of the invention is depicted in Scheme 3. The route summarized in Scheme 3 is useful for synthesizing a wide variety of A-B groups. The chemistry is similar to Scheme 1, but the second step (i.e., the conversion of B to D) introduces different substituted aniline or aminoheterocycle. By selecting an appropriately substituted aniline or aminoheteroaryl group, a wide variety of B groups can be introduced. For example, with Z is a cyano group, the corresponding imidazole and imidazoline compounds can be made using techniques known to the skilled artisan. When Z is a methyl ester or the like, the corresponding amides and ketones can be synthesized via a number of methods available to the skilled artsian. For example, an amide is prepared by hydrolyzing the ester with lithium hydroxide, treating the resulting carboxylic acid with a typical peptide coupling reagent such as HATU, followed by introduction of the desired amine.

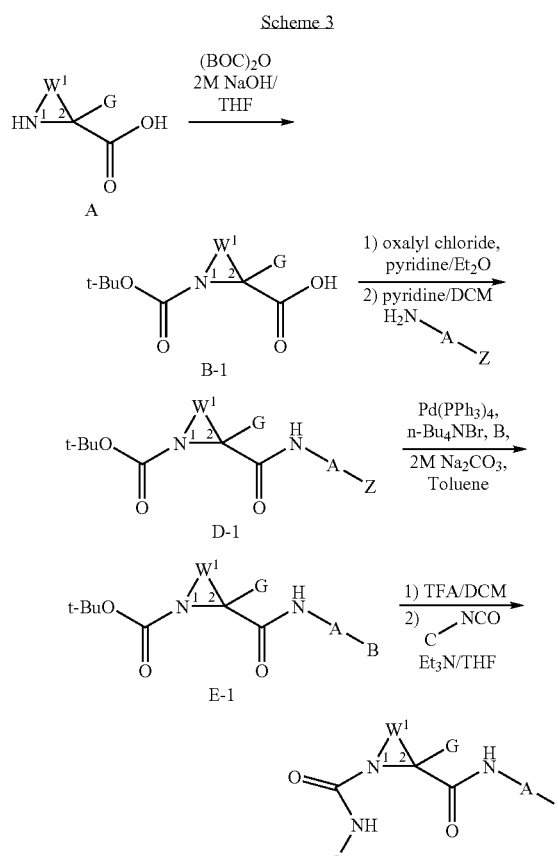

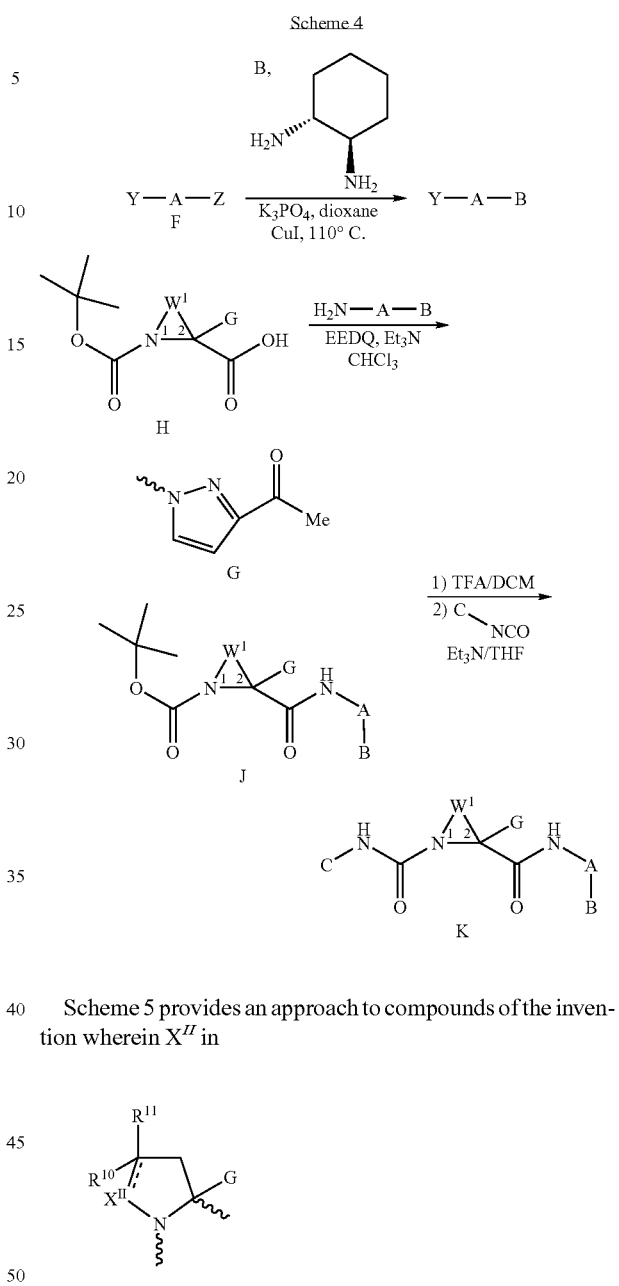

Compounds of the invention may also be prepared as provided in Scheme 4. Thus, a mixture of F (where Z is a halide and Y is an amino or nitro group), B (where B is a nitrogen-containing ring, an amine or amide), $K_3PO_4$, CuI, and trans-diaminocyclohexane is heated in dioxane at reflux to obtain compound G. In the case where Y is a nitro group, the moiety is reduced to the amino group with RaNi and EtOH under a hydrogen atmosphere. The appropriate aniline G, EEDQ, triethylamine and carboxylic acid H are heated at reflux in chloroform to produce J. Finally, a solution of compound J, TFA and DCM is stirred at room temperature for 1 h and then concentrated under reduced pressure. The resulting oil is dissolved in THF and cooled to 0° C. followed by the addition of triethylamine and the appropriate isocyanate to produce invention compound K.

Scheme 5 provides an approach to compounds of the invention wherein $X^{II}$ in

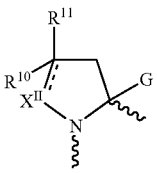

(c.f., Formulas II-X), is N and " - - - " is a bond. Thus, Aniline M is converted to an acrylamide N by the addition of acryoyl chloride and a base, such as saturated sodium bicarbonate, in a solvent such as ethyl acetate at room temperature. Alternatively, the aniline may be converted to N by the addition of an acrylic acid and adding a coupling reagent such as dicyclohexylcarbodi-imide (DCC), O-(7-Azabenzotriazol-1-yl)-N,N,N',N'-tetrarnethyluronium hexafluorophosphate (HATU), or EEDQ. The acrylamide N is added an excess of trimethylsilyl diazomethane in a solvent such as ethyl acetate or dichloromethane. The resulting dihydropyrazole O may then be treated with an isocyanate, in the presence of base such as pyridine or triethylamine, in a solvent such as dichloromethane, to afford compound P.

Scheme 5.1

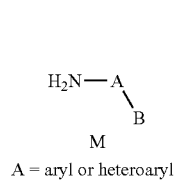

M
A = aryl or heteroaryl formation of acrylamide →

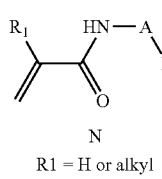

N
R1 = H or alkyl conversion to dihydropyrazole →

O reaction with isocyanate ↓

P

An alternative approach to molecules wherein $X^{II}$ in

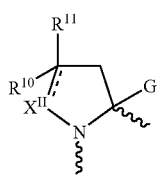

(c.f., Formulas II-X), is N and " - - - " is a bond is provided in Scheme 5.2. The chemistry for the preparation of compounds Q-T is similar to that described in Scheme 5.1. Compound T may be converted to an invention compound by a Suzuki coupling with a boronic acid, although other coupling conditions commonly known to the skilled practitioner may also be used. This route is particularly useful for compounds containing a biaryl A-B group. In situations where a tert-butylsulphonamide is present in B, which occurs in some of the particularly preferred compounds, the sulphonamide may be formed by stirring with trifluoroacetic acid for 16 h.

Scheme 5.2

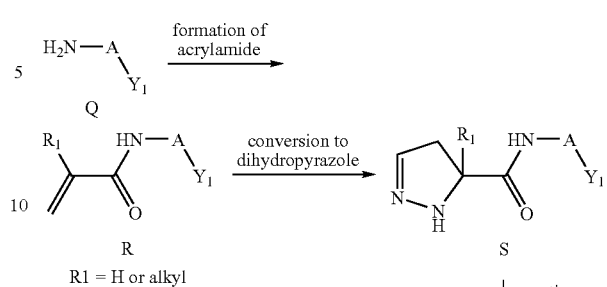

Q

R
R1 = H or alkyl conversion to dihydropyrazole →

S reaction with isocyanate ↓ coupling with compound B ←

C

Another approach to the preparation of invention compounds wherein $X^{II}$ in

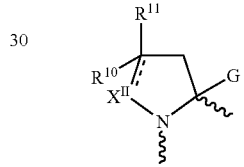

(c.f., Formulas II-X), is N and " - - - " is a bond is provided in Scheme 5.3. The synthetic routes commences with formation of acrylamide U as disclosed in Scheme 5.1. A diazoacetate such as ethyl diazoacetate is then mixed with acrylamide U to afford the appropriately substituted dihydropyrazole V. Similar chemistry to that described in Scheme 5.1 allows conversion of V to W. Reduction of the ester moiety in W is then achieved using a reducing agent such as super-hydride to afford the hydroxyl containing invention compound X.

Scheme 5.3

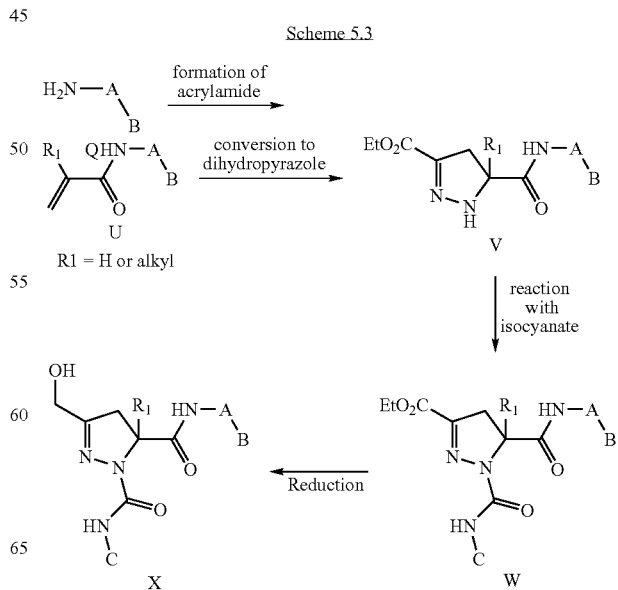

Alternatively, invention compounds wherein $X^{II}$ in

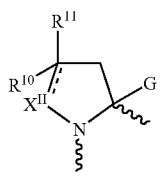

(c.f., Formulas II-X), is N and "- - -" is a bond is provided in Scheme 5.4. Here, the acrylic ester Y is reacted with a diazocompound to form the dihydropyrazole Z. Addition of a chloroformate affords compounds of formula AA. Deprotection of the ester is achieved by acid, such as TFA or hydrogen chloride to afford compounds of formula BB. Addition of an aniline with a coupling reagent such as EEDQ and base affords compounds of formula CC. Deprotection of the carbamate with Pd/C and hydrogen affords compounds of formula DD which may then be reacted with isocyanates to afford invention compounds of formula FF.

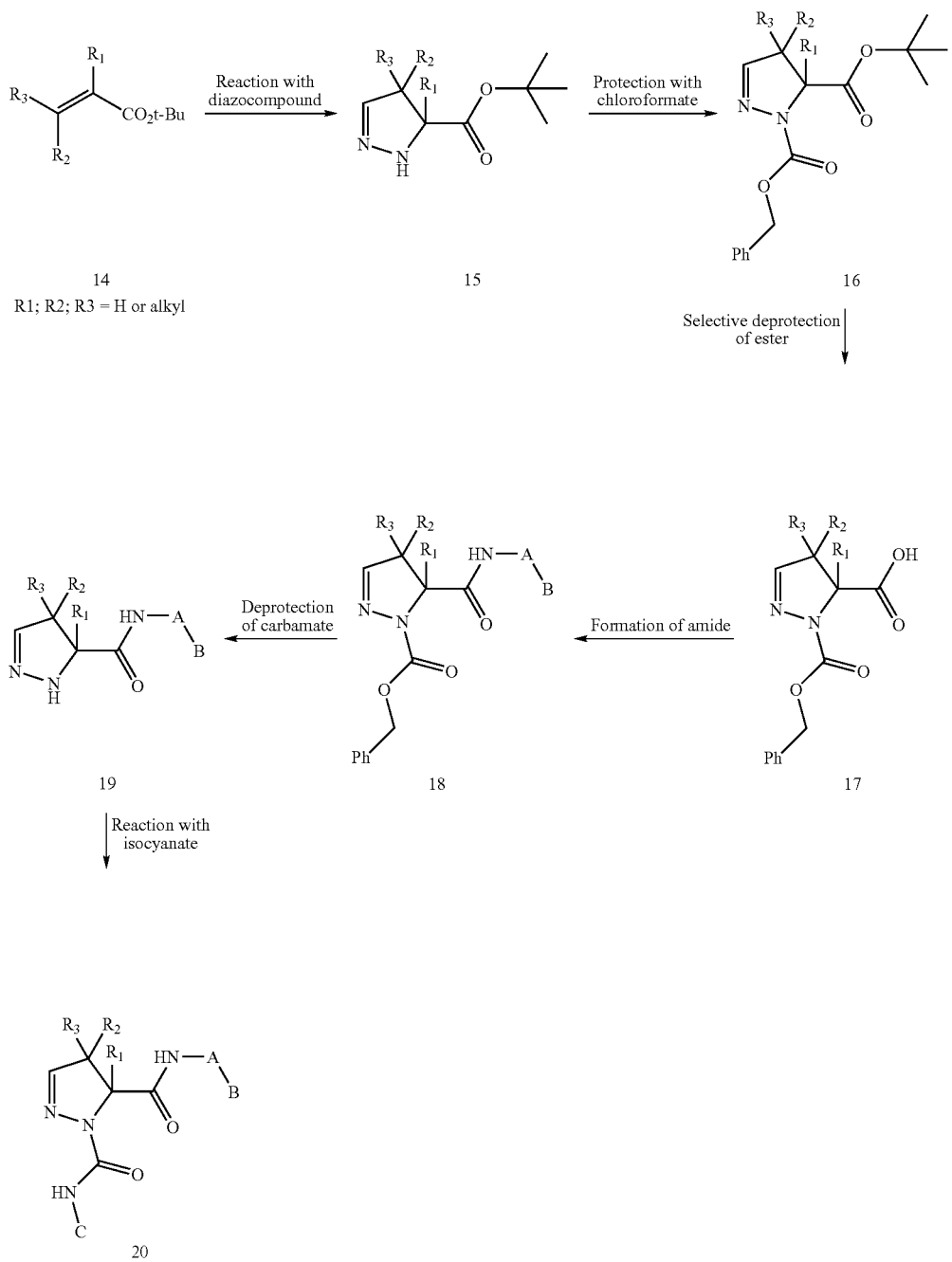

Other methods for making compounds of the invention or variations of the above Schemes are provided in the Examples section.

Not all compounds of of the invention falling into a given class may be compatible with some of the reaction conditions described. Such restrictions are readily apparent to those skilled in the art of organic synthesis, and alternative methods must then be used.

Some of the compounds of Formula I are capable of further forming pharmaceutically acceptable acid-addition and/or base salts. All of these forms are within the scope of the present invention. Thus, pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science,* 1977;66:1-19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolaamine, dicyclohexylaamine, ethylenediamine, N-methylglucamine, and procaine (see, for example, Berge S. M., supra., 1977).

The base addition salts of said acidic compounds are prepared by contacting the free acid form with a sufficient amount of the desired base to produce the salt in the conventional manner.

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms, as well as the appropriate mixtures thereof.

The compounds of Formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or Formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of Formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds of the present invention can be administered to a patient at dosage levels in the range of about 0.1 to about 2,000 mg per day. For a normal human adult having a body weight of about 70 kilograms, a dosage in the range of about 0.01 to about 10 mg per kilogram of body weight per day is preferable. However, the specific dosage used can vary. For example, the dosage can depended on a numbers of factors including the requirements of the patient, the severity of the condition being treated, and the pharmacological activity of the compound being used. The determination of optimum dosages for a particular patient is well-known to those skilled in the art.

Ideally, the active ingredient should be administered to achieve peak plasma concentrations of the active compound of from about 0.5 to about 75 µM, preferably, about 1 to 50 µM, most preferably, about 0.1 to about 5 µM. This may be achieved, for example, by the intravenous injection of a 0.05 to 5% solution of the active ingredient, optionally in saline, or orally administered as a bolus containing about 10-500 mg of the active ingredient. Desirable blood levels may be maintained by multiple oral dosing, or continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples illustrate the various embodiments of the present invention. Those skilled in the art will recognize many variations that are within the spirit of the present invention and scope of the claims.

BIOLOGICAL ASSAYS

The invention compounds have demonstrated factor Xa inhibitory activity in the standard assays commonly employed by those skilled in the art.

A. Determination of Factor Xa $IC_{50}$

The ability of compounds to act as inhibitors of human factor Xa catalytic activity is assessed by determination of that concentration of test substance that inhibits by 50% ($IC_{50}$) the ability of human factor Xa to cleave the chromogenic substrate S2765 (N—CBz-D-Arg-L-Gly-L-Arg-p-nitroanilide. 2HCl, DiaPharma). The $IC_{50}$ was determined at 3 pM and 30 pM concentrations human factor Xa (Enzyme Research Laboratories). These concentrations were achieved by diluting a 21.087 µM stock solution of factor Xa in the appropriate amount of a buffer comprising 10 µM HEPES, 150 µM NaCl, 0.1% BSA, pH 7.4 (HBSA buffer). Accordingly, 5 µL of the compound to be tested in DMSO (2% final) is added to the factor Xa/buffer solution and incubated for 60 minutes at room temperature.

The $IC_{50}$ is determined by monitoring the increase in absorbance at 390 nm exicitation, 460 nm emission, with a 455 nm cutoff, in a fluorometric plate reader. Results of the $IC_{50}$ at 3 pM and 30 pM enzyme concentrations are provided in Table 1.

TABLE 1

| EXAMPLE | FXA 3 pM IC$_{50}$ (mM) | FXA30 pM IC$_{50}$ (mM) |
|---|---|---|
| (R)-pyrrolidine-1,2-dicarboxylic acid 1-[(4-chloro-phenyl)-amide] 2-[(3-fluoro-2'-sulfamoyl-biphenyl-4-yl)-amide] | 0.0199 | 0.0270 |
| Pyrrolidine-1,2-dicarboxylic acid 1-[(4-chloro-phenyl)-amide] 2-[(3-fluoro-2'-sulfamoyl-biphenyl-4-yl)-amide] | | 0.0355 |
| Pyrrolidine-1,2-dicarboxylic acid 1-[(5-chloro-pyridin-2-yl)-amide] 2-[(3-fluoro-2'-sulfamoyl-biphenyl-4-yl)-amide] | | 0.2568 |
| Pyrrolidine-1,2-dicarboxylic acid 1-[(2,4-difluoro-phenyl)-amide] 2-[(3-fluoro-2'-sulfamoyl-biphenyl-4-yl)-amide] | | 9.1175 |
| Pyrrolidine-1,2-dicarboxylic acid 2-[(3-fluoro-2'-sulfamoyl-biphenyl-4-yl)-amide] 1-p-tolylamide | 0.3890 | |
| Pyrrolidine-1,2-dicarboxylic acid 2-[(3-fluoro-2'-sulfamoyl-biphenyl-4-yl)-amide] 1-[(4-methoxy-phenyl)-amide] | 0.8730 | |
| Pyrrolidine-1,2-dicarboxylic acid 1-[(4-bromo-phenyl)-amide] 2-[(3-fluoro-2'-sulfamoyl-biphenyl-4-yl)-amide] | 0.0333 | |
| Pyrrolidine-1,2-dicarboxylic acid 2-[(3-fluoro-2'-sulfamoyl-biphenyl-4-yl)-amide] 1-phenylamide | 0.9510 | |
| Pyrrolidine-1,2-dicarboxylic acid 1-[(3,4-difluoro-phenyl)-amide] 2-[(3-fluoro-2'-sulfamoyl-biphenyl-4-yl)-amide] | 0.6460 | |
| Pyrrolidine-1,2-dicarboxylic acid 1-[(3-fluoro-4-methyl-phenyl)-amide] 2-[(3-fluoro-2'-sulfamoyl-biphenyl-4-yl)-amide] | 0.5150 | |
| Pyrrolidine-1,2-dicarboxylic acid 1-[(5-chloro-pyridin-2-yl)-amide] 2-[(3-fluoro-2'-methanesulfonyl-biphenyl-4-yl)-amide] | 0.0804 | |
| Pyrrolidine-1,2-dicarboxylic acid 1-[(4-chloro-phenyl)-amide] 2-[(3-fluoro-2'-methanesulfonyl-biphenyl-4-yl)-amide] | 0.0172 | |
| Pyrrolidine-1,2-dicarboxylic acid 1-[(4-chloro-phenyl)-amide] 2-{[5-(2-sulfamoyl-phenyl)-pyridin-2-yl]-amide} | 0.0730 | |
| Pyrrolidine-1,2-dicarboxylic acid 2-[(3-chloro-2'-methanesulfonyl-biphenyl-4-yl)-amide] 1-[(5-chloro-pyridin-2-yl)-amide] | 0.1010 | |
| Pyrrolidine-1,2-dicarboxylic acid 2-[(3-chloro-2'-methanesulfonyl-biphenyl-4-yl)-amide] 1-[(4-chloro-phenyl)-amide] | 0.0166 | |
| Pyrrolidine-1,2-dicarboxylic acid 1-[(5-chloro-pyridin-2-yl)-amide] 2-{[5-(2-sulfamoyl-phenyl)-pyridin-2-yl]-amide} | 0.2770 | |
| (2R,4R)-4-Hydroxy-pyrrolidine-1,2-dicarboxylic acid 1-[(4-chloro-phenyl)-amide] 2-[(3-fluoro-2'-methanesulfonyl-biphenyl-4-yl)-amide] | 0.0007 | |
| Pyrrolidine-1,2-dicarboxylic acid 1-[(4-chloro-phenyl)-amide] 2-{[4-(1-methyl-4,5-dihydro-1H-imidazol-2-yl)-phenyl]-amide} | 0.1560 | |
| Pyrrolidine-1,2-dicarboxylic acid 1-[(4-chloro-phenyl)-amide] 2-[(2'-methanesulfonyl-biphenyl-4-yl)-amide] | 0.0273 | |
| Pyrrolidine-1,2-dicarboxylic acid 1-[(4-chloro-phenyl)-amide] 2-[(2'-methanesulfonyl-3-methyl-biphenyl-4-yl)-amide] | 0.0591 | |
| (2R,4R)-4-methoxy-pyrrolidine-1,2-dicarboxylic acid 1-[(4-chloro-phenyl)-amide] 2-[(3-fluoro-2'-methanesulfonyl-biphenyl-4-yl)-amide] | 0.000374833 | |
| (2R)-4-oxo-pyrrolidine-1,2-dicarboxylic acid 1-[(4-chloro-phenyl)-amide] 2-[(3-fluoro-2'-methanesulfonyl-biphenyl-4-yl)-amide] | 0.007596667 | |
| (2R,4S)-4-Fluoro-pyrrolidine-1,2-dicarboxylic acid 1-[(4-chloro-phenyl)-amide]-2-[(3-fluoro-2'-methanesulfonyl-biphenyl-4-yl)-amide] | 0.004443333 | |
| (2R,4R)-4-Hydroxy-pyrrolidine-1,2-dicarboxylic acid 2-[(3-fluoro-2'-methanesulfonyl-biphenyl-4-yl)-amide] 1-p-tolylamide | 0.01065 | |
| (2R,4R)-4-Hydroxy-pyrrolidine-1,2-dicarboxylic acid 2-[(3-fluoro-2'-methanesulfonyl-biphenyl-4-yl)-amide] 1-[(4-fluoro-phenyl)-amide] | 0.0028575 | |
| (2R,4R)-4-Hydroxy-pyrrolidine-1,2-dicarboxylic acid 1-[(5-chloro-pyridin-2-yl)-amide] 2-[(3-fluoro-2'-methanesulfonyl-biphenyl-4-yl)-amide] | 0.0071125 | |

TABLE 1-continued

| EXAMPLE | FXA 3 pM IC$_{50}$ (mM) | FXA30 pM IC$_{50}$ (mM) |
|---|---|---|
| Pyrrolidine-1,2-dicarboxylic acid 1-[(4-chloro-phenyl)-amide] 2-[(2'-methanesulfonyl-3-trifluoromethyl-biphenyl-4-yl)-amide] | 0.0806 | |
| (2R,4R)-4-Methoxy-pyrrolidine-1,2-dicarboxylic acid 1-[(4-chloro-phenyl)-amide] 2-{[2-fluoro-4-(2-oxo-piperidin-1-yl)-phenyl]-amide} | | 0.0014 |
| (2R,4R)-4-Hydroxy-pyrrolidine-1,2-dicarboxylic acid 1-[(4-chloro-phenyl)-amide] 2-{[4-(2-oxo-piperidin-1-yl)-phenyl]-amide} | | |
| (2R,4R)-4-Hydroxy-pyrrolidine-1,2-dicarboxylic acid 1-[(4-chloro-phenyl)-amide] 2-{[2-fluoro-4-(2-oxo-piperidin-1-yl)-phenyl]-amide} | 0.0025 | |
| (2R,4R)-4-Hydroxy-pyrrolidine-1,2-dicarboxylic acid 1-[(5-chloro-pyridin-2-yl)-amide] 2-{[2-fluoro-4-(2-oxo-piperidin-1-yl)-phenyl]-amide} | | 0.0041 |
| (2R,4R)-4-Methoxy-pyrrolidine-1,2-dicarboxylic acid 1-[(5-chloro-pyridin-2-yl)-amide] 2-{[2-fluoro-4-(2-oxo-piperidin-1-yl)-phenyl]-amide} | | 0.0149 |
| (2R,4R)-4-Ethoxy-pyrrolidine-1,2-dicarboxylic acid 1-[(5-chloro-pyridin-2-yl)-amide] 2-{[2-fluoro-4-(2-oxo-piperidin-1-yl)-phenyl]-amide} | | 0.0084 |
| (2R,4R)-4-Ethoxy-pyrrolidine-1,2-dicarboxylic acid 1-[(4-chloro-phenyl)-amide] 2-{[2-fluoro-4-(2-oxo-piperidin-1-yl)-phenyl]-amide} | | 0.0045 |
| (2R,4R)-4-Propoxy-pyrrolidine-1,2-dicarboxylic acid 1-[(4-chloro-phenyl)-amide] 2-{[2-fluoro-4-(2-oxo-piperidin-1-yl)-phenyl]-amide} | | 0.0008 |
| (2R,4R)-4-Propoxy-pyrrolidine-1,2-dicarboxylic acid 1-[(5-chloro-pyridin-2-yl)-amide] 2-{[2-fluoro-4-(2-oxo-piperidin-1-yl)-phenyl]-amide} | | 0.0020 |
| (2R,4R)-4-Cyano-pyrrolidine-1,2-dicarboxylic acid 1-[(4-chloro-phenyl)-amide] 2-{[2-fluoro-4-(2-oxo-piperidin-1-yl)-phenyl]-amide} | | 0.0050 |
| (2R,4R)-4-Fluoro-pyrrolidine-1,2-dicarboxylic acid 1-[(4-chloro-phenyl)-amide] 2-{[2-fluoro-4-(2-oxo-piperidin-1-yl)-phenyl]-amide} | | 0.0510 |
| (2R,4R)-4-Methoxy-pyrrolidine-1,2-dicarboxylic acid 1-[(4-chloro-phenyl)-amide] 2-{[2-fluoro-4-(2-oxo-azetidin-1-yl)-phenyl]-amide} | | 0.0110 |
| (2R,4R)-4-Methoxy-pyrrolidine-1,2-dicarboxylic acid 1-[(5-chloro-pyridin-2-yl)-amide] 2-{[2-fluoro-4-(2-oxo-azetidin-1-yl)-phenyl]-amide} | | 0.1223 |
| (2R,4R)-4-Methoxy-pyrrolidine-1,2-dicarboxylic acid 1-[(5-chloro-pyridin-2-yl)-amide] 2-{[2-fluoro-4-(2-oxo-azetidin-1-yl)-phenyl]-amide} | | 54% at 1 uM |
| (2R,4R)-4-Methoxy-pyrrolidine-1,2-dicarboxylic acid 1-[(5-chloro-pyridin-2-yl)-amide] 2-{[2-fluoro-4-(2-oxo-pyrrolidin-1-yl)-phenyl]-amide} | | 0.0040 |
| (2R,4R)-4-Methoxy-pyrrolidine-1,2-dicarboxylic acid 1-[(4-chloro-phenyl)-amide] 2-{[2-fluoro-4-(2-oxo-azepan-1-yl)-phenyl]-amide} | | 0.0294 |
| (2R,4R)-4-Methoxy-pyrrolidine-1,2-dicarboxylic acid 1-[(5-chloro-pyridin-2-yl)-amide] 2-{[2-fluoro-4-(2-oxo-azepan-1-yl)-phenyl]-amide} | | 0.0041 |
| (2R,4R)-4-Methoxy-pyrrolidine-1,2-dicarboxylic acid 1-[(5-chloro-pyridin-2-yl)-amide] 2-{[4-(2-oxo-2H-pyridin-1-yl)-phenyl]-amide} | | 0.0300 |
| (2R,4R)-4-Methoxy-pyrrolidine-1,2-dicarboxylic acid 1-[(4-chloro-phenyl)-amide] 2-{[4-(2-oxo-2H-pyridin-1-yl)-phenyl]-amide} | | 0.0013 |
| (2R,4R)-4-Ethoxy-pyrrolidine-1,2-dicarboxylic acid 1-[(4-chloro-phenyl)-amide] 2-{[2-fluoro-4-(2-oxo-2H-pyridin-1-yl)-phenyl]-amide} | | 0.0004 |
| (2R,4R)-4-Ethoxy-pyrrolidine-1,2-dicarboxylic acid 1-[(5-chloro-pyridin-2-yl)-amide] 2-{[2-fluoro-4-(2-oxo-2H-pyridin-1-yl)-phenyl]-amide} | | TBD |
| (2R,4R)-4-Methoxy-pyrrolidine-1,2-dicarboxylic acid 1-[(4-chloro-phenyl)-amide] 2-{[2-fluoro-4-(2-hydroxymethyl-5-oxo-pyrrolidin-1-yl)-phenyl]-amide} | | TBD |
| (2R,4R)-4-Hydroxy-pyrrolidine-1,2-dicarboxylic acid 1-[(4-chloro-phenyl)-amide] 2-{[4-(2,3-dimethyl-5-oxo-2,5-dihydro-pyrazol-1-yl)-phenyl]-amide} | | 0.2560 |
| 4-Hydroxy-pyrrolidine-1,2-dicarboxylic acid 1-[(4-chloro-phenyl)-amide] 2-{[4-(2-hydroxymethyl-pyrrolidin-1-yl)-phenyl]-amide} | | 0.0110 |

TABLE 1-continued

| EXAMPLE | FXA 3 pM IC$_{50}$ (mM) | FXA30 pM IC$_{50}$ (mM) |
|---|---|---|
| (2R,4R)-4-Hydroxy-pyrrolidine-1,2-dicarboxylic acid 1-[(4-chloro-phenyl)-amide] 2-[(4-pyrrolidin-1-yl-phenyl)-amide] | | 0.0640 |
| (2R,4R)-4-Hydroxy-pyrrolidine-1,2-dicarboxylic acid 1-[(4-chloro-phenyl)-amide] 2-[(4-pyrazol-1-yl-phenyl)-amide] | 0.0344 | |
| (2R,4R)-4-Hydroxy-pyrrolidine-1,2-dicarboxylic acid 1-[(4-chloro-phenyl)-amide] 2-[(2-fluoro-4-pyrazol-1-yl-phenyl)-amide] | | 0.0434 |
| (2R,4R)-4-Hydroxy-pyrrolidine-1,2-dicarboxylic acid 1-[(4-chloro-phenyl)-amide] 2-[(4-[1,2,4]triazol-1-yl-phenl)-amide] | | 0.0619 |
| (2R,4R)-4-Hydroxy-pyrrolidine-1,2-dicarboxylic acid 1-[(4-chloro-phenyl)-amide] 2-[(4-[1,2,3]triazol-2-yl-phenyl)-amide] | | 0.1903 |
| (2R,4R)-4-Hydroxy-pyrrolidine-1,2-dicarboxylic acid 1-[(4-chloro-phenyl)-amide] 2-[(4-[1,2,3]triazol-1-yl-phenyl)-amide] | | 26% at 1 uM |
| (2R,4R)-4-Hydroxy-pyrrolidine-1,2-dicarboxylic acid 2-[(4-acetylamino-phenyl)-amide] 1-[(4-chloro-phenyl)-amide] | | 0.0793 |
| (2R,4R)-4-Hydroxy-pyrrolidine-1,2-dicarboxylic acid 1-[(4-chloro-phenyl)-amide] 2-{[4-(cyclopentanecarbonyl-amino)-phenyl]-amide} | | 36% at 1 uM |
| 4-Hydroxy-pyrrolidine-1,2-dicarboxylic acid 1-[(4-chloro-phenyl)-amide] 2-[(4-pyrimidin-5-yl-phenyl)-amide] | | 32% at 1 uM |
| (2R,4R)-4-Methoxy-pyrrolidine-1,2-dicarboxylic acid 1-[(4-chloro-phenyl)-amide] 2-[(4-pyrazol-1-yl-phenyl)-amide] | | 0.041000 |
| (2R,4R)-4-Methoxy-pyrrolidine-1,2-dicarboxylic acid 1-[(4-chloro-phenyl)-amide] 2-[(2-fluoro-4-pyrazol-1-yl-phenyl)-amide] | | 0.032000 |
| (2R,4R)-4-Ethoxy-pyrrolidine-1,2-dicarboxylic acid 1-[(4-chloro-phenyl)-amide] 2-[(2-fluoro-4-pyrazol-1-yl-phenyl)-amide] | | 0.029000 |
| (2R,4R)-4-Ethoxy-pyrrolidine-1,2-dicarboxylic acid 1-[(4-chloro-phenyl)-amide] 2-[(4-pyrazol-1-yl-phenyl)-amide] | | 0.018000 |
| (2R,4R)-4-Methoxy-pyrrolidine-1,2-dicarboxylic acid 1-[(4-chloro-phenyl)-amide] 2-{[2-fluoro-4-(3-methyl-pyrazol-1-yl)-phenyl]-amide} | | 0.082000 |
| (2R,4R)-4-Hydroxy-pyrrolidine-1,2-dicarboxylic acid 1-[(4-chloro-phenyl)-amide] 2-{[2-fluoro-4-(5-methyl-pyrazol-1-yl)-phenyl]-amide} | | 0.021000 |
| (2R,4R)-4-Methoxy-pyrrolidine-1,2-dicarboxylic acid 1-[(4-chloro-phenyl)-amide] 2-{[2-fluoro-4-(5-methyl-pyrazol-1-yl)-phenyl]-amide} | | 0.009600 |
| (2R,4R)-4-Methoxy-pyrrolidine-1,2-dicarboxylic acid 1-[(4-chloro-phenyl)-amide] 2-{[4-(5-methyl-pyrazol-1-yl)-phenyl]-amide} | | 0.015000 |
| (2R,4R)-4-Hydroxy-pyrrolidine-1,2-dicarboxylic acid 1-[(4-chloro-phenyl)-amide] 2-{[4-(3,5-dimethyl-pyrazol-1-yl)-phenyl]-amide} | | 0.049000 |
| (2R,4R)-4-Methoxy-pyrrolidine-1,2-dicarboxylic acid 1-[(4-chloro-phenyl)-amide] 2-{[4-(3,5-dimethyl-pyrazol-1-yl)-phenyl]-amide} | | 0.020000 |
| (2R,4R)-4-Methoxy-pyrrolidine-1,2-dicarboxylic acid 1-[(4-chloro-phenyl)-amide] 2-{[4-(3,5-dimethyl-pyrazol-1-yl)-2-fluoro-phenyl]-amide} | | 0.010000 |
| (2R,4S)-4-Amino-pyrrolidine-1,2-dicarboxylic acid 1-[(4-chloro-phenyl)-amide] 2-[(3-fluoro-2'-methanesulfonyl-biphenyl-4-yl)-amide] | | 0.010000 |
| (2R,4R)-4-Amino-pyrrolidine-1,2-dicarboxylic acid 1-[(4-chloro-phenyl)-amide] 2-[(3-fluoro-2'-methanesulfonyl-biphenyl-4-yl)-amide] | | 0.025925 |
| (2R,4R)-4-Hydroxy-pyrrolidine-1,2-dicarboxylic acid 1-[(4-chloro-phenyl)-amide] 2-[(3-fluoro-2'-sulfamoyl-biphenyl-4-yl)-amide] | | 0.000770 |
| (2R)-4-Hydroxyimino-pyrrolidine-1,2-dicarboxylic acid 1-[(4-chloro-phenyl)-amide] 2-[(3-fluoro-2'-methanesulfonyl-biphenyl-4-yl)-amide] | | 0.002108 |
| (2R,4R)-4-Hydroxy-pyrrolidine-1,2-dicarboxylic acid 1-[(4-chloro-phenyl)-amide] 2-[(3-fluoro-2'-methylsulfamoyl-biphenyl-4-yl)-amide] | | 0.001922 |

TABLE 1-continued

| EXAMPLE | FXA 3 pM IC$_{50}$ (mM) | FXA30 pM IC$_{50}$ (mM) |
|---|---|---|
| (2R,4R)-4-Hydroxy-pyrrolidine-1,2-dicarboxylic acid 1-[(4-chloro-phenyl)-amide] 2-[(2'-dimethylsulfamoyl-3-fluoro-biphenyl-4-yl)-amide] | | 0.001188 |
| (2R,4R)-4-Methoxy-pyrrolidine-1,2-dicarboxylic acid 1-[(5-chloro-pyridin-2-yl)-amide] 2-[(3-fluoro-2'-methanesulfonyl-biphenyl-4-yl)-amide] | | 0.001021 |
| (2R,4R)-4-Methoxy-pyrrolidine-1,2-dicarboxylic acid 1-[(4-chloro-phenyl)-amide] 2-[(3-fluoro-2'-sulfamoyl-biphenyl-4-yl)-amide] | | 0.000491 |
| (2R,4R)-4-Ethoxy-pyrrolidine-1,2-dicarboxylic acid 1-[(5-chloro-pyridin-2-yl)-amide] 2-[(3-fluoro-2'-methanesulfonyl-biphenyl-4-yl)-amide] | | 0.000701 |
| (2R,4R)-4-Ethoxy-pyrrolidine-1,2-dicarboxylic acid 1-[(4-chloro-phenyl)-amide] 2-[(3-fluoro-2'-sulfamoyl-biphenyl-4-yl)-amide] | | 0.000276 |
| (2R,4S)-4-Methoxy-pyrrolidine-1,2-dicarboxylic acid 1-[(4-chloro-phenyl)-amide] 2-[(3-fluoro-2'-methanesulfonyl-biphenyl-4-yl)-amide] | | 0.001685 |
| (2R,4R)-4-Fluoro-pyrrolidine-1,2-dicarboxylic acid 1-[(4-chloro-phenyl)-amide] 2-[(3-fluoro-2'-methanesulfonyl-biphenyl-4-yl)-amide] | | 0.001200 |
| (2R)-4,4-Difluoro-pyrrolidine-1,2-dicarboxylic acid 1-[(4-chloro-phenyl)-amide] 2-[(3-fluoro-2'-methanesulfonyl-biphenyl-4-yl)-amide] | | 0.005360 |
| (2R,4R)-4-Methoxy-pyrrolidine-1,2-dicarboxylic acid 2-[(3-fluoro-2'-methanesulfonyl-biphenyl-4-yl)-amide] 1-[(4-fluoro-phenyl)-amide] | | 0.001873 |
| (2R,4R)-4-Acetylamino-pyrrolidine-1,2-dicarboxylic acid 1-[(4-chloro-phenyl)-amide] 2-[(3-fluoro-2'-methanesulfonyl-biphenyl-4-yl)-amide] | | 0.010545 |
| (2R,4R)-4-Methanesulfonylamino-pyrrolidine-1,2-dicarboxylic acid 1-[(4-chloro-phenyl)-amide] 2-[(3-fluoro-2'-methanesulfonyl-biphenyl-4-yl)-amide] | | 0.001735 |
| (2R,4S)-4-(1H-Tetrazol-5-yl)-pyrrolidine-1,2-dicarboxylic acid 1-[(4-chloro-phenyl)-amide] 2-{[2-fluoro-4-(2-oxo-piperidin-1-yl)-phenyl]-amide} | | 0.038850 |
| (2R,4S)-4-Methoxy-pyrrolidine-1,2-dicarboxylic acid 1-[(4-chloro-phenyl)-amide] 2-{[2-fluoro-4-(2-oxo-piperidin-1-yl)-phenyl]-amide} | | 0.011770 |
| (2R,4R)-4-Methoxy-pyrrolidine-1,2-dicarboxylic acid 1-[(4-chloro-phenyl)-amide] 2-{[2-fluoro-4-(2-methyl-imidazol-1-yl)-phenyl]-amide} | | 0.006210 |
| (2R,4R)-4-Cyano-pyrrolidine-1,2-dicarboxylic acid 1-[(4-chloro-phenyl)-amide] 2-{[2-fluoro-4-(2-oxo-piperidin-1-yl)-phenyl]-amide} | | 0.055475 |
| (2R,4R)-4-(1H-Tetrazol-5-yl)-pyrrolidine-1,2-dicarboxylic acid 1-[(4-chloro-phenyl)-amide] 2-{[2-fluoro-4-(2-oxo-piperidin-1-yl)-phenyl]-amide} | | 0.007973 |
| (2R,4R)-4-Trifluoromethyl-pyrrolidine-1,2-dicarboxylic acid 1-[(4-chloro-phenyl)-amide] 2-{[2-fluoro-4-(2-oxo-piperidin-1-yl)-phenyl]-amide} | | 0.032950 |
| (2R,4R)-4-Methoxy-pyrrolidine-1,2-dicarboxylic acid 1-[(4-chloro-phenyl)-amide] 2-[(2'-cyano-3-fluoro-biphenyl-4-yl)-amide] | | 0.001950 |
| (2R,4R)-4-Methoxy-pyrrolidine-1,2-dicarboxylic acid 2-[(2'-aminomethyl-3-fluoro-biphenyl-4-yl)-amide] 1-[(4-chloro-phenyl)-amide] | | 0.001633 |
| (2R,4R)-4'-{[1-(4-Chloro-phenylcarbamoyl)-4-methoxy-pyrrolidine-2-carbonyl]-amino}-3'-fluoro-biphenyl-2-carboxylic acid methyl ester | | 0.007112 |
| (2R,4R)-4-Methoxy-pyrrolidine-1,2-dicarboxylic acid 1-[(4-chloro-phenyl)-amide] 2-{[4-(2,5-dihydro-pyrrole-1-carbonyl)-phenyl]-amide} | | 0.00029 |
| (2R,4R)-4-Hydroxy-pyrrolidine-1,2-dicarboxylic acid 1-[(4-chloro-phenyl)-amide] 2-[(4-dimethylcarbamoyl-2-fluoro-phenyl)-amide] | | 0.015 |
| (2R,4R)-4-Hydroxy-pyrrolidine-1,2-dicarboxylic acid 1-[(4-chloro-phenyl)-amide] 2-{[4-(pyrrolidine-1-carbonyl)-phenyl]-amide} | | 0.0081 |
| Pyrrolidine-1,2-dicarboxylic acid 1-[(4-chloro-phenyl)-amide] 2-{[4-(pyrrolidine-1-carbonyl)-phenyl]-amide} | | 0.081 |
| (2R,4R)-4-Hydroxy-pyrrolidine-1,2-dicarboxylic acid 1-[(4-chloro-phenyl)-amide] 2-{[4-(2-methyl-pyrrolidine-1-carbonyl)-phenyl]-amide} | | 0.024 |

TABLE 1-continued

| EXAMPLE | FXA 3 pM IC$_{50}$ (mM) | FXA 30 pM IC$_{50}$ (mM) |
|---|---|---|
| (2R,4R)-4-Hydroxy-pyrrolidine-1,2-dicarboxylic acid 1-[(4-chloro-phenyl)-amide] 2-{[4-(ethyl-methyl-carbamoyl)-phenyl]-amide} | | 0.037 |
| (2R,4R)-4-Hydroxy-pyrrolidine-1,2-dicarboxylic acid 1-[(4-chloro-phenyl)-amide] 2-[(4-dimethylcarbamoyl-phenyl)-amide] | | 0.010 |
| (2R,4R)-4-Hydroxy-pyrrolidine-1,2-dicarboxylic acid 1-[(4-chloro-phenyl)-amide] 2-{[4-(2R-methyl-pyrrolidine-1-carbonyl)-phenyl]-amide} | | 0.011 |
| (2R,4R)-4-Hydroxy-pyrrolidine-1,2-dicarboxylic acid 1-[(4-chloro-phenyl)-amide] 2-{[4-(2S-methyl-pyrrolidine-1-carbonyl)-phenyl]-amide} | | 0.082 |
| (2R,4R)-4-Hydroxy-pyrrolidine-1,2-dicarboxylic acid 1-[(4-chloro-phenyl)-amide] 2-{[2-fluoro-4-(pyrrolidine-1-carbonyl)-phenyl]-amide} | | 0.0096 |
| (2R,4R)-4-Hydroxy-pyrrolidine-1,2-dicarboxylic acid 1-[(4-chloro-phenyl)-amide] 2-{[4-(pyrrolidine-1-carbonyl)-2-pyrrolidin-1-yl-phenyl]-amide} | | 0.035 |
| (2R,4R)-4-{[1-(4-Chloro-phenylcarbamoyl)-4-hydroxy-pyrrolidine-2-carbonyl]-amino}-3-pyrrolidin-1-yl-benzoic acid methyl ester | | 0.020 |
| (2R,4R)-4-Hydroxy-pyrrolidine-1,2-dicarboxylic acid 2-{[4-(azetidine-1-carbonyl)-phenyl]-amide} 1-[(4-chloro-phenyl)-amide] | | 0.061 |
| (2R,4R)-4-Hydroxy-pyrrolidine-1,2-dicarboxylic acid 1-[(5-chloro-pyridin-2-yl)-amide] 2-{[2-fluoro-4-(pyrrolidine-1-carbonyl)-phenyl]-amide} | | 0.084 |
| (2R,4R)-4-Hydroxy-pyrrolidine-1,2-dicarboxylic acid 1-[(5-chloro-pyridin-2-yl)-amide] 2-{[4-(pyrrolidine-1-carbonyl)-phenyl]-amide} | | 0.081 |
| (2R,4R)-4-Hydroxy-pyrrolidine-1,2-dicarboxylic acid 1-[(5-chloro-pyridin-2-yl)-amide] 2-[(4-dimethylcarbamoyl-phenyl)-amide] | | 0.044 |
| (2R,4R)-4-{[1-(4-Chloro-phenylcarbamoyl)-4-hydroxy-pyrrolidine-2-carbonyl]-amino}-3-dimethylamino-benzoic acid methyl ester | | 0.029 |
| (2R,4R)-4-Methoxy-pyrrolidine-1,2-dicarboxylic acid 1-[(4-chloro-phenyl)-amide] 2-{[4-(pyrrolidine-1-carbonyl)-phenyl]-amide} | | 0.0073 |
| (2R,4R)-4-Methoxy-pyrrolidine-1,2-dicarboxylic acid 1-[(4-chloro-phenyl)-amide] 2-[(4-dimethylcarbamoyl-phenyl)-amide] | | 0.0049 |
| (2R,4R)-4-Ethoxy-pyrrolidine-1,2-dicarboxylic acid 1-[(4-chloro-phenyl)-amide] 2-{[4-(pyrrolidine-1-carbonyl)-phenyl]-amide} | | 0.0057 |
| (2R,4R)-4-Ethoxy-pyrrolidine-1,2-dicarboxylic acid 1-[(4-chloro-phenyl)-amide] 2-[(4-dimethylcarbamoyl-phenyl)-amide] | | 0.0039 |
| (2R,4R)-4-Methoxy-pyrrolidine-1,2-dicarboxylic acid 1-[(4-chloro-phenyl)-amide] 2-{[2-fluoro-4-(pyrrolidine-1-carbonyl)-phenyl]-amide} | | 0.0062 |
| (2R,4R)-4-Methoxy-pyrrolidine-1,2-dicarboxylic acid 1-[(4-chloro-phenyl)-amide] 2-[(4-dimethylcarbamoyl-2-fluoro-phenyl)-amide] | | 0.0061 |
| (2R,4R)-4-Ethoxy-pyrrolidine-1,2-dicarboxylic acid 1-[(4-chloro-phenyl)-amide] 2-{[2-fluoro-4-(pyrrolidine-1-carbonyl)-phenyl]-amide} | | 0.0044 |
| (2R,4R)-4-Ethoxy-pyrrolidine-1,2-dicarboxylic acid 1-[(4-chloro-phenyl)-amide] 2-[(4-dimethylcarbamoyl-2-fluoro-phenyl)-amide] | | 0.0029 |
| (2R,4R)-4-Methoxy-pyrrolidine-1,2-dicarboxylic acid 1-[(4-chloro-phenyl)-amide] 2-{[2-methyl-4-(2-oxo-piperidin-1-yl)-phenyl]-amide} | | 0.0052 |
| (2R,4R)-4-Ethoxy-pyrrolidine-1,2-dicarboxylic acid 1-[(4-chloro-phenyl)-amide] 2-{[2-methyl-4-(2-oxo-piperidin-1-yl)-phenyl]-amide} | | 0.0020 |
| Pyrrolidine-1,2-dicarboxylic acid 1-[(4-chloro-phenyl)-amide] 2-[(2-fluoro-4-quinolin-8-yl-phenyl)-amide] | | 0.066 |
| Pyrrolidine-1,2-dicarboxylic acid 1-[(4-chloro-phenyl)-amide] 2-[(3,5-difluoro-2'-methanesulfonyl-biphenyl-4-yl)-amide] | | 0.0098 |
| Pyrrolidine-1,2-dicarboxylic acid 1-[(4-chloro-phenyl)-amide] 2-[(2'-methanesulfonyl-2-methyl-biphenyl-4-yl)-amide] | | 0.018 |

TABLE 1-continued

| EXAMPLE | FXA 3 pM IC$_{50}$ (mM) | FXA 30 pM IC$_{50}$ (mM) |
|---|---|---|
| (2R,4R)-4-Hydroxy-pyrrolidine-1,2-dicarboxylic acid 1-[(4-chloro-phenyl)-amide] 2-[(2'-methanesulfonyl-biphenyl-4-yl)-amide] | | 0.00073 |
| (2R,4R)-4-Hydroxy-pyrrolidine-1,2-dicarboxylic acid 1-[(4-chloro-phenyl)-amide] 2-[(2'-methanesulfinyl-biphenyl-4-yl)-amide] | | 0.0039 |
| (2R,4R)-4-Hydroxy-pyrrolidine-1,2-dicarboxylic acid 1-[(4-chloro-phenyl)-amide] 2-[(3-methyl-2'-methylsulfanyl-biphenyl-4-yl)-amide] | | 0.053 |
| (2R,4R)-4-Hydroxy-pyrrolidine-1,2-dicarboxylic acid 1-[(4-chloro-phenyl)-amide] 2-[(2-fluoro-2'-methanesulfonyl-biphenyl-4-yl)-amide] | | 0.0012 |
| (2R,4R)-4-Hydroxy-pyrrolidine-1,2-dicarboxylic acid 1-[(4-chloro-phenyl)-amide] 2-[(2'-methanesulfonyl-3-methyl-biphenyl-4-yl)-amide] | | 0.00068 |
| (2R,4R)-4-Hydroxy-pyrrolidine-1,2-dicarboxylic acid 1-[(4-chloro-phenyl)-amide] 2-[(2'-methanesulfonyl-3-trifluoromethyl-biphenyl-4-yl)-amide] | | 0.0015 |
| 5-Methyl-4,5-dihydro-pyrazole-1,5-dicarboxylic acid 1-[(4-chloro-phenyl)-amide] 5-[(3-fluoro-2'-sulfamoyl-biphenyl-4-yl)-amide] | | 0.005623 |
| 3-Hydroxymethyl-4,5-dihydro-pyrazole-1,5-dicarboxylic acid 1-[(4-chloro-phenyl)-amide] 5-[(3-fluoro-2'-methanesulfonyl-biphenyl-4-yl)-amide] | | 0.011267 |
| 4,5-Dihydro-pyrazole-1,5-dicarboxylic acid 1-[(4-chloro-phenyl)-amide] 5-[(3-fluoro-2'-sulfamoyl-biphenyl-4-yl)-amide] | | 0.008015 |
| (R) 4,5-Dihydro-pyrazole-1,5-dicarboxylic acid 1-[(4-chloro-phenyl)-amide] 5-[(3-fluoro-2'-sulfamoyl-biphenyl-4-yl)-amide] | | 0.007738 |
| 4,5-Dihydro-pyrazole-1,5-dicarboxylic acid 1-[(4-chloro-phenyl)-amide] 5-{[2-fluoro-4-(2-oxo-piperidin-1-yl)-phenyl]-amide} | | 0.044850 |
| 4,5-Dihydro-pyrazole-1,5-dicarboxylic acid 1-[(4-chloro-phenyl)-amide] 5-[(3-fluoro-2'-methanesulfonyl-biphenyl-4-yl)-amide] | | 0.008718 |
| 1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester | | 0.040850 |
| (2R,4R)-4-Hydroxy-pyrrolidine-1,2-dicarboxylic acid 1-[(4-chloro-phenyl)-amide] 2-[(2'-methoxy-biphenyl-4-yl)-amide] | | 0.058900 |
| (2R,4R)-4-Hydroxy-pyrrolidine-1,2-dicarboxylic acid 1-[(4-chloro-phenyl)-amide] 2-[(2'-hydroxy-biphenyl-4-yl)-amide] | | 0.074100 |
| (2R,4R)-4-Methoxy-pyrrolidine-1,2-dicarboxylic acid 1-[(4-chloro-phenyl)-amide] 2-[(2-fluoro-4-iodo-phenyl)-amide] | | 0.058575 |
| (2R,4R)-4-Methoxy-pyrrolidine-1,2-dicarboxylic acid 1-[(4-chloro-phenyl)-amide] 2-{[2-fluoro-4-(2-oxo-2H-pyridin-1-yl)-phenyl]-amide} | | 0.000404 |
| (2R,4R)-4-Methoxy-pyrrolidine-1,2-dicarboxylic acid 1-[(5-chloro-pyridin-2-yl)-amide] 2-{[2-fluoro-4-(2-oxo-2H-pyridin-1-yl)-phenyl]-amide} | | 0.001153 |
| (2R,4R)-4-Methoxy-pyrrolidine-1,2-dicarboxylic acid 1-[(4-chloro-phenyl)-amide] 2-{[2-fluoro-4-(3-hydroxy-2-oxo-piperidin-1-yl)-phenyl]-amide} | | 0.008498 |
| (2R,4R)-4-Methoxy-pyrrolidine-1,2-dicarboxylic acid 1-[(4-chloro-phenyl)-amide] 2-{[2-fluoro-4-(2-oxo-tetrahydro-pyrimidin-1-yl)-phenyl]-amide} | | 0.007665 |
| (2R,4R)-4-Methoxy-pyrrolidine-1,2-dicarboxylic acid 1-[(4-chloro-phenyl)-amide] 2-{[2-fluoro-4-(2-oxo-imidazolidin-1-yl)-phenyl]-amide} | | 0.036425 |
| (2R,4R)-4-Methoxy-pyrrolidine-1,2-dicarboxylic acid 1-[(4-chloro-phenyl)-amide] 2-{[2-fluoro-4-(2-oxo-oxazolidin-3-yl)-phenyl]-amide} | | 0.045525 |
| (2R,4R)-1-(4-{[1-(4-Chloro-phenylcarbamoyl)-4-methoxy-pyrrolidine-2-carbonyl]-amino}-3-fluoro-phenyl)-2-oxo-piperidine-3-carboxylic acid ethyl ester | | 0.011000 |
| (2R,4R)-4-Methoxy-pyrrolidine-1,2-dicarboxylic acid 1-[(4-chloro-phenyl)-amide] 2-{[2-fluoro-4-(3-methoxy-2-oxo-2H-pyridin-1-yl)-phenyl]-amide} | | 0.000862 |
| (2R,4R)-4-Methoxy-pyrrolidine-1,2-dicarboxylic acid 1-[1-(5-chloro-pyridin-2-yl)-amide] 2-{[2-fluoro-4-(3-methoxy-2-oxo-2H-pyridin-1-yl)-phenyl]-amide} | | 0.005075 |

TABLE 1-continued

| EXAMPLE | FXA 3 pM IC$_{50}$ (mM) | FXA30 pM IC$_{50}$ (mM) |
|---|---|---|
| (2R,4R)-4-Methoxy-pyrrolidine-1,2-dicarboxylic acid 1-[(4-chloro-phenyl)-amide] 2-{[4-(3-methyl-2-oxo-2H-pyridin-1-yl)-phenyl]-amide} | | 0.000383 |
| (2R,4R)-4-Methoxy-pyrrolidine-1,2-dicarboxylic acid 1-[(5-chloro-pyridin-2-yl)-amide] 2-{[4-(3-methyl-2-oxo-2H-pyridin-1-yl)-phenyl]-amide} | | 0.001793 |
| (2R,4R)-4-Methoxy-pyrrolidine-1,2-dicarboxylic acid 1-[(4-chloro-phenyl)-amide] 2-[(4-morpholin-4-yl-phenyl)-amide] | | 0.043050 |
| (2R,4R)-4-Methoxy-pyrrolidine-1,2-dicarboxylic acid 1-[(4-chloro-phenyl)-amide] 2-{[4-(2-methyl-5-oxo-pyrrolidin-1-yl)-phenyl]-amide} | | 0.002303 |
| (2R,4R)-4-Methoxy-pyrrolidine-1,2-dicarboxylic acid 1-[(5-chloro-pyridin-2-yl)-amide] 2-{[4-(2-methyl-5-oxo-pyrrolidin-1-yl)-phenyl]-amide} | | 0.011975 |
| (2R,4R)-4-Methoxy-pyrrolidine-1,2-dicarboxylic acid 1-[(4-chloro-phenyl)-amide] 2-{[2-fluoro-4-(4-methyl-2-oxo-2H-pyridin-1-yl)-phenyl]-amide} | | 0.002757 |
| (2R,4R)-4-Methoxy-pyrrolidine-1,2-dicarboxylic acid 1-[(5-chloro-pyridin-2-yl)-amide] 2-{[2-fluoro-4-(4-methyl-2-oxo-2H-pyridin-1-yl)-phenyl]-amide} | | 0.012100 |
| (2R,4R)-4-Methoxy-pyrrolidine-1,2-dicarboxylic acid 1-[(4-chloro-phenyl)-amide] 2-{[2-fluoro-4-(5-methyl-2-oxo-2H-pyridin-1-yl)-phenyl]-amide} | | 0.000743 |
| (2R,4R)-4-Methoxy-pyrrolidine-1,2-dicarboxylic acid 1-[(5-chloro-pyridin-2-yl)-amide] 2-{[2-fluoro-4-(5-methyl-2-oxo-2H-pyridin-1-yl)-phenyl]-amide} | | 0.003500 |
| (2R,4R)-4-Methoxy-pyrrolidine-1,2-dicarboxylic acid 1-[(4-chloro-phenyl)-amide] 2-{[2-fluoro-4-(4-methoxy-2-oxo-2H-pyridin-1-yl)-phenyl]-amide} | | 0.002170 |
| (2R,4R)-4-Methoxy-pyrrolidine-1,2-dicarboxylic acid 1-[(5-chloro-pyridin-2-yl)-amide] 2-{[2-fluoro-4-(4-methoxy-2-oxo-2H-pyridin-1-yl)-phenyl]-amide} | | 0.004967 |
| (2R,4R)-4-Methoxy-pyrrolidine-1,2-dicarboxylic acid 1-[(4-chloro-phenyl)-amide] 2-{[2-fluoro-4-(3-methyl-2-oxo-2H-pyridin-1-yl)-phenyl]-amide} | | TBD |
| (2R,4R)-4-Methoxy-pyrrolidine-1,2-dicarboxylic acid 1-[(5-chloro-pyridin-2-yl)-amide] 2-{[2-fluoro-4-(3-methyl-2-oxo-2H-pyridin-1-yl)-phenyl]-amide} | | TBD |
| (2R,4R)-4-Methoxy-pyrrolidine-1,2-dicarboxylic acid 1-[(4-chloro-phenyl)-amide] 2-{[2-fluoro-4-(6-methyl-2-oxo-2H-pyridin-1-yl)-phenyl]-amide} | | 0.001210 |
| (2R,4R)-4-Methoxy-pyrrolidine-1,2-dicarboxylic acid 2-{[4-(5-chloro-2-oxo-2H-pyridin-1-yl)-2-fluoro-phenyl]-amide} 1-[(4-chloro-phenyl)-amide] | | TBD |
| 4-Hydroxy-pyrrolidine-1,2-dicarboxylic acid 2-[(4-tert-butyl-phenyl)-amide] 1-[(4-chloro-phenyl)-amide] | | 0.0260 |
| 4-Hydroxy-pyrrolidine-1,2-dicarboxylic acid 1-[(4-chloro-phenyl)-amide] 2[(3,5'difluoro-2'-sulfamoyl-biphenyl-4-yl)-amide] | | 0.0006 |
| 4-Methoxy-pyrrolidine-1,2-dicarboxylic acid 1-[(4-chloro-phenyl)-amide] 2-[(2-oxo-3,4,5,6-tetrahydro-2H-[1,2']bipyridinyl-5'-yl)-amide] | | 0.0650 |
| 4-Methoxy-pyrrolidine-1,2-dicarboxylic acid 1-[(4-chloro-phenyl)-amide] 2-[(2-oxo-3,4,5,6-tetrahydro-2H-[1,3']bipyridinyl-6'-yl)-amide] | | 0.0070 |
| 4-Methoxy-pyrrolidine-1,2-dicarboxylic acid 1-[(5-chloro-pyridin-2-yl)-amide] 2-{[4-(2,3-dimethyl-5-oxo-2,5-dihydro-pyrazol-1-yl)-phenyl]-amide} | | 0.0580 |
| 4-Methoxy-pyrrolidine-1,2-dicarboxylic acid 1-[(4-chloro-phenyl)-amide] 2-{[4-(2,3-dimethyl-5-oxo-2,5-dihydro-pyrazol-1-yl)-phenyl]-amide} | | 0.0800 |
| 4-Methoxy-pyrrolidine-1,2-dicarboxylic acid 1-[(4-chloro-phenyl)-amide] 2-[(2-oxo-2H-[1,3']bipyridinyl-6'-yl)-amide] | | 0.0050 |
| 4-Methoxy-pyrrolidine-1,2-dicarboxylic acid 1-[(5-chloro-pyridin-2-yl)-amide] 2-[(2-oxo-3,4,5,6-tetrahydro-2H-[1,3']bipyridinyl-6'-yl)-amide]-TFA Salt | | 0.0900 |
| 4-Ethoxy-pyrrolidine-1,2-dicarboxylic acid 1-[(4-chloro-phenyl)-amide] 2-[(2-oxo-3,4,5,6-tetrahydro-2H-[1,3']bipyridinyl-6'-yl)-amide] | | 0.0170 |
| 4-Ethoxy-pyrrolidine-1,2-dicarboxylic acid 1-[(4-chloro-phenyl)-amide] 2-[(2-oxo-2H-[1,3']bipyridinyl-6'-yl)-amide] | | 0.0030 |

TABLE 1-continued

| EXAMPLE | FXA 3 pM IC$_{50}$ (mM) | FXA30 pM IC$_{50}$ (mM) |
|---|---|---|
| 4-Methoxy-pyrrolidine-1,2-dicarboxylic acid 1-[(4-chloro-phenyl)-amide] 2-{[2-fluoro-4-(6-oxo-6H-pyridazin-1-yl)-phenyl]-amide} | | 0.0420 |

Similarly, Table 2 provides the percent inhibition at 3 pM concentration of factor Xa and compound concentrations of 4 µM and 1 µM.

TABLE 2

| Name | Fxa 3 PM % Inhibition at 4 uM | Fxa 3 PM % Inhibition at 1 uM |
|---|---|---|
| Pyrrolidine-1,2-dicarboxylic acid 2-[(3-fluoro-2'-sulfamoyl-biphenyl-4-yl)-amide] 1-[(4-isopropyl-phenyl)-amide] | 19.22 | |
| Pyrrolidine-1,2-dicarboxylic acid 2-[(3-fluoro-2'-sulfamoyl-biphenyl-4-yl)-amide] 1-[(4-trifluoromethyl-phenyl)-amide] | 25.1 | |
| Pyrrolidine-1,2-dicarboxylic acid 2-[(3-fluoro-2'-sulfamoyl-biphenyl-4-yl)-amide] 1-[(3-methoxy-phenyl)-amide] | 36.21 | |
| Pyrrolidine-1,2-dicarboxylic acid 1-[(4-ethyl-phenyl)-amide] 2-[(3-fluoro-2'-sulfamoyl-biphenyl-4-yl)-amide] | 38.14 | |
| Pyrrolidine-1,2-dicarboxylic acid 1-[(3-acetyl-phenyl)-amide] 2-[(3-fluoro-2'-sulfamoyl-biphenyl-4-yl)-amide] | 21.04 | |
| Pyrrolidine-1,2-dicarboxylic acid 1-[(5-chloro-2-methyl-phenyl)-amide] 2-[(3-fluoro-2'-sulfamoyl-biphenyl-4-yl)-amide] | 19.84 | |
| Pyrrolidine-1,2-dicarboxylic acid 1-[(2-fluoro-phenyl)-amide] 2-[(3-fluoro-2'-sulfamoyl-biphenyl-4-yl)-amide] | 37.21 | |
| Pyrrolidine-1,2-dicarboxylic acid 1-[(3-chloro-4-fluoro-phenyl)-amide] 2-[(3-fluoro-2'-sulfamoyl-biphenyl-4-yl)-amide] | 41.07 | |
| Pyrrolidine-1,2-dicarboxylic acid 1-[(3-chloro-phenyl)-amide] 2-[(3-fluoro-2'-sulfamoyl-biphenyl-4-yl)-amide] | 55.97 | |
| Pyrrolidine-1,2-dicarboxylic acid 1-[(4-cyano-phenyl)-amide] 2-[(3-fluoro-2'-sulfamoyl-biphenyl-4-yl)-amide] | 51.86 | |
| Pyrrolidine-1,2-dicarboxylic acid 1-[(4-chloro-2-methyl-phenyl)-amide] 2-[(3-fluoro-2'-sulfamoyl-biphenyl-4-yl)-amide] | 38.88 | |
| Pyrrolidine-1,2-dicarboxylic acid 1-[(3,4-dichloro-phenyl)-amide] 2-[(3-fluoro-2'-sulfamoyl-biphenyl-4-yl)-amide] | 41.71 | |
| Pyrrolidine-1,2-dicarboxylic acid 2-[(3-fluoro-2'-sulfamoyl-biphenyl-4-yl)-amide] 1-[(3-trifluoromethyl-phenyl)-amide] | 21.61 | |
| Pyrrolidine-1,2-dicarboxylic acid 1-[(4-dimethylamino-phenyl)-amide] 2-[(3-fluoro-2'-sulfamoyl-biphenyl-4-yl)-amide] | 19.93 | |
| (2S)-Pyrrolidine-1,2-dicarboxylic acid 1-[(4-chloro-phenyl)-amide] 2-[(3-fluoro-2'-sulfamoyl-biphenyl-4-yl)-amide] | | 46.5 |
| Pyrrolidine-1,2-dicarboxylic acid 1-[(4-chloro-phenyl)-amide] 2-[(4-cyano-phenyl)-amide] | | 16.58 |
| Pyrrolidine-1,2-dicarboxylic acid 1-[(4-chloro-phenyl)-amide] 2-{[4-(1H-tetrazol-5-yl)-phenyl]-amide} | | 36.64 |

The foregoing biological tests establish that the compounds of the present invention are potent inhibitors of the Faxtor Xa. Accordingly, the compounds of the present invention are useful in pharmaceutical formulations for preventing and treating thrombotic disorders. Such disorders include venous thrombosis, deep vein thrombosis, thrombophlebitis, arterialembolism, coronary and cerebral arterial thrombosis, cerebral embolism, kidney embolism, pulmonary embolism, first or recurrent myocardial infarction, unstable angina, cerebral infarction, stroke, and atherosclerosis.

To further assist in understanding the present invention, the following non-limiting examples of such factor Xa inhibitory compounds are provided. The following examples, of course, should not be construed as specifically limiting the present invention, variations presently known or later developed, which would be within the purview of one skilled in the art and considered to fall within the scope of the present invention as described herein. Preferred synthetic routes for intermediates involved in the synthesis as well as the resulting anti-thrombotic compounds of the present invention follow.

EXAMPLE 1

(R)-pyrrolidine-1,2-dicarboxylic acid 1-[(4-chloro-phenyl)-amide]2-[(3-fluoro-2'-sulfamoyl-biphenyl-4-yl)-amide]

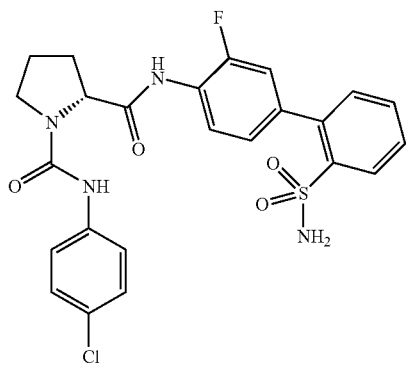

Step 1: (R)-2-(4-Bromo-2-fluoro-phenylcarbamoyl)-pyrrolidine-1-carboxylic acid 9H-fluoren-9-ylmethyl ester Fmoc-D-Pro (1.2 g, 3.56 mmol) was suspended in 10 mL dry dichloromethane (DCM), cooled in an ice water bath, and then thionyl chloride (0.78 mL, 10.7 mmol) was added slowly. After addition was complete, the ice water bath was removed and the reaction was stirred at ambient temperature overnight. The solution was concentrated to dryness. The oil was redissolved in 20 mL dry DCM under an Ar atmosphere, and 4-bromo-2-fluoroaniline (0.81 g, 4.3 mmol) was added, followed by dry pyridine (0.87 mL, 10.7 mmol). The mixture was stirred at ambient temperature for 4 hours, then concentrated. The residue was redissolved in 100 mL EtOAc, washed with 1M HCl (3×50 mL), brine (2×50 mL), dried with MgSO$_4$, filtered and concentrated to yield the title product as a sticky oil. (1.8 g, 99%) APCI (AP+): 509.2, 511.2 (M+H)$^+$.

Step 2: (R)-Pyrrolidine-2-carboxylic acid (2'-tert-butylsulfamoyl-3-fluoro-biphenyl-4-yl)-amide (R)-2-(4-Bromo-2-fluoro-phenylcarbamoyl)-pyrrolidine-1-carboxylic acid 9H-fluoren-9-ylmethyl ester (1.78 g, 3.49 mmol), 2-(N-tert-butyl)phenylsulfonamide boronic acid (1.35 g, 5.24 mmol), and tetrabutylammonium bromide (60 mg, 0.17 mmol) were combined in 40 mL toluene. 3.5 mL of an aqueous 2M sodium carbonate solution was then added, followed by tetrakistriphenylphosphine palladium(0) (200 mg, 0.17 mmol). The resulting solution was heated at reflux overnight, and cooled to room temperature, partitioned between EtOAc (250 mL) and water (150 mL). The combined organic layers were washed with water (2×100 mL), brine, dried with MgSO$_4$, filtered and concentrated. Purification by column chromatography on silica gel eluting with 10% EtOAc in hexanes, then EtOAc, and then to MeOH/NH$_5$OH/EtOAc (5:1:94) provided the title compound as an oil. (1.03 g, 70%) APCI (AP+): 420.3 (M+H)$^+$.

Step 3: (R)-pyrrolidine-1,2-dicarboxylic acid 2-[(2'-tert-butylsulfamoyl-3-fluoro-biphenyl-4-yl)-amide]1-[(4-chloro-phenyl)-amide]

(R)-Pyrrolidine-2-carboxylic acid (2'-tert-butylsulfamoyl-3-fluoro-biphenyl-4-yl)-amide (0.25 g, 0.6 mmol) and 4-chlorophenylisocyanate (90 mg, 0.6 mmol) were combined in 10 mL DCM and stirred at ambient temperature for one hour. The solution was concentrated. The residue was purified on a silica gel column eluting with 50% EtOAc in hexanes to provide the title compound as a white foam. (0.225 g, 66%) APCI (AP−): 571.3, 573.3 (M−H)$^-$.

Step 4: (R)-pyrrolidine-1,2-dicarboxylic acid 1-[(4-chloro-phenyl)-amide]2-[(3-fluoro-2'-sulfamoyl-biphenyl-4-yl)-amide]

(R)-pyrrolidine-1,2-dicarboxylic acid 2-[(2'-tert-butylsulfamoyl-3-fluoro-biphenyl-4-yl)-amide]1-[(4-chloro-phenyl)-amide] (0.22 g, 0.38 mmol) was stirred in 20 mL trifluoroacetic acid at ambient temperature overnight. The solution was concentrated, then purified on a silica gel column eluting with 50% EtOAc in hexanes, then 75% EtOAc in hexanes. The pure fractions were combined and concentrated, then redissolved in acetonitrile/water and lyophilized to yield title compound as a white solid. (0.15 g, 76%) APCI (AP−): 515.2, 517.2 (M−H)$^-$.

EXAMPLE 2

Pyrrolidine-1,2-dicarboxylic acid 1-[(4-chloro-phenyl)-amide]2-[(3-fluoro-2'-sulfamoyl-biphenyl-4-yl)-amide]

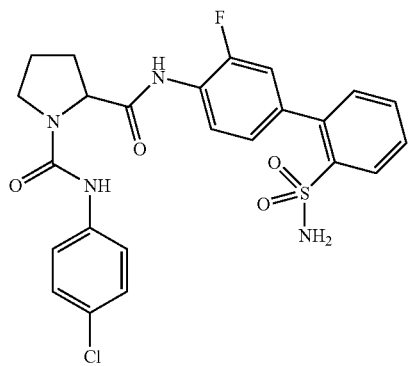

Step 1: Pyrrolidine-1,2-dicarboxylic acid 1-tert-butyl ester

DL-proline (10 g, 86.9 mmol) was dissolved in 120 mL of THF:H$_2$O (2:1), and 87 mL of a 2M NaOH solution was added, followed by Boc$_2$O (24.6 g, 113 mmol). The reaction mixture was stirred at ambient temperature overnight. The THF was removed in vacuo. The remaining aqueous mixture was acidified to pH 3 with aqueous citric acid, extracted twice with EtOAc. The combined organinc layers were washed with water, brine, dried with MgSO$_4$, filtered and concentrated to yield the title compound as a white solid. (18.7 g, quant.) APCI (AP−): 214.1 (M−H)$^-$.

Step 2: 2-(2'-tert-Butylsulfamoyl-3-fluoro-biphenyl-4-ylcarbamoyl)-pyrrolidine-1-carboxylic acid tert-butyl ester Pyrrolidine-1,2-dicarboxylic acid 1-tert-butyl ester (1.6 g, 7.4 mmol) was dissolved in 40 mL dry diethyl ether under Ar. The solution was cooled in an ice water bath as dry pyridine (3 mL, 37.2 mmol) was added, followed by the dropwise addition of oxalyl chloride (1.6 mL, 18.6 mmol). A precipitate formed immediately. The reaction was stirred vigorously at 0° C. for one hour, then at ambient temperature for one hour. 50 mL diethyl ether were added, and the mixture was filtered. The filtered off solids were washed with diethyl ether. The filtrates were combined and concentrated to give an off-white oil. The oil was redissolved in 40 mL dry DCM under Ar, cooled to 0° C., and 3 mL of pyridine were added, followed by 4'-amino-3'-fluoro-biphenyl-2-sulfonic acid tert-butylamide (2 g, 6.2 mmol). The reaction was allowed to warm to ambient temperature, stirred for 3 hours then concentrated. The concentrate was redissolved in 250 mL EtOAc, washed with 10% citric acid (2×100 mL), water (3×100 mL), brine (100 mL), dried with MgSO$_4$, filtered and concentrated. The concentrate was purified on a silica gel column eluted with 30% moving to 50% EtOAc in hexanes. Combined and concentrated pure fractions to yield title compound as a white solid. (1.4 g, 42%) APCI (AP−): 518.2 (M−H)⁻.

Step 3: Pyrrolidine-2-carboxylic acid (2'-tert-butylsulfamoyl-3-fluoro-biphenyl-4-yl)-amide 2-(2'-tert-Butylsulfamoyl-3-fluoro-biphenyl-4-ylcarbamoyl)-pyrrolidine-1-carboxylic acid tert-butyl ester (1.3 g, 2.5 mmol) was dissolved in 40 mL DCM, cooled in an ice bath, added 10 mL trifluoroacetic acid, stirred at 0° C. for 30 minutes then at ambient temperature for one hour. Concentrated solution, redissolved in EtOAc (150 mL), washed with saturated NaHCO$_3$ (2×100 mL), water (100 mL), brine (100 mL), dried with MgSO$_4$, filtered and concentrated to yield title compound as a white solid. (1 g, 91%) APCI (AP−): 418.2 (M−H)⁻.

Step 4: Pyrrolidine-1,2-dicarboxylic acid 2-[(2'-tert-butylsulfamoyl-3-fluoro-biphenyl-4-yl)-amide]1-[(4-chloro-phenyl)-amide]

Pyrrolidine-2-carboxylic acid (2'-tert-butylsulfamoyl-3-fluoro-biphenyl-4-yl)-amide (0.3 g, 0.72 mmol) was dissolved in 10 mL dry THF under Ar, added 4-chlorophenylisocyanate (0.11 g, 0.72 mmol) and stirred at ambient temperature for one hour. Concentrated solution to yield title compound. (0.42 g, quant.) APCI (AP−): 571.2, 573.2 (M−H)⁻.

Step 5: Pyrrolidine-1,2-dicarboxylic acid 1-[(4-chloro-phenyl)-amide]2-[(3-fluoro-2'-sulfamoyl-biphenyl-4-yl)-amide]

Pyrrolidine-1,2-dicarboxylic acid 2-[(2'-tert-butylsulfamoyl-3-fluoro-biphenyl-4-yl)-amide]1-[(4-chloro-phenyl)-amide] (0.4 g, 0.7 mmol) was stirred in 10 mL trifluoroacetic acid at ambient temperature overnight, concentrated solution, then purified on a silica gel column eluted with 50% moving to 75% EtOAc in hexanes. Combined and concentrated pure fractions, redissolved in acetonitrile/water and lyophilized to yield title compound as a white fluffy powder. (0.26 g, 72%) APCI (AP−): 515.1, 517.2 (M−H)⁻.

EXAMPLE 3

Pyrrolidine-1,2-dicarboxylic acid 1-[(5-chloro-pyridin-2-yl)-amide]2-[(3-fluoro-2'-sulfamoyl-biphenyl-4-yl)-amide]

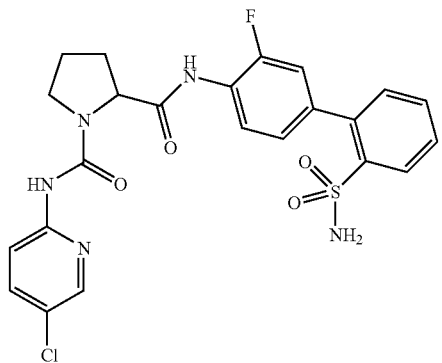

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)⁻.

Step 2: 2-(2'-tert-Butylsulfamoyl-3-fluoro-biphenyl-4-ylcarbamoyl)-pyrrolidine-1-carboxylic acid tert-butyl ester Pyrrolidine-1,2-dicarboxylic acid 1-tert-butyl ester (1.6 g, 7.4 mmol) was dissolved in 40 mL dry diethyl ether under Ar, cooled in an ice water bath, added dry pyridine (3 mL, 37.2 mmol) followed by the dropwise addition of oxalyl chloride (1.6 mL, 18.6 mmol). A precipitate forms immediately. The reaction was stirred vigorously at 0° C. for one hour, then at ambient temperature for one hour. Added 50 mL diethyl ether, filtered off solids washing with diethyl ether. Concentrated the filtrates to an off-white oil. Redissolved oil in 40 mL dry DCM under Ar, cooled to 0° C., added 3 mL pyridine followed by 4'-amino-3'-fluoro-biphenyl-2-sulfonic acid tert-butylamide (2 g, 6.2 mmol). The reaction was allowed to warm to ambient temperature, stirred for 3 hours then concentrated. Redissolved in 250 mL EtOAc, washed with 10% citric acid (2×100 mL), water (3×100 mL), brine (100 mL), dried with MgSO$_4$, filtered and concentrated. Purified on a silica gel column eluted with 30% moving to 50% EtOAc in hexanes. Combined and concentrated pure fractions to yield title compound as a white solid. (1.4 g, 42%) APCI (AP−): 518.2 (M−H)⁻.

Step 3: Pyrrolidine-2-carboxylic acid (2'-tert-butyl-sulfamoyl-3-fluoro-biphenyl-4-yl)-amide 2-(2'-tert-Butylsulfamoyl-3-fluoro-biphenyl-4-ylcarbamoyl)-pyrrolidine-1-carboxylic acid tert-butyl ester (1.3 g, 2.5 mmol) was dissolved in 40 mL DCM, cooled in an ice bath, added 10 mL trifluoroacetic acid, stirred at 0° C. for 30 minutes then at ambient temperature for one hour. Concentrated solution, redissolved in EtOAc (150 mL), washed with saturated NaHCO$_3$ (2×100 mL), water (100 mL), brine (100 mL), dried with MgSO$_4$, filtered and concentrated to yield title compound as a white solid. (1 g, 91%) APCI (AP−): 418.2 (M−H)⁻.

Step 3a: (5-Chloro-pyridin-2-yl)-carbamic acid 4-nitro-phenyl ester

2-Amino-5-chloropyridine (1.05 g, 8.2 mmol) was suspended in 15 mL dry DCM under Ar, added dry pyridine (0.66 mL, 8.2 mmol), cooled to 0° C. and added 4-nitrophenol chloroformate. A white precipitate forms rapidly. Stirred at ambient temperature for 1 hour, filtered off solid, washed with water and then DCM. A white solid recovered which is consistent with title compound. (2.1 g, 88%) $^1$H-NMR (D6-DMSO)

Step 4: Pyrrolidine-1,2-dicarboxylic acid 2-[(2'-tert-butylsulfamoyl-3-fluoro-biphenyl-4-yl)-amide]1-[(5-chloro-pyridin-2-yl)-amide]

Pyrrolidine-2-carboxylic acid (2'-tert-butylsulfamoyl-3-fluoro-biphenyl-4-yl)-amide (245 mg, 0.83 mmol) and (5-Chloro-pyridin-2-yl)-carbamic acid 4-nitro-phenyl ester (0.35 g, 0.83 mmol) were combined in 10 mL dry DMF under Ar, added diisopropylethylamine (0.15 mL, 0.83 mmol) and heated at 80° C. for 2 hours. Cooled solution, taken up in EtOAc (200 mL), washed with sat. K$_2$CO$_3$ (3×150 mL), sat. NaHCO$_3$ (3×150 mL), brine, dried with MgSO$_4$, filtered and concentrated to yield title compound as a light pink solid. (0.45 g, 94%) APCI (AP−): 572.3, 574.3 (M−H)⁻.

Step 5: Pyrrolidine-1,2-dicarboxylic acid 1-[(5-chloro-pyridin-2-yl)-amide]2-[(3-fluoro-2'-sulfamoyl-biphenyl-4-yl)-amide]

Pyrrolidine-1,2-dicarboxylic acid 2-[(2'-tert-butylsulfamoyl-3-fluoro-biphenyl-4-yl)-amide]1-[(5-chloro-pyridin-2-yl)-amide] (0.45 g, 0.78 mmol) was stirred in 10 mL trifluoroacetic acid at ambient temperature for 4 hours. Reaction is sluggish. Heated to 80° C. for 30 minutes. Cooled solution, concentrated, redissolved in 40 mL toluene and concentrated. Purified on a silica gel column eluted with 75% EtOAc in hexanes. Combined and concentrated pure fractions, redissolved in acetonitrile/water and lyophilized to yield title compound as a white fluffy powder. (0.277 g, 68%) APCI (AP−): 516.1, 518.1 (M−H)⁻.

EXAMPLE 4

Pyrrolidine-1,2-dicarboxylic acid 1-[(2,4-difluoro-phenyl)-amide]2-[(3-fluoro-2'-sulfamoyl-biphenyl-4-yl)-amide]

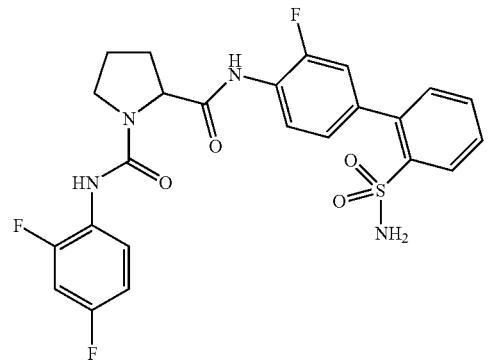

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)⁻.

Step 2: 2-(2'-tert-Butylsulfamoyl-3-fluoro-biphenyl-4-ylcarbamoyl)-pyrrolidine-1-carboxylic acid tert-butyl ester Pyrrolidine-1,2-dicarboxylic acid 1-tert-butyl ester (1.6 g, 7.4 mmol) was dissolved in 40 mL dry diethyl ether under Ar, cooled in an ice water bath, added dry pyridine (3 mL, 37.2 mmol) followed by the dropwise addition of oxalyl chloride (1.6 mL, 18.6 mmol). A precipitate forms immediately. The reaction was stirred vigorously at 0° C. for one hour, then at ambient temperature for one hour. Added 50 mL diethyl ether, filtered off solids washing with diethyl ether. Concentrated the filtrates to an off-white oil. Redissolved oil in 40 mL dry DCM under Ar, cooled to 0° C., added 3 mL pyridine followed by 4'-amino-3'-fluoro-biphenyl-2-sulfonic acid tert-butylamide (2 g, 6.2 mmol). The reaction was allowed to warm to ambient temperature, stirred for 3 hours then concentrated. Redissolved in 250 mL EtOAc, washed with 10% citric acid (2×100 mL), water (3×100 mL), brine (100 mL), dried with MgSO$_4$, filtered and concentrated. Purified on a silica gel column eluted with 30% moving to 50% EtOAc in hexanes. Combined and concentrated pure fractions to yield title compound as a white solid. (1.4 g, 42%) APCI (AP−): 518.2 (M−H)⁻.

Step 3: Pyrrolidine-2-carboxylic acid (2'-tert-butyl-sulfamoyl-3-fluoro-biphenyl-4-yl)-amide 2-(2'-tert-Butylsulfamoyl-3-fluoro-biphenyl-4-ylcarbamoyl)-pyrrolidine-1-carboxylic acid tert-butyl ester (1.3 g, 2.5 mmol) was dissolved in 40 mL DCM, cooled in an ice bath, added 10 mL trifluoroacetic acid, stirred at 0° C. for 30 minutes then at ambient temperature for one hour. Concentrated solution, redissolved in EtOAc (150 mL), washed with saturated NaHCO$_3$ (2×100 mL), water (100 mL), brine (100 mL), dried with MgSO$_4$, filtered and concentrated to yield title compound as a white solid. (1 g, 91%) APCI (AP−): 418.2 (M−H)$^-$.

Step 4: Pyrrolidine-1,2-dicarboxylic acid 1-[(2,4-difluoro-phenyl)-amide]2-[(3-fluoro-2'-sulfamoyl-biphenyl-4-yl)-amide]

To a solution of pyrrolidine-2-carboxylic acid (2'-tert-butylsulfamoyl-3-fluoro-biphenyl-4-yl)-amide (0.12 mmol/mL, 0.3 mmol) in 2.5 mL of THF was added 2,4-difluorophenylisocyanate. The reaction was shaken on an orbital shaker at ambient temperature for 2 hours, then 50 mg of trisamine resin (2.4 mmol/g) was added and shaken for 1 hour. Filtered off resin, washing with THF. The THF was blown down with a stream of nitrogen. Added 2 mL of trifluoroacetic acid and the reaction was shaken at ambient temperature overnight. The trifluoroacetic acid was blown down with a stream of nitrogen. Redissolved in 2 mL EtOAc and loaded onto a silica gel column. Eluted compound with 60% EtOAc in hexanes. Combined and concentrated pure fractions, redissolved in acetonitrile/water and lyophilized to a white fluffy powder. (0.13 g, 84%) APCI (AP−): 517.2 (M−H)$^-$.

EXAMPLE 5

Pyrrolidine-1,2-dicarboxylic acid 2-[(3-fluoro-2'-sulfamoyl-biphenyl-4-yl)-amide]1-p-tolylamide

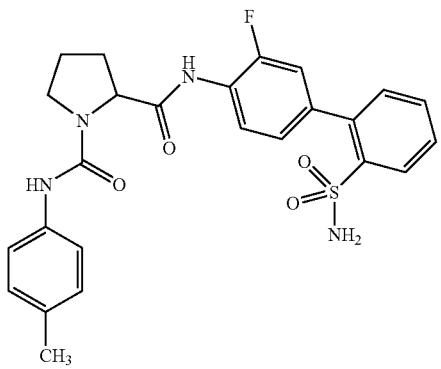

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)$^-$.

Step 2: 2-(2'-tert-Butylsulfamoyl-3-fluoro-biphenyl-4-ylcarbamoyl)-pyrrolidine-1-carboxylic acid tert-butyl ester Pyrrolidine-1,2-dicarboxylic acid 1-tert-butyl ester (1.6 g, 7.4 mmol) was dissolved in 40 mL dry diethyl ether under Ar, cooled in an ice water bath, added dry pyridine (3 mL, 37.2 mmol) followed by the dropwise addition of oxalyl chloride (1.6 mL, 18.6 mmol). A precipitate forms immediately. The reaction was stirred vigorously at 0° C. for one hour, then at ambient temperature for one hour. Added 50 mL diethyl ether, filtered off solids washing with diethyl ether. Concentrated the filtrates to an off-white oil. Redissolved oil in 40 mL dry DCM under Ar, cooled to 0° C., added 3 mL pyridine followed by 4'-amino-3'-fluoro-biphenyl-2-sulfonic acid tert-butylamide (2 g, 6.2 mmol). The reaction was allowed to warm to ambient temperature, stirred for 3 hours then concentrated. Redissolved in 250 mL EtOAc, washed with 10% citric acid (2×100 mL), water (3×100 mL), brine (100 mL), dried with MgSO$_4$, filtered and concentrated. Purified on a silica gel column eluted with 30% moving to 50% EtOAc in hexanes. Combined and concentrated pure fractions to yield title compound as a white solid. (1.4 g, 42%) APCI (AP−): 518.2 (M−H)$^-$.

Step 3: Pyrrolidine-2-carboxylic acid (2'-tert-butyl-sulfamoyl-3-fluoro-biphenyl-4-yl)-amide 2-(2'-tert-Butylsulfamoyl-3-fluoro-biphenyl-4-ylcarbamoyl)-pyrrolidine-1-carboxylic acid tert-butyl ester (1.3 g, 2.5 mmol) was dissolved in 40 mL DCM, cooled in an ice bath, added 10 mL trifluoroacetic acid, stirred at 0° C. for 30 minutes then at ambient temperature for one hour. Concentrated solution, redissolved in EtOAc (150 mL), washed with saturated NaHCO$_3$ (2×100 mL), water (100 mL), brine (100 mL), dried with MgSO$_4$, filtered and concentrated to yield title compound as a white solid. (1 g, 91%) APCI (AP−): 418.2 (M−H)$^-$.

Step 4: Pyrrolidine-1,2-dicarboxylic acid 2-[(3-fluoro-2'-sulfamoyl-biphenyl-4-yl)-amide]1-p-tolylamide To a solution of pyrrolidine-2-carboxylic acid (2'-tert-butylsulfamoyl-3-fluoro-biphenyl-4-yl)-amide (0.12 mmol/mL, 0.24 mmol) in 2 mL of TMF was added p-tolylisocyanate. The reaction was shaken on an orbital shaker at ambient temperature for 2 hours, then 50 mg of trisamine resin (2.4 mmol/g) was added and shaken for 1 hour. Filtered off resin, washing with THF. The THF was blown down with a stream of nitrogen. Added 2 mL of trifluoroacetic acid and the reaction was shaken at ambient temperature overnight. The trifluoroacetic acid was blown down with a stream of nitrogen. Loaded onto a silica gel column and eluted using an automated ISCO system with gradient of 40-100% EtOAc in hexanes over 40 minutes. Combined and concentrated pure fractions, redissolved in acetonitrile/water and lyophilized to a white fluffy powder. (0.084 g, 73%) APCI (AP−): 495.1 (M−H)$^-$.

EXAMPLE 6

Pyrrolidine-1,2-dicarboxylic acid 2-[(3-fluoro-2'-sulfamoyl-biphenyl-4-yl)-amide]1-[(4-methoxyphenyl)-amide]

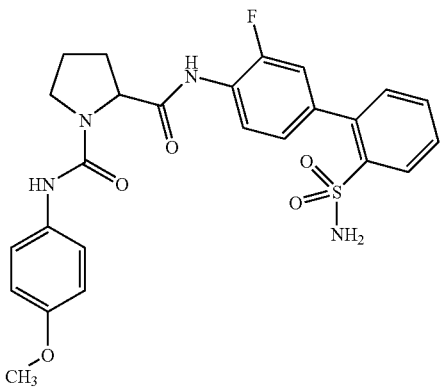

This compound was prepared using the same procedures as found for Example 5 with p-methoxyphenylisocyanate substituted for p-tolylisocyanate in step 4. (0.089 g, 72%) APCI (AP−): 511.1 (M−H)⁻.

EXAMPLE 7

Pyrrolidine-1,2-dicarboxylic acid 1-[(4-bromo-phenyl)-amide]2-[(3-fluoro-2'-sulfamoyl-biphenyl-4-yl)-amide]

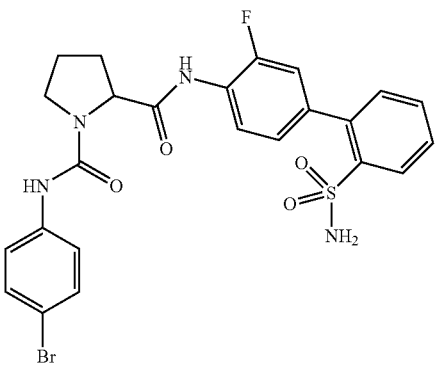

This compound was prepared using the same procedures as found for Example 5 with 4-bromophenylisocyanate substituted for p-tolylisocyanate in step 4. (0.097 g, 72%) APCI (AP−): 559.0, 561.0 (M−H)⁻.

EXAMPLE 8

Pyrrolidine-1,2-dicarboxylic acid 2-[(3-fluoro-2'-sulfamoyl-biphenyl-4-yl)-amide]1-phenylamide

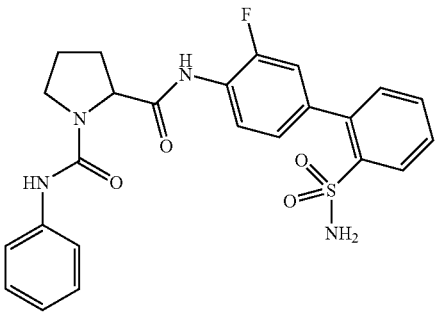

This compound was prepared using the same procedures as found for Example 5 with phenylisocyanate substituted for p-tolylisocyanate in step 4. (0.084 g, 73%) APCI (AP−): 481.1 (M−H)⁻.

EXAMPLE 9

Pyrrolidine-1,2-dicarboxylic acid 1-[(3,4-difluorophenyl)-amide]2-[(3-fluoro-2'-sulfamoyl-biphenyl-4-yl)-amide]

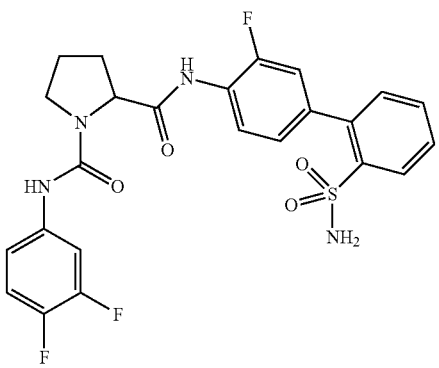

This compound was prepared using the same procedures as found for Example 5 with 3,4-difluorophenylisocyanate substituted for p-tolylisocyanate in step 4. (0.079 g, 63%) APCI (AP−): 517.0 (M−H)⁻.

EXAMPLE 10

Pyrrolidine-1,2-dicarboxylic acid 1-[(3-fluoro-4-methyl-phenyl)-amide]2-[(3-fluoro-2'-sulfamoyl-biphenyl-4-yl)-amide]

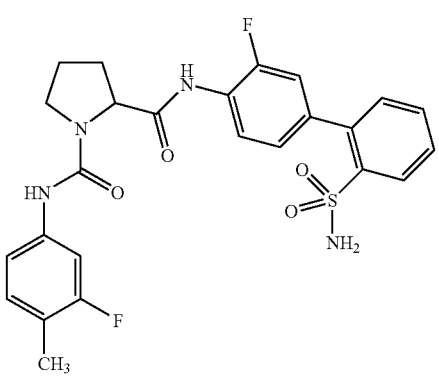

This compound was prepared using the same procedures as found for Example 5 with 3-fluoro-4-methylphenylisocyanate substituted for p-tolylisocyanate in step 4. (0.083 g, 67%) APCI (AP−): 513.0 (M−H)⁻.

EXAMPLE 11

Pyrrolidine-1,2-dicarboxylic acid 1-[(5-chloro-pyridin-2-yl)-amide]2-[(3-fluoro-2'-methanesulfonyl-biphenyl-4-yl)-amide]

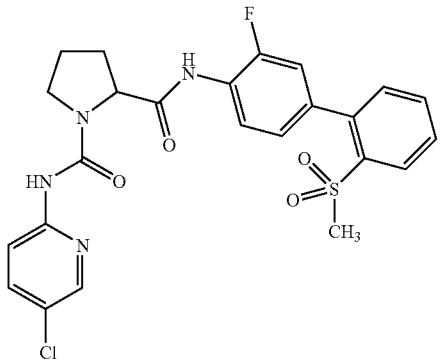

Step 1: Pyrrolidine-1,2-dicarboxylic acid 1-tert-butyl ester

DL-proline (10 g, 86.9 mmol) was dissolved in 120 mL of TBF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)⁻.

Step 2: 2-(4-Bromo-2-fluoro-phenylcarbamoyl)-pyrrolidine-1-carboxylic acid tert-butyl ester Pyrrolidine-1,2-dicarboxylic acid 1-tert-butyl ester (3.8 g, 18 mmol) was dissolved in 150 mL dry diethyl ether under Ar, cooled in an ice water bath, added dry pyridine (8.6 mL, 106 mmol) followed by the dropwise addition of oxalyl chloride (4.6 mL, 53 mmol). A precipitate formed immediately. The reaction was stirred vigorously at 0° C. for one hour, then at ambient temperature for one hour. 100 mL diethyl ether was then added. The solides were filtered off and washed with diethyl ether. The filtrates were concwentrated to an off-white oil. The solid was redissolved oil in 50 mL dry DCM under Ar, cooled to 0° C., and 6 mL pyridine was added, followed by 4-bromo-2-fluoroaniline (3.4 g, 17.7 mmol). The reaction was allowed to warm to ambient temperature, stirred for 3 hours then concentrated. The concentrate was redissolved in 250 mL EtOAc, washed with 10% HCl (3×100 mL), brine (100 mL), dried with MgSO$_4$, filtered and concentrated. The residue was purified on a silica gel column eluted with 20% moving to 40% EtOAc in hexanes to yield title compound as a white solid. (3.2 g, 47%) APCI (AP−): 385.1, 387.1 (M−H)⁻.

Step 3: 2-(3-Fluoro-2'-methylsulfanyl-biphenyl-4-ylcarbamoyl)-pyrrolidine-1-carboxylic acid tert-butyl ester 2-(4-Bromo-2-fluoro-phenylcarbamoyl)-pyrrolidine-1-carboxylic acid tert-butyl ester (2 g, 4.8 mmol), 2-(methylthio)benzene boronic acid (0.98 g, 5.8 mmol), and tetrabutylammonium bromide (78 mg, 0.24 mmol) were combined in 30 mL toluene, added 5 mL of a 2M aqueous Na$_2$CO$_3$ solution followed by tetrakistriphenylphosphine palladium (0) (0.28 g, 0.24 mmol). The reaction was heated at reflux for 4 hours, cooled, concentrated, redissolved in EtOAc (250 mL), washed with water (3×200 mL), brine (200 mL), dried with MgSO$_4$, filtered, and concentrated in the presence of 4 g coarse silica. The residue was was purified by column chromatography on silica gel eluting with 20% EtOAc in hexanes to yield title compound as a yellow foam. (1.84 g, 88%) APCI (AP−): 429.2 (M−H)⁻.

Step 4: 2-(3-Fluoro-2'-methanesulfonyl-biphenyl-4-ylcarbamoyl)-pyrrolidine-1-carboxylic acid tert-butyl ester 2-(3-Fluoro-2'-methylsulfanyl-biphenyl-4-ylcarbamoyl)-pyrrolidine-1-carboxylic acid tert-butyl ester (0.57 g, 1.32 mmol) was dissolved in 10 mL EtOAc, and m-chloroperoxybenzoic acid (1.5 g, 5.3 mmol) was added in one portion to the resulting mixture. The mixture was stirred at ambient temperature for 3 hours, then diluted with 100 mL EtOAc, washed with sat. NaHCO$_3$ (3×100 mL), brine, dried with MgSO$_4$, filtered and concentrated. The residue was purified by column chromatography on silica gel eluting with 33% moving to 50% EtOAc in hexanes to yield title compound as a yellow foam. (0.48 g, 75%) APCI (AP−): 461.2 (M−H)⁻.

Step 5: Pyrrolidine-2-carboxylic acid (3-fluoro-2'-methanesulfonyl-biphenyl-4-yl)-amide 2-(3-Fluoro-2'-methanesulfonyl-biphenyl-4-ylcarbamoyl)-pyrrolidine-1-carboxylic acid tert-butyl ester (0.45 g, 0.93 mmol) was dissolved in 15 mL DCM and 15 mL trifluoroacetic acid and the resulting mixture was stirred at ambient temperature for 1 hour. The mixture was concentrated, and the residue was redissolved in 100 mL EtOAc, washed with sat. NaCl, dried with MgSO$_4$, filtered and concentrated to yield title compound as an oil. (0.27 g, 80%) APCI (AP−): 361.1 (M−H)⁻.

Step 6: Pyrrolidine-1,2-dicarboxylic acid 1-[(5-chloro-pyridin-2-yl)-amide]2-[(3-fluoro-2'-methanesulfonyl-biphenyl-4-yl)-amide]

Pyrrolidine-2-carboxylic acid (3-fluoro-2'-methanesulfonyl-biphenyl-4-yl)-amide (0.27 g, 0.75 mmol) and (5-Chloropyridin-2-yl)-carbamic acid 4-nitro-phenyl ester (0.22 g, 0.0.75 mmol; see Example 3, step 3a) were combined in 10 mL DMF and heated at 80° C. for 4 hours, then cooled. 200 mL of water were then added and a precipitate formed. The solids were filtered off, washed with water, redissolved in EtOAc, dried with MgSO$_4$, filtered and concentrated. The residue was purified by column chromatography on silica get eluting with 70% EtOAc in hexanes to yield title compound. (220 mg, 57%) APCI (AP−): 515.1, 517.1 (M−H)[31].

EXAMPLE 12

Pyrrolidine-1,2-dicarboxylic acid 1-[(4-chloro-phenyl)-amide]2-[(3-fluoro-2'-methanesulfonyl-biphenyl-4-yl)-amide]

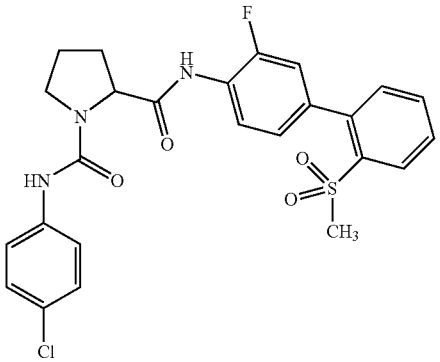

Step 1: Pyrrolidine-1,2-dicarboxylic acid 1-tert-butyl ester

DL-proline (10 g, 86.9 mmol) was dissolved in 120 mL of THF:H$_2$O (2:1), and 87 mL of a 2M NaOH solution was added to the resulting mixture, followed by Boc$_2$O (24.6 g, 113 mmol). The mixture was stirred at ambient temperature overnight. THF was removed in vacuo, and the remaining water was acidified to pH 3 with citric acid, then extracted twice with EtOAc. The combined organic layers were washed with water, brine, dried with MgSO$_4$, filtered and concentrated to yield title compound as a white solid. (18.7 g, quant.) APCI (AP−): 214.1 (M−H)⁻.

Step 2: 2-(4-Bromo-2-fluoro-phenylcarbamoyl)-pyrrolidine-1-carboxylic acid tert-butyl ester Pyrrolidine-1,2-dicarboxylic acid 1-tert-butyl ester (3.8 g, 18 mmol) was dissolved in 150 mL dry diethyl ether under Ar, and the resulting solution was cooled in an ice water bath, while dry pyridine (8.6 mL, 106 mmol) was added, followed by the dropwise addition of oxalyl chloride (4.6 mL, 53 mmol). A precipitate formed immediately. The reaction was stirred vigorously at 0° C. for one hour, then at ambient temperature for one hour. 100 mL of diethyl ether were then added, and the solids were removed by filtration washing with diethyl ether. Concentrated the filtrates to an off-white oil. Redissolved oil in 50 mL dry DCM under Ar, cooled to 0° C., added 6 mL pyridine followed by 4-bromo-2-fluoroaniline (3.4 g, 17.7 mmol). The reaction was allowed to warm to ambient temperature, stirred for 3 hours then concentrated. Redissolved in 250 mL EtOAc, washed with 10% HCl (3×100 mL), brine (100 mL), dried with MgSO$_4$, filtered and concentrated. Purified on a silica gel column eluted with 20% moving to 40% EtOAc in hexanes. Combined and concentrated pure fractions to yield title compound as a white solid. (3.2 g, 47%) APCI (AP−): 385.1, 387.1 (M−H)⁻.

Step 3: 2-(3-Fluoro-2'-methylsulfanyl-biphenyl-4-ylcarbamoyl)-pyrrolidine-1-carboxylic acid tert-butyl ester 2-(4-Bromo-2-fluoro-phenylcarbamoyl)-pyrrolidine-1-carboxylic acid tert-butyl ester (2 g, 4.8 mmol), 2-(methylthio)benzene boronic acid (0.98 g, 5.8 mmol), and tetrabutylammonium bromide (78 mg, 0.24 mmol) were combined in 30 mL toluene, added 5 mL of a 2M aqueous Na$_2$CO$_3$ solution followed by tetrakistriphenylphosphine palladium (0) (0.28 g, 0.24 mmol). Heated reaction at reflux for 4 hours, cooled, concentrated, redissolved in EtOAc (250 mL), washed with water (3×200 mL), brine (200 mL), dried with MgSO$_4$, filtered, and concentrated in the presence of 4 g coarse silica. Loaded silica onto a silica gel column, eluted with 20% EtOAc in hexanes. Combined and concentrated pure fractions to yield title compound as a yellow foam. (1.84 g, 88%) APCI (AP−): 429.2 (M−H)⁻.

Step 4: 2-(3-Fluoro-2'-methanesulfonyl-biphenyl-4-ylcarbamoyl)-pyrrolidine-1-carboxylic acid tert-butyl ester 2-(3-Fluoro-2'-methylsulfanyl-biphenyl-4-ylcarbamoyl)-pyrrolidine-1-carboxylic acid tert-butyl ester (1.2 g, 2.8 mmol) was dissolved in 30 mL EtOAc, added m-chloroperoxybenzoic acid (3.2 g, 11 mmol) in one portion and stirred at ambient temperature for 3 hours. A 10% aqueous solution (50 mL) of Na$_2$S$_2$O$_3$ was added to the vigorously stirring reaction in order to quench peroxide. After 30 minutes the solution was diluted with 100 mL EtOAc, separated layers, washed organics with sat. NaHCO$_3$ (3×100 mL), brine, dried with MgSO$_4$, filtered and concentrated. Purified on a silica gel column eluted with 50% EtOAc in hexanes. Combined and concentrated pure fractions to yield title compound as a yellow foam. (1.01 g, 78%) APCI (AP−): 461.1 (M−H)⁻.

Step 5: Pyrrolidine-2-carboxylic acid (3-fluoro-2'-methanesulfonyl-biphenyl-4-yl)-amide 2-(3-Fluoro-2'-methanesulfonyl-biphenyl-4-ylcarbamoyl)-pyrrolidine-1-carboxylic acid tert-butyl ester (1 g, 2 mmol) was dissolved in 20 mL DCM and 10 mL trifluoroacetic acid and stirred at ambient temperature for 1 hour. Concentrated solution, redissolved in 100 mL CHCl$_3$, repeated CHCl$_3$ co-concentration 3 times to yield title compound as an oil. (quant. yield) APCI (AP−): 361.1 (M−H)⁻.

Step 6: Pyrrolidine-1,2-dicarboxylic acid 1-[(4-chloro-phenyl)-amide]2-[(3-fluoro-2'-methanesulfonyl-biphenyl-4-yl)-amide]

Pyrrolidine-2-carboxylic acid (3-fluoro-2'-methanesulfonyl-biphenyl-4-yl)-amide (0.23 g, 0.64 mmol) was dissolved in 10 mL THF, added diisopropylethylamine (0.33 mL, 1.9 mmol), followed by 4-chlorophenylisocyanate (97 mg, 0.64 mmol). Stirred reaction at ambient temperature for 1 hour then concentrated. Purified on a silica gel column eluted with 70% EtOAc in hexanes. Pure fractions were combined and concentrated, redissolved in acetonitrile/water and lyophilized to yield title compound as a white powder. (0.23 g, 70%) APCI (AP−): 514.1, 516.1 (M−H)⁻.

EXAMPLE 13

Pyrrolidine-1,2-dicarboxylic acid 1-[(4-chloro-phenyl)-amide]2-{[5-(2-sulfamoyl-phenyl)-pyridin-2-yl]-amide}

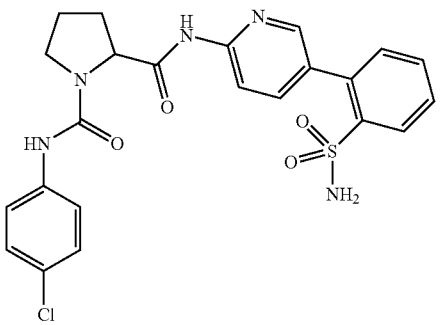

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)$^-$.

Step 2: 2-(5-Bromo-pyridin-2-ylcarbamoyl)-pyrrolidine-1-carboxylic acid tert-butyl ester Pyrrolidine-1,2-dicarboxylic acid 1-tert-butyl ester (1.97 g, 9.2 mmol) was dissolved in 150 mL dry diethyl ether under Ar, cooled in an ice water bath, added dry pyridine (3.7 mL, 45.8 mmol) followed by the dropwise addition of oxalyl chloride (2 mL, 22.9 mmol). A precipitate forms immediately. The reaction was stirred vigorously at 0° C. for 2 hours, then at ambient temperature for one hour. Added 100 mL diethyl ether, filtered off solids washing with diethyl ether. Concentrated the filtrates to an off-white oil. Redissolved oil in 100 mL dry DCM under Ar, cooled to 0° C., added 3 mL pyridine followed by 2-amino-5-bromopyridine (1.32 g, 7.6 mmol). The reaction was allowed to warm to ambient temperature, stirred for 3 hours then concentrated. Redissolved in 250 mL EtOAc, washed with 10% HCl (3×100 mL), brine (100 mL), dried with MgSO$_4$, filtered and concentrated to yield title compound as a yellow sticky solid. (2.74 g, 97%) APCI (AP−): 368.0, 370.0 (M−H)$^-$.

Step 3: 2-[5-(2-tert-Butylsulfamoyl-phenyl)-pyridin-2-ylcarbamoyl]-pyrrolidine-1-carboxylic acid tert-butyl ester 2-(5-Bromo-pyridin-2-ylcarbamoyl)-pyrrolidine-1-carboxylic acid tert-butyl ester (0.92 g, 2.48 mmol), 2-(N-tert-butyl)phenylsulfonamide boronic acid (0.64 g, 2.48 mmol), and tetrabutylammonium bromide (40 mg, 0.12 mmol) were combined in 10 mL toluene, added 2 mL of an aqueous 2M sodium carbonate solution followed by the addition of tetrakistriphenylphosphine palladium(0) (144 mg, 0.12 mmol). Refluxed solution for 4 hours, cooled to room temperature, partitioned between EtOAc (150 mL) and water (100 mL), washed organics with water (3×100 mL), brine, dried with MgSO$_4$, filtered and concentrated. Purified on a silica gel column eluted with 40% moving to 50% EtOAc in hexanes. Combined and concentrated pure fractions to yield title compound as a white solid. (0.92 g, 74%) APCI (AP−): 501.1 (M−H)$^-$.

Step 4: Pyrrolidine-2-carboxylic acid [5-(2-tert-butylsulfamoyl-phenyl)-pyridin-2-yl]-amide 2-[5-(2-tert-Butylsulfamoyl-phenyl)-pyridin-2-ylcarbamoyl]-pyrrolidine-1-carboxylic acid tert-butyl ester (0.92 g, 1.83 mmol) was dissolved in 30 mL DCM, added 10 mL trifluoroacetic acid and stirred at ambient temperature for one hour. Concentrated solution, redissolved in CHCl$_3$ and reconcentrated. Repeated co-concentration twice to yield title compound as an oil. (quant. yield) APCI (AP−): 401.1 (M−H)$^-$.

Step 5: Pyrrolidine-1,2-dicarboxylic acid 2-{[5-(2-tert-butylsulfamoyl-phenyl)-pyridin-2-yl]-amide}1-[(4-chloro-phenyl)-amide]

Pyrrolidine-2-carboxylic acid [5-(2-tert-butylsulfamoyl-phenyl)-pyridin-2-yl]-amide (0.44 g, 0.59 mmol) was dissolved in 10 mL THF, added diisopropylethylamine (0.41 mL, 2.4 mmol) followed by 4-chlorophenylisocyanate (91 mg, 0.59 mmol). Stirred at ambient temperature for 2 hours. Diluted reaction with 50 mL EtOAc, washed with 10% citric acid (3×50 mL), water (2×50 mL), brine, dried with MgSO$_4$, filtered and concentrated to yield title compound. (0.28 g, 85%) APCI (AP+): 556.2, 558.2 (M−H)$^+$.

Step 6: Pyrrolidine-1,2-dicarboxylic acid 1-[(4-chloro-phenyl)-amide]2-{[5-(2-sulfamoyl-phenyl)-pyridin-2-yl]-amide}

Pyrrolidine-1,2-dicarboxylic acid 2-{[5-(2-tert-butylsulfamoyl-phenyl)-pyridin-2-yl]-amide}1-[(4-chloro-phenyl)-amide] (0.28 g, 0.5 mmol) was stirred in 10 mL trifluoroacetic acid at ambient temperature for 20 hours. The solution was concentrated and purified on a silica gel column using an automated system with gradient of 40-100% EtOAc in hexanes over 40 minutes. Combined and concentrated pure fractions, redissolved in acetonitrile/water and lyophilized to yield title compound as a light yellow powder. (0.156 g, 62%) APCI (AP+): 500.0, 501.9 (M+H)$^+$.

EXAMPLE 14

Pyrrolidine-1,2-dicarboxylic acid 2-[(3-chloro-2'-methanesulfonyl-biphenyl-4-yl)-amide]1-[(5-chloro-pyridin-2-yl)-amide]

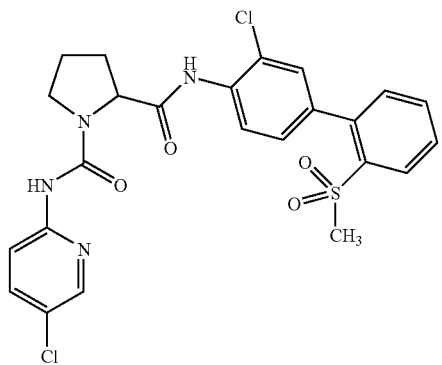

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)$^-$.

Step 2: 2-(4-Bromo-2-chloro-phenylcarbamoyl)-pyrrolidine-1-carboxylic acid tert-butyl ester Pyrrolidine-1,2-dicarboxylic acid 1-tert-butyl ester (2.2 g, 10 mmol) was dissolved in 150 mL dry diethyl ether under Ar, cooled in an ice water bath, added dry pyridine (2.8 mL, 34 mmol) followed by the dropwise addition of oxalyl chloride (1.5 mL, 17 mmol). A precipitate forms immediately. The reaction was stirred vigorously at 0° C. for 1 hours, then at ambient temperature for two hours. Added 100 mL diethyl ether, filtered off solids washing with diethyl ether. Concentrated the filtrates to an off-white oil. Redissolved oil in 100 mL dry DCM under Ar, cooled to 0° C., added 3 mL pyridine followed by 2-chloro-4-bromoaniline (1.8 g, 8.5 mmol). The reaction was allowed to warm to ambient temperature and stirred over the weekend. Concentrated reaction, redissolved in 250 mL EtOAc, washed with 10% citric acid (3×100 mL), water, (2×100 mL), brine (100 mL), dried with MgSO$_4$, filtered and concentrated. Purified on a silica gel column eluted with an automated system with gradient of 0-60% EtOAc in hexanes. Combined and concentrated pure fractions to yield title compound as a yellow solid. (2.7 g, 79%) APCI (AP−): 401.0, 403.0, 405.0 (M−H)$^-$.

Step 3: 2-(3-Chloro-2'-methylsulfanyl-biphenyl-4-ylcarbamoyl)-pyrrolidine-1-carboxylic acid tert-butyl ester 2-(4-Bromo-2-chloro-phenylcarbamoyl)-pyrrolidine-1-carboxylic acid tert-butyl ester (1 g, 2.5 mmol), 2-(methylthio)benzene boronic acid (0.5 g, 3 mmol), and tetrabutylammonium bromide (40 mg, 0.12 mmol) were combined in 10 mL toluene, added 2 mL of a 2M aqueous Na$_2$CO$_3$ solution followed by tetrakistriphenylphosphine palladium(0) (0.14 g, 0.12 mmol). Heated reaction at reflux for 5 hours, cooled, dissolved in EtOAc (150 mL), washed with water (3×50 mL), brine (50 mL), dried with MgSO$_4$, filtered, and concentrated. Purified on a silica gel column eluted using an automated system with gradient of 0-50% EtOAc in hexanes over 40 minutes. Combined and concentrated pure fractions to yield title compound as a white foam. (1.01 g, 91%) APCI (AP−): 445.1, 447.1 (M−H)$^-$.

Step 4: 2-(3-Chloro-2'-methanesulfonyl-biphenyl-4-ylcarbamoyl)-pyrrolidine-1-carboxylic acid tert-butyl ester 2-(3-Chloro-2'-methylsulfanyl-biphenyl-4-ylcarbamoyl)-pyrrolidine-1-carboxylic acid tert-butyl ester (1 g, 2 mmol) was dissolved in 20 mL EtOAc, added m-chloroperoxybenzoic acid (2.6 g, 8.9 mmol) in one portion and stirred at ambient temperature for 3 hours. A 10% aqueous solution (30 mL) of Na$_2$S$_2$O$_3$ was added to the vigorously stirring reaction in order to quench peroxide. After 20 minutes the solution was diluted with 100 mL EtOAc, separated layers, washed organics with sat. NaHCO$_3$ (3×100 mL), brine, dried with MgSO$_4$, filtered and concentrated to yield title compound as a clear oil. (1 g, 100%) APCI (AP−): 477.1, 479.1 (M−H)$^-$.

Step 5: Pyrrolidine-2-carboxylic acid (3-chloro-2'-methanesulfonyl-biphenyl-4-yl)-amide 2-(3-Chloro-2'-methanesulfonyl-biphenyl-4-ylcarbamoyl)-pyrrolidine-1-carboxylic acid tert-butyl ester (1 g, 2 mmol) was dissolved in 20 mL DCM and 20 mL trifluoroacetic acid and stirred at ambient temperature for 2 hours. Concentrated solution, redissolved in 100 mL CHCl$_3$, repeated CHCl$_3$ co-concentration 4 times to yield title compound as a yellow foam. (quant. yield) APCI (AP+): 379.1, 381.1 (M+H)$^+$.

Step 6: Pyrrolidine-1,2-dicarboxylic acid 2-[(3-chloro-2'-methanesulfonyl-biphenyl-4-yl)-amide]1-[(5-chloro-pyridin-2-yl)-amide]

Pyrrolidine-2-carboxylic acid (3-chloro-2'-methanesulfonyl-biphenyl-4-yl)-amide (0.11 g, 0.29 mmol) and (5-Chloro-pyridin-2-yl)-carbamic acid 4-nitro-phenyl ester (0.085 g, 0.29 mmol; see Example 3, step 3a) were combined in 3 mL DMF and heated at 50° C. for 2 hours, dissolved in 100 mL EtOAc, washed with sat. NaHCO$_3$ (3×50 mL), brine, dried with MgSO$_4$, filtered and concentrated. Purified on a silica gel column eluting using an automated system with gradient of 0-100% EtOAc in hexanes over 40 minutes. Combined and concentrated pure fractions, redissolved in acetonitrile/water and lyophilized to yield title compound as a white powder. (110 mg, 71%) APCI (AP+): 533.0, 535.0 (M+H)$^+$.

EXAMPLE 15

Pyrrolidine-1,2-dicarboxylic acid 2-[(3-chloro-2'-methanesulfonyl-biphenyl-4-yl)-amide]1-[(4-chloro-phenyl)-amide]

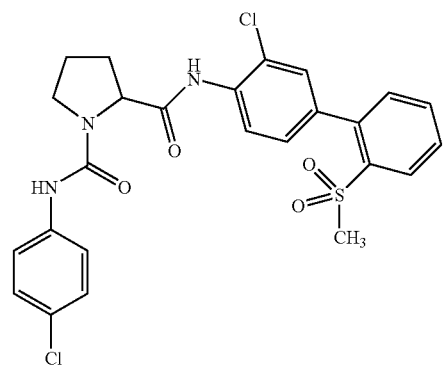

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)$^-$.

Step 2: 2-(4-Bromo-2-chloro-phenylcarbamoyl)-pyrrolidine-1-carboxylic acid tert-butyl ester Pyrrolidine-1,2-dicarboxylic acid 1-tert-butyl ester (2.2 g, 10 mmol) was dissolved in 150 mL dry diethyl ether under Ar, cooled in an ice water bath, added dry pyridine (2.8 mL, 34 mmol) followed by the dropwise addition of oxalyl chloride (1.5 mL, 17 mmol). A precipitate forms immediately. The reaction was stirred vigorously at 0° C. for 1 hours, then at ambient temperature for two hours. Added 100 mL diethyl ether, filtered off solids washing with diethyl ether. Concentrated the filtrates to an off-white oil. Redissolved oil in 100 mL dry DCM under Ar, cooled to 0° C., added 3 mL pyridine followed by 2-chloro-4-bromoaniline (1.8 g, 8.5 mmol). The reaction was allowed to warm to ambient temperature and stirred over the weekend. Concentrated reaction, redissolved in 250 mL EtOAc, washed with 10% citric acid (3×100 mL), water, (2×100 mL), brine (100 mL), dried with MgSO$_4$, filtered and concentrated. Purified on a silica gel column eluted with an automated system with gradient of 0-60% EtOAc in hexanes. Combined and concentrated pure fractions to yield title compound as a yellow solid. (2.7 g, 79%) APCI (AP−): 401.0, 403.0, 405.0 (M−H)⁻.

Step 3: 2-(3-Chloro-2'-methylsulfanyl-biphenyl-4-ylcarbamoyl)-pyrrolidine-1-carboxylic acid tert-butyl ester 2-(4-Bromo-2-chloro-phenylcarbamoyl)-pyrrolidine-1-carboxylic acid tert-butyl ester (1 g, 2.5 mmol), 2-(methylthio)benzene boronic acid (0.5 g, 3 mmol), and tetrabutylammonium bromide (40 mg, 0.12 mmol) were combined in 10 mL toluene, added 2 mL of a 2M aqueous Na$_2$CO$_3$ solution followed by tetrakistriphenylphosphine palladium(0) (0.14 g, 0.12 mmol). Heated reaction at reflux for 5 hours, cooled, dissolved in EtOAc (150 mL), washed with water (3×50 mL), brine (50 mL), dried with MgSO$_4$, filtered, and concentrated. Purified on a silica gel column eluted using an automated system with gradient of 0-50% EtOAc in hexanes over 40 minutes. Combined and concentrated pure fractions to yield title compound as a white foam. (1.01 g, 91%) APCI (AP−): 445.1, 447.1 (M−H)⁻.

Step 4: 2-(3-Chloro-2'-methanesulfonyl-biphenyl-4-ylcarbamoyl)-pyrrolidine-1-carboxylic acid tert-butyl ester 2-(3-Chloro-2'-methylsulfanyl-biphenyl-4-ylcarbamoyl)-pyrrolidine-1-carboxylic acid tert-butyl ester (1 g, 2 mmol) was dissolved in 20 mL EtOAc, added m-chloroperoxybenzoic acid (2.6 g, 8.9 mmol) in one portion and stirred at ambient temperature for 3 hours. A 10% aqueous solution (30 mL) of Na$_2$S$_2$O$_3$ was added to the vigorously stirring reaction in order to quench peroxide. After 20 minutes the solution was diluted with 100 mL EtOAc, separated layers, washed organics with sat. NaHCO$_3$ (3×100 mL), brine, dried with MgSO$_4$, filtered and concentrated to yield title compound as a clear oil. (1 g, 100%) APCI (AP−): 477.1, 479.1 (M−H)⁻.

Step 5: Pyrrolidine-2-carboxylic acid (3-chloro-2'-methanesulfonyl-biphenyl-4-yl)-amide 2-(3-Chloro-2'-methanesulfonyl-biphenyl-4-ylcarbamoyl)-pyrrolidine-1-carboxylic acid tert-butyl ester (1 g, 2 mmol) was dissolved in 20 mL DCM and 20 mL trifluoroacetic acid and stirred at ambient temperature for 2 hours. Concentrated solution, redissolved in 100 mL CHCl$_3$, repeated CHCl$_3$ co-concentration 4 times to yield title compound as a yellow foam. (quant. yield) APCI (AP+): 379.1, 381.1 (M+H)⁺.

Step 6: Pyrrolidine-1,2-dicarboxylic acid 2-[(3-chloro-2'-methanesulfonyl-biphenyl-4-yl)-amide]1-[(4-chloro-phenyl)-amide]

Pyrrolidine-2-carboxylic acid (3-chloro-2'-methanesulfonyl-biphenyl-4-yl)-amide (0.16 g, 0.42 mmol) was dissolved in 5 mL THF, added diisopropylethylamine (0.22 mL, 1.3 mmol) followed by 4-chlorophenylisocyanate (65 mg, 0.42 mmol). Stirred at ambient temperature for 20 hours. The reaction was concentrated and purified using an automated system with gradient of 0-100% EtOAc in hexanes over 40 minutes. Combined and concentrated pure fractions, redissolved in acetonitrile/water and lyophilized to yield title compound as a white powder. (0.175 g, 78%) APCI (AP+): 532.0, 534.0(M−H)⁺.

EXAMPLE 16

Pyrrolidine-1,2-dicarboxylic acid 1-[(5-chloro-pyridin-2-yl)-amide]2-{[5-(2-sulfamoyl-phenyl)-pyridin-2-yl]-amide}

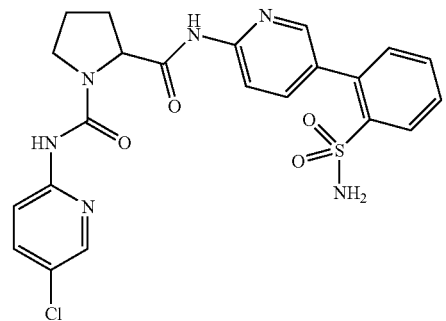

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)⁻.

Step 2: 2-(5-Bromo-pyridin-2-ylcarbamoyl)-pyrrolidine-1-carboxylic acid tert-butyl ester Pyrrolidine-1,2-dicarboxylic acid 1-tert-butyl ester (1.97 g, 9.2 mmol) was dissolved in 150 mL dry diethyl ether under Ar, cooled in an ice water bath, added dry pyridine (3.7 mL, 45.8 mmol) followed by the dropwise addition of oxalyl chloride (2 mL, 22.9 mmol). A precipitate forms immediately. The reaction was stirred vigorously at 0° C. for 2 hours, then at ambient temperature for one hour. Added 100 mL diethyl ether, filtered off solids washing with diethyl ether.

Concentrated the filtrates to an off-white oil. Redissolved oil in 100 mL dry DCM under Ar, cooled to 0° C., added 3 mL pyridine followed by 2-amino-5-bromopyridine (1.32 g, 7.6 mmol). The reaction was allowed to warm to ambient temperature, stirred for 3 hours then concentrated. Redissolved in 250 mL EtOAc, washed with 10% HCl (3×100 mL), brine (100 mL), dried with $MgSO_4$, filtered and concentrated to yield title compound as a yellow sticky solid. (2.74 g, 97%) APCI (AP−): 368.0, 370.0 (M−H)⁻.

Step 3: 2-[5-(2-tert-Butylsulfamoyl-phenyl)-pyridin-2-ylcarbamoyl]-pyrrolidine-1-carboxylic acid tert-butyl ester 2-(5-Bromo-pyridin-2-ylcarbamoyl)-pyrrolidine-1-carboxylic acid tert-butyl ester (0.92 g, 2.48 mmol), 2-(N-tert-butyl)phenylsulfonamide boronic acid (0.64 g, 2.48 mmol), and tetrabutylammonium bromide (40 mg, 0.12 mmol) were combined in 10 mL toluene, added 2 mL of an aqueous 2M sodium carbonate solution followed by the addition of tetrakistriphenylphosphine palladium(0) (144 mg, 0.12 mmol). Refluxed solution for 4 hours, cooled to room temperature, partitioned between EtOAc (150 mL) and water (100 mL), washed organics with water (3×100 mL), brine, dried with $MgSO_4$, filtered and concentrated. Purified on a silica gel column eluted with 40% moving to 50% EtOAc in hexanes. Combined and concentrated pure fractions to yield title compound as a white solid. (0.92 g, 74%) APCI (AP−): 501.1 (M−H)⁻.

Step 4: Pyrrolidine-2-carboxylic acid [5-(2-tert-butylsulfamoyl-phenyl)-pyridin-2-yl]-amide 2-[5-(2-tert-Butylsulfamoyl-phenyl)-pyridin-2-ylcarbamoyl]-pyrrolidine-1-carboxylic acid tert-butyl ester (0.92 g, 1.83 mmol) was dissolved in 30 mL DCM, added 10 mL trifluoroacetic acid and stirred at ambient temperature for one hour. Concentrated solution, redissolved in $CHCl_3$ and reconcentrated. Repeated co-concentration twice to yield title compound as an oil. (quant. yield) APCI (AP−): 401.1 (M−H)⁻.

Step 5: Pyrrolidine-1,2-dicarboxylic acid 2-{[5-(2-tert-butylsulfamoyl-phenyl)-pyridin-2-yl]-amide}1-[(5-chloro-pyridin-2-yl)-amide]

Pyrrolidine-2-carboxylic acid [5-(2-tert-butylsulfamoyl-phenyl)-pyridin-2-yl]-amide (0.17 g, 0.25 mmol) and (5-Chloro-pyridin-2-yl)-carbamic acid 4-nitro-phenyl ester (0.074 g, 0.25 mmol; see Example 3, step 3a) were combined in 3 mL DMF, added diisopropylethylamine (0.18 mL, 1 mmol) and heated at 50° C. for 2 hours. Dissolved in 100 mL EtOAc, washed with sat. $NaHCO_3$ (3×50 mL), brine, dried with $MgSO_4$, filtered and concentrated. Purified on a silica gel column eluting using an automated system with gradient of 30-100% EtOAc in hexanes over 40 minutes. Combined and concentrated pure fractions to yield title compound as a white solid. (90 mg, 64%) APCI (AP−): 555.2, 557.2 (M−H)⁻.

EXAMPLE 17

(2R,4R)-4-Hydroxy-pyrrolidine-1,2-dicarboxylic acid 1-[(4-chloro-phenyl)-amide]2-[(3-fluoro-2'-methanesulfonyl-biphenyl-4-yl)-amide]

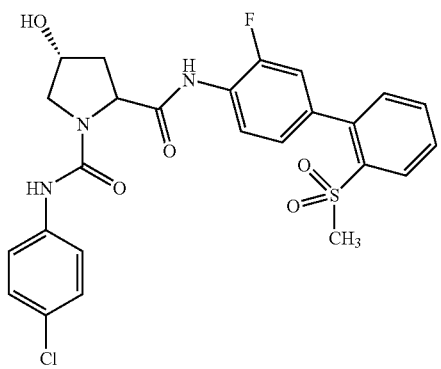

Step 1:
(2R,4R)-4-Hydroxy-pyrrolidine-1,2-dicarboxylic acid 1-tert-butyl ester

Cis-4-hydroxy-D-proline (1.1 g, 8.4 mmol) was dissolved in 18 mL of $THF/H_2O$ (2:1), added 2M aqueous NaOH solution (6.3 mL, 13 mmol), followed by $Boc_2O$. Reaction was stirred at ambient temperature over the weekend. Solution was taken up in 150 mL EtOAc, washed with 10% HCl (3×100 mL), dried organics with $MgSO_4$, filtered and concentrated to yield title compound as a white foam. (1.5 g, 77%) APCI (AP−): 230.1 (M−H)⁻.

Step 2: (2R,4R)-4-(tert-Butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (1.5 g, 6.5 mmol) was dissolved in 20 mL DMF, added imidazole (1.1 g, 16 mmol), dimethylaminopyridine (80 mg, 0.65 mmol), and tert-butyldimethylsilyl chloride (1.08 g, 7.1 mmol). Stirred at ambient temperature overnight, dissolved in 150 mL EtOAc, washed with 10% citric acid (3×100 mL), water (2×100 mL), brine, dried with $MgSO_4$, filtered, and concentrated. Redissolved in 50 mL $CHCl_3$ and reconcentrated to yield title compound as a clear oil. (1.54 g, 69%) APCI (AP−): 344.2 (M−H)⁻.

Step 3: (2R,4R)-2-(4-Bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (1.54 g, 4.5 mmol) was dissolved in 50 mL diethyl ether under an Ar atmosphere, cooled in an ice water bath, added dry pyridine (1.4 mL, 17.8 mmol), followed by the dropwise addition of oxalyl chloride (0.58 mL, 6.7 mmol). Reaction was stirred at 0° C. for 1 hour, then at ambient temperature for 1 hour. Diluted reaction with 50 mL diethyl ether, filtered off solids and concentrated filtrates. Redissolved filtrate in 30 mL dry DCM under an Ar atmosphere, cooled in an ice water bath, added 1 mL dry pyridine followed by 4-bromo-2-fluoroaniline (0.85 g, 4.5 mmol). Stirred reaction at ambient temperature for 20 hours. Concentrated solution, redissolved in EtOAc (150 mL), washed with 10% citric acid (3×100 mmL), water (2×100 mL), brine, dried with MgSO$_4$, filtered and concentrated. Purified on a silica gel column eluting with an automated system with gradient of 0-60% EtOAc in hexanes over 40 minutes. Combined and concentrated pure fractions to yield title compound as a clear oil. (0.96 g, 42%) APCI (AP−): 515.1, 517.1 (M−H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (0.95 g, 1.84 mmol), 2-(methylthio)benzene boronic acid (0.37 g, 2.2 mmol), and tetrabutylammonium bromide (30 mg, 0.09 mmol) were combined in 15 mL toluene, added 2 mL of a 2M aqueous Na$_2$CO$_3$ solution followed by tetrakistriphenylphosphine palladium(0) (0.11 g, 0.09 mmol). Heated reaction at reflux for 5 hours, cooled, dissolved in EtOAc (100 mL), washed with water (3×50 mL), brine (50 mL), dried with MgSO$_4$, filtered, and concentrated. Purified on a silica gel column eluted using an automated system with gradient of 0-60% EtOAc in hexanes over 40 minutes. Combined and concentrated pure fractions to yield title compound as a light yellow foam. (0.77 g, 74%) APCI (AP−): 559.3 (M−H)⁻.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (0.84 g, 1.35 mmol) was dissolved in 20 mL EtOAc, added added m-chloroperoxybenzoic acid (1.6 g, 5.4 mmol) in one portion and stirred at ambient temperature for 3 hours. A 10% aqueous solution (50 mL) of Na$_2$S$_2$O$_3$ was added to the vigorously stirring reaction in order to quench peroxide. After 20 minutes the solution was diluted with 100 mL EtOAc, separated layers, washed organics with sat. NaHCO$_3$ (3×100 mL), water (2×100 mL), brine, dried with MgSO$_4$, filtered and concentrated to yield title compound as a light brown foam. (0.8 g, 100%) APCI (AP−): 591.3 (M−H)⁻.

Step 6: (2R,4R)-4-Hydroxy-pyrrolidine-2-carboxylic acid (3-fluoro-2'-methanesulfonyl-biphenyl-4-yl)-amide (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (0.8 g, 1.35 mmol) was dissolved in 30 mL DCM, added 10 mL trifluoroacetic acid and stirred reaction at ambient temperature for 90 minutes. Solution was concentrated to yield title compound as an amber oil. (100% crude yield) APCI (AP−): (M−H)⁻.

Step 7: (2R,4R)-4-Hydroxy-pyrrolidine-1,2-dicarboxylic acid 1-[(4-chloro-phenyl)-amide]2-[(3-fluoro-2'-methanesulfonyl-biphenyl-4-yl)-amide]

(2R,4R)-4-Hydroxy-pyrrolidine-2-carboxylic acid (3-fluoro-2'-methanesulfonyl-biphenyl-4-yl)-amide (0.51 g, 1.35 mmol) was dissolved in 20 mL THF, added diisopropylethylamine (0.94 mL, 5.4 mmol) followed by 4-chlorophenylisocyanate (0.21 g, 1.35 mmol). Stirred at ambient temperature for 2 hours. The reaction was dissolved in 100 mL EtOAc, washed with 10% citric acid (3×50 mL), water (2×50 mL), brine, dried with MgSO$_4$, filtered and concentrated. Purified using an automated system with gradient of 50-100% EtOAc in hexanes over 40 minutes. Compound was still eluting at end of run. Switched gradient to 0-15% MeOH in EtOAc over 40 minutes. Combined and concentrated pure fractions to yield title compound as a white solid. (0.54 g, 75%) APCI (AP+): 530.1, 532.1(M−H)⁺.

EXAMPLE 18

Pyrrolidine-1,2-dicarboxylic acid 1-[(4-chloro-phenyl)-amide]2-{[4-(1-methyl-4,5-dihydro-1H-imidazol-2-yl)-phenyl]-amide}

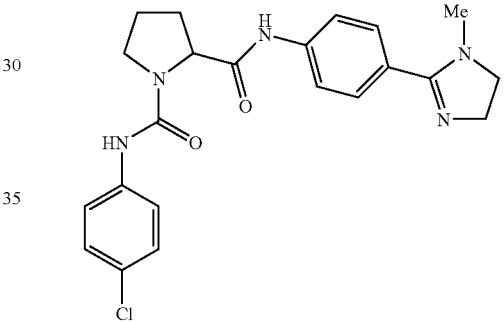

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)⁻.

Step 2: 2-(4-Cyano-phenylcarbamoyl)-pyrrolidine-1-carboxylic acid tert-butyl ester Pyrrolidine-1,2-dicarboxylic acid 1-tert-butyl ester (2.1 g, 9.8 mmol) was dissolved in 100 mL dry diethyl ether under an argon atmosphere, added dry pyridine (3.3 mL, 32.5 mmol), cooled to 0° C. then added oxalyl chloride (1.4 mL, 16.3 mmol) dropwise. A precipitate forms immediately upon addition of oxalyl chloride and therefore reaction requires vigorous stirring. Stirred at 0° C. for one hour than at ambient temperature for 2 hours. Dry diethyl ether (100 mL) was added and the solids were filtered off, washing with more diethyl ether. The filtrates were concentrated, then redissolved in dry DCM under argon, cooled to 0° C., added 1 mL dry pyridine then added 4-amino-benzonitrile (0.96 g, 8.1 mmol) in one portion. Stirred at ambient temperature for 2 hours, concentrated, redissolved in ethyl acetate (250 mL), washed with 10% citric acid (3×100 mL), water, brine, dried with MgSO$_4$, filtered and concentrated to yield title compound as a white foam. (2.4 g, 93%) APCI (AP−): 314.1 (M−H)−.

Step 3: Pyrrolidine-2-carboxylic acid (4-cyano-phenyl)-amide 2-(4-Cyano-phenylcarbamoyl)-pyrrolidine-1-carboxylic acid tert-butyl ester (3 g, 8 mmol) was dissolved in 90 mL of a 1:2 mixture of trifluoroacetic acid and dichloromethane. The reaction was stirred at ambient temperature for one hour then concentrated to yield title compound as an amber oil which was carried onto next step as is. APCI (AP−): 214.1 (M−H)−.

Step 4: Pyrrolidine-1,2-dicarboxylic acid 1-[(4-chloro-phenyl)-amide]2-[(4-cyano-phenyl)-amide]

Pyrrolidine-2-carboxylic acid (4-cyano-phenyl)-amide (0.9 g, 4 mmol) was dissolved in 25 mL tetrahydrofuran, added diisopropylethylamine (3.5 mL, 20 mmol), followed by the addition of 4-chlorophenylisocyanate (0.61 g, 4 mmol). The reaction was stirred at ambient temperature for one hour then concentrated solution. Redissolved in 100 mL ethyl acetate, washed with 10% citric acid (2×100 mL), water, brine, dried with MgSO$_4$, filtered and concentrated. Recrystallized from ethyl acetate and hexanes to yield title compound as a white powder. (1.1 g, 75%) APCI (AP−): 367.1, 369.1 (M−H)−.

Step 5: Pyrrolidine-1,2-dicarboxylic acid 1-[(4-chloro-phenyl)-amide]2-{[4-(1-methyl-4,5-dihydro-1H-imidazol-2-yl)-phenyl]-amide}

Pyrrolidine-1,2-dicarboxylic acid 1-[(4-chloro-phenyl)-amide]2-[(4-cyano-phenyl)-amide] (0.2 g, 0.54 mmol) was dissolved in 2 mL dry methanol under argon, cooled in an ice bath, bubbled in HCl(g) for 10 minutes, removed argon line and HCl line and sealed off flask. Stirred at 0° C. for 20 minutes, then at ambient temperature for 4 hours. The solution was concentrated in vacuo to a yellow foam. The foam was redissolved in 4 mL dry methanol under argon, added N-methylethylenediamine (0.048 mL, 0.54 mmol) and stirred at ambient temperature overnight. The solution was concentrated in vacuo then purified by preparatory HPLC. Combined and lyophilized pure fractions to yield the TFA salt of the title compound as a white fluffy powder. (0.2 g, 69%) APCI (AP−): 424.1, 426.1 (M−H)−.

EXAMPLE 19

Pyrrolidine-1,2-dicarboxylic acid 1-[(4-chloro-phenyl)-amide]2-[(2'-methanesulfonyl-biphenyl-4-yl)-amide]

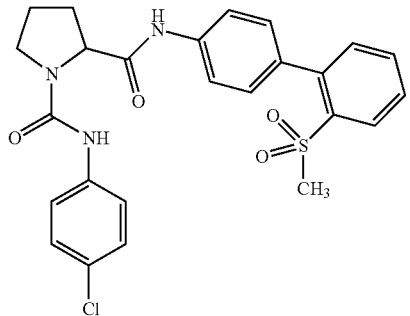

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP−): 214.1 (M−H)−.

Step 2: 2-(4-Bromo-phenylcarbamoyl)-pyrrolidine-1-carboxylic acid tert-butyl ester Pyrrolidine-1,2-dicarboxylic acid 1-tert-butyl ester (5 g, 23 mmol) was dissolved in 250 mL dry diethyl ether under Ar, cooled in an ice water bath, added dry pyridine (11.3 mL, 139 mmol) followed by the dropwise addition of oxalyl chloride (6.1 mL, 69 mmol). A precipitate forms immediately. The reaction was stirred vigorously at 0° C. for one hour, then at ambient temperature for one hour. Added 100 mL diethyl ether, filtered off solids washing with diethyl ether. Concentrated the filtrates to an off white oil. Redissolved (3.66 g, 15 mmol) oil in 40 mL dry DCM under Ar, cooled to 0° C., added 4.6 mL pyridine followed by 4-bromoaniline (2.7 g, 15 mmol). The reaction was allowed to warm to ambient temperature, stirred for 3 hours then concentrated. Redissolved in 100 mL EtOAc, washed with 1 N HCl (2×100 mL), brine (100 mL), dried with MgSO$_4$, filtered and concentrated to yield title compound. (4.56 g, 80%) APCI (AP−): 369.0, 370.0 (M−H)−.

Step 3: 2-(2'-Methylsulfanyl-biphenyl-4-ylcarbamoyl)-pyrrolidine-1-carboxylic acid tert-butyl ester 2-(4-Bromo-phenylcarbamoyl)-pyrrolidine-1-carboxylic acid tert-butyl ester (2.57 g, 6.9 mmol), 2-(methylthio)benzene boronic acid (1.4 g, 8.3 mmol), and tetrabutylammonium bromide (110 mg, 0.33 mmol) were combined in 30 mL toluene, added 6.9 mL of a 2M aqueous Na$_2$CO$_3$ solution followed by tetrakistriphenylphosphine palladium(0) (0.40 g, 0.34 mmol). Heated reaction at reflux overnight, cooled, concentrated, redissolved in EtOAc (250 mL), washed with water (3×200 mL), brine (200 mL), dried with MgSO$_4$, filtered, and concentrated. Purified on a silica gel column eluted with 20% moving to 40% EtOAc in hexanes. Combined and concentrated pure fractions to yield title compound. (1.75 g, 60%) APCI (AP−): 411.1 (M−H)−.

Step 4: 2-(2'-Methanesulfonyl-biphenyl-4-ylcarbamoyl)-pyrrolidine-1-carboxylic acid tert-butyl ester 2-(2'-Methylsulfanyl-biphenyl-4-ylcarbamoyl)-pyrrolidine-1-carboxylic acid tert-butyl ester (1.0 g, 2.4 mmol) was dissolved in 10 mL acetonitrile, added oxone (2.98 g, 4.8 mmol) in one portion and stirred at ambient temperature for 1 week and then concentrated. Redissolved in 100 mL EtOAc and 100 mL sat. NaHCO$_3$, separated layers, washed organics with brine, dried with MgSO$_4$, filtered and concentrated. Purified on a silica gel column eluted with 20% moving to 40% EtOAc in hexanes. Combined and concentrated pure fractions to yield title compound. (0.80 g, 75%) APCI (AP−): 443.1 (M−H)−.

Step 5: Pyrrolidine-2-carboxylic acid (2'-methanesulfonyl-biphenyl-4-yl)-amide 2-(2'-Methanesulfonyl-biphenyl-4-ylcarbamoyl)-pyrrolidine-1-carboxylic acid tert-butyl ester (0.8 g, 1.7 mmol) was dissolved in 25 mL DCM and 5 mL trifluoroacetic acid and stirred at ambient temperature for one hour and concentrated. Redissolved in 100 mL EtOAc and 100 mL sat. NaHCO$_3$, separated layers, washed organics with brine, dried with MgSO$_4$, filtered and concentrated to yield title compound as an oil (quant. yield) APCI (AP–): 343.1 (M–H)$^-$.

Step 6: Pyrrolidine-1,2-dicarboxylic acid 1-[(4-chloro-phenyl)-amide]2-[(2'-methanesulfonyl-biphenyl-4-yl)-amide]

Pyrrolidine-2-carboxylic acid (2'-methanesulfonyl-biphenyl-4-yl)-amide (0.61 g, 1.8 mmol) was dissolved in 20 mL THF, added diisopropylethylamine (0.92 mL, 5.3 mmol), followed by 4-chlorophenylisocyanate (270 mg, 1.7 mmol). Stirred reaction at ambient temperature for one hour then concentrated. Crystallized from EtOAc in hexanes and filtered to yield title compound as a white powder. (0.71 g, 80%) APCI (AP–): 496.1, 498.1 (M–H)$^-$.

EXAMPLE 20

Pyrrolidine-1,2-dicarboxylic acid 1-[(4-chloro-phenyl)-amide]2-[(2'-methanesulfonyl-3-methyl-biphenyl-4-yl)-amide]

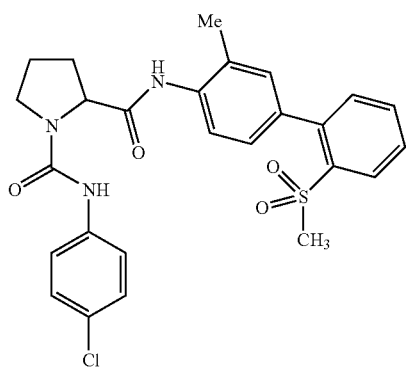

Step 1: Pyrrolidine-1,2-dicarboxylic acid 1-tert-butyl ester

DL-proline (10 g, 86.9 mmol) was dissolved in 120 mL of THF:H$_2$O (2:1), added 87 mL of a 2M NaOH solution followed by Boc$_2$O (24.6 g, 113 mmol). Stirred at ambient temperature overnight. Removed THF in vacuo, acidified water to pH 3 with citric acid, extracted twice with EtOAc, washed organics with water, brine, dried with MgSO$_4$, filtered and concentrated to yield title compound as a white solid. (18.7 g, quant.) APCI (AP–): 214.1 (M–H)$^-$.

Step 2: 2-(4-Bromo-2-methyl-phenylcarbamoyl)-pyrrolidine-1-carboxylic acid tert-butyl ester Pyrrolidine-1,2-dicarboxylic acid 1-tert-butyl ester (2 g, 9.3 mmol) was dissolved in 100 mL dry diethyl ether under Ar, cooled in an ice water bath, added dry pyridine (4.5 mL, 55 mmol) followed by the dropwise addition of oxalyl chloride (2.4 mL, 27 mmol). A precipitate forms immediately. The reaction was stirred vigorously at 0° C. for one hour, then at ambient temperature for one hour. Added 100 mL diethyl ether, filtered off solids washing with diethyl ether. Concentrated the filtrates to an off white oil. Redissolved (0.95 g, 4.0 mmol) oil in 40 mL dry DCM under Ar, cooled to 0° C., added 1.3 mL pyridine followed by 4-bromo-2-methylaniline (0.75 g, 4.0 mmol). The reaction was allowed to warm to ambient temperature, stirred overnight then concentrated. Redissolved in 100 mL EtOAc, washed with 1 N HCl (3×50 mL), brine (100 mL), dried with MgSO$_4$, filtered and concentrated to yield title compound. (1.09 g, 70%) APCI (AP–): 381.0, 383.0 (M–H)$^-$.

Step 3: 2-(3-Methyl-2'-methylsulfanyl-biphenyl-4-ylcarbamoyl)-pyrrolidine-1-carboxylic acid tert-butyl ester 2-(4-Bromo-2-methyl-phenylcarbamoyl)-pyrrolidine-1-carboxylic acid tert-butyl ester (1.07 g, 2.7 mmol), 2-(methylthio)benzene boronic acid (0.56 g, 3.3 mmol), and tetrabutylammonium bromide (322 mg, 0.13 mmol) were combined in 20 mL toluene, added 2.8 mL of a 2M aqueous Na2CO3 solution followed by tetrakistriphenylphosphine palladium (0) (0.161 g, 0.13 mmol). Heated reaction at reflux 4 hours, cooled, concentrated, redissolved in EtOAc (250 mL), washed with water (3×200 mL), brine (200 mL), dried with MgSO$_4$, filtered, and concentrated. Purified on a silica gel column eluted with 20% EtOAc in hexanes. Combined and concentrated pure fractions to yield title compound. (0.59 g, 50%) APCI (AP–): 425.1 (M–H)$^-$.

Step 4: 2-(2'-Methanesulfonyl-3-methyl-biphenyl-4-ylcarbamoyl)-pyrrolidine-1-carboxylic acid tert-butyl ester 2-(3-Methyl-2'-methylsulfanyl-biphenyl-4-ylcarbamoyl)-pyrrolidine-1-carboxylic acid tert-butyl ester (0.57 g, 1.3 mmol) was dissolved in 10 mL EtOAc, added m-chloroperoxybenzoic acid (1.76 g, 6.1 mmol) in one portion and stirred at ambient temperature for 3 hours. Reaction not complete. Concentrated and redissolved in 10 mL acetonitrile and added oxone (1.5 g, 2.4 mmol) in one portion and stirred at ambient temperature overnight and then concentrated. Redissolved in 100 mL EtOAc and 100 mL sat. NaHCO$_3$, separated layers, washed organics with brine, dried with MgSO$_4$, filtered and concentrated. Purified on a silica gel column eluted with 20% moving to 40% EtOAc in hexanes. Combined and concentrated pure fractions to yield title compound. (0.44 g, 72%) APCI (AP–): 457.1 (M–H)$^-$.

Step 5: Pyrrolidine-2-carboxylic acid (2'-methanesulfonyl-3-methyl-biphenyl-4-yl)-amide 2-(2'-Methanesulfonyl-3-methyl-biphenyl-4-ylcarbamoyl)-pyrrolidine-1-carboxylic acid tert-butyl ester (0.4 g, 0.87 mmol) was dissolved in 15 mL DCM and 5 mL trifluoroacetic acid and stirred at ambient temperature for 2 hour and concentrated. Redissolved in 100 mL EtOAc and 100 mL sat. NaHCO$_3$, separated layers, washed organics with brine, dried with MgSO$_4$, filtered and concentrated to yield title compound as an oil (0.29 g, 93%) APCI (AP–): 357.1 (M–H)$^-$.

Step 6: Pyrrolidine-1,2-dicarboxylic acid 1-[(4-chloro-phenyl)-amide]2-[(2'-methanesulfonyl-3-methyl-biphenyl-4-yl)-amide]

Pyrrolidine-2-carboxylic acid (2'-methanesulfonyl-3-methyl-biphenyl-4-yl)-amide (0.29 g, 0.80 mmol) was dissolved in 10 mL THF, added diisopropylethylamine (0.42 mL, 2.4 mmol), followed by 4-chlorophenylisocyanate (124 mg, 0.80 mmol). Stirred reaction at ambient temperature for one hour then concentrated. Purified on a silica gel column eluted with 20% moving to 40% EtOAc in hexanes. Combined and concentrated pure fractions to yield title compound. (0.32 g, 78%) APCI (AP−): 510.1, 512.1 (M−H)⁻

EXAMPLE 21

(2R,4R)-4-methoxy-pyrrolidine-1,2-dicarboxylic acid 1-[(4-chloro-phenyl)-amide]2-[(3-fluoro-2'-methanesulfonyl-biphenyl-4-yl)-amide]

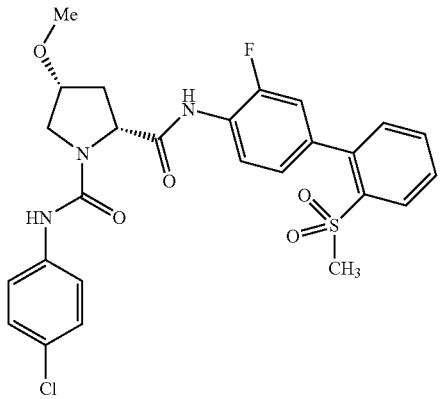

Step 1: (2R,4R)-4-hydroxy-pyrrolidine-1,2-dicarboxylic acid 1-tert-butyl ester Cis-4-hydroxy-D-proline (1.1 g, 8.4 mmol) was dissolved in 18 mL of THF/H₂O (2:1), added 2M aqueous NaOH solution (6.3 mL, 13 mmol), followed by Boc₂O. Reaction was stirred at ambient temperature over the weekend. Solution was taken up in 150 mL EtOAc, washed with 10% HCl (3×100 mL), dried organics with MgSO₄, filtered and concentrated to yield title compound as a white foam. (1.5 g, 77%) APCI (AP−): 230.1 (M−H)⁻.

Step 2: (2R,4R)-4-(tert-butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (1.5 g, 6.5 mmol) was dissolved in 2 mL DMF, added imidazole (1.1 g, 16 mmol), dimethylaminopyridine (80 mg, 0.65 mmol), and tert-butyldimethylsilyl chloride (1.08 g, 7.1 mmol). Stirred at ambient temperature overnight, dissolved in 150 mL EtOAc, washed with 10% citric acid (3×100 mL), water (2×100 mL), brine, dried with MgSO₄, filtered, and concentrated. Redissolved in 50 mL CHCl₃ and reconcentrated to yield title compound as a clear oil. (1.54 g, 69%) APCI (AP−): 344.2 (M−H)⁻.

Step 3: (2R,4R)-2-(4-bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (1.54 g, 4.5 mmol) was dissolved in 50 mL diethyl ether under an Ar atmosphere, cooled in an ice water bath, added dry pyridine (1.4 mL, 17.8 mmol), followed by the dropwise addition of oxalyl chloride (0.58 mL, 6.7 mmol). Reaction was stirred at 0° C. for 1 hour, then at ambient temperature for 1 hour. Diluted reaction with 50 mL diethyl ether, filtered off solids and concentrated filtrates. Redissolved filtrate in 30 mL dry DCM under an Ar atmosphere, cooled in an ice water bath, added 1 mL dry pyridine followed by 4-bromo-2-fluoroaniline (0.85 g, 4.5 mmol). Stirred reaction at ambient temperature for 20 hours. Concentrated solution, redissolved in EtOAc (150 mL), washed with 10% citric acid (3×100 mL), water (2×100 mL), brine, dried with MgSO₄, filtered and concentrated. Purified on a silica gel column eluting with an automated system with gradient of 0-60% EtOAc in hexanes over 40 minutes. Combined and concentrated pure fractions to yield title compound as a clear oil. (0.96 g, 42%) APCI (AP−): 515.1, 517.1 (M−H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (0.95 g, 1.84 mmol), 2-(methylthio)benzene boronic acid (0.37 g, 2.2 mmol), and tetrabutylammonium bromide (30 mg, 0.09 mmol) were combined in 15 mL toluene, added 2 mL of a 2M aqueous Na₂CO₃ solution followed by tetrakistriphenylphosphine palladium(0) (0.11 g, 0.09 mmol). Heated reaction at reflux for 5 hours, cooled, dissolved in EtOAc (100 mL), washed with water (3×50 mL), brine (50 mL), dried with MgSO₄, filtered, and concentrated. Purified on a silica gel column eluted using an automated system with gradient of 0-60% EtOAc in hexanes over 40 minutes. Combined and concentrated pure fractions to yield title compound as a light yellow foam. (0.77 g, 74%) APCI (AP−): 559.3 (M−H)⁻.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (0.84 g, 1.35 mmol) was dissolved in 20 mL EtOAc, added m-chloroperoxybenzoic acid (1.6 g, 5.4 mmol) in one portion and stirred at ambient temperature for 3 hours. A 10% aqueous solution (50 mL) of Na₂S₂O₃ was added to the vigorously stirring reaction in order to quench peroxide. After 20 minutes the solution was diluted with 100 mL EtOAc, separated layers, washed organics with sat. NaHCO₃ (3×100 mL), water (2×100 mL), brine, dried with MgSO₄, filtered and concentrated to yield title compound as a light brown foam. (0.8 g, 100%) APCI (AP−): 591.3 (M−H)⁻.

Step 6: (2R,4R)-4-hydroxy-pyrrolidine-2-carboxylic acid (3-fluoro-2'-methanesulfonyl-biphenyl-4-yl)-amide (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (0.8 g, 1.35 mmol) was dissolved in 30 mL DCM, added 10 mL trifluoroacetic acid and stirred reaction at ambient temperature for 90 minutes. Solution was concentrated to yield title compound as an amber oil. (100% crude yield) APCI (AP−): 434.1 (M−H)⁻.

Step 7: (2R,4R)-4-hydroxy-pyrrolidine-1,2-dicarboxylic acid 1-[(4-chloro-phenyl)-amide]2-[(3-fluoro-2'-methanesulfonyl-biphenyl-4-yl)-amide]

(2R,4R)-4-Hydroxy-pyrrolidine-2-carboxylic acid (3-fluoro-2'-methanesulfonyl-biphenyl-4-yl)-amide (0.51 g, 1.35 mmol) was dissolved in 20 mL THF, added diisopropylethylamine (0.94 mL, 5.4 mmol) followed by 4-chlorophenylisocyanate (0.21 g, 1.35 mmol). Stirred at ambient temperature for 2 hours. The reaction was dissolved in 100 mL EtOAc, washed with 10% citric acid (3×50 mL), water (2×50 mL), brine, dried with MgSO₄, filtered and concentrated. Purified using an automated system with gradient of 50-100% EtOAc in hexanes over 40 minutes. Compound was still eluting at end of run. Switched gradient to 0-15% MeOH in EtOAc over 40 minutes. Combined and concentrated pure fractions to yield title compound as a white solid. (0.54 g, 75%) APCI (AP+): 530.1, 532.1(M+H)⁺.

Step 8: (2R,4R)-4-methoxy-pyrrolidine-1,2-dicarboxylic acid 1-[(4-chloro-phenyl)-amide]2-[(3-fluoro-2'-methanesulfonyl-biphenyl-4-yl)-amide]

(2R,4R)-4-hydroxy-pyrrolidine-1,2-dicarboxylic acid 1-[(4-chloro-phenyl)-amide]2-[(3-fluoro-2'-methanesulfonyl-biphenyl-4-yl)-amide] (0.070 g, 0.13 mmol) was dissolved in 1.5 mL dry acetonitrile under an Argon atmosphere. Freshly prepared Ag₂O (45mg, 0.19 mmol) was added followed by methyl iodide (9 mL, 0.14 mmol). The reaction was stirred for 2 hours with no reaction seen by HPLC. Added 10 equivalents each of Ag₂O and methyl iodide. After 2 hours the reaction was complete by HPLC. The solids were filtered through celite, washing with ethyl acetate. The filtrates were concentrated, then purified by preparatory HPLC. Pure fractions were combined and lyophilized to yield title compound. (28 mg, 40%) APCI (AP−): 544.0, 546.1 (M−H)⁻.

EXAMPLE 22

(2R)-4-oxo-pyrrolidine-1,2-dicarboxylic acid 1-[(4-chloro-phenyl)-amide]2-[(3-fluoro-2'-methanesulfonyl-biphenyl-4-yl)-amide]

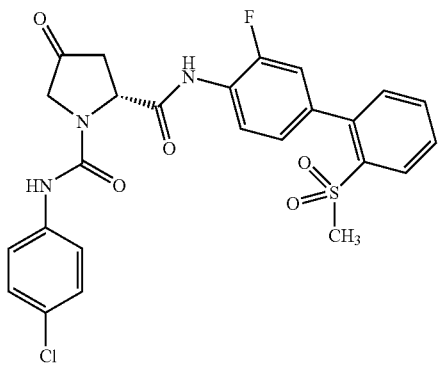

Step 1: (2R,4R)-4-hydroxy-pyrrolidine-1,2-dicarboxylic acid 1-tert-butyl ester Cis-4-hydroxy-D-proline (15 g, 114 mmol) was dissolved In 150 mL of THF/H₂O (2:1), added 2M aqueous NaOH solution (86 μmL, 172 mmol), followed by Boc₂O (27 g, 126 mmol). Reaction was stirred at ambient temperature overnight. The solution was acidified with 10% citric acid then extracted with EtOAc (2×250 mL), washed with water, brine, dried organics with MgSO₄, filtered and concentrated to yield title compound. (16 g, 61%) APCI (AP−): 230.1 (M−H)⁻.

Step 2: (2R,4R)-4-(tert-butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with MgSO₄, filtered, and concentrated to yield title compound. (20 g, 84%) APCI (AP−): 344.2 (M−H)⁻.

Step 3: (2R,4R)-2-(4-bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (4.45 g, 12.9 mmol) was dissolved in 50 mL dry CHCl₃ under an Ar atmosphere, added 4-bromo-2-fluoroaniline (2.45 g, 12.9 %mmol), EEDQ (3.8 g, 15 mmol), and triethylamine (2.6 mL, 19.3 mmol). Reaction was refluxed for 6 hours, cooled and concentrated. Redissolved in EtOAc (250 mL), washed with 10% HCl (2×200 mL), 0.1M NaOH (2×200 mL), water, brine, dried with MgSO₄, filtered and concentrated to yield title compound. (5.5 g, 82%) APCI (AP−): 515.1, 517.1 (M−H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (5.7 g, 10 mmol), 2-(methylthio)benzene boronic acid (2.1 g, 12.6 mmol), and tetrabutylammonium bromide (0.17 g, 0.52 mmol) were combined in 50 mL toluene, added 10 mL of a 2M aqueous Na₂CO₃ solution followed by tetrakistriphenylphosphine palladium(0) (0.61 g, 0.52 mmol). Heated reaction at reflux for 4 hours, cooled, dissolved in EtOAc (250 mL), washed with water (200 mL), brine, dried with MgSO₄, filtered, and concentrated in the presence of 15 g coarse silica. Slurried silica in mobile phase and loaded onto a silica gel column, eluted with 25% EtOAc in hexanes. Combined and concentrated fractions to yield title compound. (4.1 g, 70%) APCI (AP−): 559.3 (M−H)⁻.

Step 5: (2R,4R)-4-(tert-Butyl-dimethyl-silanyloxy)-
2-(3-fluoro-2'-methanesulfonyl-biphenyl-4-ylcar-
bamoyl)-pyrrolidine-1-carboxylic acid tert-butyl
ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (4.1 g, 7.3 mmol) was dissolved in 20 mL EtOAc, added m-chloroperoxybenzoic acid (7.2 g, 29 mmol) in one portion and stirred at ambient temperature for 3 hours. A 10% aqueous solution (50 mL) of $Na_2S_2O_3$ was added to the vigorously stirring reaction in order to quench peroxide. After 20 minutes the solution was diluted with 100 mL EtOAc, separated layers, washed organics with sat. $NaHCO_3$ (3×100 mL), water (2×100 mL), brine, dried with $MgSO_4$, filtered and concentrated to yield title compound. (4.3 g, 99%) APCI (AP−): 591.3 (M−H)⁻.

Step 6: (2R,4R)-4-hydroxy-pyrrolidine-1,2-dicar-
boxylic acid 1-[(4-chloro-phenyl)-amide]2-[(3-
fluoro-2'-methanesulfonyl-biphenyl-4-yl)-amide]

(2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (3.25 g, 5.5 mmol) was dissolved in 50 mL DCM, added 25 mL trifluoroacetic acid and stirred reaction at ambient temperature for 90 minutes. Solution was concentrated. The resulting oil was dissolved in 75 mL THF, added triethylamine (3.8 mL, 5.4 mmol) followed by 4-chlorophenylisocyanate (0.84 g, 5.5 mmol). Stirred at ambient temperature for 2 hours. The reaction was concentrated and purified on a silica gel column eluted with straight ethyl acetate initially moving to 5% MeOH in ethyl acetate. Combined and concentrated pure fractions to yield title compound. (2.5 g, 85%) APCI (AP−): 530.1, 532.1(M−H)⁻.

Step 7: (2R)-4-oxo-pyrrolidine-1,2-dicarboxylic acid
1-[(4-chloro-phenyl)-amide]2-[(3-fluoro-2'-methane-
sulfonyl-biphenyl-4-yl)-amide]

(2R,4R)-4-hydroxy-pyrrolidine-1,2-dicarboxylic acid 1-[(4-chloro-phenyl)-amide]2-[(3-fluoro-2'-methanesulfonyl-biphenyl-4-yl)-amide] (0.78 g, 1.5 mmol) was dissolved in 10 mL dry DCM under an Argon atmosphere, added 0.5 g celite, 0.5 g of 4 angstrom crushed molecular sieves, and pyridinium chlorochromate (0.47 g, 2.2 mmol). Stirred at ambient temperature for 6 hours, reaction appears to have stalled. Added 1 g pyridinium chlorochromate and stirred at RT overnight. HPLC did not change. Added 40 mL of a 1:1 mixture of hexanes:Et2O. Filtered through a filter funnel with silica gel. Washed with DCM. Compound did not elute. Washed with DCM:MeOH (90:10). Concentrated filtrates. Suspect pyridinium chlorochromate also eluted judged by dark color. Redissolved in DCM, washed with sat. $NaHCO_3$, dried DCM with $MgSO_4$, filtered and concentrated in vacuo. Purified on a silica gel column using an automated ISCO system with gradient of 50-100% EtOAc in hexanes over 30 minutes, then 100% EtOAc for 10 minutes. Combined and concentrated pure fractions, redissolved in acetonitrile and lyophilized to yield title compound. (0.12 g, 15%)

EXAMPLE 23

(2R,4S)-4-Fluoro-pyrrolidine-1,2-dicarboxylic acid
1-[(4-chloro-phenyl)-amide]-2-[(3-fluoro-2'-meth-
anesulfonyl-biphenyl-4-yl)-amide]

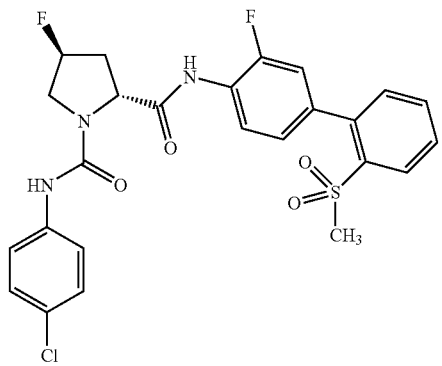

Step 1:
(2R,4R)-4-hydroxy-pyrrolidine-1,2-dicarboxylic
acid 1-tert-butyl ester

Cis4-hydroxy-D-proline (15 g, 114 mmol) was dissolved In 150 mL of $THF/H_2O$ (2:1), added 2M aqueous NaOH solution (86 mL, 172 mmol), followed by $Boc_2O$ (27 g, 126 mmol). Reaction was stirred at ambient temperature overnight. The solution was acidified with 10% citric acid then extracted with EtOAc (2×250 mL), washed with water, brine, dried organics with $MgSO_4$, filtered and concentrated to yield title compound. (16 g, 61%) APCI (AP−): 230.1 (M−H)⁻.

Step 2: (2R,4R)-4-(tert-butyl-dimethyl-silanyloxy)-
pyrrolidine-1,2-dicarboxylic acid 1-tert-butyl ester (2R,4R)-4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with $MgSO_4$, filtered, and concentrated to yield title compound. (20 g, 84%) APCI (AP−): 344.2 (M−H)⁻.

Step 3: (2R,4R)-2-(4-bromo-2-fluoro-phenylcarbam-
oyl)-4-(tert-butyl-dimethyl-silanyloxy)-pyrrolidine-
1-carboxylic acid tert-butyl ester (2R,4R)-4-(tert-Butyl-dimethyl-silanyloxy)-pyrrolidine-1,2-dicarboxylic acid 1-tert-butyl ester (4.45 g, 12.9 mmol) was dissolved in 50 mL dry $CHCl_3$ under an Ar atmosphere, added 4-bromo-2-fluoroaniline (2.45 g, 12.9 mmol), EEDQ (3.8 g, 15 mmol), and triethylamine (2.6 mL, 19.3 mmol). Reaction was refluxed for 6 hours, cooled and concentrated. Redissolved in EtOAc (250 mL), washed with 10% HCl (2×200 mL), 0.1M NaOH (2×200 mL), water, brine, dried with $MgSO_4$, filtered and concentrated to yield title compound. (5.5 g, 82%) APCI (AP−): 515.1, 517.1 (M−H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (5.7 g, 10 mmol), 2-(methylthio)benzene boronic acid (2.1 g, 12.6 mmol), and tetrabutylammonium bromide (0.17 g, 0.52 mmol) were combined in 50 mL toluene, added 10 mL of a 2M aqueous Na$_2$CO$_3$ solution followed by tetrakistriphenylphosphine palladium(0) (0.61 g, 0.52 mmol). Heated reaction at reflux for 4 hours, cooled, dissolved in EtOAc (250 mL), washed with water (200 mL), brine, dried with MgSO$_4$, filtered, and concentrated in the presence of 15 g coarse silica. Slurried silica in mobile phase and loaded onto a silica gel column, eluted with 25% EtOAc in hexanes. Combined and concentrated fractions to yield title compound. (4.1 g, 70%) APCI (AP−): 559.3 (M−H)⁻.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (4.1 g, 7.3 mmol) was dissolved in 20 mL EtOAc, added m-chloroperoxybenzoic acid (7.2 g, 29 mmol) in one portion and stirred at ambient temperature for 3 hours. A 10% aqueous solution (50 mL) of Na$_2$S$_2$O$_3$ was added to the vigorously stirring reaction in order to quench peroxide. After 20 minutes the solution was diluted with 100 mL EtOAc, separated layers, washed organics with sat. NaHCO$_3$ (3×100 mL), water (2×100 mL), brine, dried with MgSO$_4$, filtered and concentrated to yield title compound. (4.3 g, 99%) APCI (AP−): 591.3 (M−H)⁻.

Step 6: (2R,4R)-4-hydroxy-pyrrolidine-1,2-dicarboxylic acid 1-[(4-chloro-phenyl)-amide]2-[(3-fluoro-2'-methanesulfonyl-biphenyl-4-yl)-amide]

(2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (3.25 g, 5.5 mmol) was dissolved in 50 mL DCM, added 25 mL trifluoroacetic acid and stirred reaction at ambient temperature for 90 minutes. Solution was concentrated. The resulting oil was dissolved in 75 mL THF, added triethylamine (3.8 mL, 5.4 mmol) followed by 4-chlorophenylisocyanate (0.84 g, 5.5 mmol). Stirred at ambient temperature for 2 hours. The reaction was concentrated and purified on a silica gel column eluted with straight ethyl acetate initially moving to 5% MeOH in ethyl acetate. Combined and concentrated pure fractions to yield title compound. (2.5 g, 85%) APCI (AP−): 530.1, 532.1(M−H)⁻.

Step 7: (2R,4S)-4-Fluoro-pyrrolidine-1,2-dicarboxylic acid 1-[(4-chloro-phenyl)-amide]-2-[(3-fluoro-2'-methanesulfonyl-biphenyl-4-yl)-amide]

(2R,4R)-4-hydroxy-pyrrolidine-1,2-dicarboxylic acid 1-[(4-chloro-phenyl)-amide]2-[(3-fluoro-2'-methanesulfo-nyl-biphenyl-4-yl)-amide] (0.1 g, 0.19 mmol) in 3 mL dry DCM was added to a solution of [Bis(2-methoxyethyl) amino]-sulfur trifluoride (38 µl, 0.21 mmol) in 3 mL dry DCM at −78° C. under Argon. Stirred at −78° C. for 30 minutes then allowed to warm to room temperature. Stirred for one hour then concentrated reaction. Purified by preparatory HPLC, combined and lyophilized fractions to yield title compound. (0.020 g, 20%) APCI (AP−): 532.1, 534.1 (M−H)⁻.

EXAMPLE 24

(2R,4R)-4-Hydroxy-pyrrolidine-1,2-dicarboxylic acid 2-[(3-fluoro-2'-methanesulfonyl-biphenyl-4-yl)-amide]1-p-tolylamide

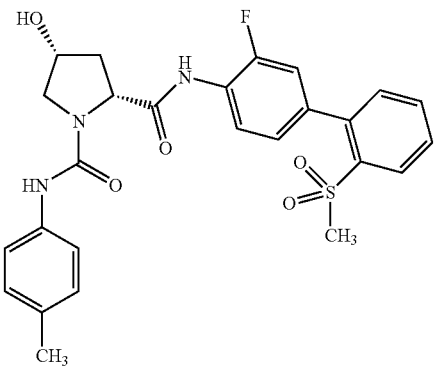

Step 1: (2R,4R)-4-hydroxy-pyrrolidine-1,2-dicarboxylic acid 1-tert-butyl ester Cis-4-hydroxy-D-proline (15 g, 114 mmol) was dissolved In 150 mL of THF/H$_2$O (2:1), added 2M aqueous NaOH solution (86 mL, 172 mmol), followed by Boc$_2$O (27 g, 126 mmol). Reaction was stirred at ambient temperature overnight. The solution was acidified with 10% citric acid then extracted with EtOAc (2×250 mL), washed with water, brine, dried organics with MgSO$_4$, filtered and concentrated to yield title compound. (16 g, 61%) APCI (AP−): 230.1 (M−H)⁻.

Step 2: (2R,4R)-4-(tert-butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with MgSO$_4$, filtered, and concentrated to yield title compound. (20 g, 84%) APCI (AP−): 344.2 (M−H)⁻.

Step 3: (2R,4R)-2-(4-bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (4.45 g, 12.9 mmol) was dissolved in 50 mL dry CHCl$_3$ under an Ar atmosphere, added 4-bromo-2-fluoroaniline (2.45 g, 12.9 mmol), EEDQ (3.8 g, 15 mmol), and triethylamine (2.6 mL, 19.3 mmol). Reaction was refluxed for 6 hours, cooled and concentrated. Redissolved in EtOAc (250 mL), washed with 10% HCl (2×200 mL), 0.1 M NaOH (2×200 mL), water, brine, dried with MgSO₄, filtered and concentrated to yield title compound. (5.5 g, 82%) APCI (AP–): 515.1, 517.1 (M–H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (5.7 g, 10 mmol), 2-(methylthio)benzene boronic acid (2.1 g, 12.6 mmol), and tetrabutylammonium bromide (0.17 g, 0.52 mmol) were combined in 50 mL toluene, added 10 mL of a 2M aqueous Na2CO3 solution followed by tetrakistriphenylphosphine palladium(0) (0.61 g, 0.52 mmol). Heated reaction at reflux for 4 hours, cooled, dissolved in EtOAc (250 mL), washed with water (200 mL), brine, dried with MgSO₄, filtered, and concentrated in the presence of 15 g coarse silica. Slurried silica in mobile phase and loaded onto a silica gel column, eluted with 25% EtOAc in hexanes. Combined and concentrated fractions to yield title compound. (4.1 g, 70%) APCI (AP–): 559.3 (M–H)⁻.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (4.1 g, 7.3 mmol) was dissolved in 20 mL EtOAc, added m-chloroperoxybenzoic acid (7.2 g, 29 mmol) in one portion and stirred at ambient temperature for 3 hours. A 10% aqueous solution (50 mL) of Na₂S₂O₃ was added to the vigorously stirring reaction in order to quench peroxide. After 20 minutes the solution was diluted with 100 mL EtOAc, separated layers, washed organics with sat. NaHCO₃ (3×100 mL), water (2×100 mL), brine, dried with MgSO₄, filtered and concentrated to yield title compound. (4.3 g, 99%) APCI (AP–): 591.3 (M–H)⁻.

Step 6: (2R,4R)-4-Hydroxy-pyrrolidine-1,2-dicarboxylic acid 2-[(3-fluoro-2'-methanesulfonyl-biphenyl-4-yl)-amide]1-p-tolylamide (2R,4R)-4-(tert-Butyl -dimethyl -silanyloxy)-2-(3-fluoro-2'-methanesulfonyl-biphenyl-4-ylcarbamoyl)-pyrrolidine-1-carboxylic acid tert-butyl ester (0.35 g, 0.59 mmol) was dissolved in 10 mL DCM, added 5 mL trifluoroacetic acid and stirred reaction at ambient temperature for 2 hours. Solution was concentrated. The resulting oil was dissolved in 20 mL THF, added triethylamine (0.41 mL, 3 mmol) followed by p-tolylisocyanate (0.079 g, 0.59 mmol). Stirred at ambient temperature for 2 hours. The reaction was concentrated and purified on a silica gel column eluted using an automated ISCO system with gradient of 0-10% MeOH in ethyl acetate over 40 minutes. Concentrated fractions then redissolved in acetonitrile/water and lyophilized to yield title compound. (0.17 g, 56%) APCI (AP–): 510.1(M–H)⁻.

EXAMPLE 25

(2R,4R)-4-Hydroxy-pyrrolidine-1,2-dicarboxylic acid 2-[(3-fluoro-2'-methanesulfonyl-biphenyl-4-yl)-amide]1-[(4-fluoro-phenyl)-amide]

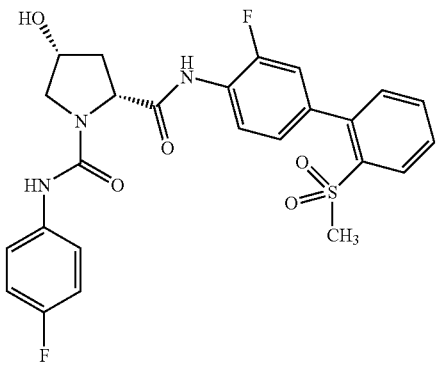

Step 1:
(2R,4R)-4-hydroxy-pyrrolidine-1,2-dicarboxylic acid 1-tert-butyl ester

Cis-4-hydroxy-D-proline (15 g, 114 mmol) was dissolved In 150 mL of THF/H₂O (2:1), added 2M aqueous NaOH solution (86 mL, 172 mmol), followed by Boc₂O (27 g, 126 mmol). Reaction was stirred at ambient temperature overnight. The solution was acidified with 10% citric acid then extracted with EtOAc (2×250 mL), washed with water, brine, dried organics with MgSO₄, filtered and concentrated to yield title compound. (16 g, 61%) APCI (AP–): 230.1 (M–H)⁻.

Step 2: (2R,4R)-4-(tert-butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with MgSO₄, filtered, and concentrated to yield title compound. (20 g, 84%) APCI (AP–): 344.2 (M–H)⁻.

Step 3: (2R,4R)-2-(4-bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (4.45 g, 12.9 mmol) was dissolved in 50 mL dry CHCl₃ under an Ar atmosphere, added 4-bromo-2-fluoroaniline (2.45 g, 12.9 mmol), EEDQ (3.8 g, 15 mmol), and triethylamine (2.6 mL, 19.3 mmol). Reaction was refluxed for 6 hours, cooled and concentrated. Redissolved in EtOAc (250 mL), washed with 10% HCl (2×200 mL), 0.1M NaOH (2×200 mL), water, brine, dried with MgSO₄, filtered and concentrated to yield title compound. (5.5 g, 82%) APCI (AP–): 515.1, 517.1 (M–H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (5.7 g, 10 mmol), 2-(methylthio)benzene boronic acid (2.1 g, 12.6 mmol), and tetrabutylammonium bromide (0.17 g, 0.52 mmol) were combined in 50 mL toluene, added 10 mL of a 2M aqueous Na$_2$CO$_3$ solution followed by tetrakistriphenylphosphine palladium(0) (0.61 g, 0.52 mmol). Heated reaction at reflux for 4 hours, cooled, dissolved in EtOAc (250 mL), washed with water (200 mL), brine, dried with MgSO$_4$, filtered, and concentrated in the presence of 15 g coarse silica. Slurried silica in mobile phase and loaded onto a silica gel column, eluted with 25% EtOAc in hexanes. Combined and concentrated fractions to yield title compound. (4.1 g, 70%) APCI (AP–): 559.3 (M–H)$^-$.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (4.1 g, 7.3 mmol) was dissolved in 20 mL EtOAc, added m-chloroperoxybenzoic acid (7.2 g, 29 mmol) in one portion and stirred at ambient temperature for 3 hours. A 10% aqueous solution (50 mL) of Na$_2$S$_2$O$_3$ was added to the vigorously stirring reaction in order to quench peroxide. After 20 minutes the solution was diluted with 100 mL EtOAc, separated layers, washed organics with sat. NaHCO$_3$ (3×100 mL), water (2×100 mL), brine, dried with MgSO$_4$, filtered and concentrated to yield title compound. (4.3 g, 99%) APCI (AP–): 591.3 (M–H)$^-$.

Step 6: (2R,4R)-4-Hydroxy-pyrrolidine-1,2-dicarboxylic acid 2-[(3-fluoro-2'-methanesulfonyl-biphenyl-4-yl)-amide]1-[(4-fluoro-phenyl)-amide]

(2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (0.35 g, 0.59 mmol) was dissolved in 10 mL DCM, added 5 mL trifluoroacetic acid and stirred reaction at ambient temperature for 2 hours. Solution was concentrated. The resulting oil was dissolved in 20 mL THF, added triethylamine (0.41 mL, 3 mmol) followed by 4-fluorophenylisocyanate (0.081 g, 0.59 mmol). Stirred at ambient temperature for 2 hours. The reaction was concentrated and purified on a silica gel column eluted using an automated ISCO system with gradient of 80-100% ethyl acetate in hexanes for 20 minutes then straight ethyl acetate for 20 minutes. Concentrated fractions then redissolved in acetonitrile/water and lyophilized to yield title compound. (0.175 g, 57%) APCI (AP–): 514.1(M–H)$^-$.

EXAMPLE 26

(2R,4R)-4-Hydroxy-pyrrolidine-1,2-dicarboxylic acid 1-[(5-chloro-pyridin-2-yl)-amide]2-[(3-fluoro-2'-methanesulfonyl-biphenyl-4-yl)-amide]

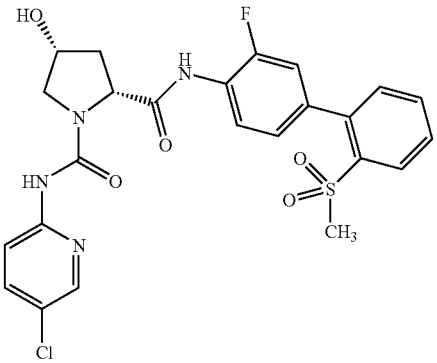

Step 1: (2R,4R)-4-hydroxy-pyrrolidine-1,2-dicarboxylic acid 1-tert-butyl ester Cis-4-hydroxy-D-proline (15 g, 114 mmol) was dissolved In 150 mL of THF/H$_2$O (2:1), added 2M aqueous NaOH solution (86 mL, 172 mmol), followed by Boc$_2$O (27 g, 126 mmol). Reaction was stirred at ambient temperature overnight. The solution was acidified with 10% citric acid then extracted with EtOAc (2×250 mL), washed with water, brine, dried organics with MgSO$_4$, filtered and concentrated to yield title compound. (16 g, 61%) APCI (AP–): 230.1 (M–H)$^-$.

Step 2: (2R,4R)-4-(tert-butyl-dimethyl-silanyloxy)-pyrrolidine-1,2-dicarboxylic acid 1-tert-butyl ester (2R,4R)-4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with MgSO$_4$, filtered, and concentrated to yield title compound. (20 g, 84%) APCI (AP–): 344.2 (M–H)$^-$.

Step 3: (2R,4R)-2-(4-bromo-2-fluoro-phenylcarbamoyl)-4-(tert-butyl-dimethyl-silanyloxy)-pyrrolidine-1-carboxylic acid tert-butyl ester (2R,4R)-4-(tert-Butyl-dimethyl-silanyloxy)-pyrrolidine-1,2-dicarboxylic acid 1-tert-butyl ester (4.45 g, 12.9 mmol) was dissolved in 50 mL dry CHCl$_3$ under an Ar atmosphere, added 4-bromo-2-fluoroaniline (2.45 g, 12.9 mmol), EEDQ (3.8 g, 15 mmol), and triethylamine (2.6 mL, 19.3 mmol). Reaction was refluxed for 6 hours, cooled and concentrated. Redissolved in EtOAc (250 mL), washed with 10% HCl (2×200 mL), 0.1M NaOH (2×200 mL), water, brine, dried with MgSO₄, filtered and concentrated to yield title compound. (5.5 g, 82%) APCI (AP–): 515.1, 517.1 (M–H)⁻.

Step 4: (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (2R,4R)-2-(4-Bromo-2-fluoro-phenylcarbamoyl)-4-(tert-butyl-dimethyl-silanyloxy)-pyrrolidine-1-carboxylic acid tert-butyl ester (5.7 g, 10 mmol), 2-(methylthio)benzene boronic acid (2.1 g, 12.6 mmol), and tetrabutylammonium bromide (0.17 g, 0.52 mmol) were combined in 50 mL toluene, added 10 mL of a 2M aqueous Na2CO3 solution followed by tetrakistriphenylphosphine palladium(0) (0.61 g, 0.52 mmol). Heated reaction at reflux for 4 hours, cooled, dissolved in EtOAc (250 mL), washed with water (200 mL), brine, dried with MgSO₄, filtered, and concentrated in the presence of 15 g coarse silica. Slurried silica in mobile phase and loaded onto a silica gel column, eluted with 25% EtOAc in hexanes. Combined and concentrated fractions to yield title compound. (4.1 g, 70%) APCI (AP–): 559.3 (M–H)⁻.

Step 5: (2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (2R,4R)-4-(tert-Butyl-dimethyl-silanyloxy)-2-(3-fluoro-2'-methylsulfanyl-biphenyl-4-ylcarbamoyl)-pyrrolidine-1-carboxylic acid tert-butyl ester (4.1 g, 7.3 mmol) was dissolved in 20 mL EtOAc, added m-chloroperoxybenzoic acid (7.2 g, 29 mmol) in one portion and stirred at ambient temperature for 3 hours. A 10% aqueous solution (50 mL) of Na₂S₂O₃ was added to the vigorously stirring reaction in order to quench peroxide. After 20 minutes the solution was diluted with 100 mL EtOAc, separated layers, washed organics with sat. NaHCO₃ (3×100 mL), water (2×100 mL), brine, dried with MgSO₄, filtered and concentrated to yield title compound. (4.3 g, 99%) APCI (AP–): 591.3 (M–H)⁻.

Step 6: (2R,4R)-4-Hydroxy-pyrrolidine-1,2-dicarboxylic acid 1-[(5-chloro-pyridin-2-yl)-amide]2-[(3-fluoro-2'-methanesulfonyl-biphenyl-4-yl)-amide]

(2R,4R)-4-(tert-Butyl-dimethyl-silanyloxy)-2-(3-fluoro-2'-methanesulfonyl-biphenyl-4-ylcarbamoyl)-pyrrolidine-1-carboxylic acid tert-butyl ester (0.35 g, 0.59 mmol) was dissolved in 10 mL DCM, added 5 mL trifluoroacetic acid and stirred reaction at ambient temperature for 2 hours. Solution was concentrated. The resulting oil was dissolved in 15 mL DMF, added triethylamine (0.41 mL, 3 mmol) followed by (5-Chloro-pyridin-2-yl)-carbamic acid 4-nitro-phenyl ester (0.17 g, 0.0.59 mmol; see Example 3, step 3a). Stirred at 50° C. for 2 hours. The reaction was cooled, dissolved in 100 mL ethyl acetate, washed with sat. NaHCO₃ (3×50 mL), 10% citric acid (2×50 mL), brine, dried with MgSO₄, filtered and concentrated. Purified on a silica gel column eluted using an automated ISCO system with gradient of 0-10% MeOH in ethyl acetate over 40 minutes. Concentrated fractions then redissolved in acetonitrile/water and lyophilized to yield title compound. (0.20 g, 64%) APCI (AP–): 531.1, 533.0(M–H)⁻.

EXAMPLE 27

Pyrrolidine-1,2-dicarboxylic acid 1-[(4-chloro-phenyl)-amide]2-[(2'-methanesulfonyl-3-trifluoromethyl-biphenyl-4-yl)-amide]

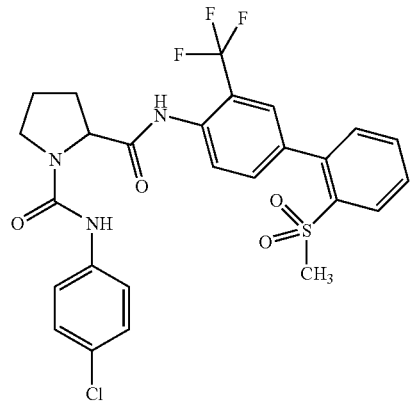

Step 1: Pyrrolidine-1,2-dicarboxylic acid 1-tert-butyl ester

DL-proline (10 g, 86.9 mmol) was dissolved in 120 mL of THF: H₂O (2:1), added 87 mL of a 2M NaOH solution followed by Boc₂O (24.6 g, 113 mmol). Stirred at ambient temperature overnight. Removed THF in vacuo, acidified water to pH 3 with citric acid, extracted twice with EtOAc, washed organics with water, brine, dried with MgSO₄, filtered and concentrated to yield title compound as a white solid. (18.7 g, quant.) APCI (AP–): 214.1 (M–H)⁻.

Step 2: 2-(4-Bromo-2-trifluoromethyl-phenylcarbamoyl)-pyrrolidine-1-carboxylic acid tert-butyl ester Pyrrolidine-1,2-dicarboxylic acid 1-tert-butyl ester (4 g, 18.6 mmol) was dissolved in 200 mL dry diethyl ether under Ar, cooled in an ice water bath, added dry pyridine (9 mL, 111 mmol) followed by the dropwise addition of oxalyl chloride (4.8 mL, 54 mmol). A precipitate forms immediately. The reaction was stirred vigorously at 0° C. for one hour, then at ambient temperature for one hour. Added 100 mL diethyl ether, filtered off solids washing with diethyl ether. Concentrated the filtrates to an off white oil. Redissolved (2 g, 8.5 mmol) oil in 40 mL dry DCM under Ar, cooled to 0° C., added 2.8 mL pyridine followed by 4-bromo-2-trifluoromethylaniline (2.05 g, 8.6 mmol). The reaction was allowed to warm to ambient temperature, stirred overnight then concentrated. Redissolved in 100 mL EtOAc, washed with 1 N HCl (3×50 mL), brine (100 mL), dried with MgSO₄, filtered and concentrated to yield title compound. (1.98 g, 53%) APCI (AP–): 435.0, 437.0 (M–H)⁻.

Step 3: 2-(2'-Methylsulfanyl-3-trifluoromethyl-biphenyl-4-ylcarbamoyl)-pyrrolidine-1-carboxylic acid tert-butyl ester 2-(4-Bromo-2-trifluoromethyl-phenylcarbamoyl)-pyrrolidine-1-carboxylic acid tert-butyl ester (1.92 g, 4.4 mmol), 2-(methylthio)benzene boronic acid (0.88 g, 5.2 mmol), and tetrabutylammonium bromide (70 mg, 0.22 mmol) were combined in 40 mL toluene, added 4.4 mL of a 2M aqueous Na2CO3 solution followed by tetrakistriphenylphosphine palladium(0) (0.253 g, 0.22 mmol). Heated reaction at reflux 4 hours, cooled, concentrated, redissolved in EtOAc (250 mL), washed with water (3×200 mL), brine (200 mL), dried with MgSO4, filtered, and concentrated. Purified on a silica gel column eluted with 20% EtOAc in hexanes. Combined and concentrated pure fractions to yield title compound. (1.8 g, 85%) APCI (AP−): 479.1 (M−H)−.

Step 4: 2-(2'-Methanesulfonyl-3-trifluoromethyl-biphenyl-4-ylcarbamoyl)-pyrrolidine-1-carboxylic acid tert-butyl ester 2-(2'-Methylsulfanyl-3-trifluoromethyl-biphenyl-4-ylcarbamoyl)-pyrrolidine-1-carboxylic acid tert-butyl ester (1.8 g, 3.7 mmol) was dissolved in 20 mL acetonitrile, and added oxone (4.6 g, 6.8 mmol) in one portion and stirred at ambient temperature 4 days and then concentrated. Redissolved in 100 mL EtOAc and 100 mL sat. NaHCO3, separated layers, washed organics with brine, dried with MgSO4, filtered and concentrated. Purified on a silica gel column eluted with 20% EtOAc in hexanes. Combined and concentrated pure fractions to yield title compound. (1.05 g, 55%) APCI (AP−): 511.1 (M−H)−.

Step 5: Pyrrolidine-2-carboxylic acid (2'-methanesulfonyl-3-trifluoromethyl-biphenyl-4-yl)-amide 2-(2'-Methanesulfonyl-3-trifluoromethyl-biphenyl-4-ylcarbamoyl)-pyrrolidine-1-carboxylic acid tert-butyl ester (0.97 g, 1.9 mmol) was dissolved in 10 mL DCM and 5 mL trifluoroacetic acid and stirred at ambient temperature overnight and concentrated. Redissolved in 100 mL EtOAc and 100 mL sat. NaHCO3, separated layers, washed organics with brine, dried with MgSO4, filtered and concentrated to yield title compound as an oil (0.78 g, 100%) APCI (AP−): 411.0 (M−H)−.

Step 6: Pyrrolidine-1,2-dicarboxylic acid 1-[(4-chloro-phenyl)-amide]2-[(2'-methanesulfonyl-3-trifluoromethyl-biphenyl-4-yl)-amide]

Pyrrolidine-2-carboxylic acid (2'-methanesulfonyl-3-trifluoromethyl-biphenyl-4-yl)-amide (0.4 g, 0.97 mmol) was dissolved in 10 mL THF, added diisopropylethylamine (0.5 mL, 2.9 mmol), followed by 4-chlorophenylisocyanate (148 mg, 0.96 mmol). Stirred reaction at ambient temperature for one hour then concentrated. Purified on a silica gel column eluted with 20% moving to 50% EtOAc in hexanes. Combined and concentrated pure fractions to yield title compound. (0.48 g, 88%) APCI (AP−): 564.0, 566.0 (M−H)−.

General Procedure for Preparation of Examples 28n et. seq.:

Step 1

Route 1

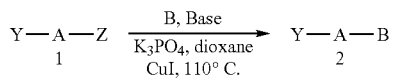

-continued

Y' = NH2 or NO2
A = substituted aryl, substituted heteroaryl
Z = Br, I, OTf

Base = 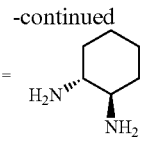

Route 2

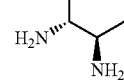

Y' = NH2 or NO2
A = substituted aryl, substituted heteroaryl
Z = Br, I, OTf

Base = 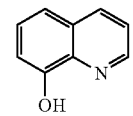

Step 2

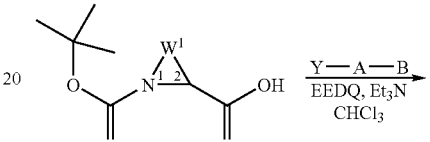

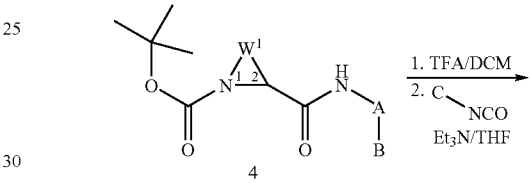

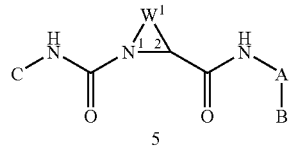

Y' = NH2
A = substituted aryl, or substituted heteroaryl

Synthesis of 2 (Step 1): As provided in Route 1, a mixture of 1 (where the structure of YAZ is as provided in the Scheme), B (where B is a nitrogen in a heteroaryl or heterocycloalkyl ring, an acyclic alkyl primary or secondary amine, or an acyclic primary or secondary amide), K3PO4, CuI, and trans-diaminocyclohexane is heated in dioxane at reflux to obtain compound 2, wherein the point of attachment of YA to B is the nitrogen of the heteroaryl or heterocycloalkyl ring, or the nitrogen of the acyclic primary or secondary alkyl amine, or the nitrogen of the acyclic primary or secondary amide. In the case where Y is a nitro group, the moiety is reduced to the amino group with RaNi and EtOH under a hydrogen atmosphere.

Alternatively, as provided in Route 2, CuI, K2CO3, and 8-hydroxyquinoline in DMSO can be used to carry out the coupling reaction.

Synthesis of 4 (Step 2): The appropriate aniline (2=YAB), N-ethoxycarbonyl-2-ethoxy-1,2-dihydroquinoline (EEDQ), triethylamine and carboxylic acid (3) are heated at reflux in chloroform to produce 4.

Synthesis of 5: A solution of compound 4, TFA and DCM is stirred at room temperature for 1 h and then concentrated under reduced pressure. The resulting oil is dissolved in THF and cooled to 0° C. followed by the addition of triethylamine and the appropriate isocyanate to produce compound 5.

EXAMPLE 28

(2R,4R)-4-Methoxy-pyrrolidine-1,2-dicarboxylic acid 1-[(4-chloro-phenyl)-amide]2-{[2-fluoro-4-(2-oxo-piperidin-1-yl)-phenyl]-amide}

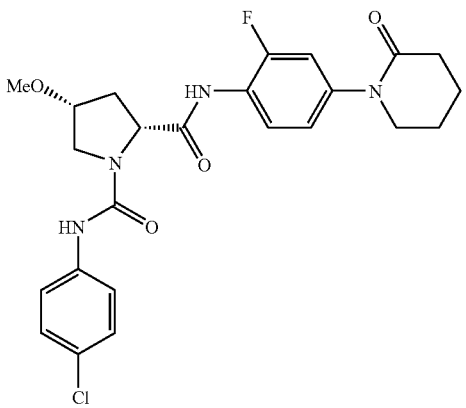

Step 1: (2R,4R)-4-Hydroxy-pyrrolidine-2-carboxylic acid methyl ester

Cis-4-Hydroxy-D-proline (15 g, 115 mmol) was suspended in 150 mL anhydrous methanol under an argon atmosphere, then cooled to 0° C. before bubbling in HCl gas for 15 minutes. The solution gradually became homogenous. The argon and HCl gas lines were removed and the solution was refluxed for 4 h. The solution was cooled and then concentrated under reduced pressure. The crude material was redissolved in 100 mL methanol and diethyl ether was added until a precipitate formed. The precipitate was filtered off, washed with diethyl ether, and dried in vacuo overnight to reveal 1 (20 g, 95%) as a white solid. MS: APCI (AP+): 146 (M)+.

Step 2: (2R,4R)-4-Hydroxy-1-trityl-pyrrolidine-2-carboxylic acid methyl ester (2)

Into a solution of 1 (10 g, 55 mmol) in anhydrous CHCl$_3$ (100mL) was added triethylamine (19 mL, 138 mmol) and triphenylmethyl chloride (14.5 g, 52 mmol). The mixture was stirred at RT for 3d before concentrating and redissolving in EtOAc. The solution was washed sequentially with 10% aq. citric acid, water, and brine before drying over MgSO$_4$ and concentrating under reduced pressure to reveal 2 (20 g, 100%) as a yellow solid.

Step 3: (2R,4R)-4-Methoxy-1-trityl-pyrrolidine-2-carboxylic acid methyl ester (3)

Into a solution of 2 (5.71 g, 14.7 mmol) in anhydrous DMF (20 mL) and anhydrous THF (20 mL) was added MeI (3.67 mL, 58.9 mmol). The solution was cooled to 0° C. in an ice bath and NaH (0.766 g, 19.2 mmol) was added in one portion. The mixture was stirred at RT for 26 h before adding EtOAc and washing sequentially with water and brine. The organic layer was dried over MgSO$_4$ and concentrated under reduced pressure. Purification of the crude material by flash chromatography revealed 3 (4.67 g, 79%) as a white solid.

Step 4: (2R,4R)-4-Methoxy-pyrrolidine-2-carboxylic acid methyl ester (4)

To a flask containing 3 (4.67 g, 11.6 mmol) was added a solution of CH$_2$Cl$_2$ (27 mL), water (0.3 mL), and TFA (3.0 mL, 38.9 mmol). The solution was stirred at RT for 3 h before concentrating under reduced pressure to reveal impure 4. MS: APCI (AP+): 160.1 (M)+.

Step 5: (2R,4R)-4-Methoxy-pyrrolidine-1,2-dicarboxylic acid 1-tert-butyl ester 2-methyl ester (5)

Into a solution of 4 (1.85 g, 11.6 mmol) in CH$_2$Cl$_2$ (20 mL) was added triethylamine (6.49 mL, 46.5 mmol), di-tert-butyl dicarbonate (5.08 g, 23.3 mmol), and dimethylaminopyridine (0.142 g, 1.16 mmol). The mixture was stirred at RT for 22 h before concentrating under reduced pressure and redissolving in EtOAc. The solution was washed sequentially with 10% aq. citric acid and brine before drying over MgSO$_4$ and concentrating under reduced pressure. The crude material was purified by flash chromatography to reveal 5 (2.54 g, 84% over two steps) as a yellow solid. MS: APCI (AP+): 260.1 (M)+.

Step 6: (2R,4R)-4-Methoxy-pyrrolidine-1,2-dicarboxylic acid 1-tert-butyl ester (6)

Into a solution of 5 (2.54 g, 9.80 mmol) in acetonitrile (20 mL) was added water (20 mL) and LiOH.H$_2$O (1.64 g, 39.2 mmol). The mixture was stirred at RT for 28 h before removing the acetonitrile under reduced pressure. EtOAc was added to the residue that was then washed with 1N HCl. The aqueous layer was extracted with additional EtOAc and the combined organic layers were washed with brine and dried over MgSO$_4$. The solution was concentrated under reduced pressure to reveal 6 (2.16 g, 90%) as a white solid. MS: APCI (AP−): 244.1 (M)−.

Step 7: 1-(4-Amino-3-fluoro-phenyl)-piperidin-2-one (7)

2-Fluoro-4-iodoaniline (10.0 g, 42.2 mmol) was combined with δ-valerolactam (6.27 g, 63.3 mmol), CuI (0.804 g, 4.22 mmol), and K$_3$PO$_4$ (22.4 g, 105 mmol). 1,4-Dioxane (60 mL) was added followed by trans-1,2-diaminocyclohexane (1.01 mL, 8.44 mmol). The mixture was heated to reflux for 22 h before cooling and diluting with EtOAc. The mixture was filtered through a plug of silica, eluting with EtOAc, and the filtrate concentrated under reduced pressure. Purification of the crude product by flash chromatography revealed 7 (3.40 g, 39%) as a brown solid. MS: APCI (AP+): 209.1 (M)+.

Step 8: (2R,4R)-2-[2-Fluoro-4-(2-oxo-piperidin-1-yl)-phenylcarbamoyl]-4-methoxy-pyrrolidine-1-carboxylic acid tert-butyl ester (8)

Into a solution of 6 (0.250 g, 1.02 mmol) in CHCl$_3$ (10 mL) was added 7 (0.212 g, 1.02 mmol), EEDQ (0.302 g, 1.22 mmol), and triethylamine (0.213 mL, 1.53 mmol). The solution was stirred at reflux for 19 h before cooling to RT and adding EtOAc. The solution was washed sequentially with 10% aq. citric acid, 1N NaOH, water, and brine, before drying over MgSO$_4$ and concentrating under reduced pressure. The crude material was purified by flash chromatography to reveal 8 (0.329 g, 74%) as a tan foam. MS: APCI (AP+): 436.1 (M)+, (AP−): 434.1 (M)−.

Step 9: (2R, 4R)-4-Methoxy-pyrrolidine-2-carboxylic acid [2-fluoro-4-(2-oxo-piperidin-1-yl)-phenyl]-amide (9)

Into a solution of 8 (0.329 g, 0.761 mmol) in anhydrous CH$_2$Cl$_2$ (5 mL) was added TFA (5 mL). The solution was stirred at RT for 0.5 h before concentrating under reduced pressure to reveal 9 (0.255 g, 100%) as a tan oil.

Step 10: (2R,4R)-4-Methoxy-pyrrolidine-1,2-dicarboxylic acid 1-[(4-chloro-phenyl)-amide]2-{[2-fluoro-4-(2-oxo-piperidin-1-yl)-phenyl]-amide}(10).

Into a solution of 9 (0.128 g, 0.380 mmol) in anhydrous THF (5 mL) at 0° C. was added triethylamine (0.265 mL, 1.90 mmol) and 4-chlorophenyl isocyanate (0.058 g, 0.380 mmol). The solution was stirred at RT for 3.5 h before concentrating under reduced pressure. The crude material was purified by flash chromatography, followed by filtration through a fritted funnel and concentration under reduced pressure. Remaining EtOAc was azeotroped off with CHCl$_3$. The resulting solid was lyophilized from acetonitrile/water to reveal 10 (0.186 g, 100%) as a white solid. MS: APCI (AP+): 489.1 (M)+, (AP−): 487.1 (M)−; CHN calc'd for C$_{24}$H$_{26}$Cl$_1$F$_1$N$_4$O$_4$: % C, 50.75; % H, 4.58; % N, 9.07. Found: % C, 50.62; % H, 4.19; % N, 9.02.

EXAMPLE 29

(2R,4R)-4-Hydroxy-pyrrolidine-1,2-dicarboxylic acid 1-[(4-chloro-phenyl)-amide]2-{[4-(2-oxo-piperidin-1-yl)-phenyl]-amide}

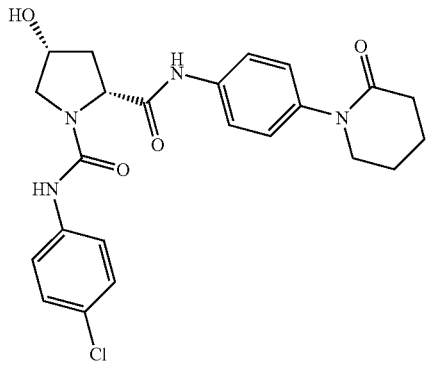

The compound was prepared as generally provided in Example 28. MS: APCI (AP+): 457.1 (M)+.

EXAMPLE 30

(2R,4R)-4-Hydroxy-pyrrolidine-1,2-dicarboxylic acid 1-[(4-chloro-phenyl)-amide]2-{[2-fluoro-4-(2-oxo-piperidin-1-yl)-phenyl]-amide}

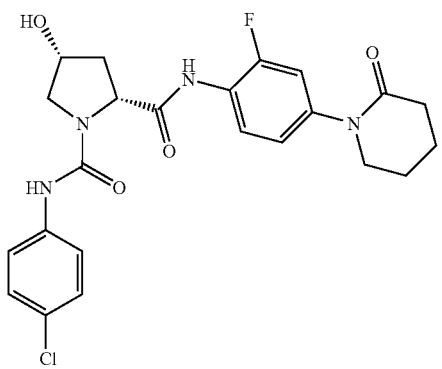

The compound was prepared as generally provided in Example 28. MS: APCI (AP+): 475.1 (M)+.

EXAMPLE 31

(2R,4R)-4-Hydroxy-pyrrolidine-1,2-dicarboxylic acid 1-[(5-chloro-pyridin-2-yl)-amide]2-{[2-fluoro-4-(2-oxo-piperidin-1-yl)-phenyl]-amide}

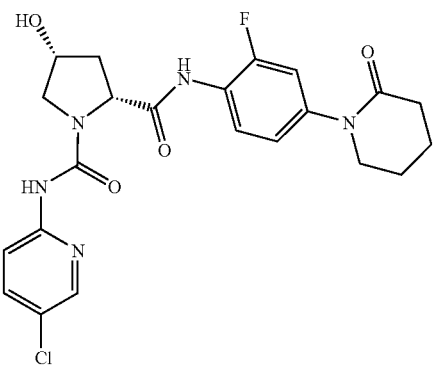

The compound was prepared as generally provided in Example 28. MS: APCI (AP+): 476.1 (M)+.

EXAMPLE 32

(2R,4R)-4-Methoxy-pyrrolidine-1,2-dicarboxylic acid 1-[(5-chloro-pyridin-2-yl)-amide]2-{[2-fluoro-4-(2-oxo-piperidin-1-yl)-phenyl]-amide}

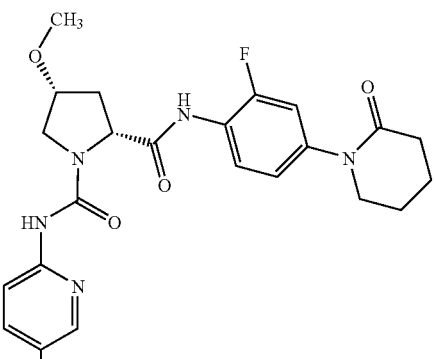

The compound was prepared as generally provided in Example 28. MS: APCI (AP+): 490.1 (M)+.

EXAMPLE 33

(2R,4R)-4-Ethoxy-pyrrolidine-1,2-dicarboxylic acid 1-[(5-chloro-pyridin-2-yl)-amide]2-{[2-fluoro-4-(2-oxo-piperidin-1-yl)-phenyl]-amide}

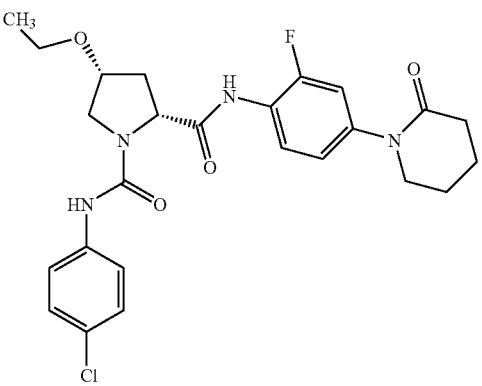

The compound was prepared as generally provided in Example 28. MS: APCI (AP+): 504.1 (M)+.

EXAMPLE 34

(2R,4R)-4-Ethoxy-pyrrolidine-1,2-dicarboxylic acid 1-[(4-chloro-phenyl)-amide]2-{[2-fluoro-4-(2-oxo-piperidin-1-yl)-phenyl]-amide}

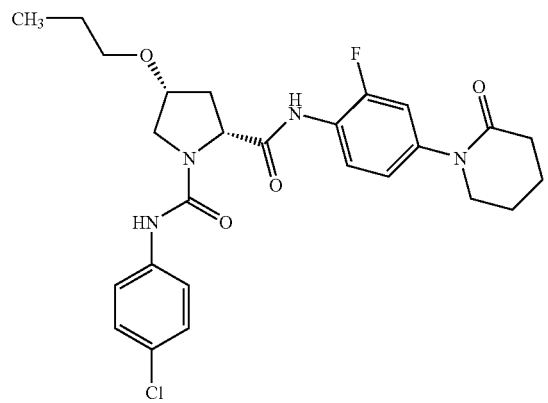

The compound was prepared as generally provided in Example 28. MS: APCI (AP+): 503.1 (M)+.

EXAMPLE 35

(2R,4R)-4-Propoxy-pyrrolidine-1,2-dicarboxylic acid 1-[(4-chloro-phenyl)-amide]2-{[2-fluoro-4-(2-oxo-piperidin-1-yl)-phenyl]-amide}

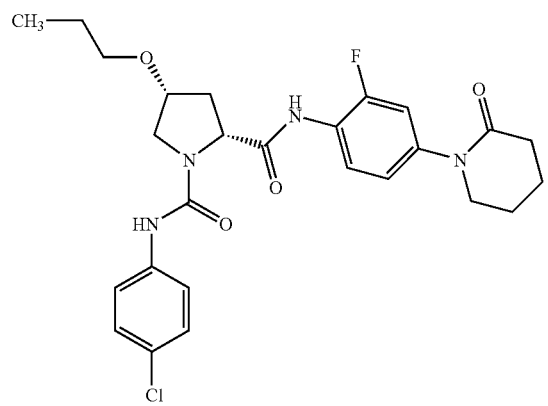

The compound was prepared as generally provided in Example 28. MS: APCI (AP+): 517.2 (M)+.

EXAMPLE 36

(2R,4R)-4-Propoxy-pyrrolidine-1,2-dicarboxylic acid 1-[(5-chloro-pyridin-2-yl)-amide]2-{[2-fluoro-4-(2-oxo-piperidin-1-yl)-phenyl]-amide}

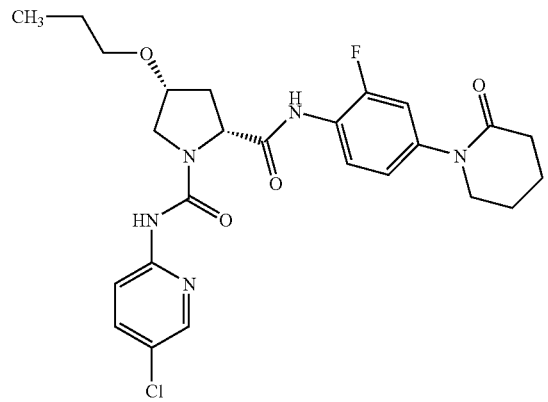

The compound was prepared as generally provided in Example 28. MS: APCI (AP+): 518.2 (M)+.

EXAMPLE 37

(2R,4R)-4-Cyano-pyrrolidine-1,2-dicarboxylic acid 1-[(4-chloro-phenyl)-amide]2-{[2-fluoro-4-(2-oxo-piperidin-1-yl)-phenyl]-amide}

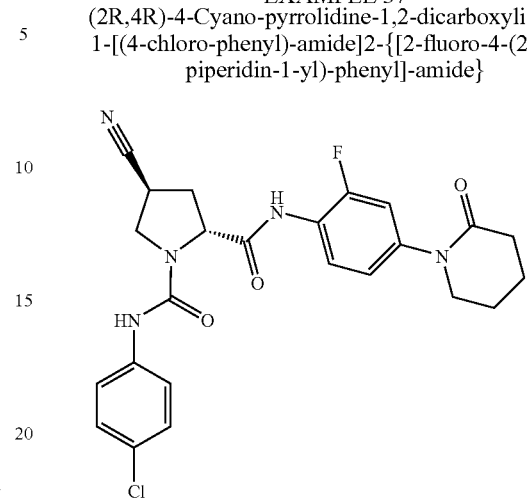

The compound was prepared as generally provided in Example 28. MS: APCI (AP+): 484.2 (M)+.

EXAMPLE 38

(2R,4R)-4-Fluoro-pyrrolidine-1,2-dicarboxylic acid 1-[(4-chloro-phenyl)-amide]2-{[2-fluoro-4-(2-oxo-piperidin-1-yl)-phenyl]-amide}

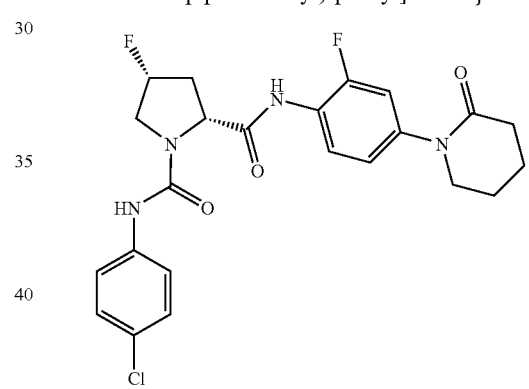

The compound was prepared as generally provided in Example 28. MS: APCI (AP+): 477.1 (M)+.

EXAMPLE 39

(2R,4R)-4-Methoxy-pyrrolidine-1,2-dicarboxylic acid 1-[(4-chloro-phenyl)-amide]2-{[2-fluoro-4-(2-oxo-azetidin-1-yl)-phenyl]-amide}

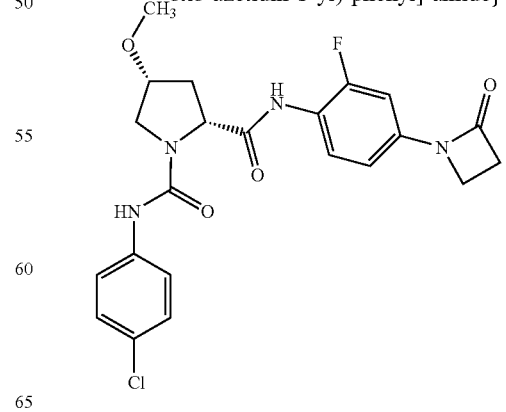

The compound was prepared as generally provided in Example 28. MS: APCI (AP+): 461.1 (M)+.

EXAMPLE 40
(2R,4R)-4-Methoxy-pyrrolidine-1,2-dicarboxylic acid 1-[(5-chloro-pyridin-2-yl)-amide]2-{[2-fluoro-4-(2-oxo-azetidin-1-yl)-phenyl]-amide}

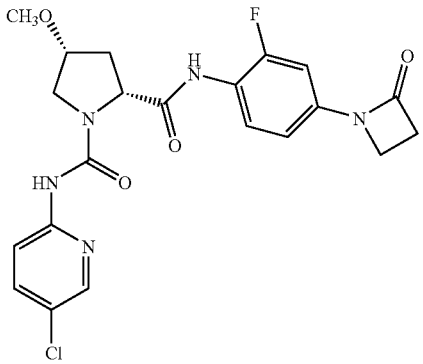

The compound was prepared as generally provided in Example 28. MS: APCI (AP+): 462.1 (M)+.

EXAMPLE 41
(2R,4R)-4-Methoxy-pyrrolidine-1,2-dicarboxylic acid 1-[(4-chloro-phenyl)-amide]2-{[2-fluoro-4-(2-oxo-pyrrolidin-1-yl)-phenyl]-amide}

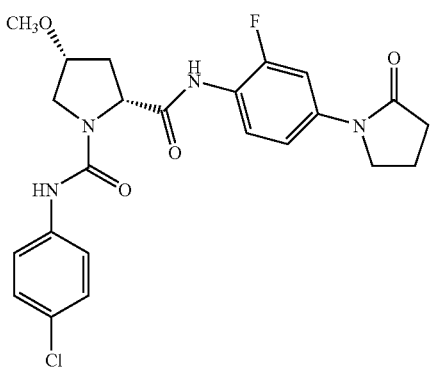

The compound was prepared as generally provided in Example 28. MS: APCI (AP+): 475.2 (M)+.

EXAMPLE 42
(2R,4R)-4-Methoxy-pyrrolidine-1,2-dicarboxylic acid 1-[(5-chloro-pyridin-2-yl)-amide]2-{[2-fluoro-4-(2-oxo-pyrrolidin-1-yl)-phenyl]-amide}

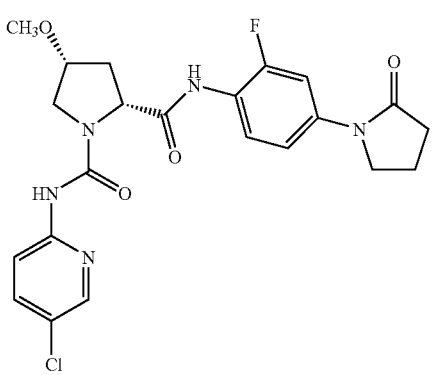

The compound was prepared as generally provided in Example 28. MS: APCI (AP+): 476.2 (M)+.

EXAMPLE 43
(2R,4R)-4-Methoxy-pyrrolidine-1,2-dicarboxylic acid 1-[(4-chloro-phenyl)-amide]2-{[2-fluoro-4-(2-oxo-azepan-1-yl)-phenyl]-amide}

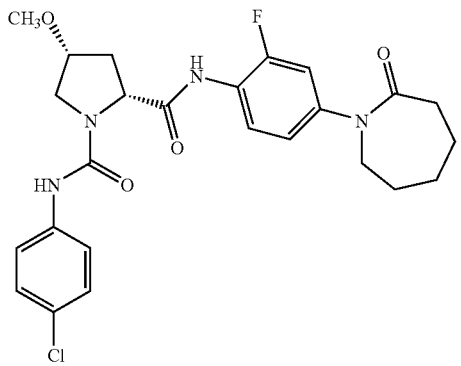

The compound was prepared as generally provided in Example 28. MS: APCI (AP+): 503.2 (M)+.

EXAMPLE 44
(2R,4R)-4-Methoxy-pyrrolidine-1,2-dicarboxylic acid 1-[(5-chloro-pyridin-2-yl)-amide]2-{[2-fluoro-4-(2-oxo-azepan-1-yl)-phenyl]-amide}

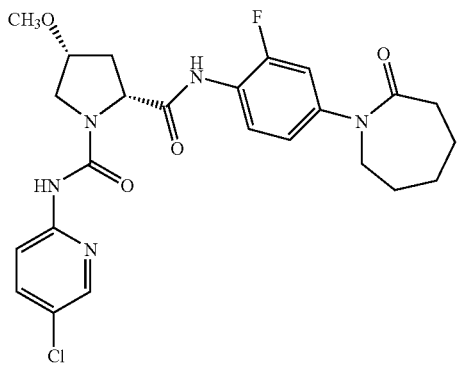

The compound was prepared as generally provided in Example 28. MS: APCI (AP+): 504.2 (M)+.

EXAMPLE 45
(2R,4R)-4-Methoxy-pyrrolidine-1,2-dicarboxylic acid 1-[(5-chloro-pyridin-2-yl)-amide]2-{[4-(2-oxo-2H-pyridin-1-yl)-phenyl]-amide}

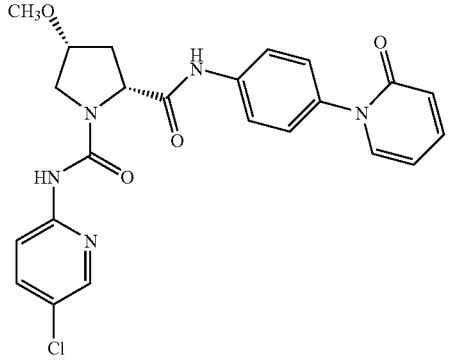

The compound was prepared as generally provided in Example 28. MS: APCI (AP+): 468.2 (M)+.

EXAMPLE 46
(2R,4R)-4-Methoxy-pyrrolidine-1,2-dicarboxylic acid 1-[(4-chloro-phenyl)-amide]2-{[4-(2-oxo-2H-pyridin-1-yl)-phenyl]-amide}

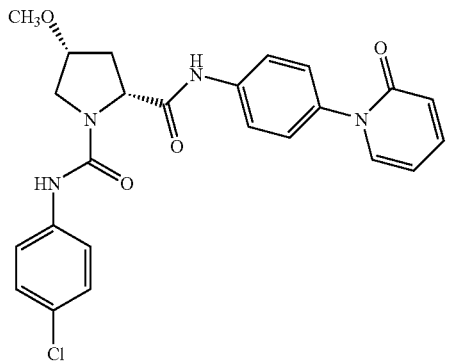

The compound was prepared as generally provided in Example 28. MS: APCI (AP+): 467.2 (M)+.

EXAMPLE 47
(2R,4R)-4-Ethoxy-pyrrolidine-1,2-dicarboxylic acid 1-[(4-chloro-phenyl)-amide]2-{[2-fluoro-4-(2-oxo-2H-pyridin-1-yl)-phenyl]-amide}

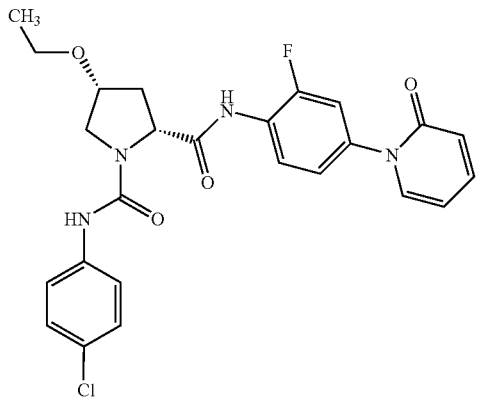

The compound was prepared as generally provided in Example 28. MS: APCI (AP+): 499.2 (M)+.

EXAMPLE 48
(2R,4R)-4-Ethoxy-pyrrolidine-1,2-dicarboxylic acid 1-[(5-chloro-pyridin-2-yl)-amide]2-{[2-fluoro-4-(2-oxo-2H-pyridin-1-yl)-phenyl]-amide}

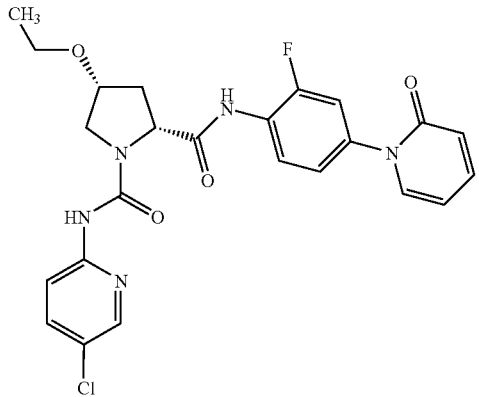

The compound was prepared as generally provided in Example 28. MS: APCI (AP+): 500.2 (M)+.

EXAMPLE 49
(2R,4R)-4-Methoxy-pyrrolidine-1,2-dicarboxylic acid 1-[(4-chloro-phenyl)-amide]2-{[2-fluoro-4-(2-hydroxymethyl-5-oxo-pyrrolidin-1-yl)-phenyl]-amide}

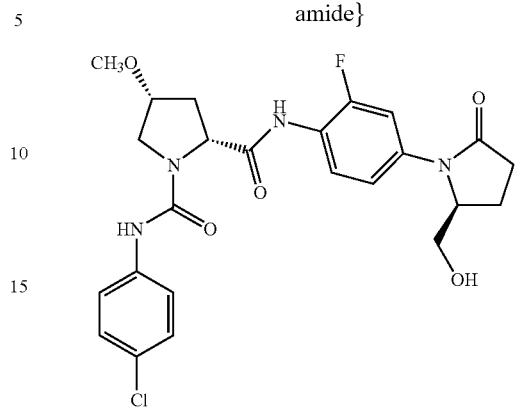

The compound was prepared as generally provided in Example 28. MS: APCI (AP+): 505.2 (M)+.

EXAMPLE 50
(2R,4R)-4-Hydroxy-pyrrolidine-1,2-dicarboxylic acid 1-[(4-chloro-phenyl)-amide]2-{[4-(2,3-dimethyl-5-oxo-2,5-dihydro-pyrazol-1-yl)-phenyl]-amide}

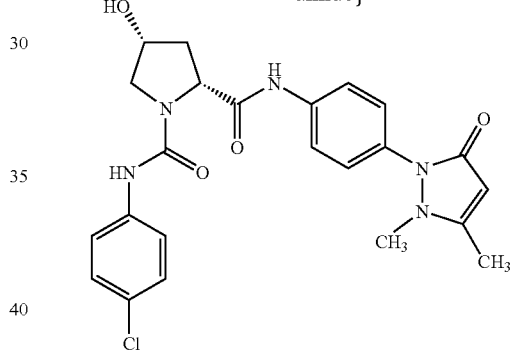

The compound was prepared as generally provided in Example 28. MS: APCI (AP+): 470.2 (M)+.

EXAMPLE 51
4-Hydroxy-pyrrolidine-1,2-dicarboxylic acid 1-[(4-chloro-phenyl)-amide]2-{[4-(2-hydroxymethyl-pyrrolidin-1-yl)-phenyl]-amide}

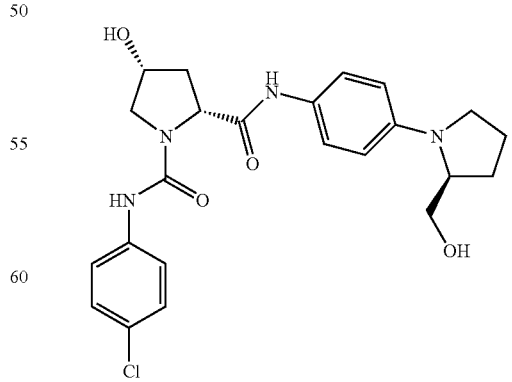

The compound was prepared as generally provided in Example 28. APCI (AP+): 459.2 (M+H)+.

EXAMPLE 52

(2R,4R)-4-Hydroxy-pyrrolidine-1,2-dicarboxylic acid 1-[(4-chloro-phenyl)-amide]2-[(4-pyrrolidin-1-yl-phenyl)-amide]

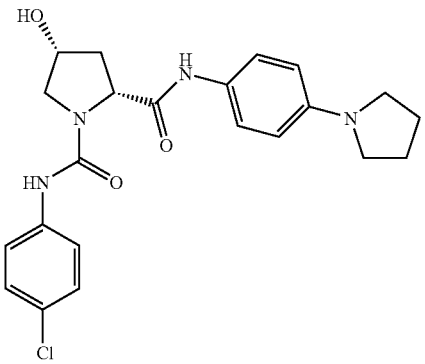

The compound was prepared as generally provided in Example 28. APCI (AP+): 429.1 (M)+.

EXAMPLE 53

(2R,4R)-4-Hydroxy-pyrrolidine-1,2-dicarboxylic acid 1-[(4-chloro-phenyl)-amide]2-[(4-pyrazol-1-yl-phenyl)-amide]

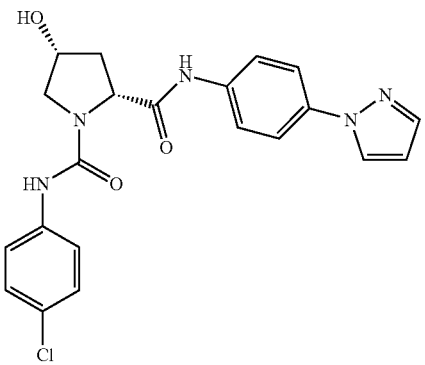

The compound was prepared as generally provided in Example 28. APCI (AP+): 426.1 (M)+.

EXAMPLE 54

(2R,4R)-4-Hydroxy-pyrrolidine-1,2-dicarboxylic acid 1-[(4-chloro-phenyl)-amide]2-[(2-fluoro-4-pyrazol-1-yl-phenyl)-amide]

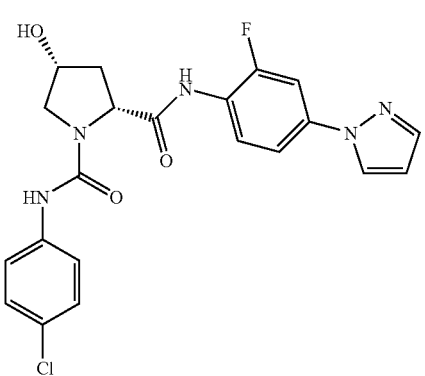

The compound was prepared as generally provided in Example 28. APCI (AP+): 444.1 (M)+.

EXAMPLE 55

(2R,4R)-4-Hydroxy-pyrrolidine-1,2-dicarboxylic acid 1-[(4-chloro-phenyl)-amide]2-[(4-[1,2,4]triazol-1-yl-phenyl)-amide]

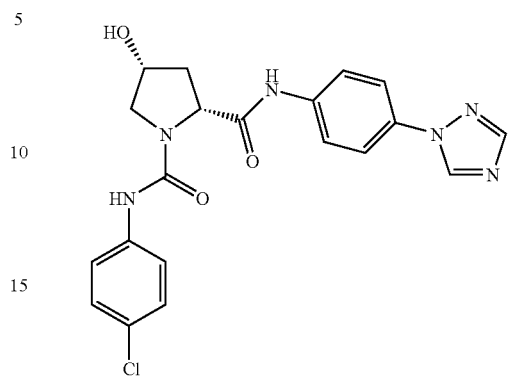

The compound was prepared as generally provided in Example 28. APCI (AP+): 427.1 (M)+.

EXAMPLE 56

(2R,4R)-4-Hydroxy-pyrrolidine-1,2-dicarboxylic acid 1-[(4-chloro-phenyl)-amide]2-[(4-[1,2,3]triazol-2-yl-phenyl)-amide]

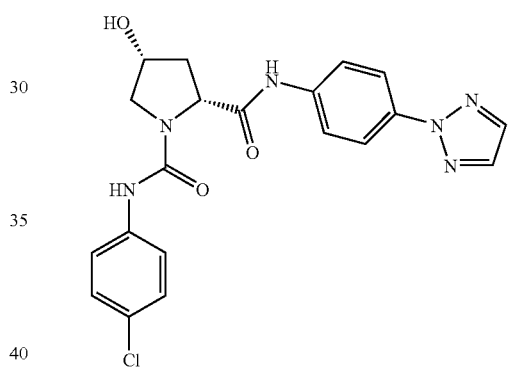

The compound was prepared as generally provided in Example 28. APCI (AP+): 427.1 (M)+.

EXAMPLE 57

(2R,4R)-4-Hydroxy-pyrrolidine-1,2-dicarboxylic acid 1-[(4-chloro-phenyl)-amide]2-[(4-[1,2,3]triazol-1-yl-phenyl)-amide]

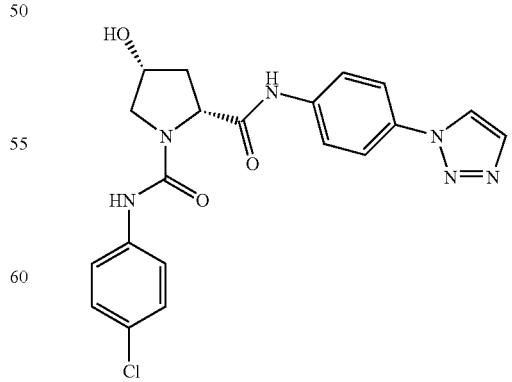

The compound was prepared as generally provided in Example 28. APCI (AP+): 427.1 (M)+.

EXAMPLE 58
(2R,4R)-4-Hydroxy-pyrrolidine-1,2-dicarboxylic acid 2-[(4-acetylamino-phenyl)-amide]1-[(4-chloro-phenyl)-amide]

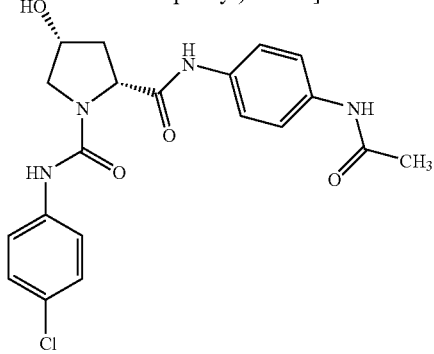

The compound was prepared as generally provided in Example 28. APCI (AP+): 417.1 (M)+.

EXAMPLE 59
(2R,4R)-4-Hydroxy-pyrrolidine-1,2-dicarboxylic acid 1-[(4-chloro-phenyl)-amide]2-{[4-(cyclopentanecarbonyl-amino)-phenyl]-amide}

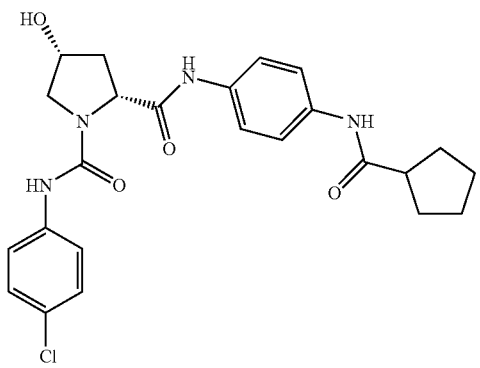

The compound was prepared as generally provided in Example 28. APCI (AP+): 471.2 (M)+.

EXAMPLE 60
4-Hydroxy-pyrrolidine-1,2-dicarboxylic acid 1-[(4-chloro-phenyl)-amide]2-[(4-pyrimidin-5-yl-phenyl)-amide]

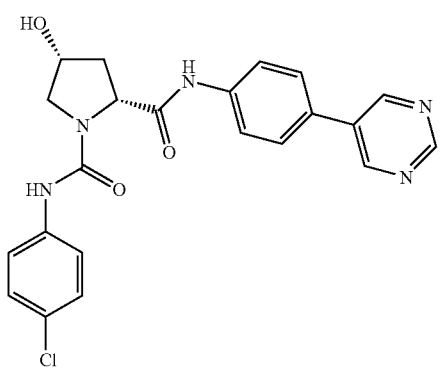

The compound was prepared as generally provided in Example 28. APCI (AP+): 484.2 (M)+.

EXAMPLE 61
(2R,4R)-4-Methoxy-pyrrolidine-1,2-dicarboxylic acid 1-[(4-chloro-phenyl)-amide]2-[(4-pyrazol-1-yl-phenyl)-amide]

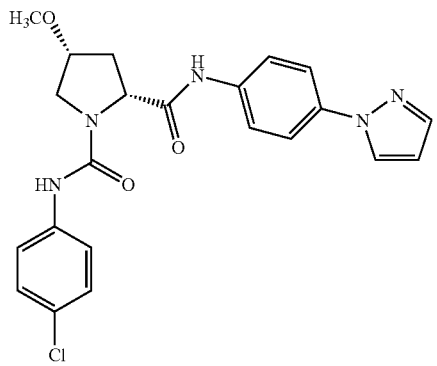

The compound was prepared as generally provided in Example 28. APCI (AP+): 440.2 (M)+.

EXAMPLE 62
(2R,4R)-4-Methoxy-pyrrolidine-1,2-dicarboxylic acid 1-[(4-chloro-phenyl)-amide]2-[(2-fluoro-4-pyrazol-1-yl-phenyl)-amide]

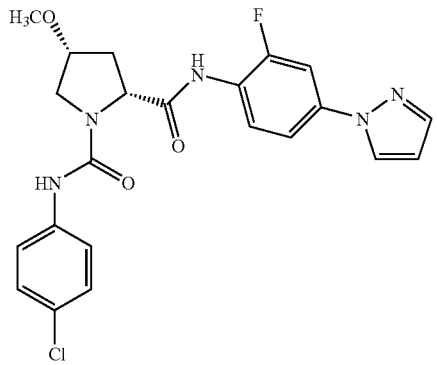

The compound was prepared as generally provided in Example 28. APCI (AP+): 458.1 (M)+.

EXAMPLE 63
(2R,4R)-4-Ethoxy-pyrrolidine-1,2-dicarboxylic acid 1-[(4-chloro-phenyl)-amide]2-[(2-fluoro-4-pyrazol-1-yl-phenyl-amide]

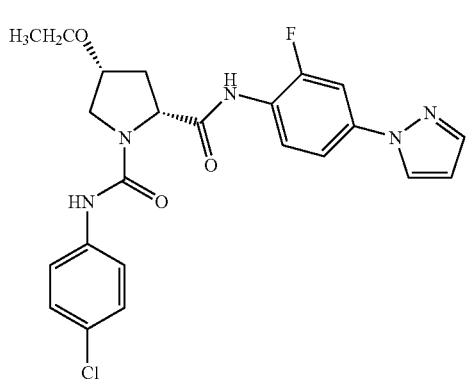

The compound was prepared as generally provided in Example 28. APCI (AP+): 472.1 (M)+.

EXAMPLE 64

(2R,4R)-4-Ethoxy-pyrrolidine-1,2-dicarboxylic acid 1-[(4-chloro-phenyl)-amide]2-[(4-pyrazol-1-yl-phenyl)-amide]

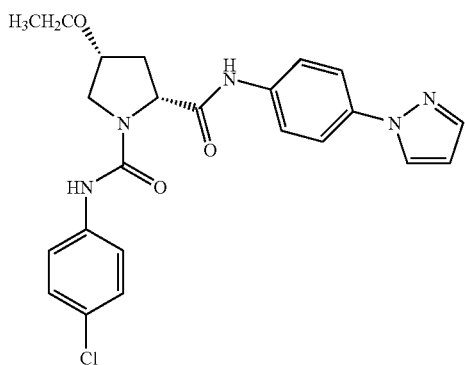

The compound was prepared as generally provided in Example 28. APCI (AP+): 454.2 (M)+.

EXAMPLE 65

(2R,4R)-4-Methoxy-pyrrolidine-1,2-dicarboxylic acid 1-[(4-chloro-phenyl)-amide]2-{[2-fluoro-4-(3-methyl-pyrazol-1-yl)-phenyl]-amide}

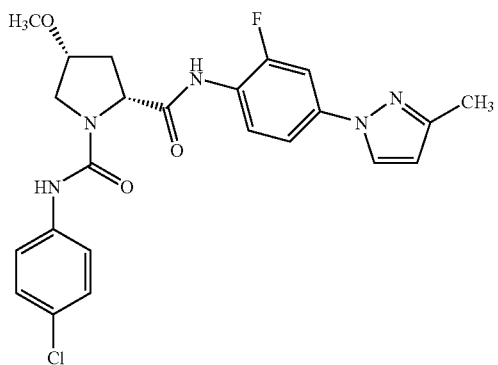

Step 1: 2-Fluoro-4-(3-methyl-pyrazol-1-yl)phenylamine (1)

2-Fluoro-4-iodoaniline (3. 0 g, 12.6 mmol), 3-methylpyrazole (1.22 mL, 15.18 mmol), Cs$_2$CO$_3$ (8.66 g, 26.58 mmol) and CuI (0.072 g, 0.379 mmol) were placed in a flask under nitrogen. The flask was evacuated under vacuum and refilled with nitrogen (5 times). 1,4-Dioxane (15 mL) was added followed by trans-1,2-diaminocyclohexane (152 μL, 1.266 mmol). The reaction mixture was heated under reflux for 36 h. Mixture cooled and filtered. Solvents removed. Residue purified by silica gel flash chromatography eluting with a gradient of EtOAc in hexanes (0 to 30%). This purification afforded 1 as a pale brown solid (0.917 g, 38%). MS: APCI (AP+): 192.0 (M)+.

From the same purification, 2-Fluoro-4-(5-methyl-pyrazol-1-yl)phenylamine (2) was obtained as pale brown solid (0.265 g, 11%). MS: APCI (AP+): 192.0 (M)+.

Step 2: (2R,4R)-2-[2-Fluoro-4-(3-methyl-pyrazol-1-yl)-phenylcarbamoyl]-4-methoxy-pyrrolidine-1-carboxylic acid tert-butyl ester (3)

(2R,4R)-4-methoxy-pyrrolidine-1,2-dicarboxylic acid 1-tert-butyl ester (0.350 g, 1.427 mmol), aniline 1 (0.273 g, 1.427 mmol) and EEDQ (0.529 g, 2.140 mmol) were dissolved in CHCl$_3$ (30 mL). Et$_3$N (0.6 mL, 4.281 mmol) was added and the reaction mixture was heated at reflux for 18 h. The mixture was allowed to cool and diluted with CHCl$_3$ (100 mL) and washed with 5% HCl, 0.5 N NaOH, water and brine (40 mL each), the organic extract was dried over MgSO$_4$, filtered and the solvent removed to give a pale tan foam. The crude product was used for the next step without purification. MS: APCI (AP+): 419.2 (M)+, (AP−): 417.2 (M)−.

Step 3: (2R, 4R)-4-Methoxy-pyrrolidine-2-carboxylic acid [2-fluoro-4-(3-methyl-pyrazol-1-yl)-phenyl]-amide (4)

Boc-amine 3 (~0.6 g, 1.427 mmol) was dissolved in 25% TFA in dichloromethane. The mixture was stirred at ambient temperature for 2 h. The solvents were removed and the residue dried under vacuum to give 4 as a tan oil (~0.450 g).

Step 4: (2R,4R)-4-Methoxy-pyrrolidine-1,2-dicarboxylic acid 1-[(4-chloro-phenyl)-amide]2-{[2-fluoro-4-(3-methyl-pyrazol-1-yl)-phenyl]-amide} (5)

A solution of amine 4 (~0.450 g, 1.427 mmol) in dichloromethane (35 mL) was cooled at 0° C. Triethylamine (1.5 mL, 10.7 mmol) was added and the mixture stirred for 15 min. Then, 4-chlorophenyl isocyanate (0.24 g, 1.569 mmol) was incorporated. The solution was stirred at ambient temperature for 18 h. The mixture was diluted with CHCl$_3$ (100 mL) and washed with 5% HCl, water, brine (40 mL each). The organic extracts were dried over MgSO$_4$, filtered and the solvent removed. The residue was purified by flash chromatography on silica gel eluting with a gradient of EtOAc in hexanes (0 to 65%) to provide 5 as white solid (0.56 g, 83% in 3 steps). MS: APCI (AP+): 472.2 (M)+, (AP−): 470.2 (M)−. Anal. calcd for C$_{23}$H$_{23}$ClFN$_5$O$_3$: C, 58.54; H, 4.91; N, 14.84. Found: C, 58.35; H, 4.59; N, 14.49.

EXAMPLE 66

(2R,4R)-4-Hydroxy-pyrrolidine-1,2-dicarboxylic acid 1-[(4-chloro-phenyl)-amide]2-{[2-fluoro-4-(5-methyl-pyrazol-1-yl)-phenyl]-amide}

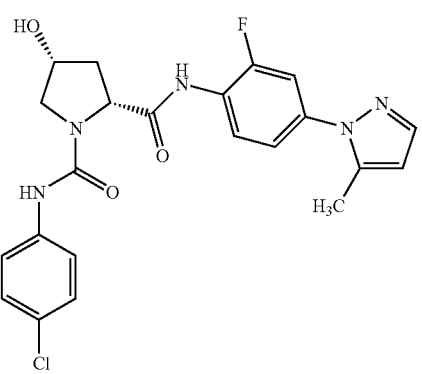

The compound was prepared as generally provided for Example 65. APCI (AP+): 458.2 (M)+.

EXAMPLE 67
(2R,4R)-4-Methoxy-pyrrolidine-1,2-dicarboxylic acid 1-[(4-chloro-phenyl)-amide]2-{[2-fluoro-4-(5-methyl-pyrazol-1-yl)-phenyl]-amide}

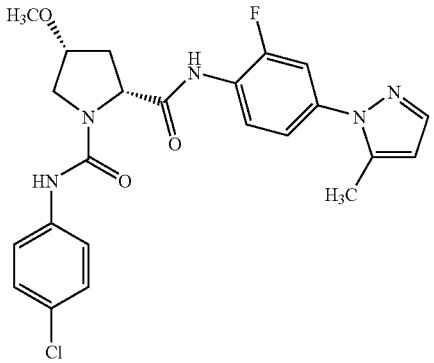

The compound was prepared as generally provided for Example 65. APCI (AP+): 472.2 (M)+.

EXAMPLE 68
(2R,4R)-4-Methoxy-pyrrolidine-1,2-dicarboxylic acid 1-[(4-chloro-phenyl)-amide]2-{[4-(5-methyl-pyrazol-1-yl)-phenyl]-amide}

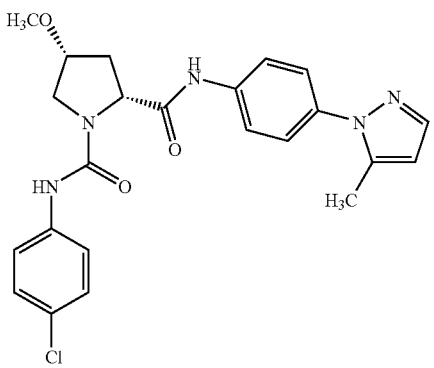

The compound was prepared as generally provided for Example 65. APCI (AP+): 454.3 (M)+.

EXAMPLE 69
(2R,4R)-4-Hydroxy-pyrrolidine-1,2-dicarboxylic acid 1-[(4-chloro-phenyl)-amide]2-{[4-(3,5-dimethyl-pyrazol-1-yl)-phenyl]-amide}

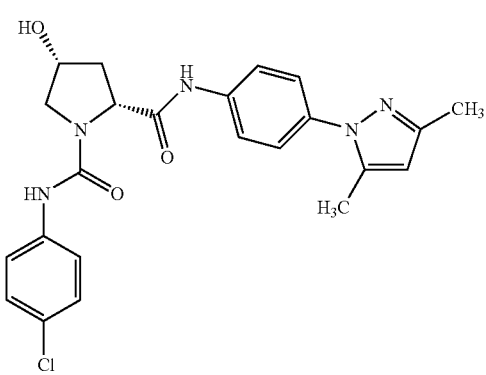

The compound was prepared as generally provided for Example 65. APCI (AP+): 454.2 (M)+.

EXAMPLE 70
(2R,4R)-4-Methoxy-pyrrolidine-1,2-dicarboxylic acid 1-[(4-chloro-phenyl)-amide]2-{[4-(3,5-dimethyl-pyrazol-1-yl)-phenyl]-amide}

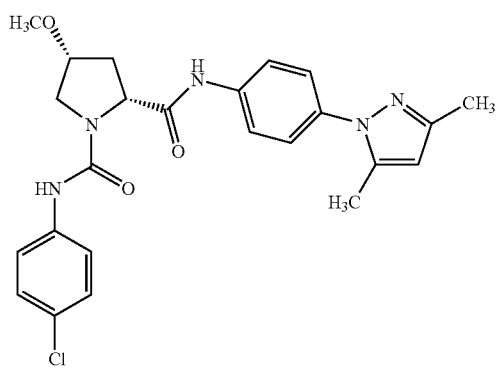

The compound was prepared as generally provided for Example 65. APCI (AP+): 468.2 (M)+.

EXAMPLE 71
(2R,4R)-4-Methoxy-pyrrolidine-1,2-dicarboxylic acid 1-[(4-chloro-phenyl)-amide]2-{[4-(3,5-dimethyl-pyrazol-1-yl)-2-fluoro-phenyl]-amide}

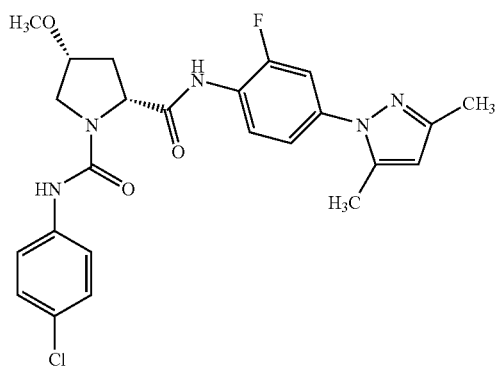

The compound was prepared as generally provided for Example 65. APCI (AP+): 486.2 (M)+.

EXAMPLE 72

1-(4-Amino-3-fluoro-phenyl)-1H-pyridin-2-one

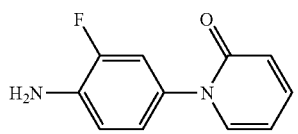

According to Route 2 for the preparation of YAB as provided in the General Procedure for the Preparation of Examples 28-60, 2-Fluoro-4-iodoaniline (10.0 g, 42.2 mmol) was combined with 1H-pyridin-2-one (1.0 g, 4.22 mmol), CuI (0.120 g, 0.633mmol), $K_2CO_3$ (0.641 g, 4.64 mmol), and 8-hydroxyquinoline (0.092 g, 0.633 mmol) in DMSO (3 mL). The mixture was degassed with a stream of argon and then heated at reflux for 20 h before cooling to ambient temperature. 10% aq. $NH_4OH$ and EtOAc were added, and the mixture was filtered through a plug of layered celite and decolorizing charcoal, eluting with EtOAc. The filtrate was concentrated under reduced pressure. Purification of the crude product by mplc revealed the title compound (0.53 g, 62%) as a yellow solid. MS: APCI (AP+): 205.1 (M)+.

EXAMPLE 73

4-Hydroxy-pyrrolidine-1,2-dicarboxylic acid 2-[(4-tert-butyl-phenyl)-amide]1-[(4-chloro-phenyl)-amide]

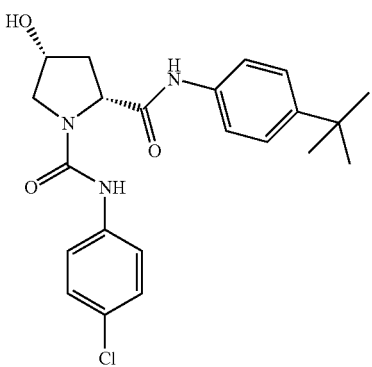

The compound was prepared as generally provided for Example 28. MS: APCI (AP+): 414.2 (M)+.

EXAMPLE 74

(2R,4R)-4-Hydroxy-pyrrolidine-1,2-dicarboxylic acid 1-[(4-chloro-phenyl)-amide]2[(3,5'difluoro-2'-sulfamoyl-biphenyl-4-yl)-amide]

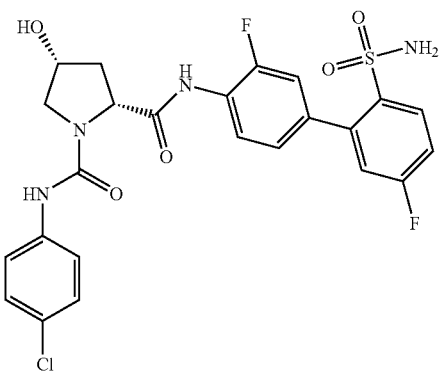

Step 1: N-tert-Butyl-4-fluoro-benzenesulfonamide

Into a DCM solution (50 mL) of tert-butylamine (5.9 mL, 56.5 mmol) and triethylamine (7.16 mL, 51.3 mmol) at 0° C. was slowly added a DCM solution (20 mL) of 4-fluoro-benzenesulfonyl chloride (10 g, 51.3 mmol), and the reaction stirred at RT for 19 h. The reaction was concentrated and the resulting solid recrystalized from ether/hexanes to get the product (9.5 g, 80%)as white crystals. MS: APCI (AP+): 230.1 (M)+.

Step 2: N-tert-Butyl-4-fluoro-benzenesulfonamide-3-boronic acid

Butyllithium (2.2 M, 4.3 mL, 9.51 mmol) was added dropwise to a 0° C. solution of N-tert-butyl-4-fluoro-benzenesulfonamide (1.0 g, 4.32 mmol), and the solution stirred for 15 min. at 0° C. and then RT for 1.5 h. Triisopropyl borate (1.19 mL, 5.18 mmol) was added, and the solution stirred at RT of 2.5 h. The mixture was cooled to 0° C., 10% aq. HCl was added slowly, and the reaction was stirred for 1.5 h. The reaction was then extracted with EtOAc three times and the organics combined and concentrated. The resulting oil was dissolved in ether and extracted with 1N NaOH three times, and the extracts combined and acidified at 0° C. with 6N HCl. The solution was extracted with ether three times and the organics were combined and dried over MgSO₄. Filtration and concentration of the organics revealed the product as an oil which formed a solid upon addition of hexanes and concentration under reduced pressure. (0.641 g, 54%) APCI (AP−): 274.1 (M)−.

Step 3: (2R, 4R)-4-(tert-Butyl-dimethyl-silanyloxy)-2-(2-fluoro-4-iodo-phenylcarbamoyl)-pyrrolidine-1-carboxylic acid tert-butyl ester 4-(tert-Butyl-dimethyl-silanyloxy)-pyrrolidine-1,2-dicarboxylic acid 1-tert-butyl ester (0.673 g, 1.94 mmol), 2-fluoro-4-iodoaniline (0.46 g, 1.94 mmol), EEDQ (0.575 g, 2.32 mmol) and triethylamine (0.408 mL, 2.91 mmol) were heated at reflux in CHCl₃ (10 mL) for 22 h. The solution was concentrated and resulting oil partitioned between EtOAc and water. The organic layer was washed with brine and dried over MgSO₄. The product was purified by mplc to produce the product as a clear oil (1.0 g, 90%). MS: APCI (AP−): 563.2 (M)−.

Step 4: (2R,4R)-4-(tert-Butyl-dimethyl-silanyloxy)-2-(2'-tert-butylsulfamoyl-3,5'-difluoro-biphenyl-4-ylcarbamoyl)-pyrrolidine-1-carboxylic acid tert-butyl ester A mixture of 4-(tert-butyl-dimethyl-silanyloxy)-2-(2-fluoro-4-iodo-phenylcarbamoyl)-pyrrolidine-1-carboxylic acid tert-butyl ester (0.56 g, 0.99 mol), Pd(PPh₃)₄ (0.11 g, 0.1 mmol), N-tert-butyl-4-fluoro-benzenesulfonamide-3-boronic acid (0.33 g, 1.19 mmol), tetrabutylammonium bromide (0.016 g, 0.05 mmol), sodium carbonate (0.210 g, 1.98 mmol), water (2.0 mL) and toluene (10 mL) was degassed with a stream of argon gas and then heated at reflux 21.5 h. The mixture was then allowed to cool to RT, concentrated and partitioned between water and EtOAc. The organic layer was washed with brine, dried over MgSO₄ and concentrated. The resulting oil was purified by mplc to reveal the product as an oil (0.119 g, 18%). MS: APCI (AP−): 666.4 (M)−.

Step 5: (2R,4R)-4-Hydroxy-pyrrolidine-1,2-dicarboxylic acid 2-[(2'-tert-butylsulfamoyl-3,5'-difluoro-biphenyl-4-yl)-amide]1-[(4-chloro-phenyl)-amide]

A solution of 4-(tert-butyl-dimethyl-silanyloxy)-2-(2'-tert-butylsulfamoyl-3,5'-difluoro-biphenyl-4-ylcarbamoyl)-pyrrolidine-1-carboxylic acid tert-butyl ester (0.228 g, 0.342 mmol) and trifluoroacetic acid (1.5 mL) in CHCl₃ (1.5 mL) was stirred at ambient temperature for 1 h. The solution was concentrated, hexanes added and then the solution concentrated again. The resulting oil was dissolved in THF and cooled 0° C. Triethylamine (0.190 mL, 1.36 mmol) was added followed by 4-chlorophenyl isocyanate (0.052 g, 0.342 mmol) and the solution stirred at RT for 5.5 h. The solution was concentrated and the oil purified by mplc to reveal the product as a solid (0.078 g, 38%). MS: APCI (AP−): 605.2 (M)−.

Step 6: (2R,4R)-4-Hydroxy-pyrrolidine-1,2-dicarboxylic acid 1-[(4-chloro-phenyl)-amide]2[(3,5'difluoro-2'-sulfamoyl-biphenyl-4-yl)-amide]

4-Hydroxy-pyrrolidine-1,2-dicarboxylic acid 2-[(2'-tert-butylsulfamoyl-3,5'-difluoro-biphenyl-4-yl)-amide]1-[(4-chloro-phenyl)-amide] (0.078 g, 0.128 mmol) was dissolved in TFA (3 mL) and stirred at RT for 1 h. The reaction was concentrated and dissolved in MeCN and water and purified by reverse phase HPLC to reveal the product as a white solid (0.05 g, 77%) after lyophilization. MS: APCI (AP+): 551.1 (M)+.

EXAMPLE 75

(2R,4R)-4-Methoxy-pyrrolidine-1,2-dicarboxylic acid 1-[(4-chloro-phenyl)-amide]2-[(2-oxo-3,4,5,6-tetrahydro-2H-[1,2']bipyridinyl-5'-yl)-amide]

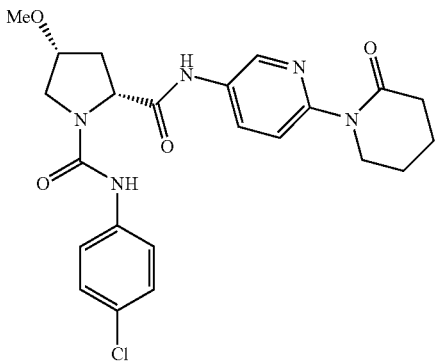

The compound was prepared as generally provided for Example 28. MS: APCI (AP+): 472.2 (M)+.

EXAMPLE 75a

Alternative Procedure

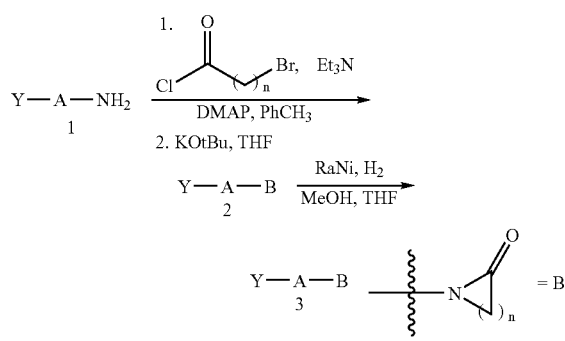

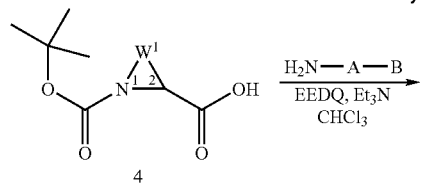

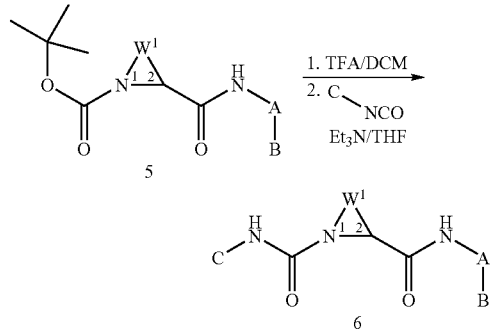

Synthesis of 2:

A solution of 1 where Y is a nitro group is treated with a halo-alkoylchloride in the presence of base and refluxing toluene to produce an intermediate halo-amide that is then cyclized in the presence of potassium tert-butoxide in THF to produce a cyclic lactam B.

Synthesis of 3:

A solution of 2 where Y is a nitro group is reduced under RaNi mediated hydrogenation to produce 3 where Y is an amino group.

Synthesis of 5 and 6:

Intermediates 5 and 6 were prepared as provided in Example 28.

EXAMPLE 76

(2R,4R)-4-Methoxy-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide]

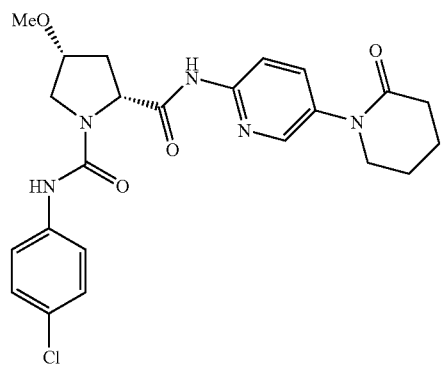

Step 1: 5'-Nitro-3,4,5,6-tetrahydro-[1,2']bipyridinyl-2-one.

See Example 75a. 2-Amino-5-nitro-pyridine (2.0 g, 14.3 mmol), 5-bromo-pentanoyl chloride (2.86 g, 14.3 mmol), triethylamine (2.39 g, 17.2 mmol), catalytic DMAP were heated at reflux in toluene (70 mL) 22 h. The reaction was allowed to cool to RT, concentrated and the resulting oil portioned between EtOAc and water. The organic layer was separated, washed with brine, dried over MgSO$_4$ and filtered.

Concentration of the filtrate produced an oil which was dissolved in THF (140 mL). Potassium tert-Butoxide (1.68 g, 15.0 mmol) was added portion-wise and the reaction stirred at RT for 2h. Water was then added, and the reaction extracted with EtOAc. The organics were then washed with brine and dried over MgSO$_4$. Purification of the crude material by mplc revealed the product as an orange solid. MS: APCI (AP+): 222.1 (M)+.

Step 2: 5'-Amino-3,4,5,6-tetrahydro-[1,2']bipyridinyl-2-one.

5'-Nitro-3,4,5,6-tetrahydro-[1,2']bipyridinyl-2-one (0.66 g, 2.98 mmol) was dissolved in 1:1 MeOH/THF (50 mL) and hydrogenated over RaNi (1 g) at 4285 psi/mole for 0.8 h. The catalyst was filtered, and the filtrate concentrated. The crude solid was purified by recrystalization from THF and hexanes to give the product as a yellow solid (0.275 g, 48%). MS: APCI (AP+): 192.1 (M)+.

Step 3: (2R,4R)-4-Methoxy-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide]

The compound was prepared as generally provided for Example 28. MS: APCI (AP+): 472.2 (M)+.

EXAMPLE 77

(2R,4R)-4-Methoxy-pyrrolidine-1,2-dicarboxylic acid 1-[(5-chloro-pyridin-2-yl)-amide]2-{[4-(2,3-dimethyl-5-oxo-2,5-dihydro-pyrazol-1-yl)-phenyl]-amide}

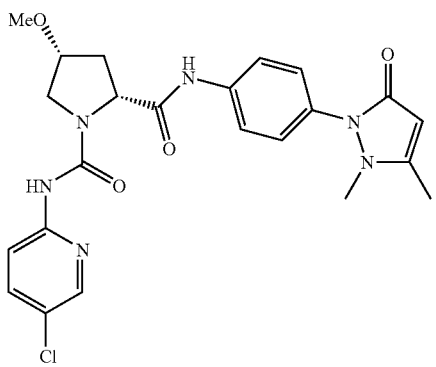

The compound was prepared as generally provided for Example 28. Formation of the 5-chloro-pyridin-2-yl moiety can be found in Example 26. MS: APCI (AP+): 485.3 (M)+.

EXAMPLE 78

(2R,4R)-4-Methoxy-pyrrolidine-1,2-dicarboxylic acid 1-[(4-chloro-phenyl)-amide]2-{[4-(2,3-dimethyl-5-oxo-2,5-dihydro-pyrazol-1-yl)-phenyl]-amide}

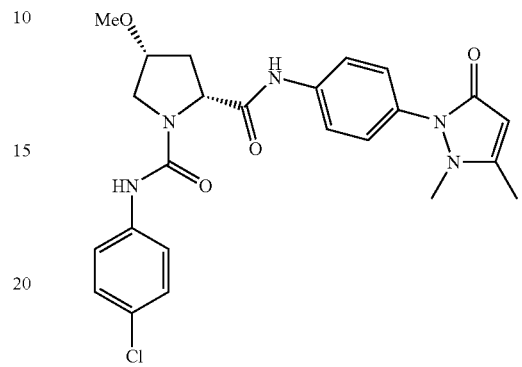

The compound was prepared as generally provided for Example 28. MS: APCI (AP+): 484.3 (M)+.

EXAMPLE 79

(2R,4R)-4-Methoxy-pyrrolidine-1,2-dicarboxylic acid 1-[(4-chloro-phenyl)-amide]2-[(2-oxo-2H-[1,3']bipyridinyl-6'-yl)-amide]

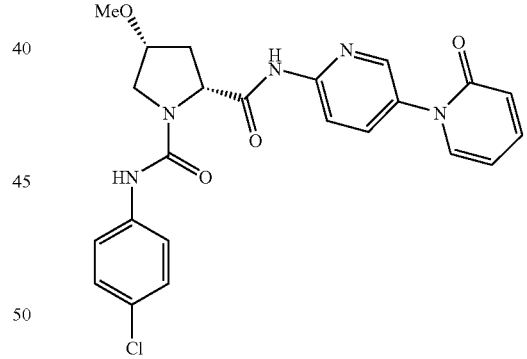

Step 1. 6'-Amino-[1,3']bipyridinyl-2-one

2-Amino-5-iodopyridine (5.0 g, 22.7 mmol) was combined with 1H-pyridin-2-one (2.59 g, 27.27 mmol), CuI (0.65 g, 3.41 mmol), K$_2$CO$_3$ (3.45 g, 24.9 mmol), and 8-hydroxyquinoline (0.49 g, 3.40 mmol) in DMSO (20 mL). The mixture was degassed with a stream of argon and then heated at reflux for 18 h before cooling to RT. 10% aq. NH$_4$OH and EtOAc were added, and the mixture was filtered through a plug of layered celite and decolorizing charcoal, eluting with EtOAc. The filtrate was concentrated under reduced pressure. Purification of the crude product by mplc revealed A (0.40 g, 10%) as a yellow solid. MS: APCI (AP+): 188.1 (M)+.

Step 2: (2R,4R)-4-Methoxy-pyrrolidine-1,2-dicarboxylic acid 1-[(4-chloro-phenyl)-amide]2-[(2-oxo-2H-[1,3']bipyridinyl-6'-yl)-amide]

The compound was prepared as generally provided for Example 28. MS: APCI (AP+): 468.3 (M)+.

EXAMPLE 80

(2R,4R)-4-Methoxy-pyrrolidine-1,2-dicarboxylic acid 1-[(5-chloro-pyridin-2-yl)-amide]2-[(2-oxo-3,4,5,6-tetrahydro-2H-[1,3']bipyridinyl-6'-yl)-amide]-TFA Salt

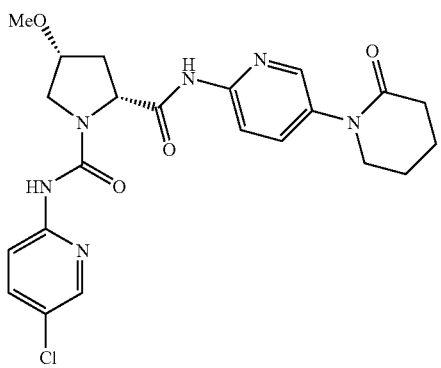

The compound was prepared as generally provided for in Examples 28 and 75a. Formation of the 5-chloro-pyridin-2-yl moiety can be found in Example 26. Purification was accomplished via reverse phase HPLC. MS: APCI (AP+): 473.2 (M)+.

EXAMPLE 81

4-Ethoxy-pyrrolidine-1,2-dicarboxylic acid 1-[(4-chloro-phenyl)-amide]2-[(2-oxo-3,4,5,6-tetrahydro-2H-[1,3']bipyridinyl-6'-yl)-amide]

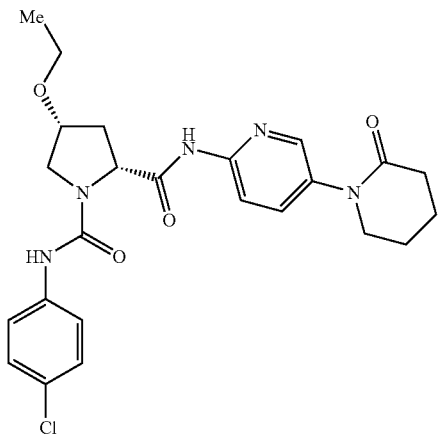

The compound was prepared as generally provided for Example 28. MS: APCI (AP+): 486.3 (M)+.

EXAMPLE 82

(2R,4R)-Ethoxy-pyrrolidine-1,2-dicarboxylic acid 1-[(4-chloro-phenyl)-amide]2-[(2-oxo-2H-[1,3']bipyridinyl-6'-yl)-amide]

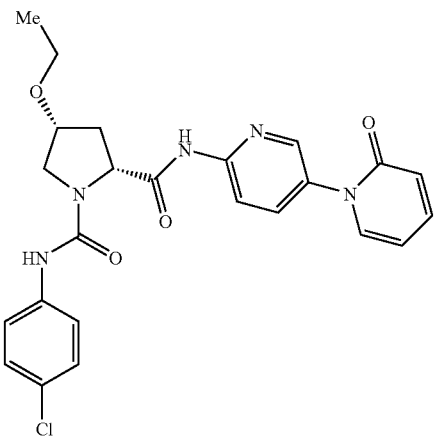

The compound was prepared as generally provided for Examples 28 and 79. MS: APCI (AP+): 482.3 (M)+.

EXAMPLE 83

(2R,4R)-4-Methoxy-pyrrolidine-1,2-dicarboxylic acid 1-[(4-chloro-phenyl)-amide]2-{[2-fluoro-4-(6-oxo-6H-pyridazin-1-yl)-phenyl]-amide}

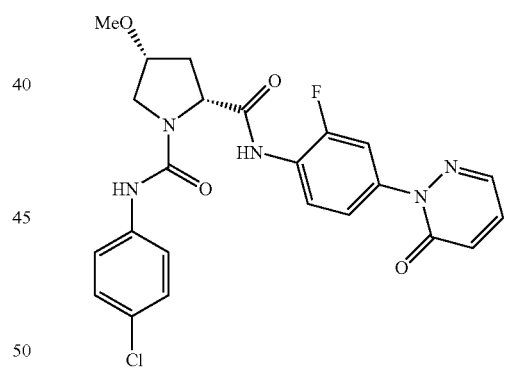

Step 1: 2-(4-Amino-3-fluoro-phenyl)-2H-pyridazin-3-one

2-Fluoro4-iodoaniline (0.5 g, 2.10 mmol) was combined with 2H-Pyridazin-3-one (0.243 g, 2.53 mmol), CuI (0.06 g, 0.315 mmol), $K_2CO_3$ (0.32 g, 2.31 mmol), and 8-hydroxyquinoline (0.046 g, 0.315 mmol) in DMSO (3 mL). The mixture was degassed with a stream of argon and then heated at reflux for 23 h before cooling to RT. 10% aq. $NH_4OH$ and EtOAc were added, and the mixture was filtered through a plug of layered celite and decolorizing charcoal, eluting with EtOAc. The filtrate was concentrated under reduced pressure. Purification of the crude product by mplc revealed A (0.16 g, 37%) as a yellow solid. MS: APCI (AP+): 206.1 (M)+.

Step 2: (2R,4R)-4-Methoxy-pyrrolidine-1,2-dicarboxylic acid 1-[(4-chloro-phenyl)-amide]2-{[2-fluoro-4-(6-oxo-6H-pyridazin-1-yl)-phenyl]-amide}

The compound was prepared as generally provided for Example 28. MS: APCI (AP+): 486.1 (M)+.

EXAMPLE 84

(2R,4S)-4-Amino-pyrrolidine-1,2-dicarboxylic acid 1-[(4-chloro-phenyl)-amide]2-[(3-fluoro-2'-methanesulfonyl-biphenyl-4-yl)-amide]

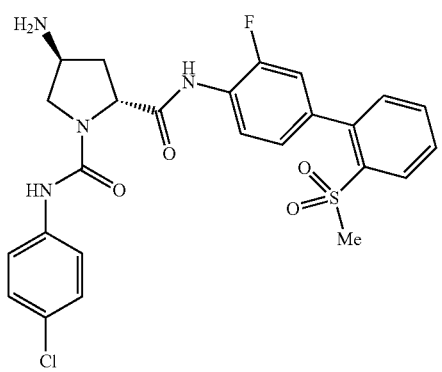

Step 1: (2R,4R)-toluene-4-sulfonic acid 1-(4-chlorophenylcarbamoyl)-5-(3-fluoro-2'-methanesulfonyl-biphenyl-4-ylcarbamoyl)-pyrrolidin-3-yl ester (2R,4R)4-Hydroxy-pyrrolidine-1,2-dicarboxylic acid 1-[(4-chloro-phenyl)-amide]2-[(3-fluoro-2'-methanesulfonyl-biphenyl-4-yl)-amide] (see example 17, 0.41 g, 0.77 mmol) was dissolved in 5 ml dry DCM, added Et3N (0.21 mL, 1.54 mmol), DMAP (10 mg, 0.8 mmol), and TsCl (0.16 g, 0.85 mmol). Stirred at ambient temperature overnight. The solution was dissolved in 100 ml EtOAc, washed with 10% citric acid (3×50 ml), sat NaHCO3 (3×50 ml), brine (100 ml), dried with MgSO4, filtered and concentrated to yield title compound. (0.54 g, 97%) MS: APCI (AP−): 684.1 (M)−.

Step 2: (2R,4S)-4-Azido-pyrrolidine-1,2-dicarboxylic acid 1-[(4-chloro-phenyl)-amide]2-[(3-fluoro-2'-methanesulfonyl-biphenyl-4-yl)-amide]

(2R,4R)-toluene-4-sulfonic acid 1-(4-chloro-phenylcarbamoyl)-5-(3-fluoro-2'-methanesulfonyl-biphenyl-4-ylcarbamoyl)-pyrrolidin-3-yl ester (0.2 g, 0.29 mmol) was dissolved in 4 ml dry DMF under Ar, added sodium azide (0.38 mg, 0.58 mmol) and stirred at 60° C. for 6 hours. The reaction was cooled, taken up in 100 ml EtOAc, washed with water, sat. NaHCO3, brine, dried with MgSO4, filtered and concentrated to yield title compound. (0.155 g, 95%) MS: APCI (AP+): 557.0 (M)+.

Step 3: (2R,4S)-4-Amino-pyrrolidine-1,2-dicarboxylic acid 1-[(4-chloro-phenyl)-amide]2-[(3-fluoro-2'-methanesulfonyl-biphenyl-4-yl)-amide]

(2R,4S)-4-Azido-pyrrolidine-1,2-dicarboxylic acid 1-[(4-chloro-phenyl)-amide]2-[(3-fluoro-2'-methanesulfonyl-biphenyl-4-yl)-amide] (0.145 g, 0.26 mmol) was shaken with Raney Nickel (300mg) in 16 mL tetrahydrofuran in a hydrogen atmosphere under pressure for 3 days. Reaction was filtered and concentrated. Purified by HPLC and lyophilized pure fractions to yield title compound. (105 mg, 76%) MS: APCI (AP−): 529.1 (M)−.

EXAMPLE 85

(2R,4R)-4-Amino-pyrrolidine-1,2-dicarboxylic acid 1-[(4-chloro-phenyl)-amide]2-[(3-fluoro-2'-methanesulfonyl-biphenyl-4-yl)-amide]

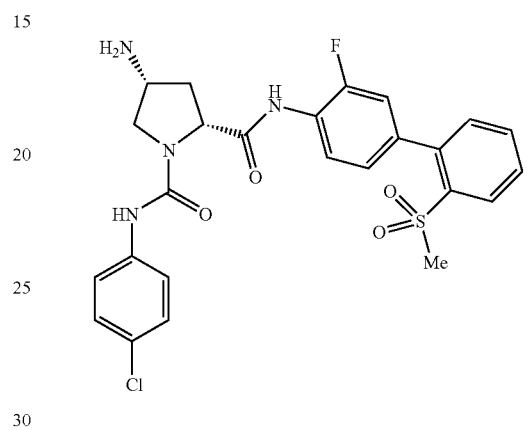

The compound was prepared as generally provided for Example 85 substituting (2R,4S)-toluene-4-sulfonic acid 1-(4-chloro-phenylcarbamoyl)-5-(3-fluoro-2'-methanesulfonyl-biphenyl-4-ylcarbamoyl)-pyrrolidin-3-yl ester for (2R,4R)-toluene-4-sulfonic acid 1-(4-chloro-phenylcarbamoyl)-5-(3-fluoro-2'-methanesulfonyl-biphenyl-4-ylcarbamoyl)-pyrrolidin-3-yl ester. MS: APCI (AP+): 531.1 (M)+.

EXAMPLE 86

(2R,4R)-4-Hydroxy-pyrrolidine-1,2-dicarboxylic acid 1-[(4-chloro-phenyl)-amide]2-[(3-fluoro-2'-sulfamoyl-biphenyl-4-yl)-amide]

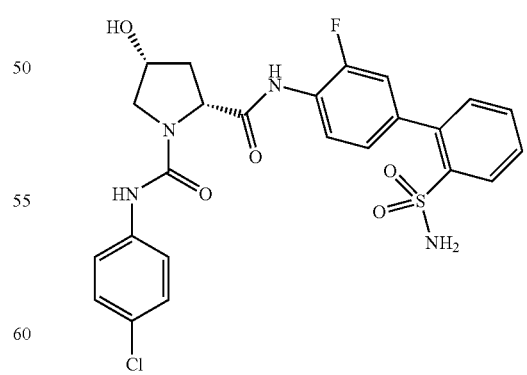

The compound was prepared as generally provided for Example 17, substituting 2-(N-tert-butyl)phenylsulfonamide boronic acid for 2-(methylthio)benzene boronic acid. MS: APCI (AP+): 533.0 (M)+.

EXAMPLE 87

(2R)-4-Hydroxyamino-pyrrolidine-1,2-dicarboxylic acid 1-[(4-chloro-phenyl)-amide]2-[(3-fluoro-2'-methanesulfonyl-biphenyl-4-yl)-amide]

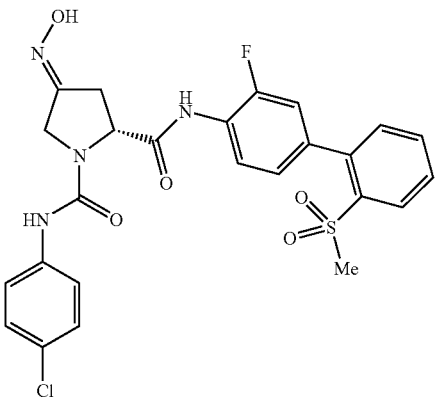

The compound was prepared as generally provided for Example 22. MS: APCI (AP+): 545.0 (M)+.

EXAMPLE 88

(2R,4R)-4-Hydroxy-pyrrolidine-1,2-dicarboxylic acid 1-[(4-chloro-phenyl)-amide]2-[(3-fluoro-2'-methylsulfamoyl-biphenyl-4-yl)-amide]

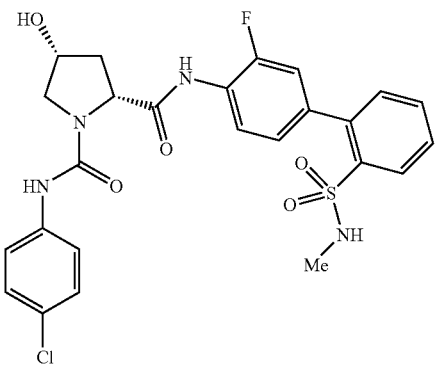

The compound was prepared as generally provided for Example 86. MS: APCI (AP+): 547.2 (M)+.

EXAMPLE 89

(2R,4R)-4-Hydroxy-pyrrolidine-1,2-dicarboxylic acid 1-[(4-chloro-phenyl)-amide]2-[(2'-dimethylsulfamoyl-3-fluoro-biphenyl-4-yl)-amide]

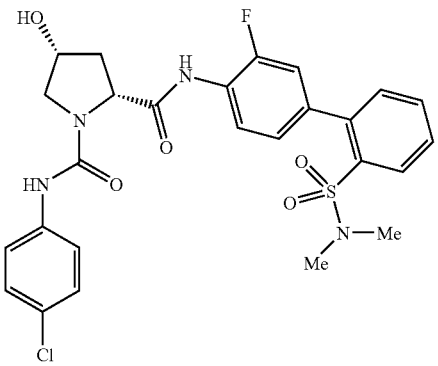

The compound was prepared as generally provided for Example 86. MS: APCI (AP+): 561.2 (M)+.

EXAMPLE 90

(2R,4R)-4-Methoxy-pyrrolidine-1,2-dicarboxylic acid 1-[(5-chloro-pyridin-2-yl)-amide]2-[(3-fluoro-2'-methanesulfonyl-biphenyl-4-yl)-amide]

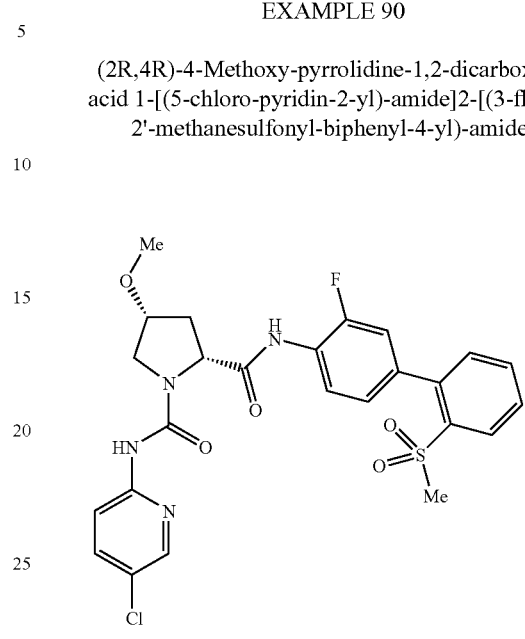

The compound was prepared as generally provided for Example 28, substituting 3-fluoro-2'-methanesulfonyl-biphenyl-4-ylamine for 1-(4-amino-3-fluoro-phenyl)-piperidin-2-one. MS: APCI (AP+): 547.1 (M)+.

EXAMPLE 91

(2R,4R)-4-Methoxy-pyrrolidine-1,2-dicarboxylic acid 1-[(4-chloro-phenyl)-amide]2-[(3-fluoro-2'-sulfamoyl-biphenyl-4-yl)-amide]

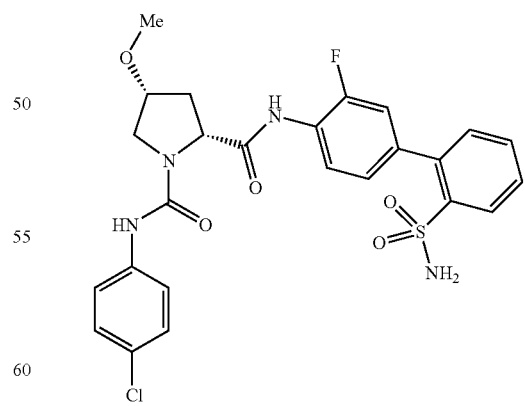

The compound was prepared as generally provided for Example 28, substituting 4'-amino-3'-fluoro-biphenyl-2-sulfonic acid tert-butylamide for 1-(4-amino-3-fluoro-phenyl)-piperidin-2-one. MS: APCI (AP+): 549.0 (M)+.

EXAMPLE 92

(2R,4R)-4-Ethoxy-pyrrolidine-1,2-dicarboxylic acid 1-[(5-chloro-pyridin-2-yl)-amide]2-[(3-fluoro-2'-methanesulfonyl-biphenyl-4-yl)-amide]

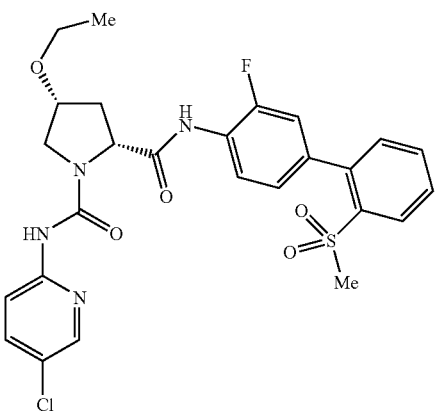

The compound was prepared as generally provided for Example 90, substituting (2R,4R)4-ethoxy-pyrrolidine-1,2-dicarboxylic acid 1-tert-butyl ester for (2R,4R)4-methoxy-pyrrolidine-1,2-dicarboxylic acid 1-tert-butyl ester. MS: APCI (AP+): 561.1 (M)+.

EXAMPLE 93

(2R,4R)-4-Ethoxy-pyrrolidine-1,2-dicarboxylic acid 1-[(4-chloro-phenyl)-amide]2-[(3-fluoro-2'-methanesulfonyl-biphenyl-4-yl)-amide]

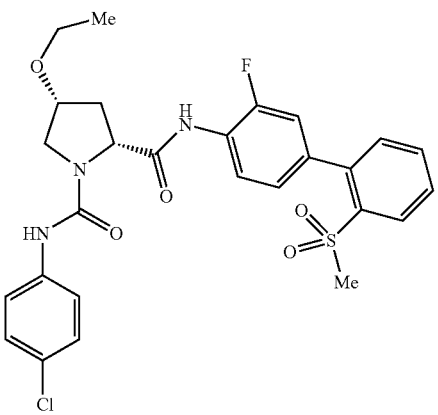

The compound was prepared as generally provided for Example 28, substituting (2R,4R)-4-ethoxy-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 560.2 (M)+.

EXAMPLE 94

(2R,4R)-4-Ethoxy-pyrrolidine-1,2-dicarboxylic acid 1-[(4-chloro-phenyl)-amide]2-[(3-fluoro-2'-sulfamoyl-biphenyl-4-yl)-amide]

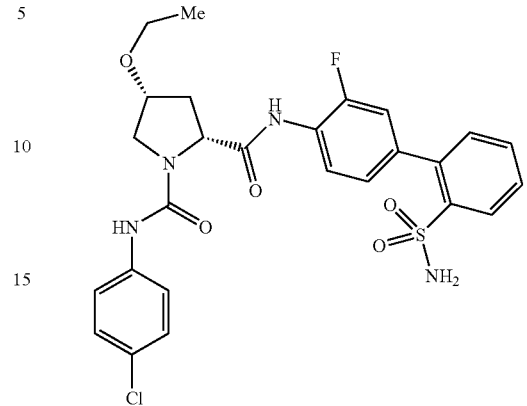

The compound was prepared as generally provided for Example 91, substituting (2R,4R)-4-ethoxy-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 561.1 (M)+.

EXAMPLE 95

(2R,4S)-4-Methoxy-pyrrolidine-1,2-dicarboxylic acid 1-[(4-chloro-phenyl)-amide]2-[(3-fluoro-2'-methanesulfonyl-biphenyl-4-yl)-amide]

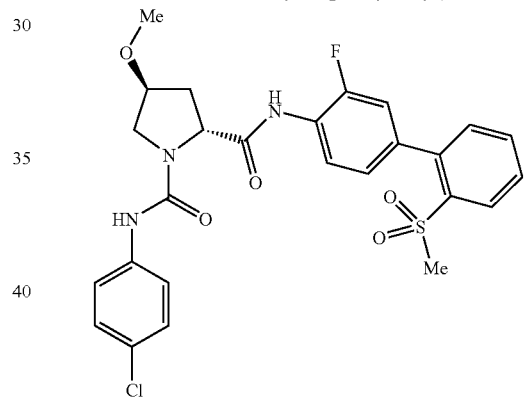

The compound was prepared as generally provided for Example 28, substituting (2R,4S)-4-methoxy-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 546.0 (M)+.

EXAMPLE 96

(2R,4R)-4-Fluoro-pyrrolidine-1,2-dicarboxylic acid 1-[(4-chloro-phenyl)-amide]2-[(3-fluoro-2'-methanesulfonyl-biphenyl-4-yl)-amide]

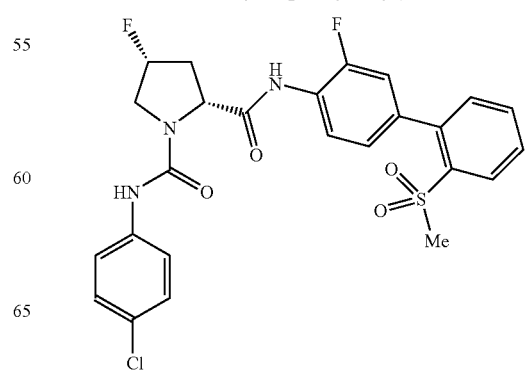

The compound was prepared as generally provided for Example 28, substituting (2R,4R)-4-ethoxy-pyrrolidine-1,2-dicarboxylic acid 1-tert-butyl ester for (2R,4R)-4-methoxy-pyrrolidine-1,2-dicarboxylic acid 1-tert-butyl ester MS: APCI (AP+): 534.0 (M)+.

EXAMPLE 97

(2R)-4,4-Difluoro-pyrrolidine-1,2-dicarboxylic acid 1-[(4-chloro-phenyl)-amide]2-[(3-fluoro-2'-methane-sulfonyl-biphenyl-4-yl)-amide]

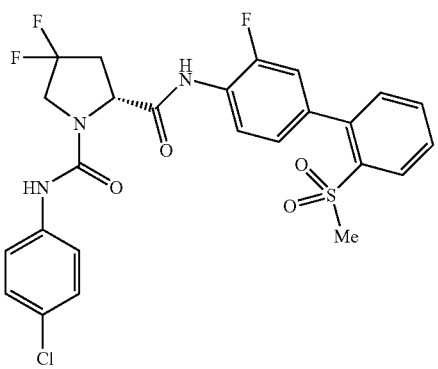

The compound was prepared as generally provided for Example 28, substituting (2R)-4-difluoro-pyrrolidine-1,2-dicarboxylic acid 1-tert-butyl ester for (2R,4R)4-methoxy-pyrrolidine-1,2-dicarboxylic acid 1-tert-butyl ester. MS: APCI (AP+): 552.0 (M)+.

EXAMPLE 98

(2R,4R)-4-Methoxy-pyrrolidine-1,2-dicarboxylic acid 2-[(3-fluoro-2'-methanesulfonyl-biphenyl-4-yl)-amide]1-[(4-fluoro-phenyl)-amide]

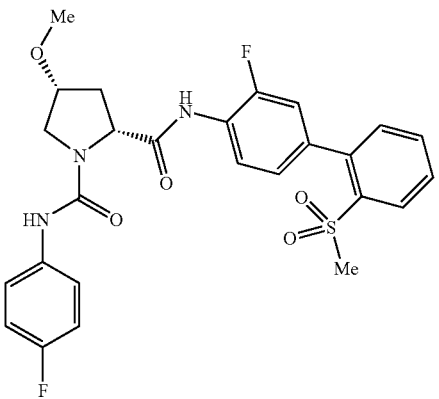

The compound was prepared as generally provided for Example 28, substituting 4-fluorophenyl isocyanate for 4-chlorophenyl isocyanate. MS: APCI (AP+): 530.2 (M)+.

EXAMPLE 99

(2R,4R)-4-Acetylamino-pyrrolidine-1,2-dicarboxylic acid 1-[(4-chloro-phenyl)-amide]2-[(3-fluoro-2'-methanesulfonyl-biphenyl-4-yl)-amide]

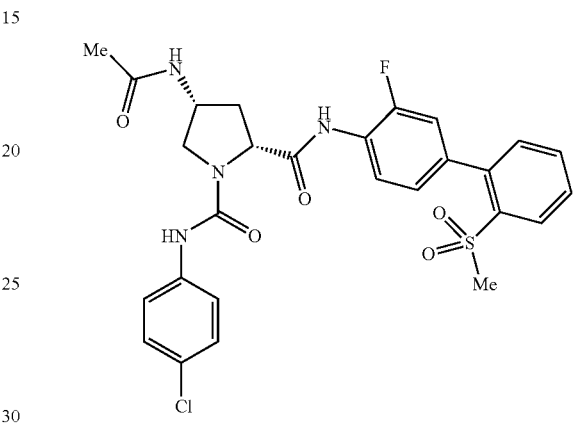

The compound was prepared as generally provided for Example 84. MS: APCI (AP+): 573.2 (M)+.

EXAMPLE 100

(2R,4R)-4-Methanesulfonylamino-pyrrolidine-1,2-dicarboxylic acid 1-[(4-chloro-phenyl)-amide]2-[(3-fluoro-2'-methanesulfonyl-biphenyl-4-yl)-amide]

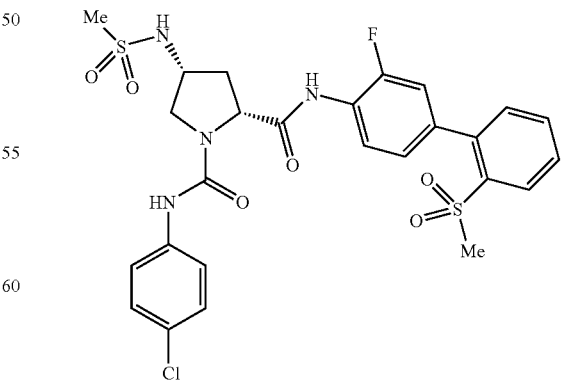

The compound was prepared as generally provided for Example 84. MS: APCI (AP+): 609.2 (M)+.

EXAMPLE 101

(2R,4S)-4-(1H-Tetrazol-5-yl)-pyrrolidine-1,2-dicarboxylic acid 1-[(4-chloro-phenyl)-amide]2-{[2-fluoro-4-(2-oxo-piperidin-1-yl)-phenyl]-amide}

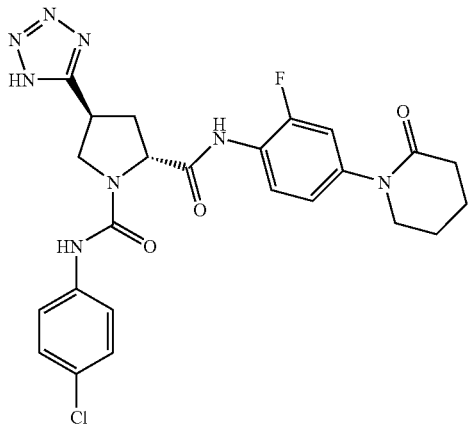

The compound was prepared as generally provided for Example 28. MS: APCI (AP+): 527.2 (M)+.

EXAMPLE 102

(2R,4S)-4-Methoxy-pyrrolidine-1,2-dicarboxylic acid 1-[(4-chloro-phenyl)-amide]2-{[2-fluoro-4-(2-oxo-piperidin-1-yl)-phenyl]-amide}

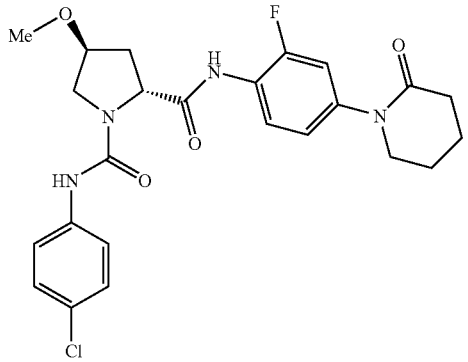

The compound was prepared as generally provided for Example 28, substituting (2R,4S)-4-methoxy-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 489.2 (M)+.

EXAMPLE 103

(2R,4R)-4-Methoxy-pyrrolidine-1,2-dicarboxylic acid 1-[(4-chloro-phenyl)-amide]2-{[2-fluoro-4-(2-methyl-imidazol-1-yl)-phenyl]-amide}

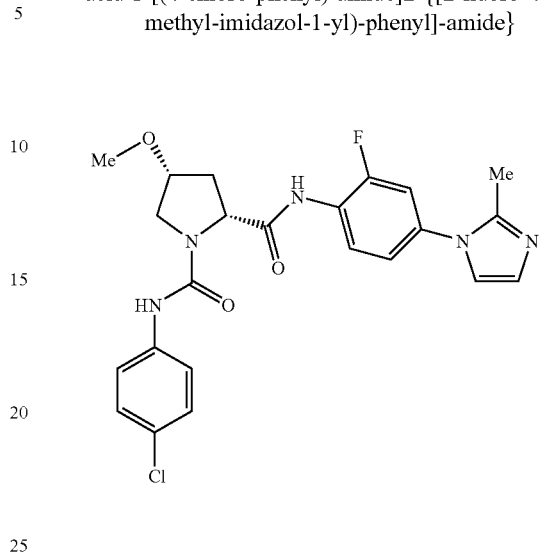

The compound was prepared as generally provided for Example 28, substituting 2-Fluoro-4-(2-methyl-imidazol-1-yl)-phenylamine for 1-(4-amino-3-fluoro-phenyl)-piperidin-2-one. MS: APCI (AP+): 472.2 (M)+.

EXAMPLE 104

(2R,4R)-4-Cyano-pyrrolidine-1,2-dicarboxylic acid 1-[(4-chloro-phenyl)-amide]2-{[2-fluoro-4-(2-oxo-piperidin-1-yl)-phenyl]-amide}

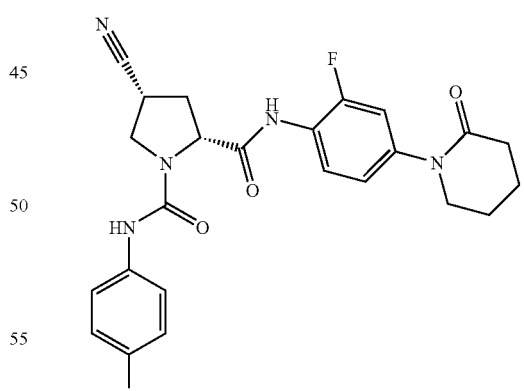

The compound was prepared as generally provided for Example 28 substituting (2R,4R)-4-cyano-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 484.2 (M)+.

EXAMPLE 105

(2R,4R)-4-(1H-Tetrazol-5-yl)-pyrrolidine-1,2-dicarboxylic acid 1-[(4-chloro-phenyl)-amide]2-{[2-fluoro-4-(2-oxo-piperidin-1-yl)-phenyl]-amide}

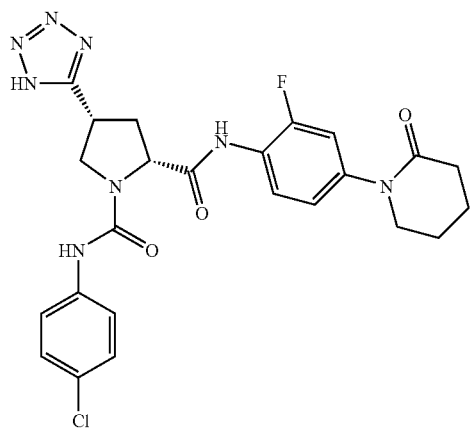

The compound was prepared as generally provided for Example 104. MS: APCI (AP−): 525.3 (M)−.

EXAMPLE 106

(2R,4R)-4-Trifluoromethyl-pyrrolidine-1,2-dicarboxylic acid 1-[(4-chloro-phenyl)-amide]2-{[2-fluoro-4-(2-oxo-piperidin-1-yl)-phenyl]-amide}

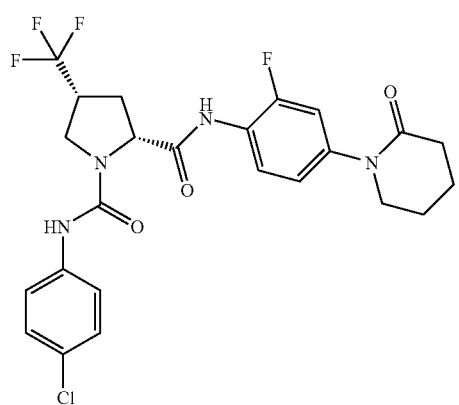

The compound was prepared as generally provided for Example 28, (2R,4R)-4-trifluoromethyl-pyrrolidine-1,2-dicarboxylic acid 1-tert-butyl ester for (2R,4R)-4-methoxy-pyrrolidine-1,2-dicarboxylic acid 1-tert-butyl ester. MS: APCI (AP+): 527.2 (M)+.

EXAMPLE 107

(2R,4R)-4-Methoxy-pyrrolidine-1,2-dicarboxylic acid 1-[(4-chloro-phenyl)-amide]2-[(2'-cyano-3-fluoro-biphenyl-4-yl)-amide]

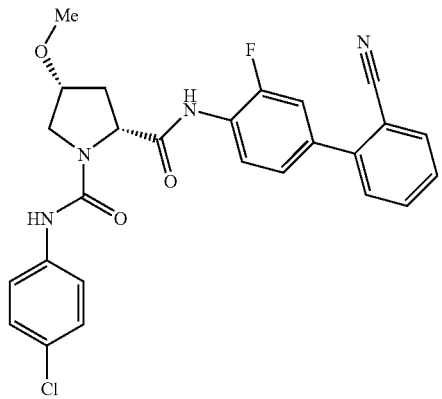

The compound was prepared as generally provided for Example 1, substituting 2-cyanobenzene boronic acid for 2-(methylthio)benzene boronic acid. MS: APCI (AP+): 493.3 (M)+.

EXAMPLE 108

(2R,4R)-4-Methoxy-pyrrolidine-1,2-dicarboxylic acid 2-[(2'-aminomethyl-3-fluoro-biphenyl-4-yl)-amide]1-[(4-chloro-phenyl)-amide]

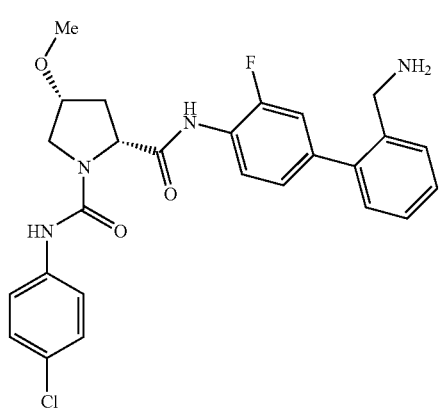

The compound was prepared as generally provided for Example 107. MS: APCI (AP+): 497.3 (M)+.

EXAMPLE 109
(2R,4R)-4'-{[1-(4-Chloro-phenylcarbamoyl)-4-methoxy-pyrrolidine-2-carbonyl]-amino}-3'-fluoro-biphenyl-2-carboxylic acid methyl ester
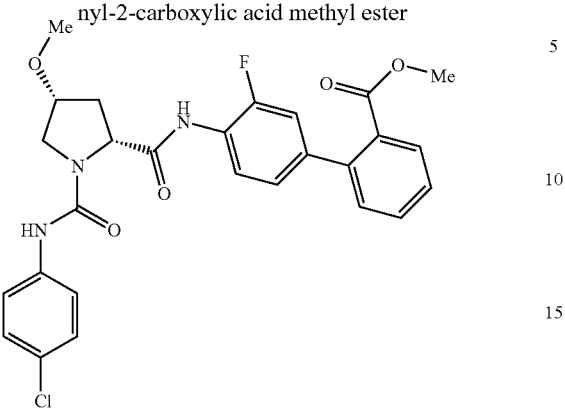
The compound was prepared as generally provided for Example 107. MS: APCI (AP+): 526.2 (M)+.
General Procedure for Example 110
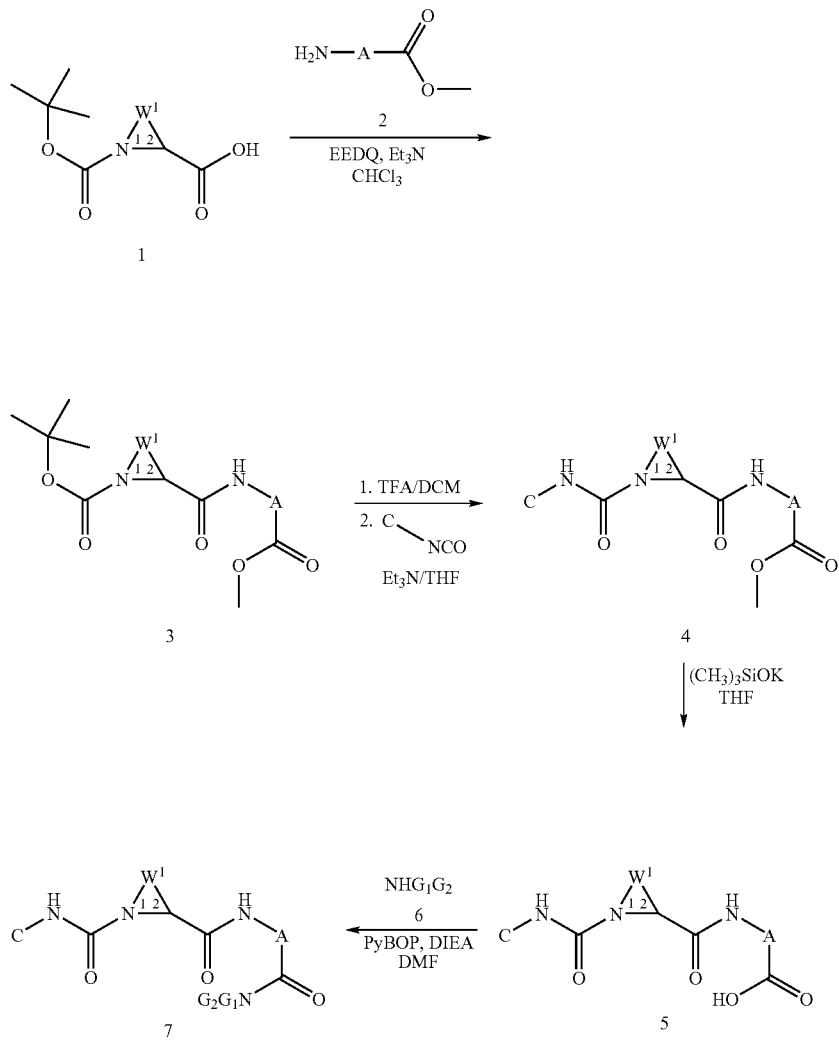

Synthesis of 3: The carboxylic acid (1), aniline or amine (2), EEDQ, and triethylamine are heated at reflux in chloroform to produce 3.

Synthesis of 4: A solution of compound 3, TFA, and DCM is stirred at room temperature for 1 h and then concentrated under reduced pressure. The resulting oil is dissolved in THF and cooled to 0° C. followed by the addition of triethylamine or N,N-diisopropylethylamine (DIEA) and the appropriate isocyanate to produce compound 4.

Synthesis of 5: To solution of compound 4 in THF is added potassium trimethylsilanolate and is stirred at room temperature overnight to produce 5.

Synthesis of 7: To solution of compound 5 in DMF is added N,N-diisopropylethylamine, PyBOP, and NHGIG$_2$ and is stirred at room temperature overnight to produce 7.

EXAMPLE 110

(2R,4R)-4-Methoxy-pyrrolidine-1,2-dicarboxylic acid 1-[(4-chloro-phenyl)-amide]2-{[4-(2,5-dihydro-pyrrole-1-carbonyl)-phenyl]-amide}

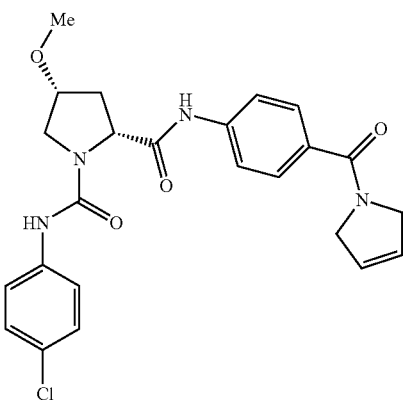

Step 1: (2R,4R)-4-Hydroxy-pyrrolidine-2-carboxylic acid methyl ester (1)

Cis-4-Hydroxy-D-proline (15 g, 115 mmol) was suspended in 150 mL anhydrous methanol under an argon atmosphere, then cooled to 0° C. before bubbling in HCl gas for 15 minutes. The solution gradually became homogenous. The argon and HCl gas lines were removed and the solution was refluxed for 4 h. The solution was cooled and then concentrated under reduced pressure. The crude material was redissolved in 100 mL methanol and diethyl ether was added until a precipitate formed. The precipitate was filtered off, washed with diethyl ether, and dried in vacuo overnight to give 1 (20 g, 95%) as a white solid. MS: APCI (AP+): 146 (M)+.

Step 2: (2R,4R)-4-Hydroxy-1-trityl-pyrrolidine-2-carboxylic acid methyl ester (2)

Into a solution of 1 (10 g, 55 mmol) in anhydrous CHCl$_3$ (100 mL) was added triethylamine (19 mL, 138 mmol) and triphenylmethyl chloride (14.5 g, 52 mmol). The mixture was stirred at RT for 3d before concentrating and redissolving in EtOAc. The solution was washed sequentially with 10% aq. citric acid, water, and brine before drying over MgSO$_4$ and concentrating under reduced pressure to give 2 (20 g, 100%) as a yellow solid.

Step 3: (2R,4R)-4-Methoxy-1-trityl-pyrrolidine-2-carboxylic acid methyl ester (3)

Into a solution of 2 (5.71 g, 14.7 mmol) in anhydrous DMF (20 mL) and anhydrous THF (20 mL) was added MeI (3.67 mL, 58.9 mmol). The solution was cooled to 0° C. in an ice bath and NaH (0.766 g, 19.2 mmol) was added in one portion. The mixture was stirred at RT for 26 h before adding EtOAc and washing sequentially with water and brine. The organic layer was dried over MgSO$_4$ and concentrated under reduced pressure. Purification of the crude material by flash chromatography revealed 3 (4.67 g, 79%) as a white solid.

Step 4: (2R,4R)-4-Methoxy-pyrrolidine-2-carboxylic acid methyl ester (4)

To a flask containing 3 (4.67 g, 11.6 mmol) was added a solution of CH$_2$Cl$_2$ (27 mL), water (0.3 mL), and TFA (3.0 mL, 38.9 mmol). The solution was stirred at RT for 3 h before concentrating under reduced pressure to reveal impure 4. MS: APCI (AP+): 160.1 (M)+.

Step 5: (2R,4R)-4-Methoxy-pyrrolidine-1,2-dicarboxylic acid 1-tert-butyl ester 2-methyl ester (5).

Into a solution of 4 (1.85 g, 11.6 mmol) in CH$_2$Cl$_2$ (20 mL) was added triethylamine (6.49 mL, 46.5 mmol), di-tert-butyl dicarbonate (5.08 g, 23.3 mmol), and dimethylaminopyridine (0.142 g, 1.16 mmol). The mixture was stirred at RT for 22 h before concentrating under reduced pressure and redissolving in EtOAc. The solution was washed sequentially with 10% aq. citric acid and brine before drying over MgSO$_4$ and concentrating under reduced pressure. The crude material was purified by flash chromatography to reveal 5 (2.54 g, 84% over two steps) as a yellow solid. MS: APCI (AP+): 260.1 (M)+.

Step 6: (2R,4R)-4-Methoxy-pyrrolidine-1,2-dicarboxylic acid 1-tert-butyl ester (6)

Into a solution of 5 (2.54 g, 9.80 mmol) in acetonitrile (20 mL) was added water (20 mL) and LiOH H$_2$O (1.64 g, 39.2 mmol). The mixture was stirred at RT for 28 h before removing the acetonitrile under reduced pressure. EtOAc was added to the residue that was then washed with 1N HCl. The aqueous layer was extracted with additional EtOAc and the combined organic layers were washed with brine and dried over MgSO$_4$. The solution was concentrated under reduced pressure to reveal 6 (2.16 g, 90%) as a white solid. MS: APCI (AP−): 244.1 (M)−.

Step 7: (2R,4R)-4-Methoxy-2-(4-methoxycarbonyl-phenylcarbamoyl)-pyrrolidine-1-carboxylic acid tert-butyl ester (7)

Into a solution of 6 (8.11 g, 33.0 mmol) in CHCl$_3$ (200 mL) was added 4-amino-benzoic acid methyl ester (5.00 g, 33.0 mmol), EEDQ (9.81 g, 39.6 mmol), and triethylamine (6.9 mL, 49.6 mmol). The solution was stirred at reflux for 19 h before cooling to RT and adding EtOAc. The solution was washed sequentially with 1N HCl, 0.1N NaOH, water, and brine, before drying over MgSO$_4$ and concentrating under reduced pressure to give 7 (12.50 g, 100%). MS: APCI (AP+): 379.3 (M)+, (AP−): 377.3 (M)−.

Step 8: (2R,4R)-4-[(4-Methoxy-pyrrolidine-2-carbonyl)-amino]-benzoic acid methyl ester (8)

Into a solution of 7 (12.5 g, 33.0 mmol) in anhydrous CH$_2$Cl$_2$ (70 mL) was added TFA (20 mL). The solution was stirred at RT overnight before concentrating under reduced pressure to give 8 (9.19 g, 100%).

Step 9: (2R,4R)-4-{[1-(4-Chloro-phenylcarbamoyl)-4-methoxy-pyrrolidine-2-carbonyl]-amino}-benzoic acid methyl ester (9)

Into a solution of 8 (9.19 g, 33.0 mmol) in anhydrous THF (200 mL) at 0° C. was added N,N-diisopropylethylamine (DIEA) (28.7 mL, 165 mmol) and 4-chlorophenyl isocyanate (5.07 g, 33.0 mmol). The solution was stirred at RT overnight before concentrating under reduced pressure. The crude material was purified on a silica gel column eluted with 10% moving to 50% EtOAc in hexanes. Combined and concentrated pure fractions. Remaining EtOAc was azeotroped off with acetonitrile and was lyophilized from acetonitrile/water to give 9 (13.37 g, 94%) as a solid. MS: APCI (AP+): 432.1 (M)+, (AP−): 430.1 (M)−.

Step 10: (2R,4R)-4-{[1-(4-Chloro-phenylcarbamoyl)-4-methoxy-pyrrolidine-2-carbonyl]-amino}-benzoic acid (10)

Into a solution of 9 (3.0 g, 6.94 mmol) in THF (50 mL) was added potassium trimethylsilanolate (3.85 g, 27.3 mmol). The solution was stirred at RT for 48 h before concentrating under reduced pressure and adding EtOAc. The solution was washed sequentially with 1N HCl, and brine, before drying over MgSO$_4$ and concentrating under reduced pressure to give 10 (2.9 g, 100%). MS: APCI (AP+): 418.1 (M)+, (AP−): 416.1 (M)−.

Step 11: (2R,4R)-4-Methoxy-pyrrolidine-1,2-dicarboxylic acid 1-[(4-chloro-phenyl)-amide]2-{[4-(2,5-dihydro-pyrrole-1-carbonyl)-phenyl]-amide} (11)

Into a solution of 10 (0.25 g, 0.589 mmol) in DMF (3 mL) was added N,N-diisopropylethylamine (DIEA) (0.4 mL, 2.32 mmol), PyBOP (0.34 g, 0.653 mmol), and 3-pyrroline (0.09 mL, 1.19 mmol). The solution was stirred at RT for 19 h and EtOAc added. The solution was washed sequentially with 1N HCl, saturated NaHCO$_3$, water, and brine, before drying over MgSO$_4$ and concentrating under reduced pressure. The crude material was purified on a silica gel column eluted with 20% EtOAc in hexanes moving to 1% MeOH in EtOAc. Combined and concentrated pure fractions. Remaining EtOAc was azeotroped off with acetonitrile and was lyophilized from acetonitrile/water to give 11 (0.116 g, 41%) as a solid. MS: APCI (AP+): 469.2 (M)+, (AP−): 468.1 (M)−.

General Procedure for Example 111

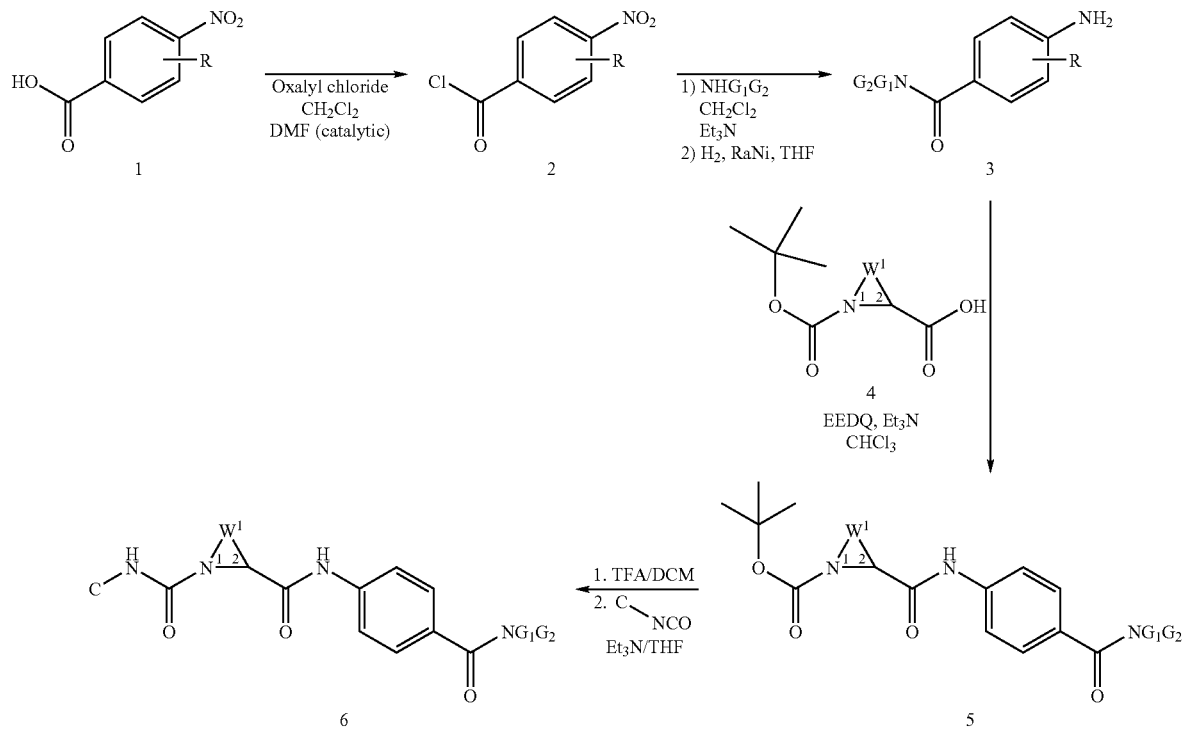

Synthesis of 2: The carboxylic acid (1) is converted to the acid chloride (2) upon treatment with oxalyl chloride and DMF (catalytic) in dichloromethane.

Synthesis of 3: To the acid chloride (2) in dichloromethane is then added NHG$_1$G$_2$ and triethylamine in dichloromethane. Alternatively NHG$_1$G$_2$ can be coupled directly to the carboxylic acid with addition of PyBOP and N,N-diisopropylethylamine in DMF. Reduction of the nitro group to the corresponding aniline is readily achieved with a transition metal such as palladium on carbon or Raney nickel and hydrogen to give 3.

Synthesis of 5: The carboxylic acid (4), aniline (3), EEDQ, and triethylamine are heated at reflux in chloroform to produce 5.

Synthesis of 6: A solution of compound 5, TFA, and DCM is stirred at room temperature for 1 h and then concentrated under reduced pressure. The resulting oil is dissolved in THF and cooled to 0° C. followed by the addition of triethylamine or N,N-diisopropylethylamine (DIEA) and the appropriate isocyanate to produce compound 6.

EXAMPLE 111

(2R,4R)-4-Hydroxy-pyrrolidine-1,2-dicarboxylic acid 1-[(4-chloro-phenyl)-amide]2-[(4-dimethylcarbamoyl-2-fluoro-phenyl)-amide]

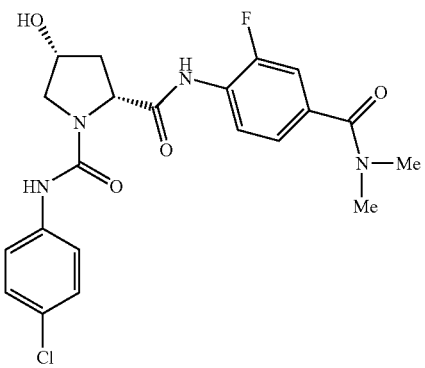

Step 1: (2R,4R)-4-hydroxy-pyrrolidine-1,2-dicarboxylic acid 1-tert-butyl ester (1)

Cis-4-hydroxy-D-proline (15 g, 114 mmol) was dissolved In 150 mL of THF/H$_2$O (2: 1), added 2M aqueous NaOH solution (86 mL, 172 mmol), followed by Boc$_2$O (27 g, 126 mmol). Reaction was stirred at ambient temperature overnight. The solution was acidified with 10% citric acid then extracted with EtOAc (2×250 mL), washed with water, brine, dried organics with MgSO$_4$, filtered and concentrated to give 1 (16 g, 61%) APCI (AP−): 230.1 (M−H)⁻.

Step 2: (2R,4R)-4-(tert-butyl-dimethyl-silanyloxy)-pyrrolidine-1,2-dicarboxylic acid 1-tert-butyl ester (2)

(2R,4R)4-Hydroxy-pyrrolidine-1,2-dicarboxylic acid 1-tert-butyl ester (16 g, 69 mmol) was dissolved in 100 mL DMF, added imidazole (12 g, 173 mmol), dimethylaminopyridine (0.85 g, 6.9 mmol), and tert-butyldimethylsilyl chloride (12.5 g, 83 mmol). Stirred at ambient temperature overnight, dissolved in 350 mL EtOAc, washed with 10% citric acid (3×200 mL), water (2×200 mL), brine, dried with MgSO$_4$, filtered, and concentrated to give 2 (20 g, 84%) APCI (AP−): 344.2 (M−H)⁻.

Step 3: 3-Fluoro-4-nitro-benzoyl chloride (3)

Into a solution of 3-fluoro-4-nitro-benzoic acid (4.0 g, 21.6 mmol) in anhydrous CH$_2$Cl$_2$ (200 mL) at 0° C. was slowly added oxalyl chloride (2.45 mL, 28.0 mmol) and a drop of DMF. The solution was stirred and allowed to warm to RT overnight before concentrating under reduced pressure to give 3 (4.39 g, 100%).

Step 4: 3-Fluoro-N,N-dimethyl-4-nitro-benzamide (4)

Into a solution of 3 (1.50 g, 7.36 mmol) in CH$_2$Cl$_2$ (30 mL) at 0° C. was added triethylamine (1.5 mL, 10.9 mmol) and dimethylamine 40% in water (0.83 mL, 7.36 mmol) dropwise. The solution was stirred and allowed to warm to RT overnight before concentrating under reduced pressure and adding EtOAc. The solution was washed sequentially with saturated NaHCO$_3$, water, and brine, before drying over MgSO$_4$ and concentrating under reduced pressure to give impure 4 (0.78 g, 50%). MS: APCI (AP+): 213.1 (M)+, (AP−): 212.1 (M)−.

Step 5: 4-Amino-3-fluoro-N,N-dimethyl-benzamide (5)

To a Parr apparatus was added 4 (0.78 g, 3.67 mmol), Raney nickel (1.2 g), and THF (50 mL). The vessel was sealed under a hydrogen atmosphere and shaken under pressure at room temperature for 15 h. The vessel was then depressurized and the solids filtered off, washing with THF. The filtrate was concentrated under reduced pressure to give impure 5 (0.66 g, 100%). MS: APCI (AP+): 183.1 (M)+, (AP−): 181.0 (M)−.

Step 6: (2R,4R)-4-(tert-Butyl-dimethyl-silanyloxy)-2-(4-dimethylcarbamoyl-2-fluoro-phenylcarbamoyl)-pyrrolidine-1-carboxylic acid tert-butyl ester (6)

Into a solution of 2 (1.25 g, 3.61 mmol) in CHCl$_3$ (25 mL) was added 5 (0.66 g, 3.61 mmol), EEDQ (1.07 g, 4.32 mmol), and triethylamine (0.74 mL, 5.33 mmol). The solution was stirred at reflux for 19 h before cooling to RT and adding EtOAc. The solution was washed sequentially with 1N HCl, 0.1N NaOH, water, and brine, before drying over MgSO$_4$ and concentrating under reduced pressure. The crude material was purified on a silica gel column eluted with 20% moving to 50% EtOAc in hexanes. Combined and concentrated pure fractions. to give 6 (0.33 g, 18%). MS: APCI (AP+): 510.3 (M)+, (AP−): 508.4 (M)−.

Step 7: (2R,4R)-4-Hydroxy-pyrrolidine-2-carboxylic acid (4-dimethylcarbamoyl-2-fluoro-phenyl)-amide (7)

Into a solution of 6 (0.33 g, 0.647 mmol) in anhydrous CH$_2$Cl$_2$ (10 mL) was added TFA (2 mL). The solution was stirred at RT for 4 h before concentrating under reduced pressure to give 7 (0.19 g, 100%).

Step 8: (2R,4R)-4-Hydroxy-pyrrolidine-1,2-dicarboxylic acid 1-[(4-chloro-phenyl)-amide]2-[(4-dimethylcarbamoyl-2-fluoro-phenyl)-amide] (8)

Into a solution of 7 (0.19 g, 0.643 mmol) in anhydrous THF (10 mL) at 0° C. was added N,N-diisopropylethylamine (DIEA) (0.56 mL, 3.21 mmol) and 4-chlorophenyl isocyanate (0.099 g, 0.643 mmol). The solution was stirred at RT overnight before concentrating under reduced pressure. Crystallized from EtOAc in hexanes and filtered to give 8 (0.12 g, 43%) as a solid. MS: APCI (AP+): 449.2 (M)+, (AP−): 447.1 (M)−.

EXAMPLE 112

(2R,4R)-4-Hydroxy-pyrrolidine-1,2-dicarboxylic acid 1-[(4-chloro-phenyl)-amide]2-{[4-(pyrrolidine-1-carbonyl)-phenyl]-amide}

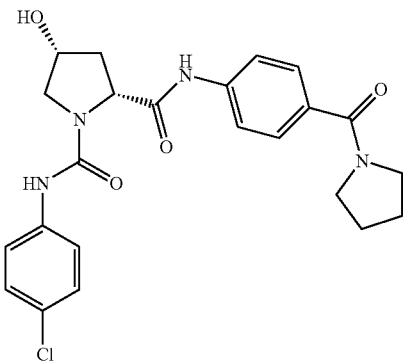

The compound was prepared as generally provided for Example 111. MS: APCI (AP+): 457.1 (M)+, (AP−): 455.1 (M)−.

EXAMPLE 113

Pyrrolidine-1,2-dicarboxylic acid 1-[(4-chloro-phenyl)-amide]2-{[4-(pyrrolidine-1-carbonyl)-phenyl]-amide}

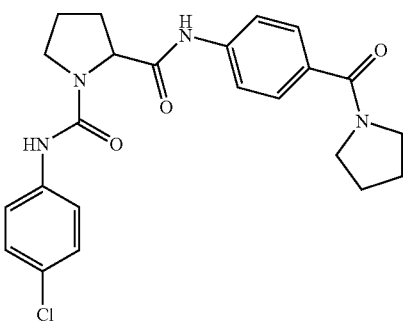

The compound was prepared as generally provided for Example 111. MS: APCI (AP+): 441.1 (M)+, (AP−): 439.1 (M)−.

EXAMPLE 114

(2R,4R)-4-Hydroxy-pyrrolidine-1,2-dicarboxylic acid 1-[(4-chloro-phenyl)-amide]2-{[4-(2-methyl-pyrrolidine-1-carbonyl)-phenyl]-amide}

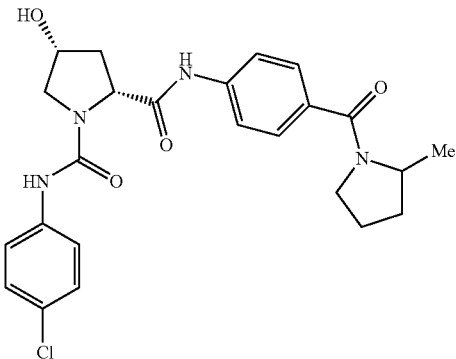

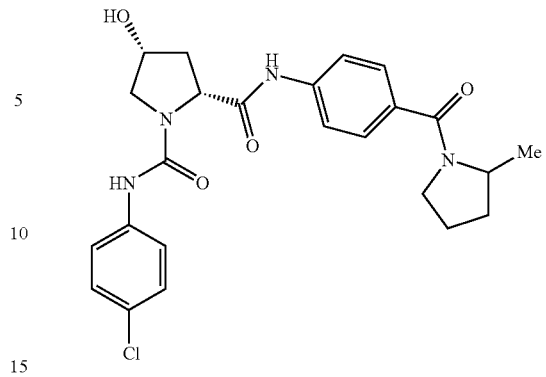

The compound was prepared as generally provided for Example 111. MS: APCI (AP+): 471.2 (M)+, (AP−): 469.2 (M)−.

EXAMPLE 115

(2R,4R)-4-Hydroxy-pyrrolidine-1,2-dicarboxylic acid 1-[(4-chloro-phenyl)-amide]2-{[4-(ethyl-methyl-carbamoyl)-phenyl]-amide}

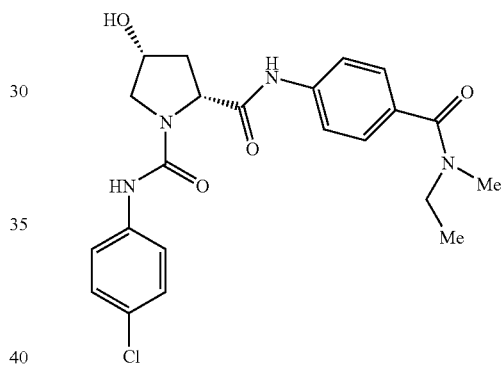

The compound was prepared as generally provided for Example 111. MS: APCI (AP+): 445.2 (M)+, (AP−): 443.1 (M)−.

EXAMPLE 116

(2R,4R)-4-Hydroxy-pyrrolidine-1,2-dicarboxylic acid 1-[(4-chloro-phenyl)-amide]2-[(4-dimethylcarbamoyl-phenyl)-amide]

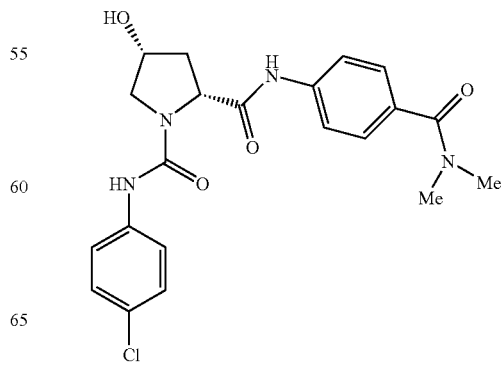

The compound was prepared as generally provided for Example 111. MS: APCI (AP+): 431.1 (M)+, (AP−): 429.1 (M)−.

EXAMPLE 117
(2R,4R)-4-Hydroxy-pyrrolidine-1,2-dicarboxylic acid 1-[(4-chloro-phenyl)-amide]2-{[4-(2R-methyl-pyrrolidine-1-carbonyl)-phenyl]-amide}

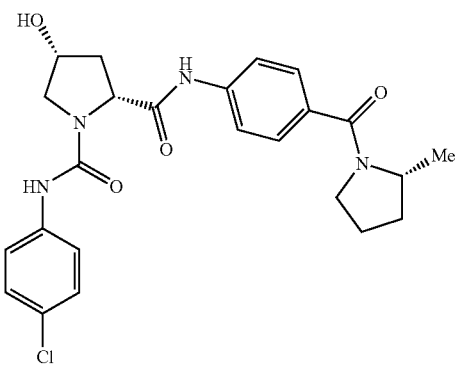

The compound was prepared as generally provided for Example 111. MS: APCI (AP+): 471.2 (M)+, (AP−): 469.2 (M)−.

EXAMPLE 118
(2R,4R)-4-Hydroxy-pyrrolidine-1,2-dicarboxylic acid 1-[(4-chloro-phenyl)-amide]2-{[4-(2S-methyl-pyrrolidine-1-carbonyl)-phenyl]-amide}

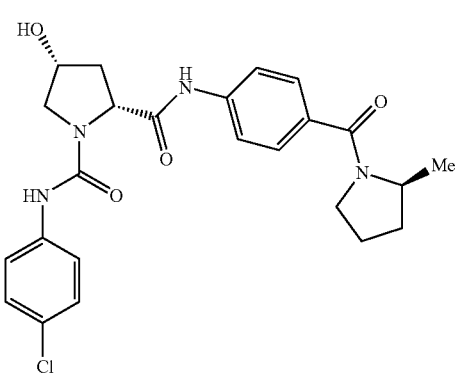

The compound was prepared as generally provided for Example 111. MS: APCI (AP+): 471.2 (M)+, (AP−): 469.2 (M)−.

EXAMPLE 119
(2R,4R)-4-Hydroxy-pyrrolidine-1,2-dicarboxylic acid 1-[(4-chloro-phenyl)-amide]2-{[2-fluoro-4-(pyrrolidine-1-carbonyl)-phenyl]-amide}

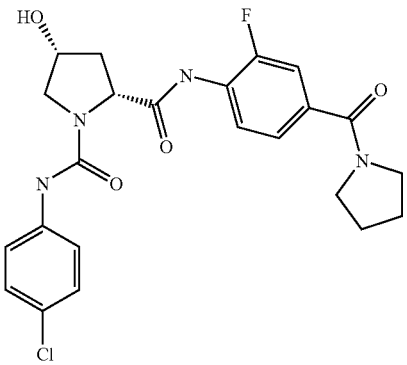

The compound was prepared as generally provided for Example 111. MS: APCI (AP+): 475.2 (M)+, (AP−): 473.1 (M)−.

EXAMPLE 120
(2R,4R)-4-Hydroxy-pyrrolidine-1,2-dicarboxylic acid 1-[(4-chloro-phenyl)-amide]2-{[4-(pyrrolidine-1-carbonyl)-2-pyrrolidin-1-yl-phenyl]-amide}

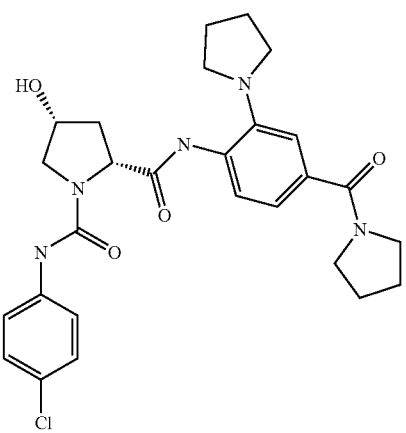

The compound was prepared as generally provided for Example 111. MS: APCI (AP+): 526.2 (M)+, (AP−): 524.3 (M)−.

EXAMPLE 121
(2R,4R)-4-{[1-(4-Chloro-phenylcarbamoyl)-4-hydroxy-pyrrolidine-2-carbonyl]-amino}-3-pyrrolidin-1-yl-benzoic acid methyl ester

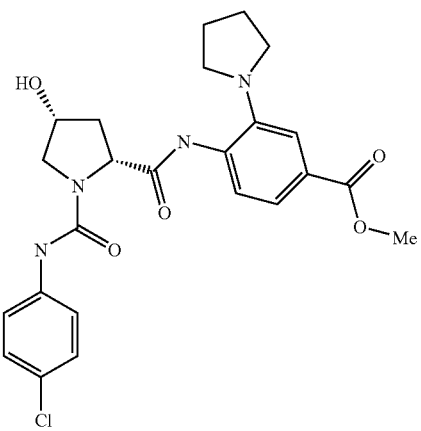

The compound was prepared as generally provided for Example 111. MS: APCI (AP+): 487.2 (M)+, (AP−): 485.2 (M)−.

EXAMPLE 122

(2R,4R)-4-Hydroxy-pyrrolidine-1,2-dicarboxylic acid 2-{[4-(azetidine-1-carbonyl)-phenyl]-amide}1-[(4-chloro-phenyl)-amide]

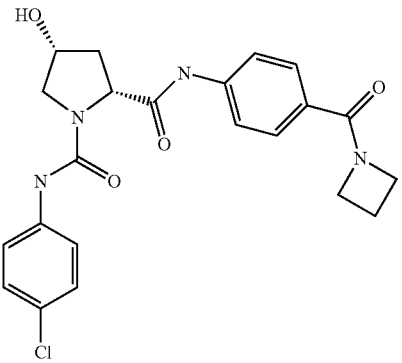

The compound was prepared as generally provided for Example 111o. MS: APCI (AP+): 443.2 (M)+, (AP−): 441.1 (M)−.

EXAMPLE 123

(2R,4R)-4-Hydroxy-pyrrolidine-1,2-dicarboxylic acid 1-[(5-chloro-pyridin-2-yl)-amide]2-{[2-fluoro-4-(pyrrolidine-1-carbonyl)-phenyl]-amide}

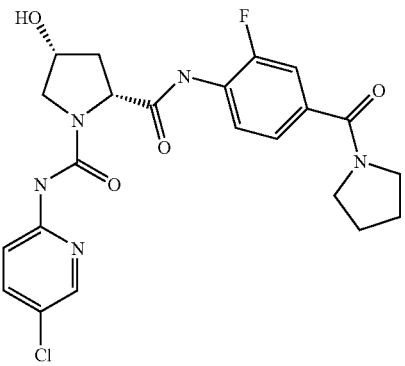

The compound was prepared as generally provided for Example 111. Formation of the 5-chloro-pyridin-2-yl moiety can be found in Example 26. MS: APCI (AP+): 476.2 (M)+, (AP−): 474.2 (M)−.

EXAMPLE 124

(2R,4R)-4-Hydroxy-pyrrolidine-1,2-dicarboxylic acid 1-[(5-chloro-pyridin-2-yl)-amide]2-{[4-(pyrrolidine-1-carbonyl)-phenyl]-amide}

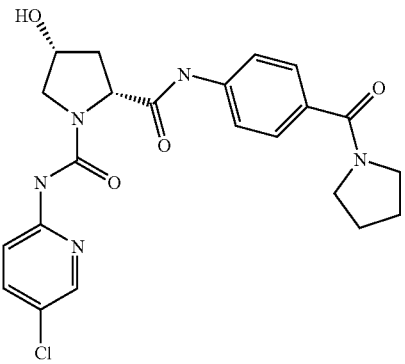

The compound was prepared as generally provided for Example 111. Formation of the 5-chloro-pyridin-2-yl moiety can be found in Example 26. MS: APCI (AP+): 458.2 (M)+, (AP−): 456.2 (M)−.

EXAMPLE 125

(2R,4R)-4-Hydroxy-pyrrolidine-1,2-dicarboxylic acid 1-[(5-chloro-pyridin-2-yl)-amide]2-[(4-dimethylcarbamoyl-phenyl)-amide]

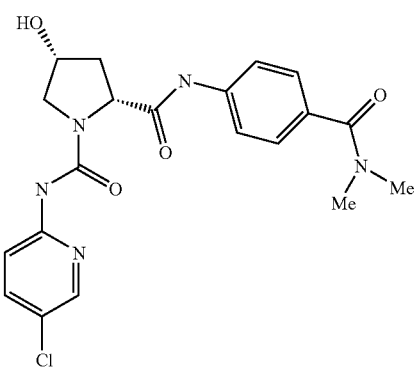

The compound was prepared as generally provided for Example 111. Formation of the 5-chloro-pyridin-2-yl moiety can be found in Example 26. MS: APCI (AP+): 432.1 (M)+, (AP−): 430.1 (M)−.

EXAMPLE 126

(2R,4R)-4-{[1-(4-Chloro-phenylcarbamoyl)-4-hydroxy-pyrrolidine-2-carbonyl]-amino}-3-dimethylamino-benzoic acid methyl ester

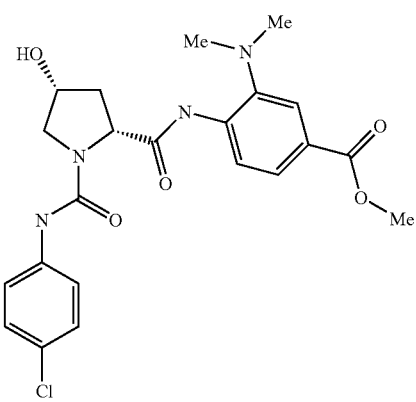

The compound was prepared as generally provided for Example 111. MS: APCI (AP+): 461.2 (M)+, (AP−): 459.1 (M)−.

EXAMPLE 127

(2R,4R)-4-Methoxy-pyrrolidine-1,2-dicarboxylic acid 1-[(4-chloro-phenyl)-amide]2-{[4-(pyrrolidine-1-carbonyl)-phenyl]-amide}

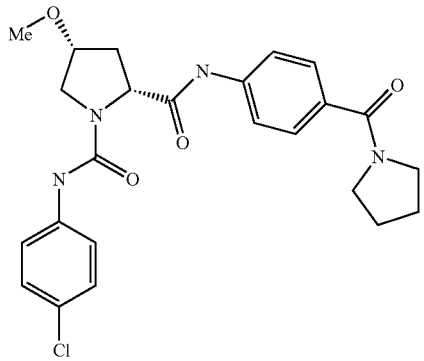

The compound was prepared as generally provided for Example 110 and/or DD-2. MS: APCI (AP+): 471.2 (M)+, (AP−): 469.2 (M)−.

EXAMPLE 128

(2R,4R)-4-Methoxy-pyrrolidine-1,2-dicarboxylic acid 1-[(4-chloro-phenyl)-amide]2-[(4-dimethylcarbamoyl-phenyl)-amide]

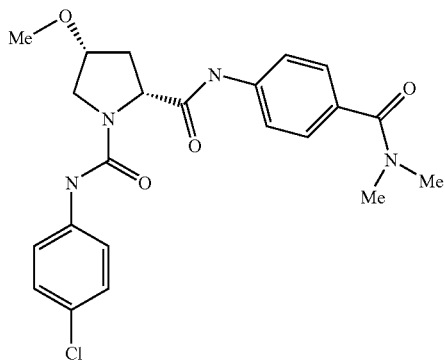

The compound was prepared as generally provided for Example 110 and/or 111. MS: APCI (AP+): 445.2 (M)+, (AP−): 443.2 (M)−.

EXAMPLE 129

(2R,4R)-4-Ethoxy-pyrrolidine-1,2-dicarboxylic acid 1-[(4-chloro-phenyl)-amide]2-{[4-(pyrrolidine-1-carbonyl)-phenyl]-amide}

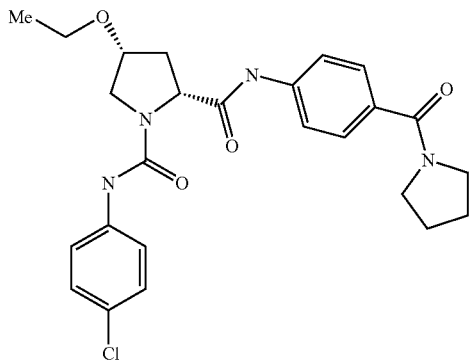

The compound was prepared as generally provided for Example 111. MS: APCI (AP+): 485.3 (M)+, (AP−): 483.3 (M)−.

EXAMPLE 130

(2R,4R)-4-Ethoxy-pyrrolidine-1,2-dicarboxylic acid 1-[(4-chloro-phenyl)-amide]2-[(4-dimethylcarbamoyl-phenyl)-amide]

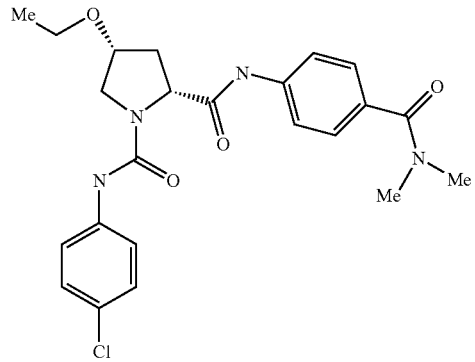

The compound was prepared as generally provided for Example 111. MS: APCI (AP+): 459.2 (M)+, (AP−): 457.2 (M)−.

EXAMPLE 131

(2R,4R)-4-Methoxy-pyrrolidine-1,2-dicarboxylic acid 1-[(4-chloro-phenyl)-amide]2-{[2-fluoro-4-(pyrrolidine-1-carbonyl)-phenyl]-amide}

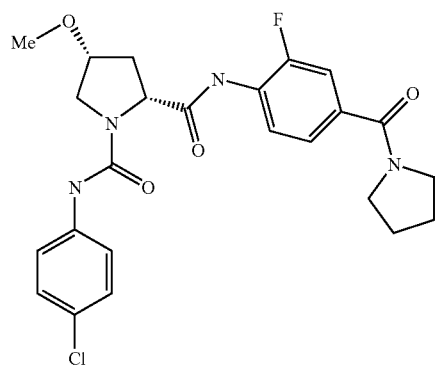

The compound was prepared as generally provided for Example 110 and/or 111. MS: APCI (AP+): 489.3 (M)+, (AP−): 487.2 (M)−.

EXAMPLE 132

(2R,4R)-4-Methoxy-pyrrolidine-1,2-dicarboxylic acid 1-[(4-chloro-phenyl)-amide]2-[(4-dimethylcarbamoyl-2-fluoro-phenyl)-amide]

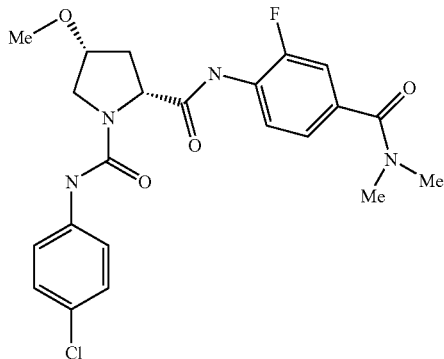

The compound was prepared as generally provided for Example 110 and/or 111. MS: APCI (AP+): 463.2 (M)+, (AP−): 461.2 (M)−.

EXAMPLE 133

(2R,4R)-4-Ethoxy-pyrrolidine-1,2-dicarboxylic acid 1-[(4-chloro-phenyl)-amide]2-{[2-fluoro-4-(pyrrolidine-1-carbonyl)-phenyl]-amide}

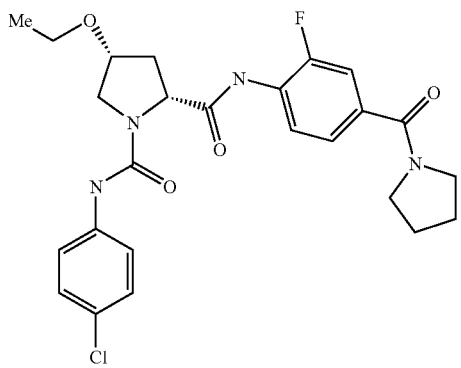

The compound was prepared as generally provided for Example 111. MS: APCI (AP+): 503.3 (M)+, (AP−): 501.3 (M)−.

EXAMPLE 134

(2R,4R)-4-Ethoxy-pyrrolidine-1,2-dicarboxylic acid 1-[(4-chloro-phenyl)-amide]2-[(4-dimethylcarbamoyl-2-fluoro-phenyl)-amide]

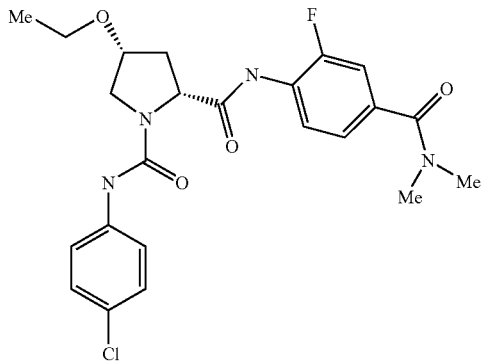

The compound was prepared as generally provided for Example 111. MS: APCI (AP+): 477.3 (M)+, (AP−): 475.2 (M)−.

EXAMPLE 135

(2R,4R)-4-Methoxy-pyrrolidine-1,2-dicarboxylic acid 1-[(4-chloro-phenyl)-amide]2-{[2-methyl-4-(2-oxo-piperidin-1-yl)-phenyl]-amide}

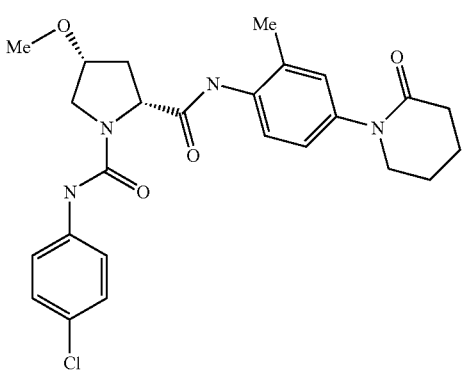

The compound was prepared as generally provided for Example 28. MS: APCI (AP+): 485.3 (M)+, (AP−): 483.3 (M)−.

EXAMPLE 136

(2R,4R)-4-Ethoxy-pyrrolidine-1,2-dicarboxylic acid 1-[(4-chloro-phenyl)-amide]2-{[2-methyl-4-(2-oxo-piperidin-1-yl)-phenyl]-amide}

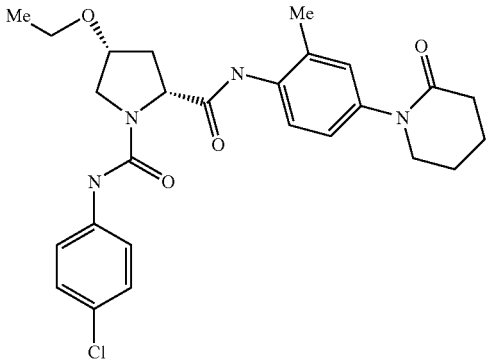

The compound was prepared as generally provided for Example 28. MS: APCI (AP+): 499.2 (M)+, (AP−): 497.2 (M)−.

EXAMPLE 137

Pyrrolidine-1,2-dicarboxylic acid 1-[(4-chloro-phenyl)-amide]2-[(2-fluoro-4-quinolin-8-yl-phenyl)-amide]

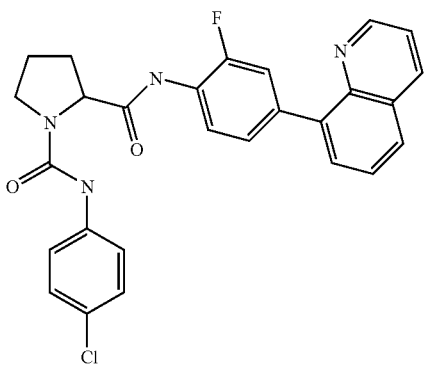

The compound was prepared as generally provided for Example 19. MS: APCI (AP+): 489.1 (M)+, (AP−): 488.1 (M)−.

EXAMPLE 138

Pyrrolidine-1,2-dicarboxylic acid 1-[(4-chloro-phenyl)-amide]2-[(3,5-difluoro-2'-methanesulfonyl-biphenyl-4-yl)-amide]

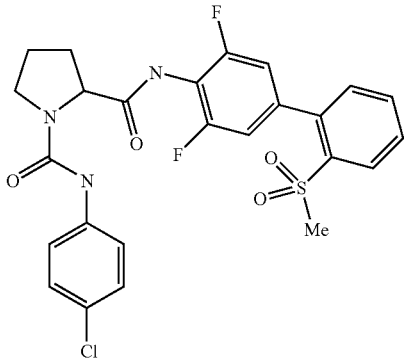

The compound was prepared as generally provided for Example 19. MS: APCI (AP+): 534.1 (M)+, (AP−): 532.0 (M)−.

EXAMPLE 139

Pyrrolidine-1,2-dicarboxylic acid 1-[(4-chloro-phenyl)-amide]2-[(2'-methanesulfonyl-2-methyl-biphenyl-4-yl)-amide]

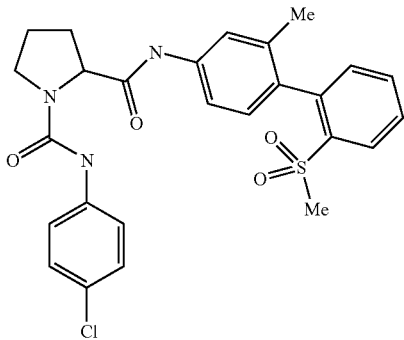

The compound was prepared as generally provided for Example 19. MS: APCI (AP+): 512.1 (M)+, (AP−): 510.1 (M)−.

EXAMPLE 140

(2R,4R)-4-Hydroxy-pyrrolidine-1,2-dicarboxylic acid 1-[(4-chloro-phenyl)-amide]2-[(2'-methanesulfonyl-biphenyl-4-yl)-amide]

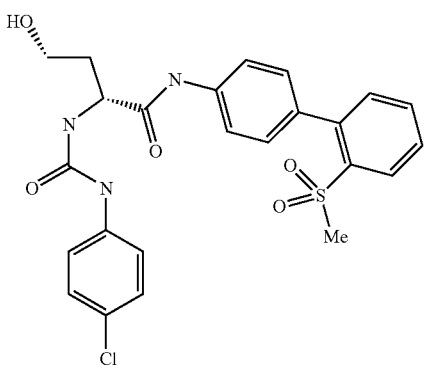

The compound was prepared as generally provided for Example 17. MS: APCI (AP+): 514.0 (M)+, (AP−): 512.0 (M)−.

EXAMPLE 142

(2R,4R)-4-Hydroxy-pyrrolidine-1,2-dicarboxylic acid 1-[(4-chloro-phenyl)-amide]2-[(2'-methanesulfinyl-biphenyl-4-yl)-amide]

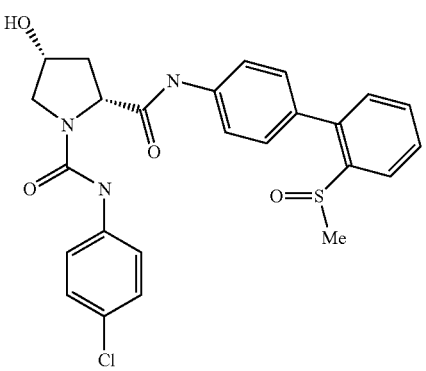

The compound was prepared as generally provided for Example 17. MS: APCI (AP+): 498.2 (M)+, (AP−): 496.2 (M)−.

EXAMPLE 143

(2R,4R)-4-Hydroxy-pyrrolidine-1,2-dicarboxylic acid 1-[(4-chloro-phenyl)-amide]2-[(3-methyl-2'-methylsulfanyl-biphenyl-4-yl)-amide]

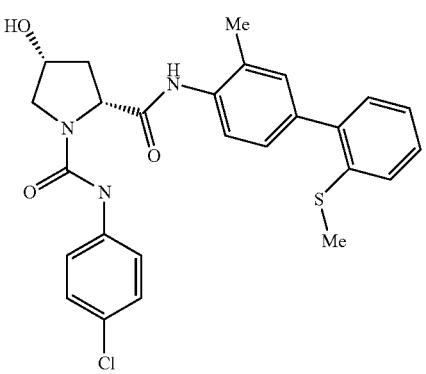

The compound was prepared as generally provided for Example 17. MS: APCI (AP+): 496.1 (M)+, (AP−): 494.1 (M)−.

EXAMPLE 144

(2R,4R)-4-Hydroxy-pyrrolidine-1,2-dicarboxylic acid 1-[(4-chloro-phenyl)-amide]2-[(2-fluoro-2'-methanesulfonyl-biphenyl-4-yl)-amide]

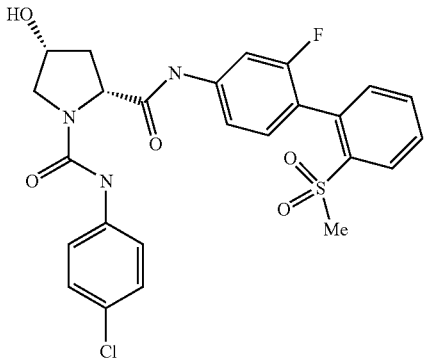

The compound was prepared as generally provided for Example 17. MS: APCI (AP+): 532.0 (M)+, (AP−): 530.0 (M)−.

EXAMPLE 145

(2R,4R)-4-Hydroxy-pyrrolidine-1,2-dicarboxylic acid 1-[(4-chloro-phenyl)-amide]2-[(2'-methanesulfonyl-3-methyl-biphenyl-4-yl)-amide]

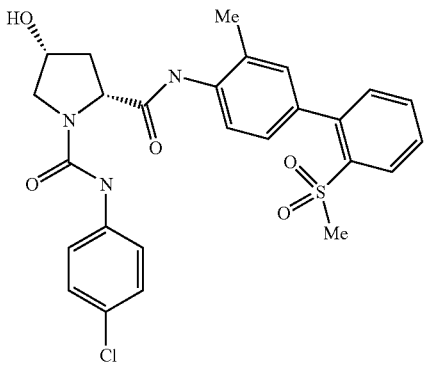

The compound was prepared as generally provided for Example 17. MS: APCI (AP+): 528.1 (M)+, (AP−): 526.1 (M)−.

EXAMPLE 146

(2R,4R)-4-Hydroxy-pyrrolidine-1,2-dicarboxylic acid 1-[(4-chloro-phenyl)-amide]2-[(2'-methanesulfonyl-3-trifluoromethyl-biphenyl-4-yl)-amide]

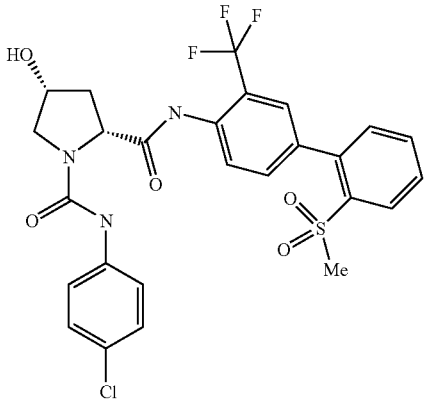

The compound was prepared as generally provided for Example 17. MS: APCI (AP+): 582.1 (M)+, (AP−): 580.1 (M)−.

EXAMPLE 147

(2R,4R)-4-Hydroxy-pyrrolidine-1,2-dicarboxylic acid 1-[(4-chloro-phenyl)-amide]2-[(2'-methoxy-biphenyl-4-yl)-amide]

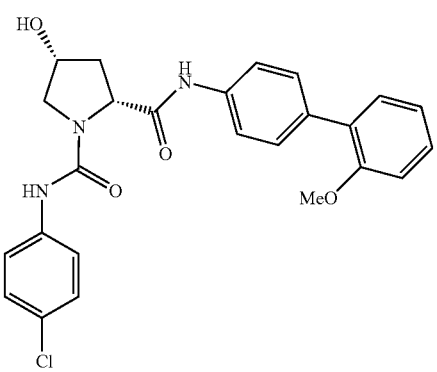

Step 1: 2-Methoxy-4'-nitro-biphenyl (147a)

1-Bromo-4-nitrobenzene (1.00 g, 4.95 mmol), 2-methoxyphenylboronic acid (1.13 g, 7.43 mmol), $K_3PO_4$ (1.58 g, 7.43 mmol), and anhydrous DMF (5 mL) were combined in a flask and degassed with argon. Tetrakistriphenylphosphine palladium(0) (0.858 g, 0.743 mmol) was added to the mixture which was again degassed with argon. The mixture was heated at 110° C. for 3 h before cooling, diluting with EtOAc, and filtering through a plug of silica gel. The solution was washed sequentially with water and brine before drying over $MgSO_4$. The solution was concentrated under reduced pressure and purified by flash chromatography to provide 147-a (1.05 g, 93%) as a yellow solid. MS: APCI (AP+): 230.1 (M)+.

Step 2: 2'-Methoxy-biphenyl-4-ylamine (147-b)

To a Parr apparatus was added 147-a (1.05 g, 4.58 mmol), Raney nickel (0.66 g), and a 4:1 mixture of THF:MeOH (50 mL). The vessel was sealed under a hydrogen atmosphere and shaken under pressure at RT for 18 h. The vessel was then depressurized and the solids filtered off, washing with THF. The filtrate was concentrated under reduced pressure to reveal an unknown amount of 147-b as a tan oil that was carried on without further purification. MS: APCI (AP+): 200.0 (M)+.

The title compound (147) was prepared from 147b as generally provided for in Examples 26 28. MS: APCI (AP+): 466.1 (M)+.

EXAMPLE 148
(2R,4R)-4-Hydroxy-pyrrolidine-1,2-dicarboxylic acid 1-[(4-chloro-phenyl)-amide]2-[(2'-hydroxy-biphenyl-4-yl)-amide]

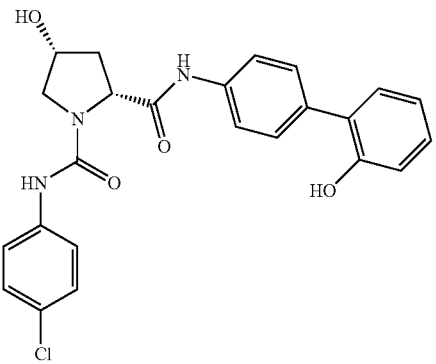

In a flask was dissolved 147a (0.100 g, 0.215 mmol) in anhydrous DCM (5 mL). At 0° C., boron tribromide (0.203 mL, 2.15 mmol) was added dropwise. The solution was stirred at RT for 25 min before concentrating under reduced pressure. The crude material was purified by silica gel flash chromatography followed by lyophilization from acetonitrile/water to provide the title compound (0.039 g, 40%) as a white solid. MS: APCI (AP+): 452.1 (M)+.

EXAMPLE 149
(2R,4R)-4-Methoxy-pyrrolidine-1,2-dicarboxylic acid 1-[(4-chloro-phenyl)-amide]2-[(2-fluoro-4-iodo-phenyl)-amide]

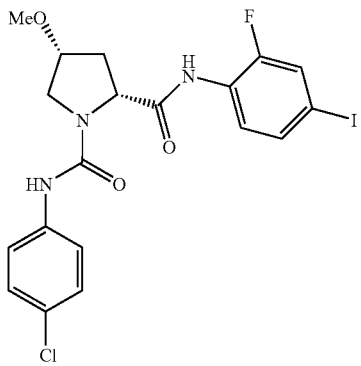

The compound was prepared as generally provided for Example 28. MS: APCI (AP+): 518.0 (M)+.

EXAMPLE 150
(2R,4R)-4-Methoxy-pyrrolidine-1,2-dicarboxylic acid 1-[(4-chloro-phenyl)-amide]2-{[2-fluoro-4-(2-oxo-2H-pyridin-1-yl)-phenyl]-amide}

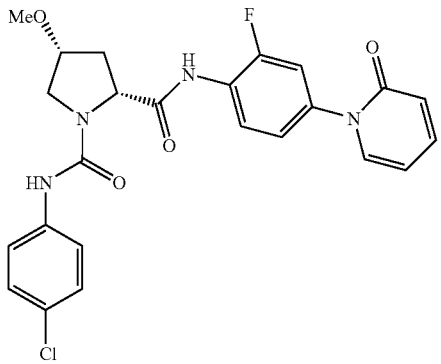

The compound was prepared as generally provided for Example 28. MS: APCI (AP+): 485.2 (M)+.

EXAMPLE 151
(2R,4R)-4-Hydroxy-pyrrolidine-1,2-dicarboxylic acid 1-[(4-chloro-phenyl)-amide]2-[(2'-hydroxy-biphenyl-4-yl)-amide]

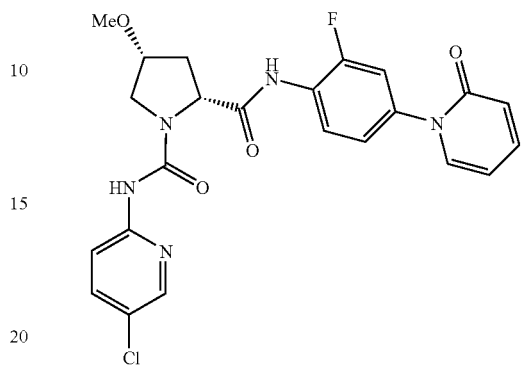

The compound was prepared as generally provided for Example 28 and Example 3, step 3a. MS: APCI (AP+): 486.2 (M)+.

EXAMPLE 152
(2R,4R)-4-Hydroxy-pyrrolidine-1,2-dicarboxylic acid 1-[(4-chloro-phenyl)-amide]2-[(2'-hydroxy-biphenyl-4-yl)-amide]

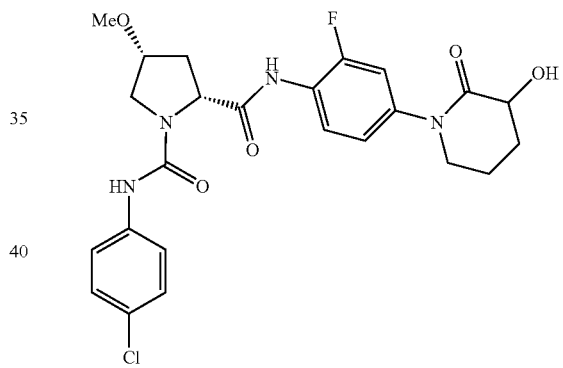

The compound was prepared as generally provided for Example 28. MS: APCI (AP+): 505.3 (M)+.

EXAMPLE 153
(2R,4R)-4-Hydroxy-pyrrolidine-1,2-dicarboxylic acid 1-[(4-chloro-phenyl)-amide]2-[(2'-hydroxy-biphenyl-4-yl)-amide]

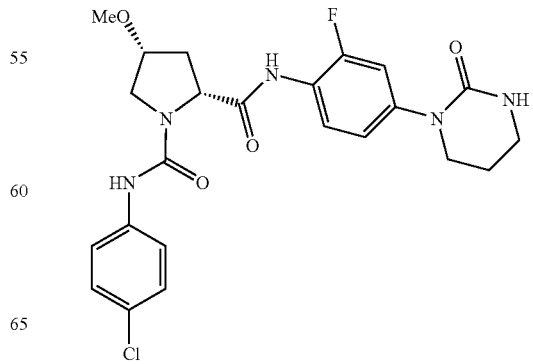

The compound was prepared as generally provided for Example 28. MS: APCI (AP+): 490.3 (M)+.

EXAMPLE 154

(2R,4R)-4-Hydroxy-pyrrolidine-1,2-dicarboxylic acid 1-[(4-chloro-phenyl)-amide]2-[(2'-hydroxy-biphenyl-4-yl)-amide]

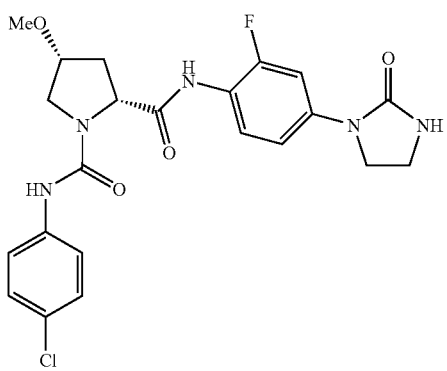

The compound was prepared as generally provided for Example 28. MS: APCI (AP+): 476.2 (M)+.

EXAMPLE 155

(2R,4R)-4-Hydroxy-pyrrolidine-1,2-dicarboxylic acid 1-[(4-chloro-phenyl)-amide]2-[(2'-hydroxy-biphenyl-4-yl)-amide]

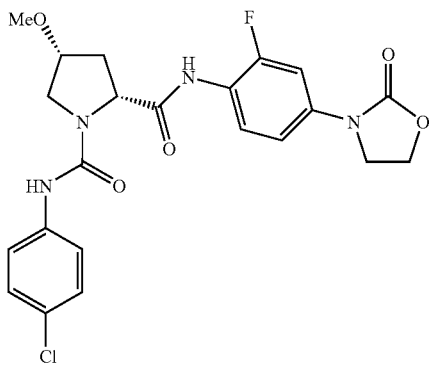

The compound was prepared as generally provided for Example 28. MS: APCI (AP+): 477.2 (M)+.

EXAMPLE 156

(2R,4R)-4-Hydroxy-pyrrolidine-1,2-dicarboxylic acid 1-[(4-chloro-phenyl)-amide]2-[(2'-hydroxy-biphenyl-4-yl)-amide]

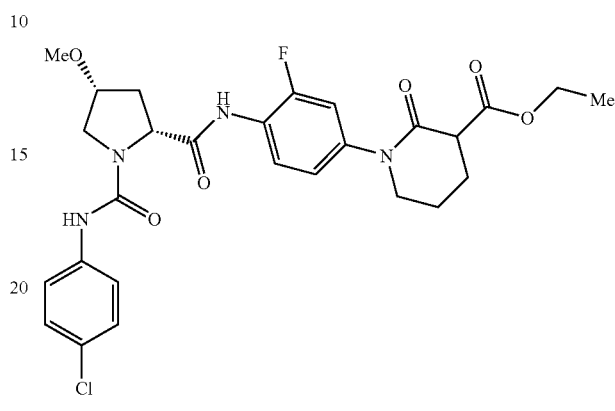

The compound was prepared as generally provided for Example 28. MS: APCI (AP+): 561.3 (M)+.

EXAMPLE 157

(2R,4R)-4-Hydroxy-pyrrolidine-1,2-dicarboxylic acid 1-[(4-chloro-phenyl)-amide]2-[(2'-hydroxy-biphenyl-4-yl)-amide]

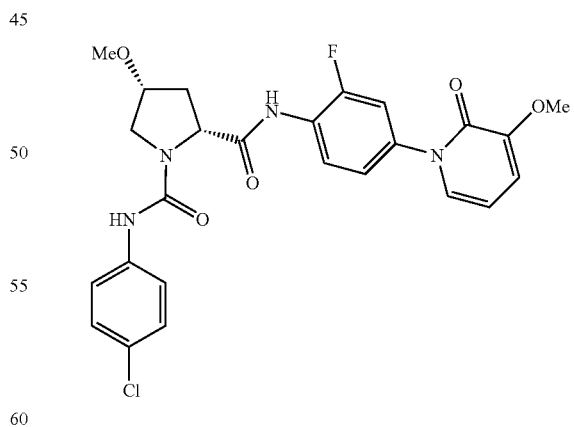

The compound was prepared as generally provided for Example 28. MS: APCI (AP+): 515.2 (M)+.

EXAMPLE 158

(2R,4R)-4-Hydroxy-pyrrolidine-1,2-dicarboxylic acid 1-[(4-chloro-phenyl)-amide]2-[(2'-hydroxy-biphenyl-4-yl)-amide]

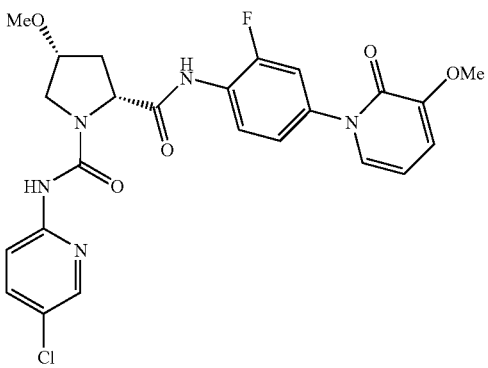

The compound was prepared as generally provided for Example 28 and Example 23, step 3a. MS: APCI (AP+): 516.2 (M)+.

EXAMPLE 159

(2R,4R)-4-Hydroxy-pyrrolidine-1,2-dicarboxylic acid 1-[(4-chloro-phenyl)-amide]2-[(2'-hydroxy-biphenyl-4-yl)-amide]

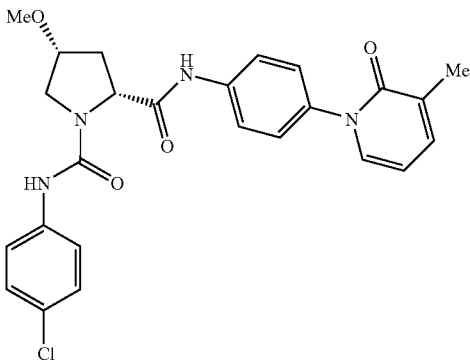

Step 1: 3-Methyl-1-(4-nitro-phenyl)-1H-pyridin-2-one (159-a)

1-Iodo-4-nitrobenzene (1.61 g, 6.45 mmol) was combined with 3-methyl-2-pyridone (0.845 g, 7.74 mmol), CuI (0.246 g, 1.29 mmol), and $K_3PO_4$ (2.74 g, 12.9 mmol). 1,4-Dioxane (6 mL) was added followed by trans-1,2-diaminocyclohexane (0.194 mL, 1.61 mmol). The mixture was heated to reflux for 19 h before cooling and diluting with EtOAc. The mixture was filtered through a plug of silica, eluting with EtOAc, and the filtrate concentrated under reduced pressure. Purification of the crude product by flash chromatography provided 159-a (0.528 g, 36%) as a brown solid. MS: APCI (AP+): 231.1 (M)+.

Step 2: 1-(4-Amino-phenyl)-3-methyl-1H-pyridin-2-one (159-b)

To a flask was added 159a (0.523 g, 2.27 mmol), glacial acetic acid (7.6 mL), conc. HCl (3.8 mL, 45.4 mmol), and mossy tin (0.539 g, 4.54 mmol). The mixture was heated to reflux for 90 min before cooling and concentrating under reduced pressure. The residue was dissolved in EtOAc and washed with aq. 1N NaOH until shown basic with pH paper. The aqueous layer was extracted twice with EtOAc and the combined organics washed with brine and dried over $MgSO_4$. After placing under vacuum, 159-b (0.407 g, 89%) was revealed as a tan solid that was carried on without further purification. MS: APCI (AP+): 201.1 (M)+.

The title compound (159) was prepared from 159-b as generally provided for Example 28. MS: APCI (AP+): 481.3 (M)+.

EXAMPLE 160

(2R,4R)-4-Hydroxy-pyrrolidine-1,2-dicarboxylic acid 1-[(4-chloro-phenyl)-amide]2-[(2'-hydroxy-biphenyl-4-yl)-amide]

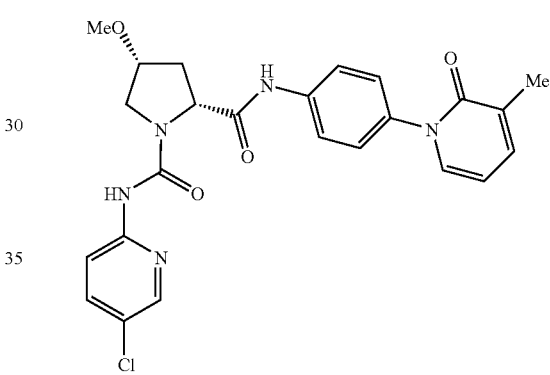

The compound was prepared as generally provided for Example 159 and Example 3, step 3a. MS: APCI (AP+): 482.3 (M)+.

EXAMPLE 161

(2R,4R)-4-Hydroxy-pyrrolidine-1,2-dicarboxylic acid 1-[(4-chloro-phenyl)-amide]2-[(2'-hydroxy-biphenyl-4-yl)-amide]

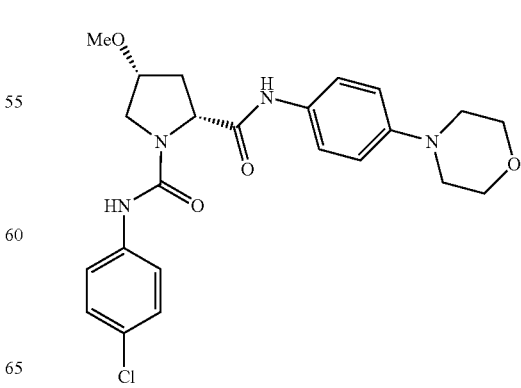

Step 1: 4-(4-Nitro-phenyl)-morpholine (161-a)

1-Fluoro-4-nitrobenzene (3.00 mL, 28.3 mmol) was combined in a flask with anhydrous 2-propanol (28 mL), triethylamine (4.34 mL, 31.1 mmol), and morpholine (2.47 mL, 28.3 mmol). The mixture was refluxed for 3.5 h before adding additional morpholine (2.47 mL, 28.3 mmol) and refluxing for 20 h. The mixture was then cooled and concentrated under reduced pressure. Purification by silica gel flash chromatography provided 161-a (6.09 g, 98%) as a 95% pure solid. MS: APCI (AP−): 207.1 (M)−.

The title compound (161) was prepared from 161-a as generally provided for 147 and Example 28. MS: APCI (AP+): 459.3 (M)+.

EXAMPLE 162

(2R,4R)-4-Hydroxy-pyrrolidine-1,2-dicarboxylic acid 1-[(4-chloro-phenyl)-amide]2-[(2'-hydroxy-biphenyl-4-yl)-amide]

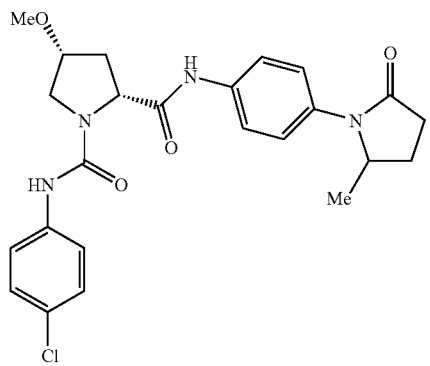

The compound was prepared as generally provided for in Example 28 and 147. MS: APCI (AP+): 471.3 (M)+.

EXAMPLE 163

(2R,4R)-4-Hydroxy-pyrrolidine-1,2-dicarboxylic acid 1-[(4-chloro-phenyl)-amide]2-[(2'-hydroxy-biphenyl-4-yl)-amide]

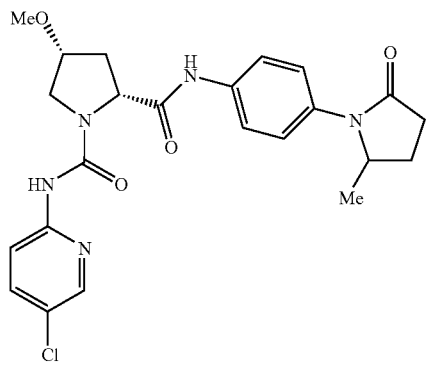

The compound was prepared as generally provided for in Example 3, step 3a, and Example 162. MS: APCI (AP+): 472.2 (M)+.

EXAMPLE 164

(2R,4R)-4-Hydroxy-pyrrolidine-1,2-dicarboxylic acid 1-[(4-chloro-phenyl)-amide]2-[(2'-hydroxy-biphenyl-4-yl)-amide]

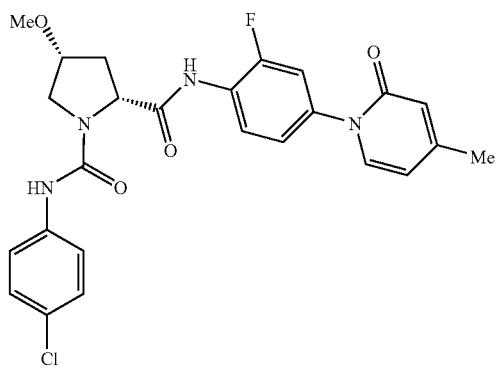

The compound was prepared as generally provided for Example 28. MS: APCI (AP+): 499.2 (M)+.

EXAMPLE 165

(2R,4R)-4-Hydroxy-pyrrolidine-1,2-dicarboxylic acid 1-[(4-chloro-phenyl)-amide]2-[(2'-hydroxy-biphenyl-4-yl)-amide]

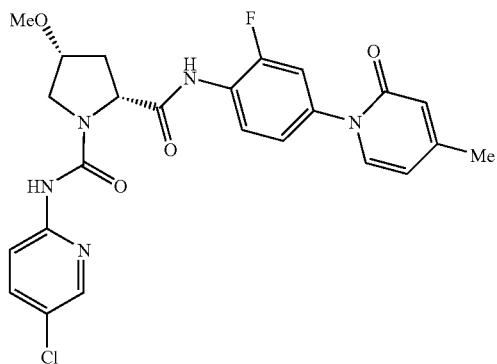

The compound was prepared as generally provided for Example 28 and Example 3, step 3a. MS: APCI (AP+): 500.2 (M)+.

GENERAL PROCEDURES FOR EXAMPLES 166-173

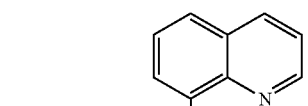

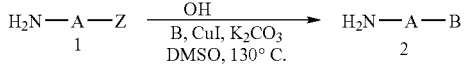

-continued

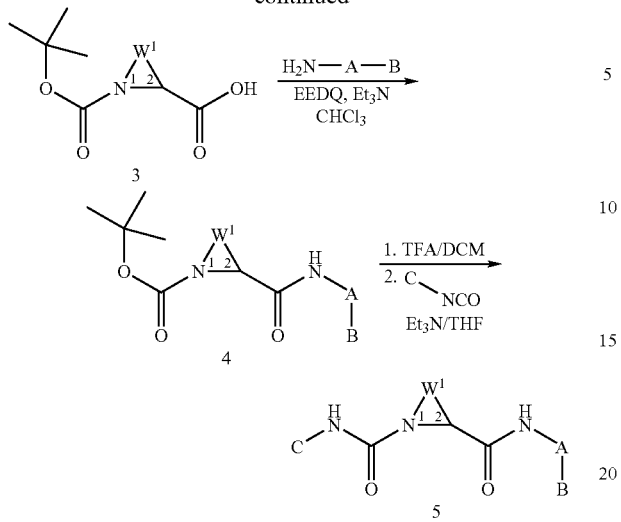

Synthesis of 2: A mixture of 1 (where Z is a halide), B (where B is a nitrogen in a ring), $K_2CO_3$, CuI, and 8-hydroxyquinoline is heated in DMSO at 130° C. to obtain compound 2.

Synthesis of 4: The appropriate aniline (2), EEDQ, triethylamine and carboxylic acid (3) are heated at reflux in chloroform to produce 4.

Synthesis of 5: A solution of compound 4, TFA and DCM is stirred at room temperature for 1 h and then concentrated under reduced pressure. The resulting oil is dissolved in THF and cooled to 0° C. followed by the addition of triethylamine and the appropriate isocyanate to produce compound 5.

EXAMPLE 167

(2R,4R)-4-Hydroxy-pyrrolidine-1,2-dicarboxylic acid 1-[(4-chloro-phenyl)-amide]2-[(2'-hydroxy-biphenyl-4-yl)-amide]

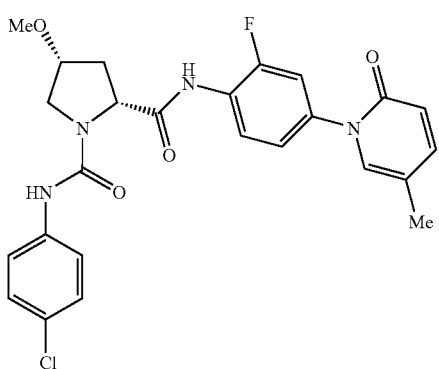

Step 1: 1-(4-Amino-3-fluoro-phenyl)-5-methyl-1H-pyridin-2-one (167-a)

2-Fluoro-4-iodoaniline (0.905 g, 42.2 mmol) was combined with 5-methyl-1H-pyridin-2-one (0.500 g, 4.58 mmol), 8-hydroxyquinoline (0.083 g, 0.573 mmol), CuI (0.109 g, 0.0.573 mmol), and $K_2CO_3$ (0.580 g, 4.20 mmol), in DMSO (3 mL). The mixture was degassed with a stream of argon and then heated at reflux for 16 h before cooling to RT. 10% aq. $NH_4OH$ and EtOAc were added, and the mixture was filtered through a plug of layered celite and decolorizing charcoal, eluting with EtOAc. The filtrate was concentrated under reduced pressure. Purification of the crude product by silica gel flash chromatography revealed 167-a (0.673 g, 81%) as a white solid. MS: APCI (AP+): 219.1 (M)+.

The title compound (167) was prepared from 167-a as generally provided for in Example 28. MS: APCI (AP+): 499.2 (M)+.

EXAMPLE 168

(2R,4R)-4-Hydroxy-pyrrolidine-1,2-dicarboxylic acid 1-[(4-chloro-phenyl)-amide]2-[(2'-hydroxy-biphenyl-4-yl)-amide]

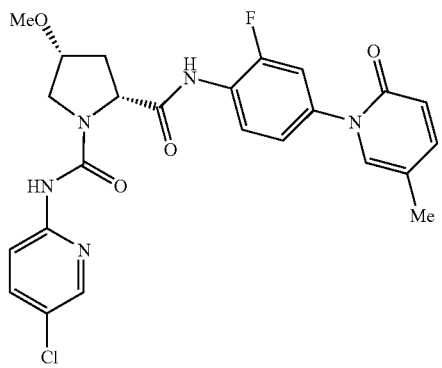

The compound was prepared as generally provided for in Example and Example 3, step 3a. MS: APCI (AP+): 500.2 (M)+.

EXAMPLE 169

(2R,4R)-4-Hydroxy-pyrrolidine-1,2-dicarboxylic acid 1-[(4-chloro-phenyl)-amide]2-[(2'-hydroxy-biphenyl-4-yl)-amide]

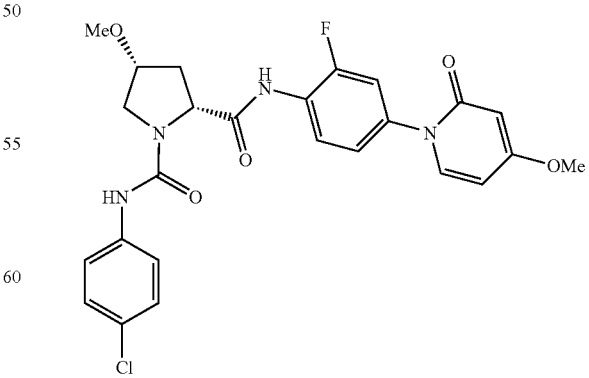

The compound was prepared as generally provided for in Example 167. MS: APCI (AP+): 515.2 (M)+.

EXAMPLE 170
(2R,4R)-4-Hydroxy-pyrrolidine-1,2-dicarboxylic acid 1-[(4-chloro-phenyl)-amide]2-[(2'-hydroxy-biphenyl-4-yl)-amide]

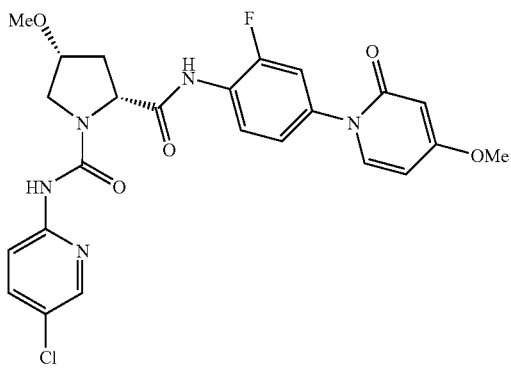

The compound was prepared as generally provided for in Example 168. MS: APCI (AP+): 516.2 (M)+.

EXAMPLE 171
(2R,4R)-4-Hydroxy-pyrrolidine-1,2-dicarboxylic acid 1-[(4-chloro-phenyl)-amide]2-[(2'-hydroxy-biphenyl-4-yl)-amide]

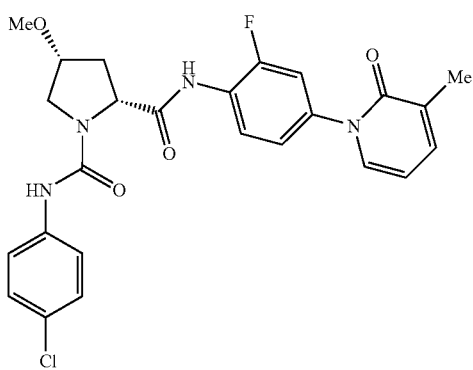

The compound was prepared as generally provided for in Example 167. MS: APCI (AP+): 499.2 (M)+.

EXAMPLE 172
(2R,4R)-4-Hydroxy-pyrrolidine-1,2-dicarboxylic acid 1-[(4-chloro-phenyl)-amide]2-[(2'-hydroxy-biphenyl-4-yl)-amide]

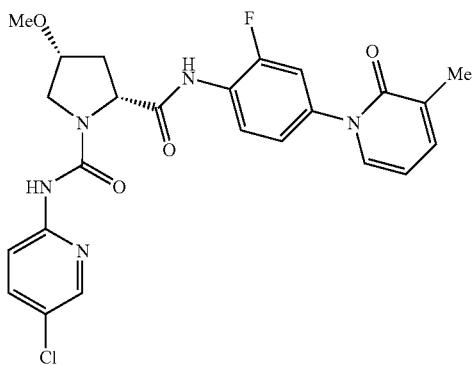

The compound was prepared as generally provided for in Example 168. MS: APCI (AP+): 500.2 (M)+.

EXAMPLE 173
(2R,4R)-4-Hydroxy-pyrrolidine-1,2-dicarboxylic acid 1-[(4-chloro-phenyl)-amide]2-[(2'-hydroxy-biphenyl-4-yl)-amide]

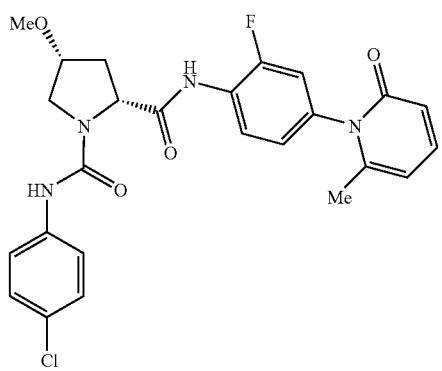

The compound was prepared as generally provided for in Example 167. MS: APCI (AP+): 499.2 (M)+.

EXAMPLE 174
(2R,4R)-4-Methoxy-pyrrolidine-1,2-dicarboxylic acid 2-{[4-(5-chloro-2-oxo-2H-pyridin-1-yl)-2-fluoro-phenyl]-amide} 1-[(4-chloro-phenyl)-amide]

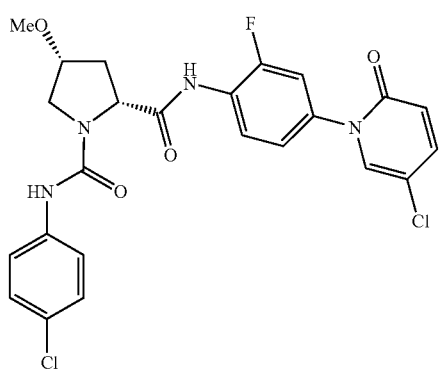

The compound was prepared as generally provided for in Example 167. MS: APCI (AP+): 519.1 (M)+.

GENERAL PROCEDURES FOR THE PREPARATION OF EXAMPLES 175-181

Route 1

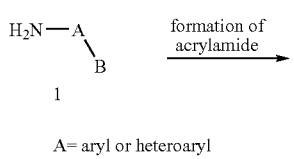

A= aryl or heteroaryl

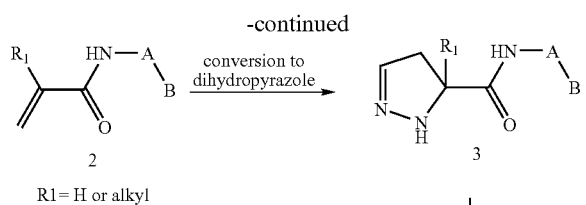

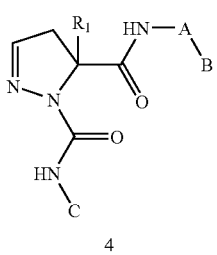

Synthesis of 2:

Aniline 1 is converted to an acrylamide 2 by the addition of acryoyl chloride and a base, such as saturated sodium bicarbonate, in a solvent such as ethyl acetate at room temperature. Alternatively, the aniline may be converted to 2 by the addition of an acrylic acid and adding a coupling reagent such as dicyclohexylcarbodi-imide (DCC), O-(7-Azabenzotriazol-1-yl)-N,N,N',N'-tetramethyluronium hexafluorophosphate (HATU), or EEDQ.

Synthesis of 3 and 4:

To the acrylamide 2 is added an excess of trimethylsilyl diazomethane in a solvent such as ethyl acetate or dichloromethane. The resulting dihydropyrazole 3 may then be treated with an isocyanate, in the presence of base such as pyridine or triethylamine, in a solvent such as dichloromethane, to afford compound 4.

Route 2

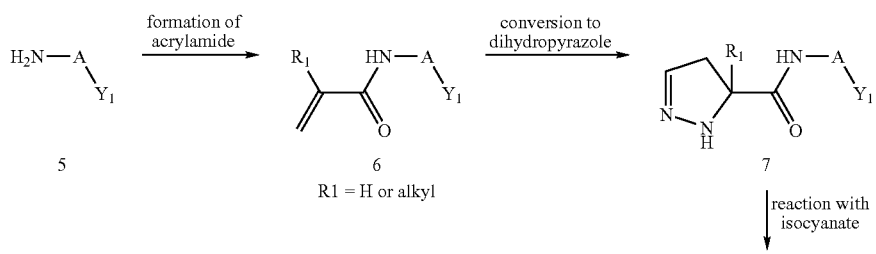

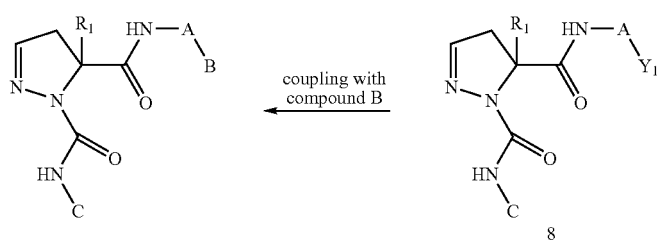

Synthesis of 5-8:

The chemistry for the preparation of compounds 5-8 is similar to that described in Route 1.

Synthesis of 9:

Compound 8 may be converted to 9 by a Suzuki coupling with a boronic acid, although other coupling conditions commonly known to the skilled practitioner may also be used. This route is particularly useful for compounds containing a biaryl A-B group. In situations where a tert-butylsulphonamide is present in B, which occurs in some of the particularly preferred compounds, the sulphonamide may be formed by stirring with trifluoroacetic acid for 16 h.

Route 4

Alternatively compounds may be prepared according to scheme 2d. Here the acrylic ester (14) is reacted with a diazocompound to form the dihydropyrazole (15). Addition of a chloroformate affords compounds of formula (16). Deprotection of the ester is achieved by acid, such as TFA or hydrogen chloride to afford compounds of formula (17). Addition of an aniline with a coupling reagent such as EEDQ and base affords compounds of formula (18). Deprotection of the carbamate with Pd/C and hydrogen affords compounds of formula (19) which may then be reacted with isocyanates to afford compounds of formula (20)

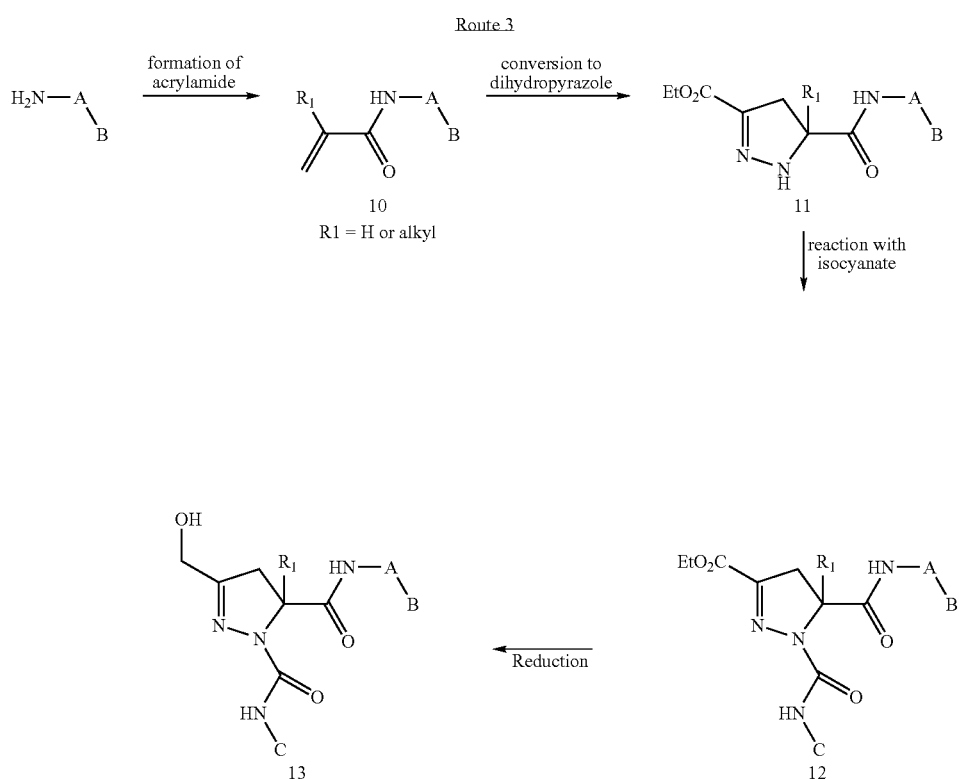

Synthesis of 10:

The synthetic routes commences with formation of acrylamide 10 as described for Route 1.

Synthesis of 11:

Ethyl diazoacetate is mixed with acrylamide 10 to afford the appropriately substituted dihydropyrazole 11.

Synthesis of 12 and 13:

Similar chemistry to that described in Route 1 allows conversion of 11 to 12. Reduction of the ester moietry in 12 is then achieved using a reducing agent such as super-hydride to afford the alcohol 13.

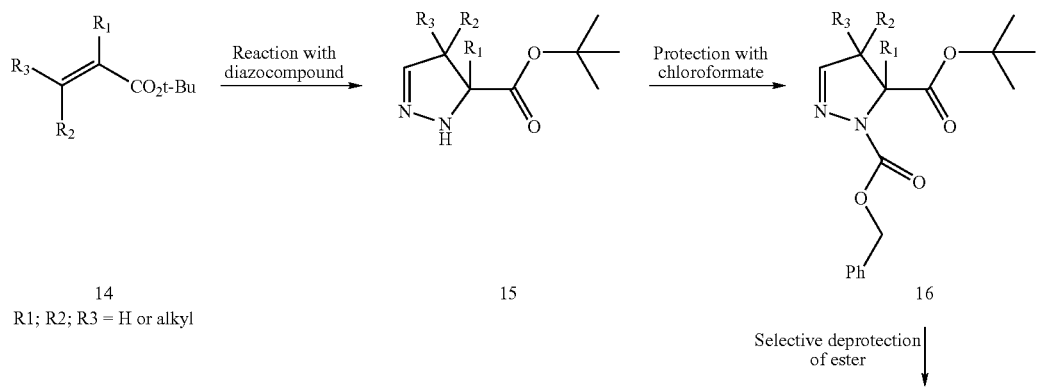
R1; R2; R3 = H or alkyl
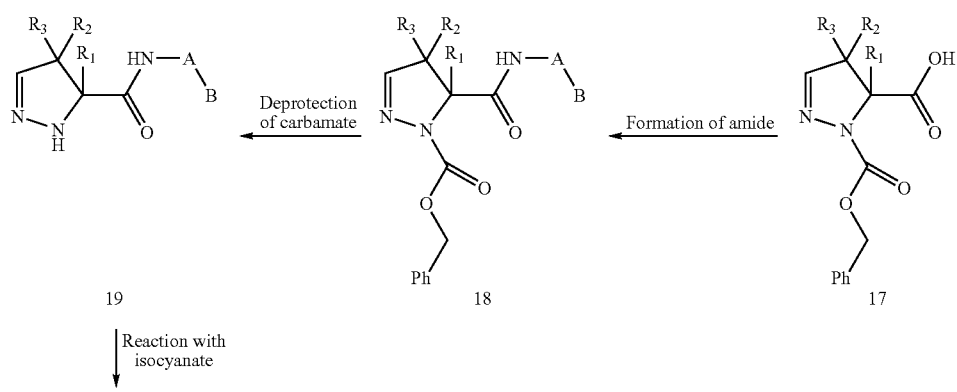
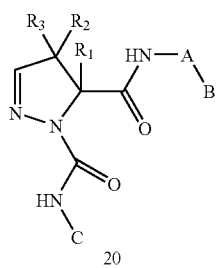

EXAMPLE 175

5-Methyl-4,5-dihydro-pyrazole-1,5-dicarboxylic acid 1-[(4-chloro-phenyl)-amide]5-[(3-fluoro-2'-sulfamoyl-biphenyl-4-yl)-amide]

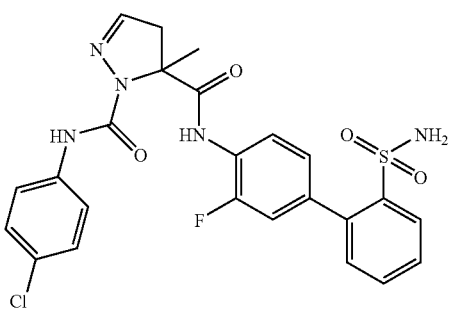

Step 1: N-(2'-tert-Butylsulfamoyl-3-fluoro-biphenyl-4-yl)-2-methyl-acrylamide To 4'-Amino-3'-fluoro-biphenyl-2-sulfonic acid tert-butylamide (5.000 g, 15.51 mmoles) at room temperature in ethyl acetate (50 ml) was added saturated sodium bicarbonate, aqueous, 50 ml and then 2-methyl-acryloyl chloride (1.25 equiv.). Stirred for 2 hours then added a further 1 ml of the acid chloride. After 2 hours an aliquot showed product by NMR. Product seems to co-run with starting material. Extracted into ethyl acetate, washed with brine, dried $MgSO_4$, and then concentrated in vacuo. Collected some crystalline product from ethyl acetate hexane, 0.48 g. Columned mother liquor to afford product. Combined with previously crystallized fraction to afford N-(2'-tert-Butylsulfamoyl-3-fluoro-biphenyl-4-yl)-2-methyl-acrylamide (4.520 g). APCI (AP+): 391 $(M+H)^+$.

Step 2: 3-Methyl-3,4-dihydro-2H-pyrazole-3-carboxylic acid (2'-tert-butylsulfamoyl-3-fluoro-biphenyl-4-yl)-amide To N-(2'-tert-Butylsulfamoyl-3-fluoro-biphenyl-4-yl)-2-methyl-acrylamide (0.525 g) in ethyl acetate (3.5 ml) was added 2M trimethylsilyl diazomethane (3.5 ml) and the mixture stirred at room temperature overnight. NMR indicated complete reaction. Evaporated and then dissolved in acetonitrile (20 ml) and treated with aq. HF (1 ml). Stirred for 1 h. Added sat. $NaHCO_3$ (5 ml), extracted into EtOAc (25 ml). Washed with brine, dried $MgSO_4$, evaporated in vacuo from methylene chloride to afford a white foam of the product: 3-Methyl-3,4-dihydro-2H-pyrazole-3-carboxylic acid (2'-tert-butylsulfamoyl-3-fluoro-biphenyl-4-yl)-amide (0.592 g). APCI (AP+): 433 $(M+H)^+$.

Step 3: 5-Methyl-4,5-dihydro-pyrazole-1,5-dicarboxylic acid 5-[(2'-tert-butylsulfamoyl-3-fluoro-biphenyl-4-yl)-amide] 1-[(4-chloro-phenyl)-amide]

To a solution of 3-methyl-3,4-dihydro-2H-pyrazole-3-carboxylic acid (2'-tert-butylsulfamoyl-3-fluoro-biphenyl-4-yl)-amide (0.416 g) in methylene chloride (4 ml) was added pyridine (1 ml) and 4-chlorophenyl isocyanate (1.25 g). Stirred at room temperature for 16 hours. A further amount of 4-chlorophenyl isocyanate (0.200 g) and pyridine (0.2 ml) was added. Stirred for 48 hours. Columned, silica gel—eluant 10-100 EtOAc in hexane over 25 mins. Affords: 5-methyl-4,5-dihydro-pyrazole-1,5-dicarboxylic acid 5-[(2'-tert-butylsulfamoyl-3-fluoro-biphenyl-4-yl)-amide] 1-[(4-chloro-phenyl)-amide]; 0.365 g

Step 4: 5-Methyl-4,5-dihydro-pyrazole-1,5-dicarboxylic acid 1-[(4-chlorophenyl)-amide]5-[(3-fluoro-2'-sulfamoyl-biphenyl-4-yl)-amide]

To 5-methyl-4,5-dihydro-pyrazole-1,5-dicarboxylic acid 5-[(2'-tert-butylsulfamoyl-3-fluoro-biphenyl-4-yl)-amide] 1-[(4-chloro-phenyl)-amide] (0.300 g) was added trifluoroacetic acid (10.0 g). Stirred at room temperature overnight and then evaporated the TFA. Redissolved in hot methanol and added water until cloudy white. Lyophilized to afford 5-methyl-4,5-dihydro-pyrazole-1,5-dicarboxylic acid 1-[(4-chloro-phenyl)-amide] 5-[(3-fluoro-2'-sulfamoyl-biphenyl-4-yl)-amide] 0.256 g. APCI (AP+): 530 $(M+H)^+$

EXAMPLE 176

3-Hydroxymethyl-4,5-dihydro-pyrazole-1,5-dicarboxylic acid 1-[(4-chlorophenyl)-amide]5-[(3-fluoro-2'-methanesulfonyl-biphenyl-4-yl)-amide]

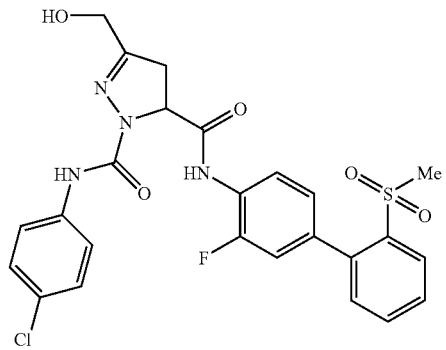

Step 1: N-(3-Fluoro-2'-methanesulfonyl-biphenyl-4-yl)-acrylamide

To 3-Fluoro-2'-methanesulfonyl-biphenyl-4-ylamine (8.510 g) in ethyl acetate (400 ml) was added sat. $NaHCO_3$ (100 ml) and then acryolyl chloride (1.3 equiv.). Stirred at room temperature for 3 hours. Washed EtOAc extract with brine, dried over $MgSO_4$ and evaporated in vacuo. Triturated with ether and then filtered to afford N-(3-fluoro-2'-methanesulfonyl-biphenyl-4-yl)-acrylamide (9.670 g, 94%).

Step 2: 5-(3-Fluoro-2'-methanesulfonyl-biphenyl-4-ylcarbamoyl)-4,5-dihydro-1H-pyrazole-3-carboxylic acid ethyl ester To N-(3-Fluoro-2'-methanesulfonyl-biphenyl-4-yl)-acrylamide (4.47 g) in ethyl acetate (150 ml) was added ethyl diazoacetate (1.5 equiv.) and the mixture heated at 60° C. for 24 hours. Evaporated and then columned: eluant 10-100 EtOAc in hexane. Collected 5-(3-fluoro-2'-methanesulfonyl-biphenyl-4-ylcarbamoyl)-4,5-dihydro-1H-pyrazole-3-carboxylic acid ethyl ester (1.67 g)

Step 3: 1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester To a solution of 5-(3-Fluoro-2'-methanesulfonyl-biphenyl-4-ylcarbamoyl)-4,5-dihydro-1H-pyrazole-3-carboxylic acid ethyl ester (1.520 g) in methylene chloride (12 ml) was added pyridine (4 equiv.) and 4-chlorophenyl isocyanate (1.25 equiv.). Stirred at room temperature for 16 hours. Evaporated and recorded crude 1H: 80156×134RM1—revealed expected product and relatively clean. Purified by silica gel chromatography, eluant 10-100% EtOAc in hexane over 25 mins. Collected 1-(4-chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester (1.480 g).

Step 4: 3-Hydroxymethyl-4,5-dihydro-pyrazole-1,5-dicarboxylic acid 1-[(4-chloro-phenyl)-amide] 5-[(3-fluoro-2'-methanesulfonyl-biphenyl-4-yl)-amide]

To a solution of 1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester (0.228 g) in THF (3 ml) at 0° C. was added a 1M solution of super-hydride in THF (1.17 ml). Stirred for 30 mins and then quenched with sat. NH$_4$Cl. Extracted into EtOAc and washed with brine. Evaporated in vacuo. Crude 1H indicated clean reaction to product. Column—eluant 0-5% methanol in ethyl acetate. Affords 3-Hydroxymethyl-4,5-dihydro-pyrazole-1,5-dicarboxylic acid 1-[(4-chloro-phenyl)-amide] 5-[(3-fluoro-2'-methanesulfonyl-biphenyl-4-yl)-amide] after lyophilization from MeCN/H2O: 0.230 g; MS (APCI) +ve: 545

EXAMPLE 177

4,5-Dihydro-pyrazole-1,5-dicarboxylic acid 1-[(4-chloro-phenyl)-amide] 5-[(3-fluoro-2'-sulfamoyl-biphenyl-4-yl)-amide]

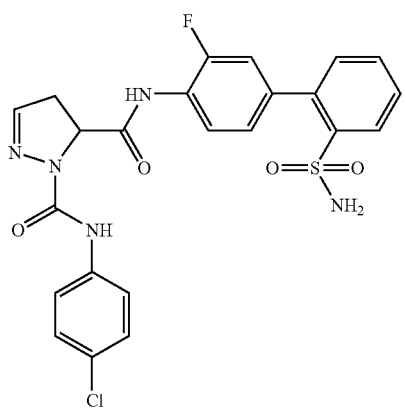

This compound was prepared using the same procedures as found for Example 175 with acryloyl chloride substituted for 2-Methyl-acryloyl chloride in step 1. APCI (AP−): 514 (M−H)⁻.

EXAMPLE 178

(5R) 4,5-Dihydro-pyrazole-1,5-dicarboxylic acid 1-[(4-chloro-phenyl)-amide]5-[(3-fluoro-2'-sulfamoyl-biphenyl-4-yl)-amide]

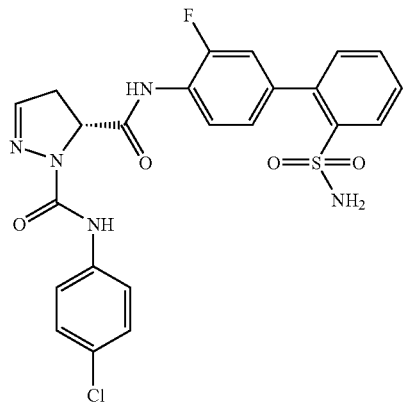

This compound was prepared using the same procedures as found for Example 177 and the enantiomers separated by chiral HPLC Column: Chrial Pak AD 250×4.6 mm; 254 nm, mobile phase: Hexane (20); Ethanol (20); Methanol (60) Affords: (R) enantiomer @11.038 mins APCI (AP−): 514 (M−H)⁻ and (S) enantiomer @36.084 mins APCI (AP−): 514 (M−H)⁻.

EXAMPLE 179

4,5-Dihydro-pyrazole-1,5-dicarboxylic acid 1-[(4-chloro-phenyl)-amide] 5-{[2-fluoro-4-(2-oxo-piperidin-1-yl)-phenyl]-amide}

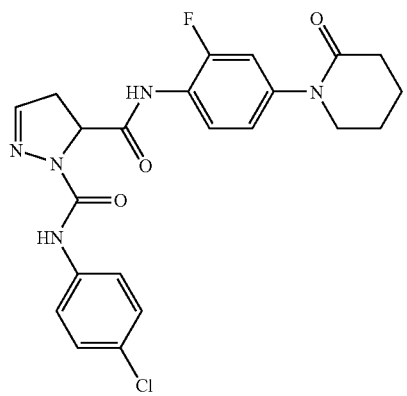

This compound was prepared using the same procedures as found for Example 175 with acryloyl chloride substituted for 2-Methyl-acryloyl chloride in step 1 and 1-(4-Amino-3-fluoro-phenyl)-piperidin-2-one substituted for 4'-Amino-3'-fluoro-biphenyl-2-sulfonic acid tert-butylamide. APCI (AP−): 456 (M−H)⁻.

EXAMPLE 180

4,5-Dihydro-pyrazole-1,5-dicarboxylic acid 1-[(4-chloro-phenyl)-amide] 5-[(3-fluoro-2'-methanesulfonyl-biphenyl-4-yl)-amide]

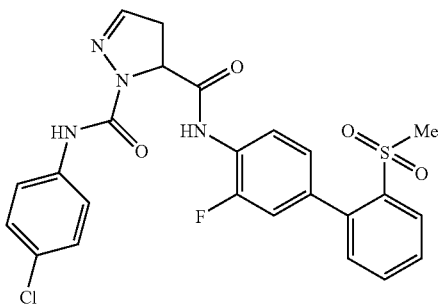

This compound was prepared using the same procedures as found for Example 177 with acryloyl chloride substituted for 2-Methyl-acryloyl chloride in step 1 and 3-Fluoro-2'-methanesulfonyl-biphenyl-4-ylamine substituted for 4'-Amino-3'-fluoro-biphenyl-2-sulfonic acid tert-butylamide. APCI (AP−): 513 (M−H)−.

EXAMPLE 181

1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester

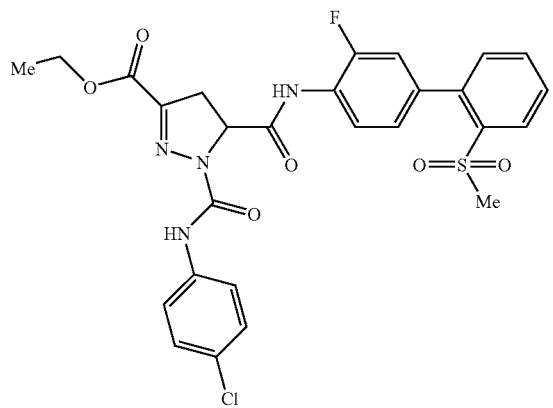

This compound was prepared using the same procedures as found for Example 176 wherein step 4 was omitted. APCI (AP−): 585 (M−H)−.

EXAMPLE 182

Formulations

The compounds of the present invention can be administered alone or in combination with one or more therapeutic agents. These include, for example, other anticoagulant, anti-platelet, or platelet inhibitory agents which include non-steroidal anti-inflammatory agents such as aspirin, ibuprofen, naproxen sodium, indomethacin, piroxica, and ticlopidine; thrombin inhibitors such as argatroban, efegatran, inogatran, factor VIIa inhibitors, thrombolytic or fibrinolytic agents such as tissue plasminogen activator, urokinase or streptokinase; GP IIb-IIIa antagonists, and P2Y12 antagonists.

The compounds are thus well suited to formulation for convenient administration to mammals for the prevention and treatment of such disorders.

The following examples further illustrate typical formulations provided by the invention.

| Formulation 1 | |
|---|---|
| Ingredient | Amount |
| compound of Formulas I-V | 0.5 to 800 mg |
| sodium benzoate | 5 mg |
| isotonic saline | 1000 mL |

The above ingredients are mixed and dissolved in the saline for IV administration to a human suffering from, for example, arterial thrombosis.

| Formulation 2 | |
|---|---|
| Ingredient | Amount |
| compound of Formulas I-V | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a human for preventing, for example, cerebral infarction.

| Formulation 3 | |
|---|---|
| Ingredient | Amount |
| compound of Formulas I-I | 0.5 to 800 mg |
| starch, dried | 250 mg |
| magnesium stearate | 10 mg |

The ingredients are combined and milled to afford material suitable for filling hard gelatin capsules administered to humans suffering from, for example, venous thrombosis.

| Formulation 4 | |
|---|---|
| Ingredient | Amount % wt./(total wt.) |
| compound of Formulas I-I | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound of formula X:

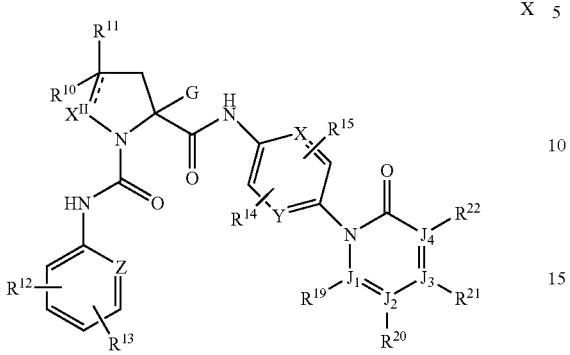

or a pharmaceutically acceptable salt thereof wherein
" - - - " is a bond;

Z is C—H, C-halo, C—$(C_1$-$C_6)$alkyl, C-halo$(C_1$-$C_6)$alkyl, C—$(C_1$-$C_6)$alkoxy, or N;

G is H, halo, $(C_1$-$C_6)$alkyl, halo$(C_1$-$C_6)$alkyl, hydroxy$(C_1$-$C_6)$alkyl, —$CH_2O$—$(C_1$-$C_6)$alkyl, —$CH_2$—$CO_2(C_1$-$C_6)$alkyl, —$CH_2$—$CONH_2$, or —$CH_2$—$CONH(C_1$-$C_6)$alkyl;

$X^{II}$ is N;

$R^{11}$ is absent, and $R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$;

$R^2$ is each independently H or $(C_1$-$C_6)$alkyl; and $R^3$ and $R^4$ are each independently H, $(C_1$-$C_6)$alkyl, aralkyl, aryl, monocyclic heteroaryl, alkoxycarbonyl, aralkoxycarbonyl, —$SO_2$alkyl, or are joined together to form an optionally substituted saturated or unsaturated 3 to 7 membered ring;

$R^{12}$ and $R^{13}$ are each independently H, halo, $(C_1$-$C_6)$alkyl, or halo$(C_1$-$C_6)$alkyl, or $(C_1$-$C_6)$alkoxy;

$R^{14}$ and $R^{15}$ are each independently H, halo, alkyl, or haloalkyl, or $NR^8R^9$ wherein $R^8$ and $R^9$ are as defined for $R^3$ and $R^4$;

X and Y are each independently C or N, provided that when one of X or Y is N, $R^{14}$ or $R^{15}$ is absent at that position;

$J_1$, $J_2$, $J_3$, and $J_4$ are C or one of $J_1$, $J_2$, $J_3$, and $J_4$ is N;

$R^{19}$, $R^{20}$, $R^{21}$, and $R^{22}$ are each independently H, halo, hydroxy, $NH_2$, $NR^{23}R^{24}$, $NO_2$, SH, $(C_1$-$C_6)$alkyl, halo$(C_1$-$C_6)$alkyl, $(C_1$-$C_6)$alkanoyl, $(C_1$-$C_6)$alkoxycarbonyl, or $(C_1$-$C_6)$alkoxy, wherein $R^{23}$ and $R^{24}$ are each independently H, $(C_1$-$C_6)$alkyl, aralkyl, aryl, monocyclic heteroaryl, alkoxycarbonyl, aralkoxycarbonyl, —$SO_2$alkyl, or are joined together to form an optionally substituted saturated or unsaturated 3 to 7 membered ring, or $R^{19}$ and $R^{20}$, $R^{20}$ and $R^{21}$, or $R^{21}$ and $R^{22}$, together with the carbons to which they are attached, form a 5, 6, or 7 membered saturated or unsaturated cycloalkyl or heterocycloalkyl ring, or an aryl or heteroaryl ring; provided that when any of $J_1$, $J_2$, $J_3$, or $J_4$ is N, $R^{19}$, $R^{20}$, $R^{21}$, or $R^{22}$ is absent at that position.

2. The compound of claim 1, wherein
$R^{10}$ is H or —$CH_2OR^2$, or —$CO_2R^2$, wherein $R^2$ is each independently H or$(C_1$-$C_6)$alkyl;
$R^{12}$ and $R^{13}$ are each independently H, fluoro, chloro, bromo, methyl, or methoxy;
$R^{14}$ and $R^{15}$ are each independently H, fluoro, chloro, methyl, or trifluoromethyl;
X and Y are each independently C, or N, provided that X or Y is N, $R^{14}$ or $R^{15}$ is absent at that position; and

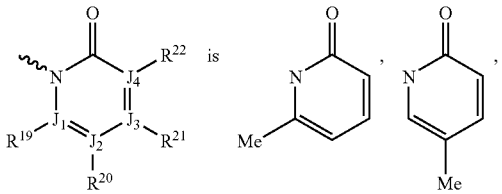

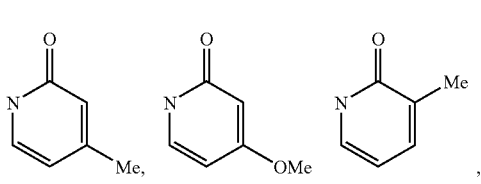

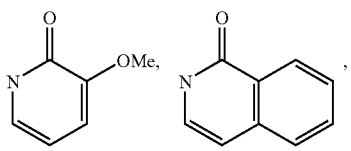

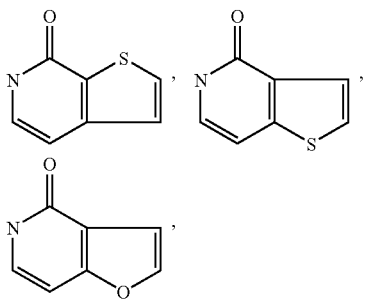

wherein

" ~~~ "

indicates the point of attachment.

3. A pharmaceutical composition comprising a compound of formula I

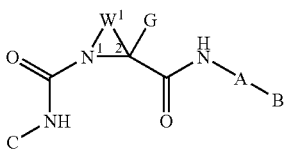

or a pharmaceutically acceptable salt thereof wherein:

A is aryl or substituted aryl or monocyclic heteroaryl or substituted monocyclic heteroaryl;

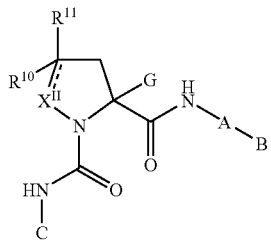

($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, or heteroaryl, any of which may be optionally substituted;
C is phenyl or heteroaryl, wherein phenyl or heteroaryl is optionally substituted with one or more substituents selected from halogen, hydroxy, —$CO_2R^2$, —$COR^2$, —$CONR^2R^{2'}$, alkoxy, alkyl, —CN, haloalkyl, amino, alkylamino, amidino, amido, or sulfonamido;
G is H, halo, ($C_1$-$C_6$)alkyl, halo($C_1$-$C_6$)alkyl, hydroxy($C_1$-$C_6$)alkyl, —$CH_2$O—($C_1$-$C_6$)alkyl, —$CH_2$—$CO_2$($C_1$-$C_6$)alkyl, —$CH_2$—$CONH_2$, or —$CH_2$—$CONH$($C_1$-$C_6$)alkyl;
$W^1$ is —N=$CR^5$—$CH_2$— wherein $W^1$ connects the nitrogen atom at position 1 to the carbon atom at position 2 to form a five membered ring;
$R^1$ is ($C_1$-$C_6$)alkoxy, ($C_3$-$C_7$)cycloalkyl, ($C_3$-$C_7$)heterocycloalkyl, ($C_4$-$C_7$)cycloalkenyl, ($C_4$-$C_7$)heterocycloalkenyl, aryl, monocyclic heteroaryl, or —$NR^3R^4$;
$R^2$ and $R^{2'}$ are each independently H or ($C_1$-$C_6$)alkyl; and
$R^3$ and $R^4$ are each independently H, ($C_1$-$C_6$)alkyl, aralkyl, aryl, monocyclic heteroaryl, alkoxycarbonyl, aralkoxycarbonyl, —$SO_2$alkyl, or joined together to form a saturated or unsaturated 3 to 7 membered ring;
$R^5$ is —OH, alkyl, halo($C_1$-$C_6$)alkyl, —$NR^3R^4$, —$OR^2$, halo, —CN, —$CH_2OR^2$, —$CH_2$—$NR^3R^4$, aryl, monocyclic heteroaryl, alkylaryl, —$CONR^3R^4$, —$COR^2$, halo($C_1$-$C_6$)alkyl, or —$CO_2R^2$; admixed with a carrier, diluent, or excipient.

4. A compound which is:
4,5-Dihydro-pyrazole-1,5-dicarboxylic acid 1-[(4-chloro-phenyl)-amide] 5-[(3-fluoro-2'-methanesulfonyl-biphenyl-4-yl)-amide];
4,5-Dihydro-pyrazole-1,5-dicarboxylic acid 1-[(4-chloro-phenyl)-amide] 5-{[4-(2-oxo-piperidin-1-yl)-phenyl]-amide};
4,5-Dihydro-pyrazole-1,5-dicarboxylic acid 1-[(5-chloro-pyridin-2-yl)-amide] 5-{[2-fluoro-4-(2-oxo-piperidin-1-yl)-phenyl]-amide};
4,5-Dihydro-pyrazole-1,5-dicarboxylic acid 1-[(5-chloro-pyridin-2-yl)-amide] 5-{[4-(2-oxo-piperidin-1-yl)-phenyl]-amide};
4,5-Dihydro-pyrazole-1,5-dicarboxylic acid 1-[(4-chloro-phenyl)-amide] 5-[(2-oxo-3,4,5,6-tetrahydro-2H-[1,3']bipyridinyl-6'-yl)-amide];
4,5-Dihydro-pyrazole-1,5-dicarboxylic acid 1-[(5-chloro-pyridin-2-yl)-amide] 5-[(2-oxo-3,4,5,6-tetrahydro-2H-[1,3']bipyridinyl-6'-yl)-amide];
5-Methyl-4,5-dihydro-pyrazole-1,5-dicarboxylic acid 1-[(4-chloro-phenyl)-amide] 5-[(3-fluoro-2'-sulfamoyl-biphenyl-4-yl)-amide];
3-Hydroxymethyl-4,5-dihydro-pyrazole-1,5-dicarboxylic acid 1-[(4-chloro-phenyl)-amide] 5-[(3-fluoro-2'-methanesulfonyl-biphenyl-4-yl)-amide];
4,5-Dihydro-pyrazole-1,5-dicarboxylic acid 1-[(4-chloro-phenyl)-amide] 5-[(3-fluoro-2'-sulfamoyl-biphenyl-4-yl)-amide];
(R) 4,5-Dihydro-pyrazole-1,5-dicarboxylic acid 1-[(4-chloro-phenyl)-amide] 5-[(3-fluoro-2'-sulfamoyl-biphenyl-4-yl)-amide];
4,5-Dihydro-pyrazole-1,5-dicarboxylic acid 1-[(4-chloro-phenyl)-amide] 5-{[2-fluoro-4-(2-oxo-piperidin-1-yl)-phenyl]-amide};
4,5-Dihydro-pyrazole-1,5-dicarboxylic acid 1-[(4-chloro-phenyl)-amide] 5-[(3-fluoro-2'-methanesulfonyl-biphenyl-4-yl)-amide];
1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester;
4,5-Dihydro-pyrazole-1,5-dicarboxylic acid 1-[(4-chloro-phenyl)-amide] 5-{[2-fluoro-4-(2-oxo-2H-pyridin-1-yl)-phenyl]-amide};
3-Hydroxymethyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};
5-Methyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};
3-Methoxymethyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};
4,5-Dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};
3-Hydroxymethyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};
5-Methyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};
3-Methoxymethyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};
or a pharmaceutically acceptable salt thereof.

5. A pharmaceutical composition comprising one or more compounds or a pharmaceutically acceptable salt thereof selected from the group consisting of:
4,5-Dihydro-pyrazole-1,5-dicarboxylic acid 1-[(4-chloro-phenyl)-amide] 5-[(3-fluoro-2'-methanesulfonyl-biphenyl-4-yl)-amide];
4,5-Dihydro-pyrazole-1,5-dicarboxylic acid 1-[(4-chloro-phenyl)-amide] 5-{[4-(2-oxo-piperidin-1-yl)-phenyl]-amide};
4,5-Dihydro-pyrazole-1,5-dicarboxylic acid 1-[(5-chloro-pyridin-2-yl)-amide] 5-{[2-fluoro-4-(2-oxo-piperidin-1-yl)-phenyl]-amide};
4,5-Dihydro-pyrazole-1,5-dicarboxylic acid 1-[(5-chloro-pyridin-2-yl)-amide] 5-{[4-(2-oxo-piperidin-1-yl)-phenyl]-amide};
4,5-Dihydro-pyrazole-1,5-dicarboxylic acid 1-[(4-chloro-phenyl)-amide] 5-[(2-oxo-3,4,5,6-tetrahydro-2H-[1,3']bipyridinyl-6'-yl)-amide];
4,5-Dihydro-pyrazole-1,5-dicarboxylic acid 1-[(5-chloro-pyridin-2-yl)-amide] 5-[(2-oxo-3,4,5,6-tetrahydro-2H-[1,3']bipyridinyl-6'-yl)-amide];
5-Methyl-4,5-dihydro-pyrazole-1,5-dicarboxylic acid 1-[(4-chloro-phenyl)-amide] 5-[(3-fluoro-2'-sulfamoyl-biphenyl-4-yl)-amide];

3-Hydroxymethyl-4,5-dihydro-pyrazole-1,5-dicarboxylic acid 1-[(4-chloro-phenyl)-amide] 5-[(3-fluoro-2'-methanesulfonyl-biphenyl-4-yl)-amide];

4,5-Dihydro-pyrazole-1,5-dicarboxylic acid 1-[(4-chloro-phenyl)-amide] 5-[(3-fluoro-2'-sulfamoyl-biphenyl-4-yl)-amide];

(R) 4,5-Dihydro-pyrazole-1,5-dicarboxylic acid 1-[(4-chloro-phenyl)-amide] 5-[(3-fluoro-2'-sulfamoyl-biphenyl-4-yl)-amide];

4,5-Dihydro-pyrazole-1,5-dicarboxylic acid 1-[(4-chloro-phenyl)-amide] 5-{[2-fluoro-4-(2-oxo-piperidin-1-yl)-phenyl]-amide};

4,5-Dihydro-pyrazole-1,5-dicarboxylic acid 1-[(4-chloro-phenyl)-amide] 5-[(3-fluoro-2'-methanesulfonyl-biphenyl-4-yl)-amide];

1-(4-Chloro-phenylcarbamoyl)-5-(3-fluoro-2'-methanesulfonyl-biphenyl-4-ylcarbamoyl)-4,5-dihydro-1H-pyrazole-3-carboxylic acid ethyl ester;

4,5-Dihydro-pyrazole-1,5-dicarboxylic acid 1-[(4-chloro-phenyl)-amide] 5-{[2-fluoro-4-(2-oxo-2H-pyridin-1-yl)-phenyl]-amide};

3-Hydroxymethyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};

5-Methyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};

3-Methoxymethyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide};

4,5-Dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};

3-Hydroxymethyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};

5-Methyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide}; and 3-Methoxymethyl-4,5-dihydro-pyrazole-1,5-dicarboxylic acid 1-[(5-chloro-pyridin-2-yl)-amide] 5-{[2-fluoro-4-(2-oxo-2H-pyridin-1-yl)-phenyl]-amide};

and a carrier, diluent, or excipient.

6. The compound 5-Methyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amine} or a pharmaceutically acceptable salt thereof.

7. A pharmaceutical composition comprising (5-Methyl-4,5-dihydro-pyrazole-1,5-dicarboxylic acid 1-[(4-chloro-phenyl)-amide] 5-{[2-fluoro-4-(2-oxo-2H-pyridin-1-yl)-phenyl]-amide}or a pharmaceutically acceptable salt thereof and a carrier, diluent, or excipient.

8. The compound 5-Methyl-4,5-dihydro-pyrazole-1,5-dicarboxylic acid 1-[(4-chloro-phenyl)-amide] 5-[(3-fluoro-2'-sulfamoyl-biphenyl-4-yl)-amide] or a pharmaceutically acceptable salt thereof.

9. A pharmaceutical composition comprising 5-Methyl-4,5-dihydro-pyrazole-1, 5-dicarboxylic acid 1-[(4-chloro-phenyl)-amide] 5-[(3-fluoro-2'-sulfamoyl-biphenyl-4-yl)-amide]or a pharmaceutically acceptable salt thereof and a carrier, diluent, or excipient.

10. The compound (R) 4,5-Dihydro-pyrazole-1,5-dicarboxylic acid 1-[(4-chloro-phenyl)-amide] 5-[(3-fluoro-2'-sulfamoyl-biphenyl-4-yl)-amide] or a pharmaceutically acceptable salt thereof.

11. The compound (R) 4,5-Dihydro-pyrazole-1,5-dicarboxylic acid 1-[(4-chloro-phenyl)-amide] 5-[(3-fluoro-2'-sulfamoyl-biphenyl-4-yl)-amide] or a pharmaceutically acceptable salt thereof and a carrier, diluent, or excipient.

12. A compound of formula IV:

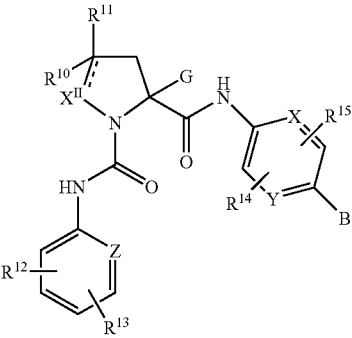

IV or a pharmaceutically acceptable salt thereof wherein

" - - - " is a bond;

Z is C—H, C-halo, C—$(C_1-C_6)$alkyl, C-halo$(C_1-C_6)$alkyl, C—$(C_1-C_6)$alkoxy, or N;

G is H, halo, $(C_1-C_6)$alkyl;

$X^{II}$ is N;

$R^{11}$ is absent;

$R^{10}$ is H, —OH, halo, alkyl, haloalkyl, —$NR^8R^9$, —$OR^2$, —CN, —$CH_2OH$, —$CH_2$—$NR^3R^4$, aryl, monocyclic heteroaryl, alkylaryl, —CH=O, —$CH_2OR^2$, —$COR^2$, —$CO_2R^2$, or —$CONR^3R^4$;

$R^2$ is each independently H or $(C_1-C_6)$alkyl;

$R^3$ and $R^4$ are each independently H, $(C_1-C_6)$alkyl, aralkyl, aryl, monocyclic heteroaryl, alkoxycarbonyl, aralkoxycarbonyl, —$SO_2$alkyl, or are joined together to form an optionally substituted saturated or unsaturated 3 to 7 membered ring;

$R^{12}$ and $R^{13}$ are each independently H, halo, $(C_1-C_6)$alkyl, or halo$(C_1-C_6)$alkyl, or $(C_1-C_6)$alkoxy;

$R^{14}$ and $R^{15}$ are each independently H, halo, alkyl, or haloalkyl, or $NR^8R^9$ wherein $R^8$ and $R^9$ are as defined for $R^3$ and $R^4$;

X and Y are each independently C or N, provided that when one of X or Y is N, $R^{14}$ or $R^{15}$ is absent at that position; and B is $(C_3-C_7)$ cycloalkyl, $(C_3-C_7)$heterocycloalkyl, $(C^4-C^7)$ cycloalkenyl, $(C_4-C_7)$heterocycloalkenyl, aryl, or heteroaryl, any of which may be optionally substituted by halo, $(C_1-C_6)$alkyl, halo$(C_1-C_6)$alkyl, oxo, —O—$(C_1-C_6)$alkyl, —CN, —$NH_2$, —$NR^{23}R^{24}$, —$SO_2$alkyl, or —$SO_2NR^{23}R^{24}$ wherein $R^{23}$ and $R^{24}$ are each independently H, $(C_1-C_6)$alkyl, aralkyl, aryl, monocyclic heteroaryl, alkoxycarbonyl, aralkoxycarbonyl, or are joined together to form an optionally substituted saturated or unsaturated 3 to 7 membered ring.

13. The compound of claim 12, wherein

G is H, F, or methyl;

$R^{10}$ is H, —$CO_2R^2$, —$CH_2OR^2$ wherein each $R^2$ is independently H or $(C_1-C_6)$alkyl;

$R^{12}$ and $R^{13}$ are each independently H, fluoro, chloro, bromo, methyl, or methoxy;

$R^{14}$ and $R^{15}$ are each independently H, fluoro, chloro, methyl, or trifluoromethyl;

X and Y are each independently C or N, provided that X or Y is N, $R^{14}$ or $R^{15}$ is absent at that position; and B is phenyl optionally substituted by —$SO_2$alkyl or —$SO_2$$NR^{23}R^{24}$ wherein $R^{23}$ and $R^{24}$ are each independently H or ($C_1$-$C_6$)alkyl.

* * * * *